US006713457B2

(12) United States Patent
Farrar et al.

(10) Patent No.: US 6,713,457 B2
(45) Date of Patent: *Mar. 30, 2004

(54) STRATEGY FOR SUPPRESSING THE EXPRESSION OF AN ENDOGENEOUS GENE BY USING COMPOUNDS THAT ARE ABLE TO BIND TO THE NON-CODING REGIONS OF THE GENE TO BE SUPPRESSED

(76) Inventors: Gwenyth Jane Farrar, 9 The Crescent, Monkstown D20, County Dublin (IE); Peter Humphries, 5 Holmwood, Cabinteely D15, County Dublin (IE); Paul Francis Kenna, 176 New Cabra Road, Dublin 7 (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 171 days.

(21) Appl. No.: 09/043,506
(22) PCT Filed: Sep. 23, 1996
(86) PCT No.: PCT/GB96/02357
  § 371 (c)(1), (2), (4) Date: Sep. 21, 1998
(87) PCT Pub. No.: WO97/11169
  PCT Pub. Date: Mar. 27, 1997

(65) Prior Publication Data
  US 2003/0096767 A1 May 22, 2003

(30) Foreign Application Priority Data
  Sep. 21, 1995 (GB) .............................. 9519299

(51) Int. Cl.[7] ............................... A01N 43/04
(52) U.S. Cl. ................... 514/44; 435/6; 435/91.31; 435/91.1; 435/325; 435/375; 435/320.1; 536/23.1; 536/24.5; 536/24.31; 536/23.2
(58) Field of Search .................. 514/44; 435/6, 435/91.1, 91.31, 440.1, 320.1, 325, 366, 375; 536/23.1, 23.2, 24.5, 24.31

(56) References Cited

U.S. PATENT DOCUMENTS

| | | | | |
|---|---|---|---|---|
| 5,223,391 A | * | 6/1993 | Coen et al. ..................... | 435/5 |
| 5,240,846 A | | 8/1993 | Collins et al. ............ | 435/240.1 |
| 5,814,500 A | | 9/1998 | Dietz ....................... | 435/172.3 |
| 5,977,296 A | * | 11/1999 | Nielsen et al. .............. | 530/300 |
| 6,482,803 B1 | * | 11/2002 | Roth et al. .................... | 514/44 |

FOREIGN PATENT DOCUMENTS

| | | |
|---|---|---|
| EP | 0414134 B1 | 2/1991 |
| EP | 0475623 A1 | 3/1992 |
| WO | 92/12262 | 7/1992 |
| WO | 93/12257 | 6/1993 |
| WO | 93/21202 | 10/1993 |
| WO | 94/03596 | 2/1994 |
| WO | 94/11494 | 5/1994 |
| WO | 94/22487 | 10/1994 |
| WO | 94/26887 | 11/1994 |
| WO | 95/34573 | 12/1995 |
| WO | 97/11169 | 3/1997 |

OTHER PUBLICATIONS

Nathan et al. Cell 1983. 34:807–814.*
Reichenberger et al. FEBS 311 (3)305–310.*
Connell et al. Biochem. 1990. 29: 4691–4698.*
Robinson–Benion et al., "Gene transplantation: Combined antisense inhibition and gene replacement strategies", Leukemia, vol. 8, Apr. 1994, pp. s152–s155.
Chang et al., "Antisense RNA complementary to 3' coding and noncoding sequences of creatine kinase . . . ", Proceedings of National Academy of Sciences, vol. 86, 1989, pp. 10006–10010.
Postel et al., "Evidence that a triplex–forming oligodeoxyribonucleotide binds to the c–myc promoter in HeLa cells", Proceedings of the National Academy of Sciences, vol. 88, 1991, pp. 8227–8231.
Marini et al., "Antisense oligonucleotides selectively suppress production in mutant alpha2(I) collagen . . . ", Pediatric Research, vol. 37, No. 4, Apr. 1995, p. 150.
Blaese et al., "Stratagies for Gene Therapy." Pathol. Biol. (Paris), 1993, 41(8): 672–6.
Bordignon et al., "Transfer of the ADA Gene into Bone Marrow Cells and Peripheral Blood Lymphocytes for the Treatment of Patients Affected by ADA–Deficient SCID." Hum. Gene Ther., 1993, 4(4): 513–20.
Carter et al., "Antisense Technology for Cancer Therapy: Does it Make Sense?" Cancer Res., 1993, 67:869–876.
Cazenave et al., "Comparative inhibition of rabbit globin mRNA translation by modified antisense oligodeoxynucleotides." Nuc. Acid Res., 1989, 17:4255–4273.
Chertkov et al., "The Hematopoietic Stromal Microenvironment Promotes Retrovirus–Mediated Gene Transfer into Hematopoietic Stem Cells." Stem Cells, 1993, 11(3): 218–27.
Cournoyer et al., "Gene Therapy of the Immune System." Ann. Rev. Immunol., 1993, 11: 297–329.

(List continued on next page.)

Primary Examiner—Andrew Wang
Assistant Examiner—James Douglas Schultz
(74) Attorney, Agent, or Firm—Testa, Hurwitz & Thibeault, LLP

(57) ABSTRACT

The invention provides strategy for suppressing expression of an endogenous gene, wherein said strategy comprises providing suppression effectors able to bind to the non-coding regions of a gene to be suppressed, to prevent the functional expression thereof. The suppression effectors may be antisense nucleic acids, and the non-coding regions can include the transcribed but non-translated regions of a gene. The strategy can also introduce a replacement gene.

39 Claims, 70 Drawing Sheets

OTHER PUBLICATIONS

Figure 1:
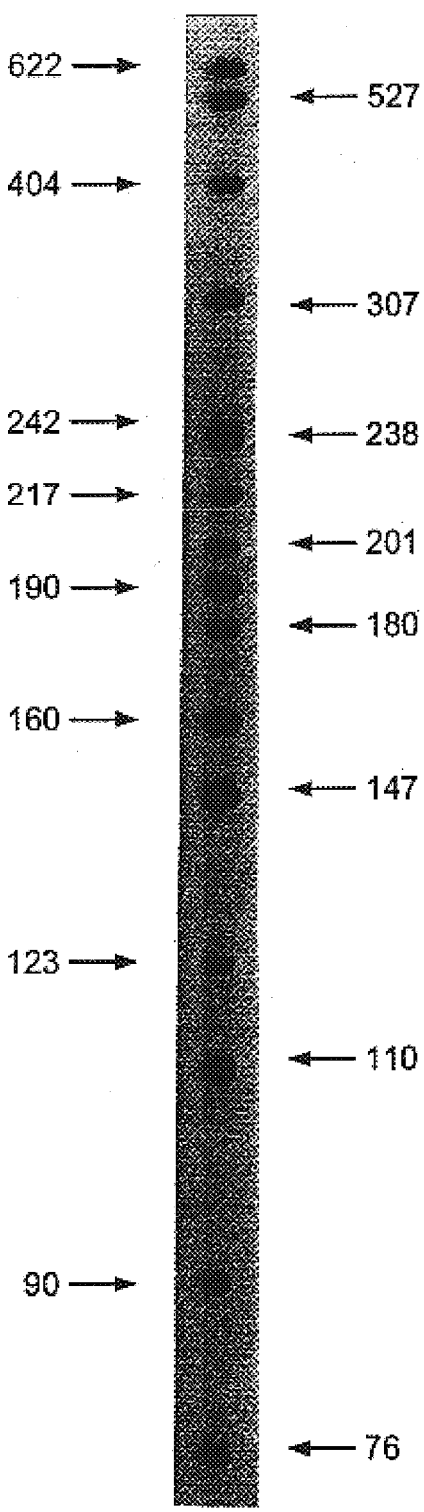

Couture et al., "Retorviral Vectors Containing Chimeric Promoter/Enhancer Elements Exhibit Cell–Type Specific Gene Expression." *Hum. Gen. Ther.*, 1994, 5(6): 667–77.

Dosaka–Akita et al., "Inhibition of Proliferation by L–*myc* Antisens DNA for the Translational Initiation Site in Huma Small Cell Lung Cancer." *Cancer Res.* 1995, 55:1559–1564.

Dryja et al., "A point mutation of the rhodospin gene in one form of retinitis pigmenosa." *Nature*, 1990, 343:364–366.

Duval–Valentin et al., "Specific inhibition of transcription by triple helix–forming oligonucleotides." *Proc. Natl. Acad. Sci. USA*, 1992, 89:504–508.

Ellis et al., "Design and specificity of hammerhead ribozymes against calretinin mRNA." *Nuc. Acid Res.*, 1993, 21:5171–5178.

Fairbanks et al., "Biochemical and Immunological Status Following Gene Therapy and PEG–ADA Therapy for Adenosine Deaminase (ADA) Deficiency." *Adv. Exp. Med. Biol.*, 1994, 370: 391–4.

Farrar et al., "A three–base–pair deletion in the peripherin–RDS gene in one form of retinitis pigmentosa." *Nature*, 1991, 354:478–480.

Farrar et al., "Autosomal Dominant Retinitis Pigmentosa: A Novel Mutation at the Peripherin/RDS Locus in the Original 6p–Linked Pedigree." *Genomics*, 1991, 14:805–807.

Farrar et al., "Progress in Genetic Linkage for Retinitis Pigmentosa and Gene Delivery to Ocular Tissues." *Invest Ophthamol Vis. Sci. (ARVO)*, 1995, 36:(4).

Feng et al., "Neoplastic Reversion Accomplished by High Efficiency Adenoviral–mediated Delivery of an Anti–ras Ribozyme." *Can. Res.*, 1995, 55:2024–2028.

Friedmann, "Overcoming the Obstacles to Gene Therapy." *Sci. Am.*, 1997, 96–101.

Gaughan et al., "Ribozyme Mediated Cleavage of Acute Phase Serum Amyloid A (A–SAA) mRNA in vitro." *FEBS Letters*, 1995, 374:241–245.

Grossman et al., "Successful ex vivo Gene Therapy Directed to Liver in a Patient with Familial Hypercholesterolaemia." *Nature Gen.*, 1994, 6: 335–341.

Hart et al., "The introduction of two silent mutations into the CFTR cDNA construct allows improved detection of exogenous mRNA in gene transfer experiments," *Human Mol. Gen.* (1995) vol. 4 (9), pp. 1597–1602.

Hanvey et al., "Antisense and Antigene Properties of Peptide Nucleic Acids." *Science*, 1992, 258:1481–1485.

Hardenbol et al., "Sequence specificity of triplex DNA formation: Analysis by a combinatorial approach, restriction endonuclease protection selection and amplification." *Proc. Natl. Acad. Sci. USA*, 1996, 93:2811–2816.

Herrmann, F., "Cancer gene therapy: principles, problems, and perspectives." *Mol. Med.*, 1995, 73:157–163.

Herschlag et al., "An RNA chaperone activity of non–specific RNA binding proteins in hammerhead ribozyme catalysis." *EMBO*, 1994, 13:(12):2913–2924.

Hershfield, "PEG–ADA Replacement Therapy for Adenosine Deaminase Deficiency: An Update After 8.5 Years." *Clin. Immunol. Immunopathol.*, 1995, 76: S228–32.

Herskowitz, "Functional inactivation of genes by dominant negative mutations." *Nature*, 1987, 329:219–222.

Hughes et al., "Delivery of a Secretable Adenosine Deaminase Through Microcapsules–A Novel Approach to Somatic Gene Therapy." *Hum. Gene Tehr.*, 1994, 5(12): 1445–55.

Jankowsky et al., "Oligonucleotide facilitators may inhibit or activate a hammerhead ribozyme." *Nuc. Acid. Res.*, 1996, 24:(3):423–429.

Jones et al., "Tagging ribozyme reaction sites to follow *trans*–splicing in mammalian cells." *Nature Medicine*, 1996, 2:643–648.

Jordan et al., "Localization of an autosomal dominant retinitis pigmentosa gene to chromosome 7q." *Nature Genetics*, 1993, 4:54–58.

Kajiwara et al, "Mutation in the human retinal degeneration slow gene in autosomal dominant retinitis pigmentosa." *Nature*, 1991, 354:480–483.

Knudsen et al., "Antisense properties of duplex–and triplex–forming PNAs." *Nuc. Acid Res.*, 1996, 24:(3):494–500.

Kuo et al., "Efficient Gene Transfer into Primary Murine Lymphocytes Obviating the Need for Drug Selection." *Blood*, 1993, 82(3): 845–52.

Lange et al., "In Vitro and In Vivo Effects of Synthetic Ribozymes Targeted Against BCR/ABL mRNA." *Leukemia*, 1993, 7:1786–1794.

Lyons et al., "An Improved Retroviral Vector Encoding the Herpes Simplex Virus Thymidine Kinase Gene Increases Antitumor Efficacy In Vivo."*Cancer Gene Ther.*, 1995, 2(4): 273–80.

Mansergh et al., "Evidence for genetic heterogeneity in Best's vitelliform macular dystrophy." *J. Med. Genet*, 1995, 32:855–858.

Mashhour et al., "In Vivo Adenovirus–Meidated Gene Transfer Into Ocular Tissues." *Gene Therapy*, 1994, 1:122–126.

McKay et al., "Enhanced activity of an antisense oligonucleotide targeting murine protein kinase C–[alpha] by the incorporation of 2'–O–propyl modifications." *Nuc. Acid Res.*, 1996, 24:(3):411–417.

McWilliam et al., "Autosomal Dominant Retinitis Pigmentosa (ADRP): Localization of an ADRP Gene to the Long Arm of Chromosome 3." *Genetics*, 1989, 5:612–619.

Mickish et al., "From Laboratory Expertise to Clinical Practics: Multidrug–Resistance Based Gene Therapy Becomes Available for Urologist." *World J. Urol.*, 1994, 12(2): 104–11.

Mitani, et al., "Gene transfer therapy for heritable disease: cell and expression targeting," *Philos Trans. R. Soc. Lond. B. Biol. Sci.* 1993, 339:217–24.

Mitani, et al., "Transduction of Human Bone Marrow by Adenoviral Vector." *Hum. Gene Ther.*, 1994, 5(8): 941–8.

Mitani et al., "Long–term Expression of Retroviral–Transduced Adenosine Deaminase in Human Primitive Hematopoietic Progenitors." *Hum. Gene Ther.*, 1993, 4(1) 9–16.

Moritz et al., "Human Cord Blood Cells as Targets for Gene Transfer: Potential Use in Genetic Therapies of Severe Combined Immunodefiency Disease." *J. Exp. Med.*, 1993, 178(2): 529–36.

Nabel et al., "Direct Gene Transfer for Treatment of Human Cancer." *Ann. N. Y. Acad. Sci.*, 1995, 772: 227–31.

Nimgaonkar et al., "Long–term Expression of the Glucocerebrosidase Gene in Mouse and Human Hematopoietic Progenitors." Department of Medicine, University of Pittsburgh Medical Center, PA, USA. *Leukemia*, 1995, 9 Suppl 1: S38–42.

Ohta et al., "Tissue–specific expression of an anti–*ras*ribozyme inhibits proliferation of human malignant melanoma cells." *Nuc. Acid Res.*, 1996, 24:(5):938–942.

Orkin et al., "Report and Recommendations of the Panel to Assess the NIH Investment in Research on Gene Therapy." http://ww.nih.gov/news/panelrep.html, Dec. 7, 1995.

Ott et al., "Localizing multiple X chromosome–linked retinitis pigmentosa loci using multilocus homogeneity tests." *Pro. Natl. Acad. Sci.*, 1990, 87:701–704.

Oyama et al., "N–ras Mutation of Thyroid Tumor with Special Reference to the Folicular Type." *Pathol. Int.*, 1995, 45:45–50.

Porumb et al., "Temporary ex Vivo Inhibition of the Expression of the Human Oncogene HER2 (NEU) by a Triple Helix–forming Oligonucleotide." *Can. Res.*, 1996, 56:515–522.

Postel et al., "Evidence that a triplex–forming oligodeoxyribonucleotide binds to the c–myc promoter in HeLa cells, thereby reducing c–myc mRNA levels." *Proc. Natl. Acad. Sci. USA*, 1991, 88:8227–8231.

Quatrrone et al., "Reversion of the Invasive Phenotype of Transformed Human Fibroblast by Anti–Messenger Oligonucleotide Inhibition of Urokinase Receptor Gene Expression." *Can. Res.*, 1995, 55:90–95.

Ramesh et al., "High–Level Human Adenosine Deaminase Expression in Dog Skin Fibroblasts is not Sustained Following Transplantation." *Human Gene Ther.*, 1993, 4(1): 3–7.

Ramesh et al., "High Level Expression from a Cytomegalovirus Promoter in Macrophage Cells." *Human Gen. Ther.*, 1995, 6(10): 1323–1327.

Ramsey et al., "Retrovirus Mediated Gene Transfer as Therapy for Adenosine Deaminase (ADA) Deficiency." *Leukemia*, 1995, 9 Suppl 1:S70.

Rimsky et al., "*Trans*–dominant inactivation of HTLV–1 and HIV–1 gene expression by mutation of the HTLV–1 Rex transactivator." *Nature*, 1989, 341:453–456.

Sullenger et al., "Ribozyme Mediated Repair of Defective mRMA by Target Trans–splicing." *Nature*, 1994, 371: 619–622.

Sun et al., "Sequence–specific intercalating agents: Intercalation at specific sequences on duplex DNA via major groove recognition by oligonucleotide–intercalator conjugations." *Proc. Natl. Acad. Sci USA*, 1989, 86:9198–9202.

Takaku [Recent Trends of Gene Therapy of Human Patients] *Nippon Rinsho*, 1993, 51(7): 1915–22. Japanese. English language summary.

Tolstoshev, "Gene Therapy, Concepts, Current Trials and Future Directions." *Ann. Rev. Pharmacol. Toxicol.*, 1993, 32: 573–96.

Trauger et al., "Recognition of DNA by designed ligands at subnanomolar concentrations." *Nature*, 1996, 382:559–561.

Valera et al., "Expression of GLUT–2 Antisense RNA in β Cells of Transgenic Mice Leads to Diabetes." *J. Biol. Chem.*, 1994, 269:28543–28546.

Van Soest et al., "Assignment of a Gene for Autosomal Recessive Retinitis Pigmentosa (RP12) to Chromosome 1q31–q32.1 in an Inbred and Genetically Heterogenous Disease Population." *Genomics*, 1994, 22:499–504.

Vaulont et al., "Disruption of the Adenosine Deaminase (ADA) Gene Using a Dicistronic Promoterless Construct: Production of an ADA–Deficient Homozygote ES Cell Line." *Transgenic Res.*, 1995, 4(4): 247–55.

Verma et al., "Gene Therapy–Promises, Problems, and Prospects." *Nature*, 1987, 389:239–242.

Wei et al., "Hybridization properties of oligodeoxynucleotide pairs bridged by polyarginine peptides." *Nuc. Acid Res.*, 1996, 24:(4):655–661.

Welsh et al., "Adenovirus–Mediated Gene Transfer for Cystic Fibrosis: Part A. Safety of Dose and Repeat Administration in the Nasal Epithelium. Part B. Clinical Efficacy in the Maxillary Sinus."*Hum. Gene Ther.*, 1995, 6(2): 205–18.

Welsh et al., "Cystic Fibrosis Gene Therapy Using an Adenovirus Vector: In Vivo Safety and Efficacy in Nasal Epithelium." *Hum. Gene Ther.*, 1994, 5(2): 209–19.

Yu et al., "Liposome–Mediated in vivo E1A Gene Transfer Suppressed Dissemination of Ovarian Cancer Cells that Overexpress HER–2/neu." *Oncogene*, 1995, 11(7): 1383–8.

Zabner et al, "Adenovirus–Mediated Gene Transfer Corrects the Chloride Transport Defect in Nasal Epithelia of Patients with Cystic Fibrosis." *Cell.*, 1993, 75(2): 207–16.

Zabner et al., "Correction of cAMP–Stimulated Fluid Secretion in Cystic Fibrosis Airway Epithelia: Efficiency of Adenovirus–Mediated Gene Transfer In Vitro." *Hum. Gene Ther.*, 1994, 5(5): 585–93.

Zabner et al., "Safety and Efficacy of Repetitive Adenovirus–Mediated Transfer of CFTR cDNA to Airway Epithelia of Primates and Cotton Rats." *Nature Gen.*, 1994, 6(1): 75–83.

Zhao et al, "Generating Loss–of–Function Phenotypes of the *Fushi Tarazu* Gene with a Targeted Ribozyme in *Drosophila*." *Nature*, 1993, 365: 448–51.

\* cited by examiner

STRATEGY FOR SUPPRESSING THE EXPRESSION OF AN ENDOGENEOUS GENE BY USING COMPOUNDS THAT ARE ABLE TO BIND TO THE NON-CODING REGIONS OF THE GENE TO BE SUPPRESSED

FIELD OF THE INVENTION

The present invention relates to a strategy and medicaments for suppressing a gene. In particular the invention relates to the suppression of mutated genes which give rise to a dominant or deleterious effect either monogenically or polygenically. The invention relates to a strategy for suppressing a gene or disease allele such that (if required) a replacement gene, gene product or alternative gene therapy can be introduced.

The invention also relates to a medicament or medicaments for use in suppressing a gene or disease allele which is present in a genome of one or more individuals or animals. The said medicament(s) may also introduce the replacement gene sequence, product or alternative therapy.

Generally the strategy of the present invention will be useful where the gene, which is naturally present in the genome of a patient, contributes to a disease state. Generally, the gene in question will be mutated, that is, will possess alterations in its nucleotide sequence that affect the function or level of the gene product. For example, the alteration may result in an altered protein product from the wild type gene or altered control of transcription and processing. Inheritance or the somatic acquisition of such a mutation can give rise to a disease phenotype or can predispose an individual to a disease phenotype. However the gene of interest could also be of wild type phenotype, but contribute to a disease state in another way such that the suppression of the gene would alleviate or improve the disease state.

BACKGROUND OF THE INVENTION

Studies of degenerative hereditary ocular conditions, including Retinitis Pigmentosa (RP) and various macular dystrophies have resulted in a substantial elucidation of the molecular basis of these debilitating human eye disorders. In a collaborative study, applying the approach of genetic linkage, two x-linked RP genes were localised to the short arm of the X chromosome (Ott et al. 1990). In autosomal dominant forms of RP (adRP) three genes have been localised. The first adRP gene mapped on 3q close to the gene encoding the photoreceptor specific protein rhodopsin (McWilliam et al. 1989; Dryja et al. 1990). Similarly, an adRP gene was placed on 6p close to the gene encoding the photoreceptor specific protein peripherin/RDS (Farrar et al. 1991a,b; Kajiwara et al. 1991). A third adRP gene mapped to 7q (Jordan et al. 1993); no known candidate genes for RP reside in this region of 7q. In addition, the disease gene segregating in ha Best's macular dystrophy family was placed on 11q close to the region previously shown to be involved in some forms of this dystrophy (Mansergh et al. 1995). Recently, an autosomal recessive RP gene was placed on 1q (Van Soest et al. 1994). Genetic linkage, in combination with techniques for rapid mutational screening of candidate genes, enabled subsequent identification of causative mutations in the genes encoding rhodopsin and peripherin/RDS proteins. Globally about 100 rhodopsin mutations have now been found in patients with RP or congenital stationary night blindness. Similarly about 40 mutations have been characterised in the peripherin/RDS gene in patients with RP or with various macular dystrophies.

Knowledge of the molecular aetiology of some forms of human inherited retinopathies has stimulated the establishment of methodologies to generate animal models for these diseases and to explore methods of therapeutic intervention; the goal being the development of treatments for human retinal diseases (Farrar et al. 1995). Surgical procedures enabling the injection of sub-microlitre volumes of fluid intravitinally or sub-retinally into mouse eyes have been developed by Dr. Paul Kenna. In conjunction with the generation of animal models, optimal systems for delivery of gene therapies to retinal tissues using viral (inter alia Adenovirus, Adeno Associated Virus, Herpes Simplex Type 1 Virus) and non-viral (inter alia liposomes, dendrimers) vectors alone or in association with derivatives to aid gene transfer are being investigated.

Generally, gene therapies utilising both viral and non-viral delivery systems have been applied in the treatment of a number of inherited disorders; of cancers and of some infectious disorders. The majority of this work has been undertaken on animal models, although, some human gene therapies have been approved. Many studies have focused on recessively inherited disorders, the rationale being, that the introduction and efficient expression of the wild type gene may be sufficient to result in a prevention/amelioration of disease phenotype. In contrast gene therapy for dominant disorders will require the suppression of the dominant disease allele. Notably the majority of characterised mutations that cause inherited retinal degenerations such as RP are inherited in an autosomal dominant fashion. Indeed there are over 1,000 autosomal dominantly inherited disorders in man. In addition there are many polygenic disorders due to the co-inheritance of a number of genetic components which together give rise to a disease phenotype. Effective gene therapy in dominant or polygenic disease will require suppression of the disease allele while in many cases still maintaining the function of the normal allele.

Strategies to differentiate between normal and disease alleles and to selectively switch off the disease allele using suppression effectors inter alia antisense DNA/RNA, ribozymes or triple helix DNA, targeted towards the disease mutation may be difficult in many cases and impossible in others—frequently the disease and normal alleles may differ by only a single nucleotide. For example, the disease mutation may not occur at a ribozyme cleavage site. Similarly the disease allele may be difficult to target specifically by antisense DNA/RNA or triple helix DNA if there are only small sequence differences between the disease and normal alleles. A further difficulty inhibiting the development of gene therapies is the heterogeneous nature of some dominant disorders—many different mutations in the same gene give rise to a similar disease phenotype. The development of specific gene therapies for each of these would be extremely costly. To circumvent the dual difficulties associated with specifically targeting the disease mutation and the genetic heterogeneity present in some inherited disorders, the present invention aims to provide a novel strategy for gene suppression and replacement exploiting the noncoding and control regions of a gene.

Suppression effectors have been used previously to achieve specific suppression of gene expression. Antisense DNA and RNA has been used to inhibit gene expression in many instances. Many modifications, such as phosphorothioates, have been made to antisense oligonucleotides to increase resistance to nuclease degradation, binding affinity and uptake (Cazenave et al. 1989; Sun et al. 1989; McKay et al. 1996; Wei et al. 1996). In some instances, using antisense and ribozyme suppression stategies has led to the reversal of the tumor phenotype by greatly reducing the expression of a gene product or by cleaving a mutant transcript at the site of the mutation (Carter and Lemoine 1993; Lange et al. 1993; Valera et al. 1994; Dosaka-Akita et al. 1995; Feng et al. 1995; Quattrone et al. 1995; Ohta et al. 1996). For example, neoplastic reversion was obtained using a ribozyme targeted to the codon 12 H-ras mutation in bladder carcinoma cells (Feng et al. 1995). Ribozymes have also been proposed as a means of both inhibiting gene expression of a mutant gene and of correcting the mutant by targeting trans-splicing (Sullenger and Cech 1994; Jones et al. 1996). Ribozymes can be designed to elict autocatalytic cleavage of RNA targets. However the inhibitory effect of some ribozymes may be due in part to an antisense effect of the variable antisense sequences flanking the catalytic core which specify the target site (Ellis and Rodgers 1993; Jankowsky and Schwenzer 1996). Ribozyme activity may be augmented by the use of non-specific nucleic acid binding protiens or facilitator oligonucleotides (Herschlag et al. 1994; Jankowsky and Schwenzer 1996). Triple helix approaches have also been investigated for sequence specific gene suppression—triplex forming oligonucleotides have been found in some cases to bind in a sequence specific manner (Postel et al. 1991; Duval-Valentin et al. 1992; Hardenbol and Van Dyke 1996; Porumb et al. 1996). Similarly peptide nucleic acids have been shown in some instances to inhibit gene expression (Hanvey et al. 1992; Knudson and Nielson 1996). Minor groove binding polyamides have been shown to bind in a sequence specific manner to DNA targets and hence may represent useful small molecules for future suppression at the DNA level (Trauger et al. 1996). In addition, suppression has been obtained by interference at the protein level using dominant negative mutant peptides and antibodies (Herskowitz 1987; Rimsky et al. 1989; Wright et al. 1989). In some cases suppression strategies have lead to a reduction in RNA levels without a concomitant reduction in proteins, whereas in others, reductions in RNA levels have been mirrored by reductions in protein levels.

The present invention aims to circumvent the shortcomings in the prior art by using a two step approach for suppression and replacement.

According to the present invention there is provided a strategy for suppressing expression of an endogenous gene, wherein said strategy comprises providing suppression effectors able to bind to the non-coding regions of a gene to be suppressed, to prevent the functional expression thereof. Preferably the suppression effectors are antisense nucleic acids. Preferably the targetted non-coding regions include the transcribed but non-translated regions of a gene.

Generally the term suppression effectors includes nucleic acids, peptide nucleic acids (PNAs) or peptides which can be used to silence or reduce gene expression in a sequence specific manner.

The antisense nucleic acids can be DNA or RNA, can be directed to 5' and/or 3' untranslated regions and/or to introns and/or to control regions or to any combination of such untranslated regions. However targetted the binding of the antisense nucleic acid prevents or lowers the functional expression of the endogenous gene. Chimeric antisense nucleic acids including a small proportion of translated regions of a gene can be used in some cases to help to optimise suppression. Likewise chimeric antisense nucleic acids including a small proportion of promoter regions of a gene can be used in some cases to help to optimise suppression.

Generally the term 'functional expression' means the expression of a gene product able to function in a manner equivalent to or better than a wild type product. In the case of a mutant gene 'functional expression' means the expression of a gene product whose presence gives rise to a deleterious effect.

In a particular embodiment of the invention the strategy further employs ribozymes. These can be designed to elicit cleavage of target RNAs.

The strategy further employs nucleotides which form triple helix DNA.

Nucleic acids for antisense, ribozymes and triple helix may be modified to increase stability, binding efficiencies and uptake as discussed earlier. Nucleic acids can be incorporated into a vector. Vectors include DNA plasmid vectors, RNA or DNA virus vectors. These can be combined with lipids, polymers or other derivatives to aid gene delivery and expression.

The invention further provides the use of antisense nucleotides, ribozymes, triple helix nucleotides or other suppression effectors alone or in a vector or vectors, wherein the nucleic acids are able to bind specifically to untranslated regions of a gene such as the 5' and 3' UTRs to prevent the functional expression thereof, in the preparation of a medicament for the treatment of an autosomal dominant disease.

In a further embodiment the non-coding regions of the gene can include promoter regions which are untranslated.

According to the present invention there is provided a strategy for suppressing an endogenous gene and introducing a replacement gene, said strategy comprising the steps of:

1. providing antisense nucleic acid able to bind to at least one non-coding or untranslated region of a gene to be suppressed and
2. providing genomic DNA or cDNA encoding a replacement gene sequence, wherein the antisense nucleic acid is unable to bind to equivalent non-coding or untranslated regions in the genomic DNA or cDNA to prevent expression of the replacement gene sequence.

The replacement nucleic acids will not be recognised by the suppression nucleic acid. The control sequences of the replacement nucleic acid may belong to a different mammalian species, may belong to a different human gene or may be similar but altered from those in the gene to be suppressed and may thus permit translation of the part of the replacement nucleic acid to be initiated.

By control sequences is meant sequences which are involved in the control of gene expression or in the control of processing and/or sequences present in mature RNA transcripts and/or in precursor RNA transcripts, but not including protein coding sequences.

In a particular embodiment of the invention there is provided a strategy for gene suppression targeted towards the non-coding regions of a gene and using a characteristic of one of the alleles of a gene, for example, the allele carrying a disease mutation. Suppressors are targeted to non-coding regions of a gene and to a characteristic of one allele of a gene such that suppression in specific or partially specific to one allele of the gene. The invention further provides for replacement nucleic acids containing altered non-coding sequences such that replacement nucleic acids cannot be recognised by suppressors which are targeted towards the non-coding regions of a gene. Replacement nucleic acids provide the wild type or an equivalent gene product but are protected completely or in part from suppression effectors targeted to non-coding regions.

In a further embodiment of the invention there is provided replacement nucleic acids with altered non-coding sequences such that replacement nucleic acids cannot be recognised by naturally occurring endogenous suppressors present in one or more individuals, animals or plants. Replacement nucleic acids with altered non-coding sequences provide the wild type or equivalent gene product but are completely or partially protected from suppression by naturally occurring endogenous suppression effectors.

In an additional embodiment of the invention there is provided replacement nucleic acids with altered non-coding sequences such that replacement nucleic acids provide a wild type or equivalent gene product or gene product with beneficial characteristics. For example, the 3° non-coding sequences of the replacement nucleic acids could be altered to modify the stability and turn over the RNA expressed from the replacement nucleic acids thereby sometimes affecting levels of resulting gene product.

The invention further provides the use of a vector or vectors containing suppression effectors in the form of nucleic acids, said nucleic acids being directed towards untranslated regions or control sequences of the target gene and vector(s) containing genomic DNA or cDNA encoding a replacement gene sequence to which nucleic acids for suppression are unable to bind, in the preparation of a combined medicament for the treatment of an autosomal dominant disease. Nucleic acids for suppression or replacement gene nucleic acids may be provided in the same vector or in separate vectors. Nucleic acids for suppression or replacement gene nucleic acids may be provided as a combination of nucleic acids alone or in vectors. The vector may contain antisense nucleic acid with or without, ribozymes.

The invention further provides a method of treatment for a disease caused by an endogenous mutant gene, said method comprising sequential or concomitant introduction of (a) antisense nucleic acids to the non-coding regions of a gene to be suppressed; to the 5' and/or 3' untranslated regions of a gene or intronic regions or to the non-control regions of a gene to be suppressed, (b) replacement gene sequence with control sequences which allow it to be expressed.

The nucleic acid for gene suppression can be administered before or after or at the same time as the replacement gene is administered.

The invention further provides a kit for use in the treatment of a disease caused by an endogenous mutation in a gene, the kit comprising nucleic acids for suppression able to bind to the 5' and/or 3' untranslated regions or intronic regions or control regions of the gene to be suppressed and (preferably packaged separately thereto) a replacement nucleic acid to replace the mutant gene having a control sequence to allow it to be expressed.

Nucleotides can be administered as naked DNA or RNA, with or without ribozymes and/or with dendrimers. Ribozymes stabilise DNA and block transcription. Dendrimers (for example dendrimers of methylmethacrylate) can be utilised, it is believed the dendrimers mimic histones and as such are capable of transporting nucleic acids into cells. Oligonucleotides can be synthesized, purified and modified with phosphorothioate linkages and 2'0-allyl groups to render them resistant to cellular nucleases while still supporting RNase H medicated degradation of RNA. Also, nucleic acids can be mixed with lipids to increase efficiency of delivery to somatic tissues.

Nucleotides can be delivered in vectors. Naked nucleic acids or nucleic acids in vectors can be delivered with lipids or other derivatives which aid gene delivery. Nucleotides may be modified to render them more stable, for example, resistant to cellular nucleases while still supporting RNaseH mediated degradation of RNA or with increased binding efficiencies as discussed earlier.

Suppression effectors and replacement sequences can be injected sub-sectionally, or may be administered systemically.

There is now an armament with which to obtain gene suppression. This, in conjunction with a better understanding of the molecular etiology of disease, results in an ever increasing number of disease targets for therapies based on suppression. In many cases, complete (100%) suppression of gene expression has been difficult to achieve. Possibly a combined approach using a number of suppression effectors may be required. For some disorders it may be necessary to block expression of a disease allele completely to prevent disease symptoms whereas for others low levels of mutant protein may be tolerated. In parallel with an increased knowledge of the molecular defects causing disease has been the realisation that many disorders are genetically heterogeneous. Examples in which multiple genes and/or multiple mutations within a gene can give rise to a similar disease phenotype include osteogenesis imperfecta, familial hypercholesteraemia, retinitis pigmentosa, and many others.

The invention addresses some shortcomings of the prior art and aims to provide a novel approach to the design of suppression effectors directed to target mutant genes. Suppression of every mutation giving rise to a disease phenotype may be costly, problematic and sometimes impossible. Disease mutations are often single nucleotide changes. As a result differentiating between the disease and normal alleles may be difficult. Furthermore some suppression effectors require specific sequence targets, for example, ribozymes can only cleave at NUX sites and hence will not be able to target some mutations. Notably, the wide spectrum of mutations observed in many diseases adds an additional layer of complexity in the development of therapeutic strategies for such disorders. A further problem associated with suppression is the high level of homology present in coding sequences between members of some gene families. This can limit the range of target sites for suppression which will enable specific suppression of a single member of such a gene family.

The strategy described herein has applications for alleviating autosomal dominant diseases. Complete silencing of a disease allele may be difficult to achieve using antisense, ribozyme and triple helix approaches or any combination of these. However small quantities of mutant product may be tolerated in some autosomal dominant disorders. In others a significant reduction in the proportion of mutant to normal product may result in an amelioration of disease symptoms. Hence this strategy may be applied to any autosomal dominantly inherited disease in man where the molecular basis of the disease has been established. This strategy will enable the same therapy to be used to treat a wide range of different disease mutations within the same gene. The development of strategies will be important to future gene therapies for some autosomal dominant diseases, the key to a general strategy being that it circumvents the need for a specific therapy for every dominant mutation in a given disease-causing gene. This is particularly relevant in some disorders, for example, rhodopsin linked autosomal dominant RP (adRP), in which to date about 100 different mutations in the rhodopsin gene have been observed in adRP patients. The costs of developing designer therapies for each individual mutation which may be present in some cases in a single patient are prohibitive at present. Hence strategies such as this using a more universally applicable approach for therapy will be required.

This strategy may be applied in gene therapy approaches for biologically important polygenic disorders affecting large proportions of the world's populations such as age related macular degeneration (ARMD) glaucoma, manic depression, cancers having a familial component and indeed many others. Polygenic diseases require the inheritance of more than one mutation (component) to give rise to the disease phenotype. Notably an amelioration in disease symptoms may require reduction in the presence of only one of these components, that is, suppression of one of the genotypes which, together with others, leads to the disease phenotype, may be sufficient to prevent or ameliorate symptoms of the disease. In some cases the suppression of more than one component giving rise to the disease pathology may be required to obtain an amelioration in disease symptoms. The strategy described here may be applied broadly to possible future interventive therapies in common polygenic diseases to suppress a particular genotype(s) and thereby suppress the disease phenotype.

In the present invention suppression effectors are designed specifically to target the non-coding regions of genes, for example, the 5' and 3' UTRs. This provides sequence specificity for gene suppression. In addition it provides greater flexibility in the choice of target sequence for suppression in contrast to suppression strategies directed towards single disease mutations. Furthermore it allows suppression effectors to target non-coding sequences 5' or 3' of the coding region thereby allowing the possibility of including the ATG start site in the target site for suppression and hence presenting an opportunity for suppression at the level of translation or inducing instability in RNA by, for example, cleavage of the RNA before the polyA tail.

Notably the invention has the advantage that the same suppression strategy when directed to the 5' and 3' non-coding sequences could be used to suppress, in principle, any mutation in a given gene. This is particularly relevant when large numbers of mutations within a single gene cause a disease pathology. Suppression targeted to non-coding sequences allows, when necessary, the introduction of a replacement gene(s) with the same or similar coding sequences to provide the normal gene product. The replacement gene can be designed to have altered non-coding sequences and hence can escape suppression as it does not contain the target site(s) for suppression. The same replacement gene could in principle be used in conjunction with the suppression of any disease mutation in a given gene. In the case of suppression of an individual member of a gene family, the non-coding regions typically show lower levels of homology between family members thereby providing more flexibility and specificity in the choice of target sites for suppression. In relation to this aspect of the invention, the use of intronic sequences for suppression of an individual member of a family of genes has been described in a previous invention (REF: WO 92/07071). However the use of 5' and 3' non-coding sequences as targets for suppression holds the advantage that these sequences are present not only in precursor messenger RNAs. but also in mature messenger RNAs, thereby enabling suppressors to target all forms of RNA. In contrast, intronic sequences are spliced out of mature RNAS.

In summary the invention can involve gene suppression and replacement such that the replacement gene cannot be suppressed. Both the same suppression and replacement steps can be used for many and in some cases all of the disease mutations identified in a given gene. Therefore the invention enables the same approach to be used to suppress a wide range of mutations within the same gene. Suppression and replacement can be undertaken in conjunction with each other or separately.

EXAMPLES

The present invention is exemplified using four different genes: human rhodopsin, human peripherin, mouse rhodopsin and mouse peripherin. While all four genes are retinal specific there is no reason why the present invention could not be deployed in the suppression of other genes. Notably the 5'UTR and part of the coding sequence of the COL1A2 gene has been cloned together with a ribozyme to target the 5'UTR of the gene emphasizing the broad utility of the invention in gene suppression. The 5'UTR and part of the coding sequence of the COL1A2 gene in which there are many mutations have previously been identified which give rise to autosomal dominant osteogenesis imperfecta, has begun but was not completed at the time of submission. Many examples of mutant genes which give rise to disease phenotypes are available from the prior art—these all represent disease targets for this invention. The present invention is exemplified using ribozymes with antisense arms to elicit RNA cleavage. There is no reason why other suppression effectors directed towards the non-coding regions of genes could not be used to achieve gene suppression. Many examples from the prior art detailing the use of suppression effectors inter alia antisense RNA/DNA, triple helix, PNAs, peptides to achieve suppression of gene expression are reported as discussed earlier. The present invention is exemplified using ribozymes with antisense arms to elicit cleavage of template RNA transcribed from one vector and non-cleavage of replacement RNAs with altered untranslated region sequences transcribed from a second vector. There is no reason why both the suppression and replacement steps could not be in the same vector. In addition there is no reason why ribozymes could not be used to combine both the suppression and replacement steps, that is, to cleave the target RNA and to ligate to the cleavage product, a replacement RNA with an altered sequence, to prevent subsequent cleavage by ribozymes which are frequently autocatalytic as discussed. The present invention is exemplified using suppression effectors directed to target the 5' untranslated region of the above named genes. There is no reason why other non-coding regions of a gene inter alia the 3' untranslated region or the regions involved in the control of gene expression such as promoter regions or any combination of non-coding regions could not be used to achieve gene suppression. Suppression targeted to any non-coding region of a gene would allow the expression of a replacement gene with altered sequences in the non-coding region of the gene to which the suppression effector(s) was targeted.

Materials and Methods

Cloning Vectors cDNA templates, cDNA hybrids with altered non-coding sequences, ribozymes and antisense DNA fragments were cloned into commercial expression vectors (pcDNA3, pZeoSV or pBluescript) which enable expression in a test tube from T7, T3 or SP6 promoters or expression in cells from CMV or SV40 promoters. Inserts were placed into the multiple cloning site (MCS) of these vectors typically at or near the terminal ends of the MCS to delete most of the MCS and thereby prevent any possible problems with efficiency of expression subsequent to cloning.

Sequencing Protocols

Clones containing template cDNAs, hybrid cDNAs with altered non-coding sequences, ribozymes and antisense were sequenced by ABI automated sequencing machinery using standard protocols.

Expression of RNAs

RNA was obtained from clones in vitro using a commercially available Ribomax expression system (Promega) and standard protocols. RNA purifications were undertaken using the Bio-101 RNA purification kit or a solution of 0.3M sodium acetate and 0.2% SDS. Cleavage reactions were performed using standard protocols with varying $MgCl_2$ concentrations (0–15 mM) at 370° C. typically for 3 hours. Time points were performed at the predetermined optimal $MgCl_2$ concentrations for up to 5 hours. Radioactively labeled RNA products were obtained by incorporating $\alpha$-$P^{32}$ rUTP (Amersham) in the expression reactions (Gaughan et al. 1995). Labeled RNA products were run on polyacrylamide gels before cleavage reactions were undertaken for the purposes of RNA purification and subsequent to cleavage reactions to establish if RNA cleavage had been achieved.

The exact base at which transcription starts has not been defined fully for some promoters (pcDNA3 Invitrogen) hence the sizes of the RNA products may vary slightly from those predicted in Table 1. In addition multiple rounds of cloning of a cDNA results is inserts carrying extra portions of MCS again, sometimes altering marginally the size of expressed RNA products. Typically 4–8% polyacrylamide gels were run to resolve RNA products.

RNA Secondary Structures

Predictions of the secondary structures of human rhodopsin, mouse rhodopsin, human peripherin, mouse peripherin and human type I Collagen COLIA2 mRNAs where obtained using the RNAPlotFold program. Ribozyme and antisense was designed to target areas of the RNA that were predicted to be accessible to suppression effectors and which were composed of non-coding sequence. The integrity of open loop structures was evaluated from the 15 most probable RNA structures. Additionally RNA structures for truncated RNA products were generated and the integrity of open loops between full length and truncated RNAs compared.

Template/Hybrid/Ribozyme and Antisense Constructs

EXAMPLES

Various products of the examples are illustrated in FIGS. 1 to 20 and are explained in the results sections.

Sequences

In each case the most relevant sequences have been underlined. The position of the ATG start in each sequence is highlighted by an arrow. Sequences 1 to 18 (SEQ ID NOS:1–18, respectively) below are represented in FIGS. 21 to 39 respectively.

| | |
|---|---|
| Sequence 1: | Mouse Rhodopsin CDNA sequences mouse rhodopsin 5'UTR sequences/the ATG start site/mouse rhodopsin coding sequences are shown. |
| Sequence 2: (F + R) | Mouse Rhodopsin cDNA with altered non-coding sequences mouse rhodopsin 5'UTR sequences with a 1 base change/the ATG start site/mouse rhodopsin coding sequences are shown. |
| Sequence 3: (F + R) | Mouse Rhodopsin cDNA with altered non-coding sequences mouse rhodopsin 5'UTR sequences with a 1 base change/the ATG start site/mouse rhodopsin coding sequences are shown. |
| Sequence 4: | Ribozyme 3 |
| Sequence 5: | Human Rhodopsin cDNA sequence human rhodopsin 5'UTR sequences/the ATG start site/human rhodopsin coding sequences are shown. |
| Sequence 6: | Human Rhodopsin cDNA with altered non-coding sequences human rhodopsin 5'UTR sequences (shorter UTR)/the ATG start site/human rhodopsin coding sequences are shown. |
| Sequence 7: | Ribozyme 15 |
| Sequence 8: | Mouse peripherin cDNA sequences mouse peripherin 5'UTR sequences/the ATG start site/mouse peripherin coding sequences are shown. |
| Sequence 9: | Mouse peripherin cDNA with altered non-coding sequences mouse rhodopsin 5'UTR sequences/the ATG start site/mouse peripherin coding sequences are shown. |
| Sequence 10: | Ribozyme 17 |
| Sequence 11: | Human peripherin cDNA sequences human peripherin 5'UTR sequences/the ATG start site/human peripherin coding sequences are shown. |
| Sequence 12: | Human peripherin cDNA with altered non-coding sequences Partial human and mouse peripherin 5'UTR sequences/the ATG start site/human peripherin coding sequences are shown. |
| Sequence 13: | Ribozyme 8 |
| Sequence 14: | Ribozyme 9 |
| Sequence 15: | Human type I collagen (COL1A2) sequence - 5'UTR and exon 1 sequence |
| Sequence 16: | Ribozyme 18 |
| Sequence 17: | Antisense construct containing 127bp of antisense sequence targeting the 5'UTR of the mouse peripherin gene. |
| Sequence 18: | Sense construct containing 127bp of sense sequence from the 5'UTR of the mouse peripherin gene. |

Mouse Rhodopsin
Template cDNA

A full length mouse rhodopsin cDNA was generated from a partial cDNA clone missing the sequence coding for the first 20 amino acids of the protein and a partial genomic clone, which enabled the production of a full length cDNA (kindly donated by Dr. Wolfgang Baehr). The full length cDNA was cloned into the EcoRI site of pcDNA3 in a 5' to 3' orientation allowing subsequent expression of RNA from the T7 or CMV promoters in the vector. The full length 5'UTR sequence was present in this clone. In addition to the full length 5' UTR sequence the clone contains additional 5' upstream sequence of the mouse rhodopsin gene as the clone was generated using the EcoRI site present at position 1120 (Accession number: M55171). (SEQ ID NO:1)

Hybrid cDNAs with Altered Non-coding Regions
Hybrid I

The mouse rhodopsin hybrid cDNA sequence was altered in the non-coding sequences by PCR primer directed mutagenesis and cloned into the Hindlll and EcoRI sites of pcDNA3 in a 5' to 3' orientation allowing subsequent expression of RNA from the T7 or CMV promoters in the vector. PCR mutagenesis was undertaken using a Hindlll (in the MCS of pcDNA3) to Eco47111 (in Exon 2 of the gene) DNA fragment. The 5'UTR was altered significantly—the mouse rhodopsin 5'UTR was completely replaced by the 5'UTR of the human peripherin gene, that is, by 5'UTR sequence from a different gene (peripherin) and from a different species (human) but from a gene expressed in the same tissue as mouse rhodopsin, i.e., photoreceptor cells (SEQ ID NO:2). The sequence of the mouse rhodopsin cDNA is present in the clone from the ATG start onwards.

Hybrid 2

The mouse rhodopsin hybrid cDNA sequence was altered in the non-coding sequences to eliminate the GUC ribozyme binding site targeted in the 5'UTR of mouse rhodopsin. The U of the target was changed to G, that is, GUC→GGC (nucleotides 340–342 of SEQ ID NO:3). Again PCR mutagenesis was primer driven and was undertaken using a HindIII (in pcDNA3) to Eco47111 (in the coding sequence of the mouse rhodopsin cDNA) DNA fragment.

Ribozyme Constructs

A hammerhead ribozyme (termed Rib3) designed to target an open loop structure in the RNA in the 5' non-coding region of the gene was cloned into the HindIII and XbaI sites of pcDNA3 again allowing subsequent expression of RNA from the T7 or CMV promoters in the vector (SEQ ID NO:4). The target site was GUC at position 1393–1395 of the mouse rhodopsin sequence (Accession number: M55171). Antisense flanks are underlined.

Rib3: CUUCGUACUGAUGAGUCCGUGAGGAC-GAAACAGAGAC (nucleotides 95–131 of SEQ ID NO:4)

Human Rhodopsin

Template cDNA

The human rhodopsin CDNA was cloned into the HindIII and EcoRI sites of the MCS of pcDNA3 in a 5' to 3' orientation allowing subsequent expression of RNA from the T7 or CMV promoters in the vector. The full length 5'UTR sequence was inserted into this clone using primer driven PCR mutagenesis and a HindIII (in pcDNA3) to BstEII (in the coding sequence of the human rhodopsin cDNA) DNA fragment (SEQ ID NO:5)

Hybrid cDNAs with Altered Non-coding Regions

The human rhodopsin hybrid cDNA with altered non-coding sequences was cloned into the EcoRI site of pcDNA3 in a 5' to 3' orientation allowing subsequent expression of RNA from the T7 or CMV promoters in the vector. The 5'UTR of this clone included only the first 21 bases of the non-coding region of human rhodopsin before the ATG start site (SEQ ID NO:6).

Ribozyme Constructs

A hammerhead ribozyme (termed Rib15) designed to target an open loop structure in the RNA from the non-coding regions of the gene was cloned subsequent to synthesis and annealing into the HindIII and XbaI sites of pcDNA3 again allowing subsequent expression of RNA from the T7 or CMV promoters in the vector (SEQ ID NO:7). The target site was AUU (the NUX rule) at position 249–251 of the human rhodopsin sequence (Accession number: K02281). Antisense flanks are underlined.

Rib15: ACCCAAGCUGAUGAGUCCGUGAGGAC-GAAAUGCUGC (nucleotides 104–139 of SEQ ID NO:7)

Mouse Peripherin

Template cDNA

A mouse peripherin CDNA was cloned into the HindIII and EcoRV sites of pcDNA3. The clone is in a 5' to 3' orientation allowing subsequent expression of RNA from the T7 or CMV promoters in the vector (SEQ ID NO:8). The clone contains the complete 5'UTR sequence together with 27 bases of additional sequence 5' of this UTR sequence left probably from other cloning vectors.

Hybrid cDNAs with Altered Non-coding Regions

The mouse peripherin hybrid cDNA was altered in the 5'non-coding region. Using primer driven PCR mutagenesis the mouse rhodopsin 5'UTR sequence was replaced by the sequence of the mouse peripherin 5'UTR (SEQ ID NO:9). The PCR mutagenesis was achieved using a HindIII (in pcDNA3) to SacII (in the coding sequence of the mouse peripherin cDNA) DNA fragment.

Ribozyme Constructs

A hammerhead ribozyme (termed Rib17) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:10). The target site was AUU at position 162–164 of the mouse peripherin sequence (Accession number: X14770). Antisense flanks are underlined.

Rib17: CACUCCUCUGAUGAGUCCGUGAGGAC-GAAAUCCGAGU (nucleotides 99–136 of SEQ ID NO:10)

Antisense Constructs

Antisense and sense constructs were PCR amplified and cloned into pcDNA3 and pZEOSV for expression in vitro and in vivo. For example, a 127bp fragment from the 5'UTR sequence of mouse peripherin was cloned in both orientations into the above stated vectors. The effectiveness of antisense at suppression is under evaluation. The altered hybrid cDNA clones are being used to establish if RNAs expressed from these altered clones are protected from antisense suppression effects (SEQ ID NOS:17 and 18).

Human Peripherin

Template cDNA

A human peripherin cDNA cloned into the EcoRI site of the commercially available vector pBluescript was kindly provided by Dr. Gabriel Travis. The clone is in a 5' to 3' orientation allowing subsequent expression of RNA from the T7 promoter in the vector. The full length 5'UTR sequence is present in this clone (SEQ ID NO:11).

Hybrid cDNAs with Altered Non-coding Regions

The hybrid clone with altered non-coding sequences was generated as follows. The hybrid clone contains human RDS 5'UTR sequences until the BamHI site in the human peripherin 5'UTR sequence. From this site the clone runs into mouse RDS 5'UTR sequence until the ATG start site where it returns to human RDS sequence (SEQ ID NO:12). The clone was generated using primer driven PCR mutagenesis of a BamHI (in the 5'UTR sequence) to Bgl1 (in the coding sequence of the human peripherin cDNA) DNA fragment.

Ribozyme Constructs

Hammerhead ribozymes (termed Rib8 and Rib9) designed to target open loop structures in the RNA from the non-coding regions of the gene were cloned into the HindIII and XbaI sites of pcDNA3 which again allows subsequent expression of RNA from the T7 or CMV promoters in the vector (SEQ ID NOS:13 and 14). The target sites were CUA and GUU at positions 234–236 and 190–192 respectively of the human peripherin sequence (Accession number: M62958).

Rib8: CCAAGUGCUGAUGAGUCCGUGAGGAC-GAAAGUCCGG (nucleotides 93–128 of SEQ ID NO:13)

Rib9: CAAACCUUCUGAUGAGUCCGUGAGGAC-GAAACGAGCC (nucleotides 94–130 of SEQ ID NO:14)

Antisense flanks are underlined.

Human Type I Collagen—COL1A2

Template cDNA

A partial human type I collagen 1A2 cDNA sequence including the 5'UTR sequence and exon 1 was cloned after PCR amplification into the HindIII and XbaI sites of pcDNA3. The clone is in a 5' to 3' orientation allowing subsequent expression of RNA from the T7 and or CMV promoters in the vector (SEQ ID NO:15). The clone contains the complete 5'UTR sequence together with Exon I of COL1A2.

Ribozyme Constructs

A hammerhead ribozyme (termed Rib18) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:16). The target site was GUC at position 448–450 of the human type I collagen 1A2 sequence (Accession number: J03464; M18057; X02488). Antisense flanks are underlined.

Rib18: A<u>GACAUGCC</u>UGAUGAGUCCGUGAGGAC<u>GAAACUCCUU</u> (nucleotides 85–121 of SEQ ID NO:16)

Results

Human and mouse rhodopsin and peripherin cDNAs were expressed in vitro. Likewise human and mouse rhodopsin and peripherin cDNAs with altered 5'non-coding sequences were expressed in vitro. Ribozymes targeting the 5'UTRs of these retinal cDNAs were also expressed in vitro. cDNA clones were cut with various restriction enzymes resulting in the production of differently sized RNAs after expression. This aided in differentiating between RNAs expressed from the original cDNAs or from altered hybrid cDNAs. The sites used to cut each clone, the predicted sizes of the resulting RNAs and the predicted sizes of cleavage products after cleavage by target ribozymes are given below in Table 1.

TABLE 1

| | Restriction Enzyme | RNA Size | Cleavage Products |
|---|---|---|---|
| Example 1 | | | |
| Mouse rhodopsin | Eco47111 | 778 bases | 336 + 442 bases |
| Mouse rhodopsin hybrid 1 | Eco47111 | 643 bases | |
| Mouse rhodopsin hybrid 2 | Fsp 1 | 577 bases | |
| Rib 3 (See Table 1; sequences 1–4; FIGS. 1–6; FIGS. 1–6) | Xho 1 | 60 bases | |
| Example 2 | | | |
| Human rhodopsin | BstEll Acy 1 | 8511 bases 1183 bases | 61 + 790 bases 61 + 1122 bases |
| Human rhodopsin hybrid | BstEll Acy 1 Fspl | 841 bases 1173 bases 300 bases | |
| Rib 15 (See Table 1; sequences 5–7; FIGS. 7–11) | Xba1 | 55 bases | |
| Example 3 | | | |
| Mouse peripherin | Bgl1 | 488 bases | 201 + 287 bases |
| Mouse peripherin hybrid | Bgl1 | 344 bases | |
| Rib 17 (See Table 1; sequences 8–10; FIGS. 12–16) | Xba1 | 60 bases | |
| Example 4 | | | |
| Human peripherin | Bgl1 | 489 bases | 238 + 251 (Rib 8) 194 + 295 (Rib 9) |
| Human peripherin hybrid | Avrll | 331 bases | |
| Rib 8 | Xbal | 55 bases | |
| Rib 9 (see Table 1; sequence 11–14; FIGS. 16–19) | Xbal | 55 bases | |

TABLE 1-continued

| | Restriction Enzyme | RNA Size | Cleavage Products |
|---|---|---|---|
| Example 5 | | | |
| Collagen 1A2 | Xhol | | |
| Rib 18 (See Table 1; sequences 15 and 16) | Xbal | | |
| Example 6 | | | |
| Antisense constructs (See Table 1; sequences 17 and 18) | | | |

The examples of the invention are illustrated in the accompanying figures wherein:

FIG. 1 pBR322 was cut with MspI, radioactively labeled and run on a polyacrylamide gel to enable separation of the resulting DNA fragments. The sizes of these fragments are given in FIG. 1. This DNA ladder was then used on subsequent polyacrylamide gels to provide an estimate of the size of the RNA products run on the gels.

FIG. 2

A: Mouse rhodopsin cDNA was expressed from the T7 promoter to the Eco47III site in the coding sequence. The RNA was mixed with Rib3 RNA with varying concentrations of magnesium chloride. Lane 1–4: Rhodopsin RNA and Rib3 RNA after incubation for 3 hours at 37° C. with 0 mM, 5 mM, 10 mM and 15 mM magnesium chloride. The sizes of the expressed RNAs and cleavage products are as expected (Table 1). Complete cleavage of mouse rhodopsin RNA was obtained with a small residual amount of intact RNA present at 5 mM magnesium chloride. Note at 0 mM magnesium chloride before activation of Rib3 RNA no cleavage products were observed.

B: Mouse rhodopsin cDNA was expressed from the T7 promoter to the Eco47III site in the coding sequence. Resulting RNA was mixed with Rib3 RNA with varying concentrations of magnesium chloride. Lane 1: DNA ladder as in FIG. 1. Lane 2: intact mouse rhodopsin RNA. Lane 3–6: Rhodopsin RNA and Rib3 RNA after incubation for 3 hours at 37° C. with 0 mM, 5 mM, 10 mM and 15 mM magnesium chloride. Again complete cleavage of mouse rhodopsin RNA was obtained with a small residual amount of intact RNA present at 5 mM magnesium chloride. Lane 7: DNA ladder as in FIG. 1.

FIG. 3

Mouse rhodopsin cDNA was expressed from the T7 promoter to the Eco47III site in the coding sequence. Lane 1: intact mouse rhodopsin RNA. Lanes 2–7: Mouse rhodopsin RNA was mixed with Rib3 RNA with 15 mM magnesium chloride and incubated at 37° C. for 0, 30, 60, 90, 120 and 180 minutes. The sizes of the expressed RNAs and cleavage products are as expected (Table 1). Complete cleavage of mouse rhodopsin RNA was obtained. Notably cleavage was observed immediately after the addition of the divalent ions which activated Rib3 RNA (see Lane 2: 0 minutes).

FIG. 4

Mouse rhodopsin cDNA with altered 5'UTR sequence was expressed from the T7 promoter to the Eco47III site in the coding sequence. The resulting RNA was mixed with Rib3 RNA using varying concentrations of magnesium chloride. Lane 1: DNA ladder as in FIG. 1. Lane 2: intact altered mouse rhodopsin RNA. Lane 3 6: altered mouse rhodopsin RNA and Rib3 RNA after incubation for 3 hours at 37° C. with 0 mM, 5 mM, 10 mM and 15 mM magnesium chloride. No cleavage of the altered hybrid RNA occurred.

FIG. 5

Mouse rhodopsin cDNA with altered 5'UTR sequence was expressed from the T7 promoter to the Eco47III site in the coding sequence. The resulting RNA was mixed with Rib3 RNA with 10 mM magnesium chloride and incubated at 37° C. Lane 1: intact altered mouse rhodopsin RNAs. Lane 2–6: altered mouse rhodopsin RNA and Rib3 RNA after incubation for 0, 30, 60,120, 180 minutes. No cleavage of the hybrid RNA was obtained. Notably after 3 hours incubation with Rib3 RNA the adapted mouse rhodopsin RNA was as intense as at 0 minutes. Lane 7: DNA ladder as in FIG. 1.

FIG. 6

A: The unadapted mouse rhodopsin cDNA and the mouse rhodopsin cDNA with altered 5'UTR sequence were expressed from the T7 promoter to the Eco47III site in the coding sequence. The resulting RNAs were mixed together with Rib3 RNA and 10 mM magnesium chloride. Lane 1: intact unadapted and altered mouse rhodopsin RNAs which can clearly be differentiated by size as predicted (Table 1). Lane 2–6: unadapted and altered mouse rhodopsin RNAs and Rib3 RNA after incubation for 0, 30, 60,120,180 minutes with 10 mM magnesium chloride at 37° C. No cleavage of the altered hybrid RNA was obtained. The hybrid was of equal intensity after 3 hours as it was at 0 minutes. Notably the majority of the unadapted mouse rhodopsin RNA is cleaved immediately by Rib3 RNA even in the presence of the altered mouse rhodopsin RNA. The cleavage products are highlighted with arrows. The background is due to a small amount of RNA degradation. B: In a separate experiment the three RNAs (unadapted, altered mouse rhodopsin RNAs and Rib3 RNA) were incubated at 15 mM magnesium chloride for 5 hours. The altered hybrid RNA remains intact but the unadapted mouse rhodopsin RNA has been cleaved completely.

FIG. 7

A second altered mouse rhodopsin cDNA involving a single base change at the ribozyme cleavage site was generated. This adapted mouse rhodopsin cDNA was expressed from the T7 promoter to the FspI site in the coding sequence. Likewise the unadapted mouse rhodopsin cDNA was expressed from the T7 promoter to the Eco47III site in the coding sequence. These two RNAs were mixed with Rib3 RNA and incubated at 37° C. with 15 mM magnesium chloride. Lane 1: Intact mouse rhodopsin RNA. Lane 2: Intact altered mouse rhodopsin RNA (2nd alteration). Lane 3: DNA ladder as in FIG. 1. Lanes 4–7: Unadapted and altered mouse rhodopsin RNAs and Rib3 RNA after incubation for 0, 60, 120 and 180 minutes with 15 mM magnesium chloride at 37° C. Note the reduction of the unadapted RNA product over time in the presence of the altered RNA (Lanes 4 and 5). The adapted RNA remains intact and maintains equal intensity at each time point indicating that it is resistant to cleavage by Rib3 RNA. Again, as with all other altered RNAs, no additional cleavage products were observed. Lane 8: The unadapted and adapted mouse rhodopsin RNA without ribozyme. Lane 9: DNA ladder as in FIG. 1.

FIG. 8

Human rhodopsin was expressed from the T7 promoter to the BstEII site in Exon IV. The resulting RNA was mixed with Rib15 RNA with varying concentrations of magnesium chloride. Lane 1: intact rhodopsin RNA alone. Lane 2: Rib15 alone. Lane 3: DNA ladder as in FIG. 1. Lanes 4–7: Rhodopsin RNA and Rib15 RNA after incubation for 3 hours at 37° C. with the 0 mM, 5 mM, 10 mM and 15 mM magnesium chloride. Predicted cleavage products are 61 and 790 bases (Table 1). Lane 8: DNA ladder. Partial cleavage of the RNA was obtained—a doublet representing the intact RNA and the larger cleavage product is present (most clearly in lane 5). The gel was run a shorter distance than the gel presented in FIGS. 9–12 to show the presence of Rib15 RNA at the bottom of the gel and to demonstrate that one of the cleavage products cannot be visualized due to the presence of the labeled ribozyme which runs at approximately the same size. Subsequent gels were run further to achieve better separation of these two RNA fragments.

FIG. 9

Both the unadapted human rhodopsin cDNA and the altered cDNA were expressed from the T7 promoter to the BstEII site in Exon IV. The resulting RNA was mixed with Rib15 RNA with varying concentrations of magnesium chloride. Lane 1: intact human rhodopsin RNA alone. Lane 2: DNA ladder as in FIG. 1. Lane 3–6: Rhodopsin RNA and Rib15 RNA after incubation together for 3 hours at 37° C. with 0 mM, 5 mM, 10 mM and 15 mM magnesium chloride. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodbpsin RNA with altered 5'UTR sequence alone. The predicted cleavage products for human rhodopsin are 61 and 790 bases (Table 1)—the larger cleavage product is clearly visible when the ribozyme becomes active after the addition of magnesium chloride (Lanes 4–6). This larger cleavage product is highlighted by an arrow.

FIG. 10

Human rhodopsin cDNA was expressed from the T7 promoter to the BstEII site in Exon IV. Likewise the altered human rhodopsin cDNA was expressed from the T7 promoter to the Fspl site in Exon 1. Both resulting RNAs were mixed together with Rib15 RNA with varying concentrations of magnesium chloride. Lane 1: DNA ladder as in FIG. 1. Lanes 2–5: Rhodopsin RNA, altered rhodopsin RNA and Rib15 RNA after incubation for 3 hours at 37° C. with 0 mM, 5 mM, 10 mM and 15 mM magnesium chloride. The sizes of the expressed RNAs and cleavage products are as expected (Table 1). Partial cleavage of the unadapted RNA was obtained after magnesium was added to the reaction. The altered human rhodopsin RNA was protected from cleavage in all reactions. If cleavage of the altered human rhodopsin RNA had occurred the products rationally would most likely be of a different size than those observed with the unadapted RNA. Notably no additional cleavage products were observed. Moreover there was no change in intensity of the altered RNA when the ribozyme was active (in the presence of magnesium chloride) or inactive (at OmM magnesium chloride). In contrast the undapted human rhodopsin RNA is less intense in lanes 3–5 after cleavage than in lane 2 before the addition of magnesium to activate Rib15. Lane 6: intact human rhodopsin RNA. Lane 7: intact human rhodopsin RNA with altered 5'UTR sequence. Lane 8: DNA ladder.

FIG. 11

Human rhodopsin cDNA was expressed from the T7 promoter to the BstEII site in Exon IV. Likewise the altered human rhodopsin cDNA was expressed from the T7 promoter to the Acyl in the 3'rhodopsin sequence after the stop codon. Both resulting RNAs were mixed together with Rib15 RNA with varying concentrations of magnesium chloride. Lane 1: DNA ladder as in FIG. 1. Lanes 2–5:

Rhodopsin RNA, altered rhodopsin RNA and Rib15 RNA after incubation for 3 hours at 37° C. with 0 mM, 5 mM, 10 mM and 15 mM magnesium chloride. Lane 6: Intact human rhodopsin RNA. Lane 7: DNA ladder as in FIG. 1. Note that neither RNAs or cleavage products are present in Lane 5 as too little sample may have been loaded in this lane.

FIG. 12

Human rhodopsin cDNA and the cDNA with altered 5'sequence were expressed from the T7 promoter to the AcyI site after the coding sequence of human rhodopsin.

The resulting RNA was mixed with Rib15 RNA with varying concentrations of magnesium chloride. Lane 1: DNA ladder as in FIG. 1. Lane 2–5: Human rhodopsin RNA and Rib15 RNA after incubation together for 3 hours at 37° C. with 0 mM, 5 mM, 10 mM and 15 mM magnesium chloride. Lane 6: Intact human rhodopsin RNA. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodopsin RNA with altered 5'UTR sequence alone. Lane 13: DNA ladder as in FIG. 1. The larger of the predicted cleavage products is present in lanes 3–5 and is highlighted by an arrow. The adapted human rhodopsin RNA again was protected from cleavage by Rib15 RNA. Note that in Lane 12 too little sample may have been loaded.

FIG. 13

Mouse peripherin CDNA was expressed from the T7 promoter to the BglII site in the coding sequence. The RNA was mixed with Rib17 RNA with varying concentrations of magnesium chloride. Lane 1: DNA ladder as in FIG. 1. Lane 2: intact mouse peripherin RNA. Lanes 3–6: Mouse peripherin RNA and Rib17 RNA after incubation for 3 hours at 37° C. with 0 mM, 5 mM, 10 mM and 15 mM magnesium chloride. The sizes of the expressed RNAs and cleavage products are as expected (Table 1). Partial cleavage of mouse rhodopsin RNA was obtained once Rib17 RNA was activated with magnesium chloride. Possibly some of the RNA was in a conformation that was inaccessible to Rib17 RNA. It should be noted that in the absence of magnesium chloride the ribozyme was inactive and no cleavage products were observed.

FIG. 14

Mouse peripherin cDNA was expressed from the T7 promoter to the BglII site in the coding sequence. The resulting RNA was mixed with Rib17 RNA with 15 mM magnesium chloride and incubated at 37° C. for varying times. Lane 1: DNA ladder as in FIG. 1. Lane 2: intact mouse peripherin RNA. Lanes 3–6: Mouse peripherin RNA and Rib17 RNA after incubation together with 15 mM magnesium chloride at 37° C. for 0,1, 2 and 3 hours respectively. The sizes of the expressed RNAs and cleavage products are as expected (Table 1). Partial cleavage of mouse rhodopsin RNA was obtained with Rib17 after 1 hour. The proportion of the RNA cleaved increased over time. The intensity of the mouse rhodopsin RNA band decreased visibly on the gel by 3 hours and similarly the cleavage products visibly increased in intensity. It is possible that further cleavage might be obtained over longer time periods. Lane 7: DNA ladder as in FIG. 1.

FIG. 15

Mouse peripherin CDNA with altered 5'sequences was expressed from the T7 promoter to the BglII site in the coding sequence. The resulting RNA was mixed with Rib17 RNA with varying concentrations of magnesium chloride. Lane 1: intact altered mouse peripherin RNA with no ribozyme. Lanes 2–5: Mouse peripherin RNA with altered 5'sequence and Rib17 RNA after incubation for 3 hours at 37° C. with 0 mM, 5 mM, 10 mM and 15 mM magnesium chloride. The sizes of the expressed RNAs are as expected (Table 1). No cleavage of the adapted mouse rhodopsin RNA was obtained before or after Rib17 RNA was activated with magnesium chloride. Lane 6: DNA ladder as in FIG. 1.

FIG. 16

Both the unadapted and adapted mouse peripherin cDNAs were expressed from the T7 promoter to the BglII site in the coding sequence. The resulting RNAs were mixed together with Rib17 RNA with 15 mM magnesium chloride and incubated at 37° C. for varying times. Lane 1: DNA ladder as in FIG. 1. Lane 2: intact unadapted and altered mouse peripherin RNA. Lanes 3–6: Unadapted mouse peripherin RNA, altered mouse peripherin RNA and Rib17 RNA after incubation together with 15 mM magnesium chloride at 37° C. for 0, 30, 90 and 180 minutes respectively. The sizes of the expressed RNAs and cleavage products are as expected (Table 1). Partial cleavage of the unadapted mouse peripherin RNA was obtained with Rib17 RNA after 1 hour. The intensity of the larger unadapted mouse peripherin RNA product decreases slightly over time. In contrast the cleavage products increase in intensity. The intensity of the smaller altered mouse peripherin RNA product remains constant over time indicating that the RNA is not cleaved by Rib17 RNA. Lane 7: DNA ladder as in FIG. 1.

FIG. 17

Both the unadapted and adapted human peripherin cDNAs were expressed from the T7 promoter to the BglII site in the coding sequence. The resulting RNAs were mixed together with Rib8 RNA with varying concentrations of magnesium chloride and incubated at 37° C. for 3 hours. Lane 1: Unadapted human peripherin without ribozyme. Lanes 2–5: Unadapted human peripherin RNA and Rib8 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib8 RNA after 3 hours. The intensity of the larger unadapted human peripherin RNA product decreases over time. Lanes 6–9: Altered human peripherin RNA and Rib8 RNA after incubation together with 0, 5,10,15 mM magnesium chloride respectively at 37° C. for 3 hours. The sizes of the expressed RNAs are as expected (Table 1). No cleavage of the altered human peripherin RNA was obtained with Rib8 RNA even after 3 hours. The intensity of the smaller altered mouse peripherin RNA product remains constant (with the exception of lane 9 in which less sample may have been loaded) indicating that the RNA is not cleaved by Rib8 RNA. In addition no cleavage products were observed. Lane 10: Intact unadapted human peripherin RNA alone. Lane 11: Intact altered human peripherin RNA alone. Lane 12: DNA ladder as in FIG. 1.

FIG. 18

The unadapted and altered human peripherin cDNAs were expressed from the T7 promoter to the BglII site in the coding sequence. The resulting RNAs were mixed together with Rib8 RNA for varying times with 15 mM magnesium chloride and incubated at 37° C. Lane 1: DNA ladder as in FIG. 1. Lane 2–5: Unadapted and altered human peripherin RNAs and Rib8 RNA after incubation together for 0,1, 2 and 3 hours respectively at 37° C. with 15 mM magnesium chloride. The sizes of the expressed RNAs and cleavage products are as expected (Table 1). Almost complete cleavage of the larger unadapted human peripherin RNA was obtained with Rib8 RNA after 3 hours. The intensity of the larger unadapted human peripherin RNA product decreases over time. Altered human peripherin RNA was not cleaved by Rib8 RNA even after 3 hours. The intensity of the smaller altered mouse peripherin RNA product remains constant over time indicating that the RNA is not cleaved by Rib8 RNA. In addition no additional cleavage products were observed. Lane 6: Intact unadapted and altered human peripherin RNA together without ribozyme. Lane 7: DNA ladder as in FIG. 1.

FIG. 19

Both the unadapted and adapted human peripherin cDNAs were expressed from the T7 promoter to the BglII site in the coding sequence. The resulting RNAs were mixed together with Rib9 RNA with varying concentrations of magnesium chloride and incubated at 37° C. for 3 hours. Lane 1: DNA ladder as in FIG. 1. Lanes 2–5: Unadapted human peripherin RNA and Rib9 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib9 RNA. The intensity of the larger unadapted human peripherin RNA product decreases greatly. Lanes 6–9: Altered human peripherin RNA and Rib9 RNA after incubation together with 0, 5, 10, 15 mM magnesium chloride respectively at 37° C. for 3 hours. The sizes of the expressed RNAs are as expected (Table 1). No cleavage of the altered human peripherin RNA was obtained with Rib17 RNA even after 3 hours. The intensity of the smaller altered mouse peripherin RNA was observed—the product remains constant over time indicating that the RNA is not cleaved by Rib9 RNA. Lane 10: Intact unadapted human peripherin RNA alone. Lane 11: Intact altered human peripherin RNA alone. Lane 12: DNA ladder as in FIG. 1. Rib9 RNA was designed to target a different loop structure in the 5'sequence of human peripherin. It may result in slightly more efficient cleavage of RNA than Rib8 RNA.

FIG. 20

The unadapted and altered human peripherin cDNAs were expressed from the T7 promoter to the BglII site in the coding sequence. The resulting RNAs were mixed together with Rib9 RNA for varying times with 15 mM magnesium chloride and incubated at 37° C. Lane 1: Intact unadapted human peripherin RNA without ribozyme. Lane 2: Intact altered human peripherin RNA without ribozyme. Lanes 3 and 4: DNA ladder as in FIG. 1. Lane 5–8: Unadapted and altered human peripherin RNAs and Rib9 RNA after incubation together for 0,1, 2 and 3 hours, respectively, at 37° C. with 15 mM magnesium chloride. The sizes of the expressed RNAs and cleavage products are as expected (Table 1). Cleavage products were observed at time zero. Almost complete cleavage of the larger unadapted human peripherin RNA was obtained with Rib9 RNA after 1 hour. The intensity of the larger unadapted human peripherin RNA product decreased quickly over time. The altered human peripherin RNA was not cleaved by Rib9 RNA even after 3 hours. The intensity of the smaller altered human peripherin RNA product remains constant over time indicating that the RNA is not cleaved by Rib9 RNA. In addition, no additional cleavage products were observed. Lane 9: Intact unadapted and altered human peripherin RNA together without ribozyme. Lane 10: DNA ladder as in FIG. 1.

Example 1
Mouse Rhodopsin

Rib3 RNA targeting the mouse rhodopsin 5'non-coding sequence was cut with Xho I and expressed in vitro. The mouse rhodopsin cDNA and hybrid cDNA with altered 5'non-coding sequence (with the human peripherin 5'UTR sequence in place of the mouse rhodopsin 5'UTR sequence) were cut with Eco47111, expressed and both RNAs mixed separately and together with Rib3 RNA to test for cleavage. RNAs were mixed with varying concentrations of $MgCl_2$ and for varying amounts of time to optimise cleavage of RNA by Rib3 RNA (FIGS. 2–7). Likewise, a second hybrid with a small modification of the 5'UTR sequence was cut with Fspl, expressed and tested for cleavage with Rib3 RNA alone and together with the original unadapted mouse rhodopsin RNA. This alteration is a single base change at the ribozyme cleavage site involving a U→G, that is, altering the ribozyme cleavage site from GUC to GGC thereby removing the target site. In all cases the expressed RNA was the correct size. In all cases cleavage of the larger unadapted mouse rhodopsin RNA product was achieved. In some cases cleavage was complete and all cleavage products were of the predicted size. Notably hybrid mouse rhodopsin RNAs with altered 5'UTR sequences were not cleaved by Rib3 RNA either when mixed alone with Rib3 RNA or when combined with Rib3 RNA and the unadapted mouse rhodopsin RNA (FIGS. 2–7). This highlights the sequence specificity of the Rib3 RNA target in that small sequence alterations may be all that is required to prevent cleavage. Likewise small modifications in the targets for the antisense arms of ribozymes or more generally for any antisense may result in the inability of a suppression effector to attack the modified RNA. The first hybrid described above could be used to prevent ribozyme cleavage or antisense binding of many ribozymes or antisense suppression effectors and therefore would be particularly useful if more than one suppression effector was required to achieve suppression.

Example 2
Human Rhodopsin

The human rhodopsin cDNA clone (with a full length 5'UTR) and the human rhodopsin hybrid cDNA clone with altered 5'non-coding sequence (shorter 5'UTR) were cut with BstEII and expressed in vitro. The Rib15 clone was cut with Xbal and expressed in vitro. The resulting ribozyme and human rhodopsin RNAs were mixed with varying concentrations of $MgCl_2$ to optimize cleavage of the template RNA by Rib15 RNA. (FIGS. 8–12). The human rhodopsin cDNA and hybrid cDNA with altered 5'non-coding sequence were cut with Acyl, expressed and both RNAs mixed separately (due to their similar sizes) with Rib15 RNA to test for cleavage (FIGS. 8–12). The human rhodopsin cDNA was cut with BstEII and the hybrid cDNA with altered 5'non-coding sequence cut with Fspl, expressed and mixed separately and together with Rib15 RNA to test for cleavage (FIGS. 8–12). In all cases the expressed RNA was the correct size. Similarly in all cases the unadapted RNA template was cut into cleavage products of the predicted sizes. The cleavage of the unadapted RNA template was incomplete with some residual uncleaved RNA remaining. This may be due, for example, to the inability of the ribozyme to access RNA in some conformations. In all cases RNA expressed from the altered hybrid human rhodopsin cDNA with a shorter 5'UTR remained intact, that is, it was not cleaved by Rib15 RNA. It is worth noting that Acyl enzyme cuts after the stop codon of the coding region of the gene and therefore the resulting RNA includes all of the coding sequence that gives rise to the protein. The RNA from the original unadapted human rhodopsin cDNA clone cut with Acyl is cleaved by Rib15 RNA. In contrast, RNA from the hybrid clone with an altered 5'UTR sequence is not cleaved by Rib15 RNA. (FIGS. 8–12). The sequence of the ribozyme target site and of the antisense flanks are not present in the altered human rhodopsin RNA. Clearly, altering the sequence in non-coding regions masks the resulting altered gene from being suppressed by antisense or ribozymes targeting sites in non-coding regions.

Example 3

Mouse Peripherin

Rib17 targeting mouse peripherin 5'non-coding sequence was cut with XbaI and expressed in vitro. The mouse peripherin cDNA and mouse peripherin hybrid cDNA with an altered 5'non-coding sequence (in which the mouse peripherin 5'UTR sequence has been replaced by mouse rhodopsin 5'UTR sequence) were cut with BglII, expressed in vitro and both RNAs mixed separately and together with Rib17 RNA to test for cleavage. RNAs were mixed with varying concentrations of $MgCl_2$ and for varying times to optimize cleavage of RNAs by Rib17 RNA(FIGS. 13–16). Partial cleavage of the unadapted mouse peripherin RNA by Rib17 RNA was obtained—all RNAs expressed and all cleavage products were the predicted sizes. Partial cleavage may be due to the inaccessibility of some RNA conformations to antisense binding and/or ribozyme cleavage. In contrast the adapted hybrid mouse peripherin RNA containing mouse rhodopsin non-coding sequences remained intact (FIGS. 13–16). This again highlights that RNAs can be designed so that they code for a correct protein, in this case, mouse peripherin and such that they are masked from a suppression effector(s), in this case, a ribozyme with antisense flanks.

Example 4

Human Peripherin

Rib8 and Rib9 clones targeting human peripherin 5'non-coding sequence were cut with XbaI and expressed in vitro. The human peripherin cDNA and human peripherin hybrid cDNA with altered 5'non-coding sequence (with part of the human peripherin 5'UTR sequence replaced by mouse peripherin 5'UTR sequence) were cut with BglII and AvrII respectively, expressed in vitro and both RNAs mixed separately and together with Rib9 RNA to test for cleavage. RNAs were mixed with varying concentrations of $MgCl_2$ to optimise cleavage of RNAs by Rib9 RNA (FIGS. 17–20). Notably the majority of the larger unadapted RNA product was cleaved while the adapted RNA product with altered noncoding sequence remained intact (FIGS. 17–20). Similar results were obtained with Rib8 RNA which targets a different open loop than Rib9 RNA in the non-coding sequence of human peripherin. However, in the case of Rib8 RNA, the extent of the cleavage was significantly less than Rib9 RNA (FIGS. 17–20) suggesting the important role of RNA structure in antisense binding and RNA cleavage.

Example 5

Human COL1A2

Rib18 which has been cloned into pcDNA3 (SEQ ID NO:16) targets the 5'UTR sequence of the human type I collagen COL1A2 gene, multiple mutations in which can cause autosomal dominantly inherited osteogenesis imperfecta involving bone fragility, amongst other symptoms. A clone containing the 5'UTR sequence together with exon I of the human COLlA2 gene has also been generated (SEQ ID NO:15) to apply suppression and replacement strategies to this human gene.

Antisense Constructs

A number of constructs have been generated in pcDNA3 and pZEOSV containing tracks of sense and antisense sequence from the non-coding regions of the mouse rhodopsin and peripherin genes. An example of these sequences is given in SEQ ID NOS:17 and 18. Antisense effects are under evaluation.

Discussion

In the first four examples outlined above, RNA was expressed from cDNAs coding for four different proteins: mouse and human rhodopsin and mouse and human peripherin. All four RNAs have been significantly attacked in vitro using suppression effectors directed towards the non-coding regions of the RNA. In all four examples the ribozymes directed to 5'UTR sequences were successful in cleaving target RNAs in the predicted manner. Antisense targeting non-coding sequences was used successfully to elicit binding and cleavage of target RNAs in a sequence specific manner.

In some cases it is possible that cleavage of the RNA at the 5'UTR would not effect the functioning of the resulting RNA cleavage products in generating protein. Moreover although lowering RNA levels may often lead to a parallel lowering of protein levels this is not always the case. In some situations mechanisms may prevent a significant decrease in protein levels despite a substantial decrease in levels of RNA. However in many instances suppression at the RNA level has been shown to be effective (see prior art). In some cases it is thought that ribozymes elicit suppression not only by cleavage of RNA but also by an antisense effect due to the antisense arms in the ribozyme. Notably we have demonstrated sequence specific attack of target RNAs in non-coding regions, which is an important stage in gene suppression.

In the four examples provided ribozymes were designed to target 5'UTR sequences, however, they could be readily designed to target any non-coding sequences. Suppression could be achieved using antisense or ribozymes targeting for example, the 3'UTR sequences or any combination of non-coding sequences.

Additionally, in all four examples, cDNAs with altered sequences in the non-coding regions targeted by ribozymes were generated. RNAs expressed from altered cDNAs were protected entirely from cleavage due the absence of the ribozyme target by each of the ribozymes tested. Alterations involved replacement of UTR sequence with UTR sequence from another gene expressed in the same tissue or UTR sequence from the same gene but from a different mammalian species (e.g. mouse peripherin, human peripherin, mouse rhodopsin). In one case the target site was deleted (human rhodopsin). Of particular interest is the second mouse rhodopsin hybrid cDNA for Rib3 which contains a single base change thereby preventing RNA cleavage. In some cases the non-coding sequences of a gene may be essential to the overall efficient expression and functioning of the gene. Therefore it may be useful to alter replacement genes in subtle ways to prevent ribozyme cleavage or nucleic acid binding. Changing a few nucleotides in many instances may be sufficient to prevent nucleolytic attack.

As highlighted before in this text using this invention the same method of suppression (targeting non-coding sequences) and gene replacement (using a gene with altered non-coding sequences) may be used as a therapeutic approach for any mutation within a given gene.

REFERENCES

Carter G and Lemoine N R. (1993) Cancer Res. 67: 869–876.
Cazenave et al. (1989) Nucl. Acid Res. 17: 42554273.
Dosaka-Akita H et al. (1995) Cancer Res. 55: 1559–1564.
Dryja T P et al. (1990) Nature 343: 364–366.
Duval-Valentin et al. (1992) Proc. Natl. Acad. Sci. USA 89: 504–508.
Ellis and Rodgers (1993) Nucl. Acid Res. 21: 5171–5178.

Farrar G J et al. (1991) Nature 354: 478–480.
Farrar G J et al. (1991) Genomics 14: 805–807.
Farrar G J et al. (1995) Invest. Ophthamol. Vis. Sci. (ARVO) 36: (4).
Feng M, Cabrera G, Deshane J, Scanlon K and Curiel D T. (1995) Cancer Res. 55: 2024–2028.
Gaughan D J, Steel D M, and Whitehead S A. (1995) FEBS Letters 374: 241–245.
Hanvey J C et al. (1992) Science 258:1481–1485.
Hardenbol P and Van Dyke M W. (1996) Proc. Natl. Acad. Sci. USA 93: 2811–2816.
Herschlag D, Khosla M, Tsuchihashi Z and Karpel R L. (1994) EMBO 13: (12) 29132924.
Herskowitz et al. (1987) Nature 329: 219–222.
Jankowsky E and Schwenzer B. (1996) Nucl. Acid Res. 24: (3) 423 429.
Jones J T, Lee S-W and Sullenger B A. (1996) Nature Medicine 2: 643–648.
Jordan S A et al. (1993) Nature Genetics 4: 54–58.
Quattrone A, Fibbi G, Anichini E, Pucci M et al. (1995) Cancer Res. 55: 90–95.
Kajiwara et al. (1991) Nature 354: 480–483.
Knudsen H and Nielsen P E. (1996) Nucl. Acid Res. 24: (3) 494–500.
Lange W et al. (1993) Leukemia 7: 1786–1794.
Mansergh F et al. (1995) J. Med. Genet. 32: 855–858.
Mashhour B et al. (1994) Gene Therapy 1:122–126.
McKay R A, Cummins L L, Graham M J, Lesnik E A et al. (1996) Nuc Acid Res 24: (3) 411–417.
McWilliam P et al. (1989) Genomics 5: 612–619.
Ohta Y, Kijima H, Ohkawa T, Kashani-Sabet M and Scanlon K J. (1996) Nucl. Acid. Res. 24: (5) 938–942.
Ott J et al. (1989) Proc. Natl. Acad. Sci. 87: 701–704.
Oyama T et al. (1995) Pathol. Int. 45: 45–50.
Postel et al. (1991) Proc. Natl. Acad. Sci. USA 88: 8227–8231.
Porumb H, Gousset, Letellier R, Salle V, et al. (1996) Cancer Res. 56: 515–522.
Rimsky et al. (1989) Nature 341: 453–456.
Sullenger B A and Cech T R. (1994) Nature 371: 619–622.
Sun J S et al. (1989) Proc. Natl. Acad. Sci. USA 86: 9198–9202.
Trauger J W, Baird E E and Dervan P B. (1996) Nature 382: 559–561.
Valera A et al. (1994) J. Biol. Chem. 269: 28543–28546.
Van Soest S et al. (1994) Genomics 22: 499–504.
Wei Z, Tung C-H, Zhu T, Dickerhof W A et al. (1996) Nucl. Acid Res. 24: (4) 655–661.

SEQUENCE LISTING

```
<160> NUMBER OF SEQ ID NOS: 18

<210> SEQ ID NO 1
<211> LENGTH: 624
<212> TYPE: DNA
<213> ORGANISM: mammalian
<220> FEATURE:
<221> NAME/KEY: n
<222> LOCATION: (1)..(624)
<223> OTHER INFORMATION: any

<400> SEQUENCE: 1
nnnncttnct tanngcttgg taccganctc ggatccacta gtnaacggcc gccagtgtgc      60
tggaaattcc cagaggnact ctggggcaga caagatgaga caccctttcc tttctttacc    120
taagggcctc cacccgatgt caccttggcc cctctgcaag ccaattaggc cccggtggca    180
gcagtgggat tagcgttagt atgatatctc gcggatgctg aatcagcctc tggcttaggg    240
agagaaggtc actttataag ggtctggggg gggtcagtgc ctggagttgc gctgtgggag    300
ccgtcagtgg ctgagctcgc caagcagcct tggtctctgt ctacgaaaan cccgtggggc    360
agcctcnana accgcagcca tgaacggcac agaaggcccc aattttatg tgcccttctc     420 caacgtcaca ngcgtggtgc ggaacccctt cnancanccg cagtactacc tggcggaacc    480
atggcagttc tccatgctgg cancgtacat gtcctgctca tcgtgctggg nttcccatca    540
actcctcacg ctctagttca ccgtaaanna naaaaaactg cgcaacccct caactaaatc    600
ctgctcaatt gggcgtgggt gaac                                           624

<210> SEQ ID NO 2
<211> LENGTH: 624
<212> TYPE: DNA
<213> ORGANISM: mammalian
<220> FEATURE:
<221> NAME/KEY: n
<222> LOCATION: (1)..(624)
<223> OTHER INFORMATION: any
```

-continued

```
<400> SEQUENCE: 2
tncctttttt tncaatttcc ttcnanaccc aggancacga tatccctgc tcaagctgtg      60 attccgaaac ccctgccacc actactgcat tcacggggta tcccaggcta gtgggactcn    120
acatgggtag cccccagggc agctccctac agcttgggcc atctgcactt ttcccaaggc    180
cctaagtctc cgcctctggg ctcgttaagg tttggggtgg gagctgtgct gtgggaagca    240
acccggacta cacttggcaa gcatgaacgg cacagagggc cccaatttttt atgtgcccctt   300 ctccaacgtc acaggcgtgg tgcggancccc cttcgagcag ccgcagtact acctggcgga   360
accatggcag ttctccatgc tgggcancgt tacatgttcc tggcccatcg tgctgggctt    420
ccccatcaac ttcctcacgc tctacgtcan cgtacagcan aaaaanctgc gcacacccct    480
caactacatc ctgctcaact ttgggcgtgg ctgacccttc atggtctcgg aagatcacac    540
caccctctaa catcactcca tggctaattc ctctttnggg ccanaggcnt gtaatcncna    600
aggnttcttt gccancttgg aggt                                          624

<210> SEQ ID NO 3
<211> LENGTH: 620
<212> TYPE: DNA
<213> ORGANISM: mammalian
<220> FEATURE:
<221> NAME/KEY: n
<222> LOCATION: (1)..(620)
<223> OTHER INFORMATION: any

<400> SEQUENCE: 3 tgnnttncttt aaangcttgg ttaccgagct cggatccact nagtaacggc cgccagtgtg    60
ctggaaattc ccagaggcac tctggggcag acaagatgag acacccttttc ctttctttac   120 ctaagggcct ccacccgatg tcaccttggc ccctctgcaa gccaattagg ccccggtggc    180
agcagtggga ttagcgttag tatgatatct cgcggatgct gaatcagcct ctggcttagg    240
gagagaangt cactttataa gggtctgggg ggggtcagtg cctggagttg cgctgtggga   300
gccgtcagtg gctgagctcg ccaagcagcc ttggtctctg gctacnaaaa ncccgtgggg   360
cancctcnaa anccgcancc atgaacggca cagaaggccc caatttttat gtttcccttc    420
tccaacgtca cangcgtngt gcggaacctc ttcaacaac cgcaatncta cctggcggaa    480
ccatggcagt tctccatgct ggcancgtaa tnttctgctc atcgtgctgg gttcccatca    540
anttcctcac ccctaatttc cgtnaanaaa aaaactgccc caccccaaa taattctgnn    600 caanttggcg tggtnaccct                                               620

<210> SEQ ID NO 4
<211> LENGTH: 705
<212> TYPE: DNA
<213> ORGANISM: mammalian
<220> FEATURE:
<221> NAME/KEY: n
<222> LOCATION: (1)..(705)
<223> OTHER INFORMATION: any

<400> SEQUENCE: 4
ngnttnnnnn nttacaganc nctcgctaan tagagaacca ctgcttactg gcttatcgaa     60
attaatcgga ctcactatag ggagacccaa gcttcttcgt actgatgagt ccgtgaggac    120
gaaacagaga ctcgagcatg catctagagg gccctattct atagtgtcac ctaaatgcta    180
gagctcgctg atcagcctcg actgtgcctt ctagttgcca gccatctgtt gtttgcccct    240
cccccgtgcc ttccttgacc ctggaangtg ccactcccac tgtccttttcc taataaaatg    300
```

```
aggaaattgc atcgcattgt ctgagtangt gtcattctat tctgggggt ggggtggggc    360 anggacanca aggggggaaga ttgggaaaaa caatancagg catgctgggg gatncngtgg    420
ggctctatgg cttctgangc ggaaagaaca actggggctc tangggggtat ccccacncgc    480 cctgtaacgg cgcattaaac cccgcgggtg ttgtngttac cccacnttac cgctacactt    540
gccancgcct acgcccctcc tttcccttct ccttcctt ctcccacttc ccgcttccc       600 ctcaactcta atcgggggccc cttaggttcc attaattctt acggncccca ccccaaaact   660
nataggtang gtcccttntt ggccnccct anaanggttt tccct                     705
```

```
<210> SEQ ID NO 5
<211> LENGTH: 617
<212> TYPE: DNA
<213> ORGANISM: mammalian
<220> FEATURE:
<221> NAME/KEY: n
<222> LOCATION: (1)..(617)
<223> OTHER INFORMATION: any

<400> SEQUENCE: 5
tcccttntgn tagattgcan nncccaataa aanaaggncc cgcttaaagg cttatcgaaa    60
ttaatacgac tcactatang gagacccaag cttagagtca tccagctgga gccctgagtg   120
gctgagctca ggccttcgca gcattcttgg gtgggagcag ccacgggtca gccacaaggg   180
ccacagccat gaatggcaca gaaggcccta acttctacgt gcccttctcc aatgcgacgg   240
gtgtggtacg cagccccttc gagtacccac agtactacct ggctgagcca tggcagttct   300
ccatgctggc cgcctacatg tttctgctga tcgtgctggg cttccccatc aacttcctca   360
cgctctacgt caccgtccag cacaagaagc tgcgcacgcc tctcaactac atcctggctc   420
aacctagccg tggctgaact cttcatggtc ctangtggct tcaccagcac ctctacanct   480
ctctgcatgg atactcgtct tcgggcccac aggatgcaat tggangggctc tttgcacctg   540 gngggaaatt gcctgtggtc ctngtggtcn ggncaccaac gtactggtng tgtntanccc   600
agaacaactc cgctccg                                                   617
```

```
<210> SEQ ID NO 6
<211> LENGTH: 574
<212> TYPE: DNA
<213> ORGANISM: mammalian
<220> FEATURE:
<221> NAME/KEY: n
<222> LOCATION: (1)..(574)
<223> OTHER INFORMATION: any

<400> SEQUENCE: 6
nnacttcttc nggaatacct gcgganaata nagaaccact gcttactggc ttatcgaaat    60
taatacgact cactatagg agacccaagc ttggtaccga gctcggatcc actagtaacg   120
gccgccagtg tgctggaatt ccggaaggcc tgagctcagc cacaagggcc acagccatga  180
atggcacaga aggccctaac ttctacgtgc ccttctccaa tgcgacgggt gtggtacgca  240
gccccttcga gtacccacag tactacctgg ctgagccatg gcagttctcc atgctggccg  300
cctacatgtt tctgctgatc gtgctgggct tccccatcaa cttcctcacg ctctacgtca  360
ccgtccagca caagaagctg cgcacgcctc tcaactacat cctggctcaa cctanccgtg  420
ggtgaactct tcatggtcct aggtgggttc accaacaccc tctaaaacct ctctgcatgg  480
atattcgtct tcgggccaca ggatgcaatt ggagggttc ttggcacctg ggngggaaat   540
gcctgtggtc ctgggngntc nggccaccaa cggt                              574
```

```
<210> SEQ ID NO 7
<211> LENGTH: 601
<212> TYPE: DNA
<213> ORGANISM: mammalian
<220> FEATURE:
<221> NAME/KEY: n
<222> LOCATION: (1)..(601)
<223> OTHER INFORMATION: any

<400> SEQUENCE: 7
cntncttttn anntttngnt cgcactctct ggctaactca gagaacccac tgcttactgg      60
cttatcgaaa ttaatacgac tcactatagg gagacccaag cttacccaag ctgatgagtc     120
cgtgaggacg aaatgctgct ctagagggcc ctattctata gtgtcaccta aatgctagag     180
ctcgctgatc agcctcgact gtgccttcta gttgccagcc atctgttgtt tgcccctccc     240
ccgtgccttc cttgaccctg aaggtgcca ctcccactgt cctttcctaa taaaatgagg      300
aaattgcatc gcattgtctg agtaagtgtc attctattct gggggtggg gtnggcang       360 acaacnaggg gaagattggg aananaataa caggcatgct ggggatgcng tgggctctat     420
ggcttcctga gcggaaaga aacactnggn tctagggtn tccccccncc ctgtacnggc       480
attaacncgn ggtttgtngt taccccacnn acctaattc accctacccc cttcctctc      540 ctcttnccat tccggttccc taacntangg ggccttngtc caatattttn gccccccca      600 a                                                                    601

<210> SEQ ID NO 8
<211> LENGTH: 626
<212> TYPE: DNA
<213> ORGANISM: mammalian
<220> FEATURE:
<221> NAME/KEY: n
<222> LOCATION: (1)..(626)
<223> OTHER INFORMATION: any

<400> SEQUENCE: 8
ttcnntgnaa attgcgccna aaananaagg gcngcttact ggcttatcna anttaatacg      60
actcactata gggagaccca agcttgcatg cctgcagggg gggggaagg actctgcaga     120 tacggcggcc taattaact ccggctaccg ttactgantt aacgggatc ccaagctagg       180 gaggccccaa aatgggcaac tccctgcagc ttgggcccat ggtgctcttc cctanacct     240 agcggtccag ccccgganct cactcggatt angagtggaa gctgaaccgt gggangctgc    300
tgaacgcact cngtaagcat ggcgctgctc aaagtcnagt ttgaccagaa gaaacnggtc    360
aagttggccc aagggctctg gctttatgaa ctggctgtcc gtgttnggcg gcatcgtccc    420
tcntcagctt ggggctgttc ttgaanattg aactttcccc aagaagaacc aaagtgatga    480
ataatttctg aaanccnctt ttgtncccaa ctccctgata ggggtgggg tcctgtccnt     540 nttcttnact ctctggctgg gaaaatttgc tnttnaancc ctggancccg ccaantncnc    600
cnnttggaaa ccctgctcga aaccct                                         626

<210> SEQ ID NO 9
<211> LENGTH: 617
<212> TYPE: DNA
<213> ORGANISM: mammalian
<220> FEATURE:
<221> NAME/KEY: n
<222> LOCATION: (1)..(617)
<223> OTHER INFORMATION: any
```

```
<400> SEQUENCE: 9
tnaccattcg nntaaanctn tcnnnccta ananaaccca ctggcttact ggcttatcga      60
aattaatacg actcactata gggagaccca agcttgagtt gcgctgtggg agccgtcagt    120
ggctgagctc gccaagcagc cttggtctct gtctacgaag agcccgtggg gcagcctcga   180
gagccgcagc catggcgctg ctcaaagtca agtttgacca agaagcgg gtcaagttgg     240
cccagggct ctggcttatg aactggctgt ccgtgttggc cggcatcgtc ctcttcagct    300
tggggctgtt cttgaagatt gaacttcgca agagagcga agtgatgaat aattctgaga    360
gccactttgt gcccaactcc ctgatanggg tgggggtcct gtcctgtgtc ttcaactctc    420
tggctgggaa gatctgctat gatgccctgg aaccggccaa gtacgccaag tggaancccct   480
ggctgaagcc gtacctggct gtctgcatct tctttaacgt catcctcttc cggtggntct   540
ctgctgcttc tgttgcgggg tccctggaaa acaccnggct tacggacnca aaatngggat    600
gaatttttttt cnggata                                                617

<210> SEQ ID NO 10
<211> LENGTH: 610
<212> TYPE: DNA
<213> ORGANISM: mammalian
<220> FEATURE:
<221> NAME/KEY: n
<222> LOCATION: (1)..(610)
<223> OTHER INFORMATION: any

<400> SEQUENCE: 10
nnctnnntnt ttnatcgccc tctctggcta antcanagaa cccactgctt actggcttat    60
cgaaattaat acgactcact atagggtaga cccaagcttc actcctctga tgagtccgtg   120
aggacgaaat ccgagttcta gagggcccta ttctatagtg tcacctaaat gctagagctc   180
gctgatcagc ctcgactgtg ccttctagtt gccagccatc tgttgtttgc ccctcccccg    240
tgccttcctt gaccctggaa ggtgccactc ccactgtcct ttcctaataa aatgaggaaa    300
ttgcatcgca ttgtctgagt aagtgtcatt ctattctggg gggtggggtg gggcangaca    360
acaagggga agattgggaa acaataaca ggcatgctgg ggatgcggtg ggctctatgg     420
ctcctgaagc gaaaaaacca ctggggctct aggggtttcc ccccccctg tacngccatt    480
aacncgnggt ntgtggtacc ccacnnacgt aattgcaccc taccncttc ntctcctctt     540
ctccattcng gttcccccaa cnaagggggc ccttggttca atttttttnn gcccccccna    600
nntnaagttc                                                          610

<210> SEQ ID NO 11
<211> LENGTH: 630
<212> TYPE: DNA
<213> ORGANISM: mammalian
<220> FEATURE:
<221> NAME/KEY: n
<222> LOCATION: (1)..(630)
<223> OTHER INFORMATION: any

<400> SEQUENCE: 11
nnncttntta ttcttcagcg tgccngacca ngantatccc ctgctcaagc tgtgattccg     60
agacccctgc caccactact gcattcacgg ggnatcccag gctagtggga ctcgacatgg    120
gtancccca gggcagctcc ctacagcttg ggccatctgc acttttccca aggccctaag   180
tctccgcctc tgggctcgtt aaggtttggg gtgggagctg tgctgtggga agcaacccgg    240
actacacttg gcaagcatgg cgctactgaa agtcaagttt gaccaaaaaa agcgggtcaa    300
```

```
gttggcccaa gggctctggc tcatgaactg gttctccgtg ttggctggca tcatcatctt    360
cagcctagga ctgttcctga anattgaact ccgaaagaag ancgatgtga tgaataaatt    420
ctgaaaccaa ttttgtgccc aactcattga tanggatggg ggtgctatcc tgtgtcttca    480
actcnctggn tgggaanatc tgctacaacg ccctggaacc anccaatttg ccaaatggaa    540
ccctggctga aaccgtacct ggctatctgt nttcncctcc aaatcatccc cttccttgtg    600
ggtctctgct gctttccngc tccggggccc                                    630

<210> SEQ ID NO 12
<211> LENGTH: 611
<212> TYPE: DNA
<213> ORGANISM: mammalian
<220> FEATURE:
<221> NAME/KEY: n
<222> LOCATION: (1)..(611)
<223> OTHER INFORMATION: any

<400> SEQUENCE: 12
cnctattcaa acttgnccct gcaagtcgac nntanaggat cttcccagcc agcgagttga     60
agacacagga tagcaccccc atccctatca atgagttggg cacaaaatgg ctctcagaat    120
tattcatcac atcgctcctc tttcggagtt cgatcttcag gaacagtcct aggctgaaga    180
tgatgatgcc agccaacacg gagaaccant tcatgagcca gagcccttgg gccaacttga    240
cccgcttctc tggtcaaact tgactttcag tagcgccatg cttaccgagt gcgttcagca    300
gcctcccacg gttcagcttc cactcctaat ccgagtgagc tccggggctg gaccgctang    360
gtctaaggaa nancaccatg ggcccaagct gcagggantt gcccattttg gggcctggat    420
ccccgtgaat gcantaatgg tggcagggt ctcggaatca cagcttgagc agggatagtc    480
ctggtcctgg gcgctgaaaa aatcnccat antgagtcgt atacaatcac tgggcgtcgt    540
ttacaacgtc tgaatgggaa accctggntt acccaactta atcgcctgga acacatcccc    600
tttcncanct g                                                        611

<210> SEQ ID NO 13
<211> LENGTH: 619
<212> TYPE: DNA
<213> ORGANISM: mammalian
<220> FEATURE:
<221> NAME/KEY: n
<222> LOCATION: (1)..(619)
<223> OTHER INFORMATION: any

<400> SEQUENCE: 13
ctcnnntttn aacaganctg cngctaacta nagaaccact gcttactggc ttatcgaaat     60
taatacgact cactataggg agacccaagc ttccaagtgc tgatgagtcc gtgaggacga    120
aagtccggtc tagagggccc tattctatag tgtcacctaa atgctagagc tcgctgatca    180
gcctcgactg tgccttctag ttgccagcca tctgttgttt gccctcccc cgtgccttcc    240 ttgaccctgg aangtgccac tcccactgtc ctttcctaat aaaatgagga aattgcatcg    300
cattgtctga gtaggtgtca ttctattctg ggggtggg tgggcanga cancaagggg    360 gaagattggg aagacaatan cangcatgct ggggatgcgg tgggctctat ggcttctgaa    420
gcggaaagaa ccanctgggg ctctaagggg tatccccacg cncctgtaa cggcgcatta    480 acccgcggt gttgttgtta ccccaacnt gaccgctaca cttgccaacc cctaaccccg    540
ctcctttcct ttcttcttc cttctcncac tttcccngct tccntcaac tctaatcggg    600 gcccttagg ttcaattat                                                619
```

<210> SEQ ID NO 14
<211> LENGTH: 760
<212> TYPE: DNA
<213> ORGANISM: mammalian
<220> FEATURE:
<221> NAME/KEY: n
<222> LOCATION: (1)..(760)
<223> OTHER INFORMATION: any

<400> SEQUENCE: 14

| | | | | | |
|---|---|---|---|---|---|
| nnnnnntttt | naacaganct | ccggctaact | anagaaccac | tgcttactgg | cttatcgaaa | 60 |
| ttaatacgac | tcactatagg | gagacccaag | cttcaaacct | tctgatgagt | ccgtgaggac | 120 |
| gaaacgagcc | tctagagggc | cctattctat | agtgtcacct | aaatgctaga | gctcgctgat | 180 |
| cagcctcgac | tgtgccttct | agttgccagc | catctgttgt | ttgcccctcc | ccgtgcctt | 240 |
| ccttgaccct | ggaangtgcc | actcccactg | tcctttccta | ataaaatgag | gaaattgcat | 300 |
| cgcattgtct | gagtangtgt | cattctattc | tgggggtgg | ggtggggcaa | ggacancaag | 360 |
| ggggaagatt | gggaagacaa | tancangcat | gctggggatg | cggtgggctc | tatggcttct | 420 |
| gaagcggaaa | gaaccanctg | gggctctaag | gggtatcccc | acgcgccctg | taaccgcgca | 480 |
| ttaacccgc | nggtntgttg | gttaccccca | cgtgaccgct | acacttgcca | accctaacc | 540 |
| ccgctccttt | cccttcttc | cttccttctc | ccactttcc | ggnttcccct | caactctaat | 600 |
| cngggcncct | taggttcaat | tatcttacgn | cncanccaaa | atgataggta | angtcntttt | 660 |
| ggccncccta | aaaggtttc | ccttnattga | tcccttctta | natgancttt | ccaatgaaaa | 720 |
| ccaccnncgt | cttcttaata | angattgcat | cgccttgtaa | | | 760 |

<210> SEQ ID NO 15
<211> LENGTH: 622
<212> TYPE: DNA
<213> ORGANISM: mammalian
<220> FEATURE:
<221> NAME/KEY: n
<222> LOCATION: (1)..(622)
<223> OTHER INFORMATION: any

<400> SEQUENCE: 15

| | | | | | |
|---|---|---|---|---|---|
| cnnctnnntn | ttttntngcn | tctcnggcta | acngacagaa | cccactgctt | actggcttat | 60 |
| cgaaattaat | acgactcact | atagggagac | ccaagcttag | caccacggca | gcaggaggtt | 120 |
| tcggctaagt | tggaggtact | ggccacgact | gcatgcccgc | gcccgccagg | tgatacctcc | 180 |
| gccggtgacc | cagggctct | cgacacaag | gagtctgcat | gtctaagtgc | tagacatgct | 240 |
| cagctttgtg | gatacgcgga | ctttgttgct | gcttgcagta | acctcatgcc | tagcaacatg | 300 |
| ccaatctcga | gcatgcatct | ananggccct | attctatagt | gtcncctana | tgctaganct | 360 |
| cgctgatnag | cctcgactgt | gccttctaat | tgccagccat | ctgtngtttg | gccctccccc | 420 |
| gtgccttcct | tgaacctgga | aggtgccact | cccactgtcc | tttcctaata | aaatgaagaa | 480 |
| attgcatcnc | atgtctgant | agtgtcatct | atctgggggt | gggtnggca | gganaccagg | 540 |
| gagatggaaa | aaatacagct | tctgggaacg | tggcctatgc | tctnagngaa | aaaactgggg | 600 |
| ctagggttcc | cccccntnc | gc | | | | 622 |

<210> SEQ ID NO 16
<211> LENGTH: 621
<212> TYPE: DNA
<213> ORGANISM: mammalian

<220> FEATURE:
<221> NAME/KEY: n
<222> LOCATION: (1)..(621)
<223> OTHER INFORMATION: any

<400> SEQUENCE: 16

| | | | | | |
|---|---|---|---|---|---|
| agcagantct | ctggctaact | anagaaccca | ctgcttactg | gcttatcgaa | attaatacga | 60 |
| ctcactatag | ggagacccaa | gcttagacat | gcctgatgag | tccgtgagga | cgaaactcct | 120 |
| ttctagaggg | ccctattcta | tagtgtcacc | taaatgctag | agctcgctga | tcagcctcga | 180 |
| ctgtgccttc | tagttgccag | ccatctgttg | tttgccnctc | cccgtgcct | tccttgaccc | 240 |
| tggaaggtgc | cactcccact | gtcctttcct | aataaaatga | ggaaattgca | tcgcattgtc | 300 |
| tgagtaggtg | tcattctatt | ctgggggtg | ggtggggca | ngacancaag | ggggangatt | 360 |
| gggaagacaa | tancangcat | gctggggatg | cggtgggctc | tatggcttct | gangcggaaa | 420 |
| gaaccanctg | gggctctagg | ggtatcccca | cnccctgta | ccggccatta | agcccgcggt | 480 |
| gttgtngtta | ccccaantga | cgctacactg | ccacgcctac | gccctccttc | cttctccctc | 540 |
| cttctcccat | tcccggttc | ccctcancct | aatcggggcc | cttaggttcc | aatattctta | 600 |
| cgncnccacc | caaantaatn | g | | | | 621 |

<210> SEQ ID NO 17
<211> LENGTH: 644
<212> TYPE: DNA
<213> ORGANISM: mammalian
<220> FEATURE:
<221> NAME/KEY: n
<222> LOCATION: (1)..(644)
<223> OTHER INFORMATION: any

<400> SEQUENCE: 17

| | | | | | |
|---|---|---|---|---|---|
| atggttatcg | aattaatacg | actcactata | nggagaccca | agcttccatg | cttaccgagt | 60 |
| gcgttcagca | gcctcccacg | gttcagcttc | cactcctaat | ccgagtgagc | tccggggctg | 120 |
| gaccgctagg | gtctanggaa | gagcaccatt | ctagagggcc | ctattctata | gtgtcaccta | 180 |
| aatgctagag | ctcgctgatc | agcctcgact | gtgccttcta | nttgccagcc | atctgttgtt | 240 |
| tgcccctccc | ccgtgccttc | cttgaccctg | gaangtgcca | ctcccactgt | nctttcctaa | 300 |
| aaaaatgagg | aaattgcatc | gcattgtctg | actaagtgtc | attctattct | ggggtgtggg | 360 |
| gtggggcacg | acaacaangg | ggaagattgg | gaanacaata | acacgcatgc | ngggatgcc | 420 |
| gtggggctct | atggcttctg | aagcggaaag | aacaactggg | gcnctagggg | tatcccacac | 480 |
| gccctgtacc | gggctttaac | gcggnggtgt | tgtggttacc | ccaacttgac | gctacacttt | 540 |
| ccaacgccta | ncgccgctct | ttcctttctt | ccctccattc | cccaattcc | ccgntttccc | 600 |
| cccnnnnnnn | nnnncncnc | nnnaantnng | ggggcccctn | nggg | | 644 |

<210> SEQ ID NO 18
<211> LENGTH: 603
<212> TYPE: DNA
<213> ORGANISM: mammalian
<220> FEATURE:
<221> NAME/KEY: n
<222> LOCATION: (1)..(603)
<223> OTHER INFORMATION: any

<400> SEQUENCE: 18

| | | | | | |
|---|---|---|---|---|---|
| nngnnnnnn | ncntatggtt | atcgaattaa | tacgactcac | tataggggaga | cccaagctta | 60 |
| tggtgctctt | ccctanaccc | tancggtcca | gccccggagc | tcactcggat | taggagtgga | 120 |

-continued

```
agctgaaccg tgggaggctg ctgaacgcac tcggtaagca tggtctanag ggccctattc      180
tatagtgtca cctaaatgct agagctcgct gatcagcctc gactgtgcct tctagttgcc      240
agccatctgt tgtttgcccc tcccccgtgc cttccttgac cctggaaggt gccactccca      300
ctgtcctttc ctaataaaat gaggaaattg catcgcattg tctgagtaag tgtcattcta      360
ttctgggggg tggggtgggg cangacaaca aggggggaaga ttgggaanac aataacangc      420
atgctgggga tgccgtgggc tctatggctt ctgaagcgga aanaaccact ggggctctaa      480
ggggtatccc caccccctg taccggccat aaccccgcgg tttgtggtta ccccactnac       540
gtaccttgca cgcctacccc cnccttcctc ttcctccttc cccnttccgg ttcccnnann      600 nnn                                                                    603
```

What is claimed is:

1. A therapeutic composition for treating a genetic disease, the composition comprising:
   a) a suppression effector binds to an untranslated region of a mature RNA encoding a mutant allele, wherein said suppression effector inhibits the expression of the mutant allele; and
   b) a replacement nucleic acid that encodes a wild-type or non-disease causing allele and that is not inhibited by the suppression effector.

2. The composition of claim 1, wherein the suppression effector is a nucleic acid or peptide nucleic acid (PNA).

3. The composition of claim 1, wherein the suppression effector is a peptide.

4. The composition of claim 1, wherein the suppression effector is an antisense nucleic acid.

5. The composition of claim 1, wherein the suppression effector cleaves or degrades mRNA.

6. The composition of claim 1, wherein the suppression effector is a ribozyme.

7. The composition of claim 1, wherein the suppression effector is a nucleic acid that forms a triple helix with a portion of the untranslated region of the mutant allele.

8. The composition of claim 1, wherein the suppression effector is specific for mammalian rhodopsin RNA.

9. The composition of claim 1, wherein the suppression effector is specific for mammalian peripherin RNA.

10. The composition of claim 1, wherein the suppression effector is specific for mammalian collagen RNA.

11. The composition of claim 1, wherein the replacement nucleic acid does does not hybridize with, or is only partially suppressed by, the suppression effector.

12. The composition of claim 1, wherein the replacement nucleic acid encodes a protein selected from the group consisting of mammalian rhodopsin, collagen 1A2 and peripherin.

13. The composition of claim 1, wherein the suppression effector comprises a nucleic acid sequence selected from the group consisting of SEQ ID NOS: 7, 13, 14 and 16.

14. The composition of claim 1, wherein suppression effector is operatively linked to an expression vector.

15. The composition of claim 1, wherein the replacement nucleic acid is operatively linked to an expression vector.

16. The composition of claim 1, wherein the suppression effector and the replacement nucleic acid are operatively linked to the same expression vector.

17. The composition of claim 1, wherein the untranslated region is essentially a 5' untranslated region.

18. The composition of claim 1, wherein the untranslated region is essentially a 3' untranslated region.

19. The composition of claim 17 or 18, wherein the suppression effector binds to said untranslated region and to a portion of the coding sequence.

20. The composition of claim 1, wherein the genetic disease is an autosomal dominant disease or a polygenic disease.

21. The composition of claim 1, wherein the genetic disease is osteogenesis imperfecta, retinitis pigmentosa, age-related macular degeneration, glaucoma, manic depression or cancer.

22. A therapeutic composition for suppressing the expression of a mutant allele of a protein, the composition comprising:
   a) a ribozyme that targets an untranslated region of a mature RNA encoding a mutant allele; and
   b) a replacement nucleic acid that encodes a wild-type or non-disease causing allele and that is not targeted by the ribozyme.

23. The composition of claim 22, wherein the ribozyme cleavage site is an NUX site.

24. The composition of claim 22, wherein the ribozyme is specific for mammalian rhodopsin RNA.

25. The composition of claim 22, wherein the ribozyme is specific for mammalian peripherin RNA.

26. The composition of claim 22, wherein the ribozyme is specific for mammalian collagen RNA.

27. The composition of claim 22, wherein the replacement nucleic acid does not hybridize with, or is only partially suppressed by, the ribozyme.

28. The composition of claim 22, wherein the replacement nucleic acid encodes a protein selected from the group consisting of mammalinan rhodopsin, collagen 1A2 and peripherin..

29. The composition of claim 22, wherein the suppression effector comprises a nucleic acid sequence selected from the group consisting of SEQ ID NOS: 7, 13, 14 and 16.

30. The composition of claim 22, wherein the ribozyme is operatively linked to an expression vector.

31. The composition of claim 22, wherein the replacement nucleic acid is operatively linked to an expression vector.

32. The composition of claim 22, wherein the ribozyme and the replacement nucleic acid are operatively linked to the same expression vector.

33. The composition of claim 22, wherein the untranslated region is essentially a 5' untranslated region.

34. The composition of claim 22, wherein the untranslated region is essentially a 3' untranslated region.

35. The composition of claim 33 or 34, wherein the ribozyme binds to said untranslated region and to a portion of the coding sequence.

36. The composition of claim 22, wherein the genetic disease is an autosomal dominant disease or a polygenic disease.

37. The composition of claim 22, wherein the genetic disease is osteogenesis imperfecta, retinitis pigmentosa, age-related macular degeneration, glaucoma, manic depression or cancer.

38. The composition of claim 1, wherein the suppression effector suppresses an endogenous gene.

39. The composition of claim 22, wherein the ribozyme suppresses an endogenous gene.

* * * * *

UNITED STATES PATENT AND TRADEMARK OFFICE
CERTIFICATE OF CORRECTION

PATENT NO. : 6,713,457 B2
DATED : March 30, 2004
INVENTOR(S) : Farrar et al.

It is certified that error appears in the above-identified patent and that said Letters Patent is hereby corrected as shown below:

Columns 1-46 should be deleted and replaced with the attached pages consisting of columns 1-46.

Signed and Sealed this

Seventh Day of February, 2006

JON W. DUDAS
*Director of the United States Patent and Trademark Office*

STRATEGY FOR SUPPRESSING THE EXPRESSION OF AN ENDOGENEOUS GENE BY USING COMPOUNDS THAT ARE ABLE TO BIND TO THE NON-CODING REGIONS OF THE GENE TO BE SUPPRESSED

REFERENCE TO RELATED APPLICATIONS

This application was filed under 35 U.S.C. §371 for, and claims priority to, PCT/GB96/02357, filed Sep. 23, 1996, which claims priority to GB9519299.3, filed Sep. 21, 1995, the disclosures of which are incorporated by reference herein.

FIELD OF THE INVENTION

The present invention relates to a strategy and medicaments for suppressing a gene. In particular the invention relates to the suppression of mutated genes which give rise to a dominant or deleterious effect either monogenically or polygenically. The invention relates to a strategy for suppressing a gene or disease allele such that (if required) a replacement gene, gene product or alternative gene therapy can be introduced.

The invention also relates to a medicament or medicaments for use in suppressing a gene or disease allele which is present in a genome of one or more individuals or animals. The said medicament(s) may also introduce the replacement gene sequence, product or alternative therapy.

Generally the strategy of the present invention will be useful where the gene, which is naturally present in the genome of a patient, contributes to a disease state. Generally, the gene in question will be mutated, that is, will possess alterations in its nucleotide sequence that affect the function or level of the gene product. For example, the alteration may result in an altered protein product from the wild type gene or altered control of transcription and processing. Inheritance or the somatic acquisition of such a mutation can give rise to a disease phenotype or can predispose an individual to a disease phenotype. However the gene of interest could also be of wild type phenotype, but contribute to a disease state in another way such that the suppression of the gene would alleviate or improve the disease state.

BACKGROUND OF THE INVENTION

Studies of degenerative hereditary ocular conditions, including Retinitis Pigmentosa (RP) and various macular dystrophies have resulted in a substantial elucidation of the molecular basis of these debilitating human eye disorders. In a collaborative study, applying the approach of genetic linkage, two x-linked RP genes were localized to the short arm of the X chromosome (Ott et al. 1990). In autosomal dominant forms of RP (adRP) three genes have been localized. The first adRP gene mapped on 3q close to the gene encoding the photoreceptor specific protein rhodopsin (Mcwilliam et al. 1989; Dryja et al. 1990). Similarly, an adRP gene was placed on 6p close to the gene encoding the photoreceptor specific protein peripherin/RDS (Farrar et al. 1991a,b; Kajiwara et al. 1991). A third adRP gene mapped to 7q (Jordan et al. 1993); no known candidate genes for RP reside in this region of 7q. In addition, the disease gene segregating in a Best's macular dystrophy family was placed on 11q close to the region previously shown to be involved in some forms of this dystrophy (Mansergh et al. 1995). Recently, an autosomal recessive RP gene was placed on 1q (Van Soest et al. 1994). Genetic linkage, in combination with techniques for rapid mutational screening of candidate genes, enabled subsequent identification of causative mutations in the genes encoding rhodopsin and peripherin/RDS proteins. Globally about 100 rhodopsin mutations have now been found in patients with RP or congenital stationary night blindness. Similarly about 40 mutations have been characterised in the peripherin/RDS gene in patients with RP or with various macular dystrophies.

Knowledge of the molecular etiology of some forms of human inherited retinopathies has stimulated the establishment of methodologies to generate animal models for these diseases and to explore methods of therapeutic intervention; the goal being the development of treatments for human retinal diseases (Farrar et al. 1995). Surgical procedures enabling the injection of sub-microliter volumes of fluid intravitreally or sub-retinally into mouse eyes have been developed by Dr. Paul Kenna. In conjunction with the generation of animal models, optimal systems for delivery of gene therapies to retinal tissues using viral (inter alia Adenovirus, Adeno Associated Virus, Herpes Simplex Type 1 Virus) and non-viral (inter alia liposomes, dendrimers) vectors alone or in association with derivatives to aid gene transfer are being investigated.

Generally, gene therapies utilizing both viral and non-viral delivery systems have been applied in the treatment of a number of inherited disorders; of cancers and of some infectious disorders. The majority of this work has been undertaken on animal models, although, some human gene therapies have been approved. Many studies have focused on recessively inherited disorders, the rationale being, that the introduction and efficient expression of the wild type gene may be sufficient to result in a prevention/amelioration of disease phenotype. In contrast gene therapy for dominant disorders will require the suppression of the dominant disease allele. Notably the majority of characterised mutations that cause inherited retinal degenerations such as RP are inherited in an autosomal dominant fashion. Indeed there are over 1,000 autosomal dominantly inherited disorders in man. In addition there are many polygenic disorders due to the co-inheritance of a number of genetic components which together give rise to a disease phenotype. Effective gene therapy in dominant or polygenic disease will require suppression of the disease allele while in many cases still maintaining the function of the normal allele.

Strategies to differentiate between normal and disease alleles and to selectively switch off the disease allele using suppression effectors inter alia antisense DNA/RNA, ribozymes or triple helix DNA, targeted towards the disease mutation may be difficult in many cases and impossible in others—frequently the disease and normal alleles may differ by only a single nucleotide. For example, the disease mutation may not occur at a ribozyme cleavage site. Similarly the disease allele may be difficult to target specifically by antisense DNA/RNA or triple helix DNA if there are only small sequence differences between the disease and normal alleles. A further difficulty inhibiting the development of gene therapies is the heterogeneous nature of some dominant disorders—many different mutations in the same gene give rise to a similar disease phenotype. The development of specific gene therapies for each of these would be extremely costly. To circumvent the dual difficulties associated with specifically targeting the disease mutation and the genetic heterogeneity present in some inherited disorders, the present invention aims to provide a novel strategy for gene suppression and replacement exploiting the noncoding and control regions of a gene.

Suppression effectors have been used previously to achieve specific suppression of gene expression. Antisense DNA and RNA has been used to inhibit gene expression in many instances. Many modifications, such as phosphorothioates, have been made to antisense oligonucleotides to increase resistance to nuclease degradation, binding affinity and uptake (Cazenave et al. 1989; Sun et al. 1989; McKay et al. 1996; Wei et al. 1996). In some instances, using antisense and ribozyme suppression strategies has led to the reversal of the tumor phenotype by greatly reducing the expression of a gene product or by cleaving a mutant transcript at the site of the mutation (Carter and Lemoine 1993; Lange et al. 1993; Valera et al. 1994; Dosaka-Akita et al. 1995; Feng et al. 1995; Quattrone et al. 1995; Ohta et al. 1996). For example, neoplastic reversion was obtained using a ribozyme targeted to the codon 12 H-ras mutation in bladder carcinoma cells (Feng et al. 1995). Ribozymes have also been proposed as a means of both inhibiting gene expression of a mutant gene and of correcting the mutant by targeted trans-splicing (Sullenger and Cech 1994; Jones et al. 1996). Ribozymes can be designed to elicit autocatalytic cleavage of RNA targets. However the inhibitory effect of some ribozymes may be due in part to an antisense effect of the variable antisense sequences flanking the catalytic core which specify the target site (Ellis and Rodgers 1993; Jankowsky and Schwenzer 1996). Ribozyme activity may be augmented by the use of non-specific nucleic acid binding proteins or facilitator oligonucleotides (Herschlag et al. 1994; Jankowsky and Schwenzer 1996). Triple helix approaches have also been investigated for sequence specific gene suppression—triplex forming oligonucleotides have been found in some cases to bind in a sequence specific manner (Postel et al. 1991; Duval-Valentin et al. 1992; Hardenbol and Van Dyke 1996; Porumb et al. 1996). Similarly peptide nucleic acids have been shown in some instances to inhibit gene expression (Hanvey et al. 1992; Knudson and Nielsen 1996). Minor groove binding polyamides have been shown to bind in a sequence specific manner to DNA targets and hence may represent useful small molecules for future suppression at the DNA level (Trauger et al. 1996). In addition, suppression has been obtained by interference at the protein level using dominant negative mutant peptides and antibodies (Herskowitz 1987; Rimsky et al. 1989; Wright et al. 1989). In some cases suppression strategies have lead to a reduction in RNA levels without a concomitant reduction in proteins, whereas in others, reductions in RNA levels have been mirrored by reductions in protein levels.

SUMMARY OF THE INVENTION

The present invention aims to circumvent the shortcomings in the prior art by using a two step approach for suppression and replacement.

According to the present invention there is provided a strategy for suppressing expression of an endogenous gene, wherein said strategy comprises providing suppression effectors able to bind to the non-coding regions of a gene to be suppressed, to prevent the functional expression thereof. Preferably the suppression effectors are antisense nucleic acids. Preferably the targeted non-coding regions include the transcribed but non-translated regions of a gene.

Generally the term suppression effectors includes nucleic acids, peptide nucleic acids (PNAs) or peptides which can be used to silence or reduce gene expression in a sequence specific manner.

The antisense nucleic acids can be DNA or RNA, can be directed to 5' and/or 3' untranslated regions and/or to introns and/or to control regions or to any combination of such untranslated regions. However targeted the binding of the antisense nucleic acid prevents or lowers the functional expression of the endogenous gene. Chimeric antisense nucleic acids including a small proportion of translated regions of a gene can be used in some cases to help to optimize suppression. Likewise chimeric antisense nucleic acids including a small proportion of promoter regions of a gene can be used in some cases to help to optimize suppression.

Generally the term 'functional expression' means the expression of a gene product able to function in a manner equivalent to or better than a wild type product. In the case of a mutant gene 'functional expression' means the expression of a gene product whose presence gives rise to a deleterious effect.

In a particular embodiment of the invention the strategy further employs ribozymes. These can be designed to elicit cleavage of target RNAs.

The strategy further employs nucleotides which form triple helix DNA.

Nucleic acids for antisense, ribozymes and triple helix may be modified to increase stability, binding efficiencies and uptake as discussed earlier. Nucleic acids can be incorporated into a vector. Vectors include DNA plasmid vectors, RNA or DNA virus vectors. These can be combined with lipids, polymers or other derivatives to aid gene delivery and expression.

The invention further provides the use of antisense nucleotides, ribozymes, triple helix nucleotides or other suppression effectors alone or in a vector or vectors, wherein the nucleic acids are able to bind specifically to untranslated regions of a gene such as the 5' and 3' UTRs to prevent the functional expression thereof, in the preparation of a medicament for the treatment of an autosomal dominant disease.

In a further embodiment the non-coding regions of the gene can include promoter regions which are untranslated.

According to the present invention there is provided a strategy for suppressing an endogenous gene and introducing a replacement gene, said strategy comprising the steps of:

1. providing antisense nucleic acid able to bind to at least one non-coding or untranslated region of a gene to be suppressed and
2. providing genomic DNA or cDNA encoding a replacement gene sequence, wherein the antisense nucleic acid is unable to bind to equivalent non-coding or untranslated regions in the genomic DNA or cDNA to prevent expression of the replacement gene sequence.

The replacement nucleic acids will not be recognized by the suppression nucleic acid. The control sequences of the replacement nucleic acid may belong to a different mammalian species, may belong to a different human gene or may be similar but altered from those in the gene to be suppressed and may thus permit translation of the part of the replacement nucleic acid to be initiated.

By control sequences is meant sequences which are involved in the control of gene expression or in the control of processing and/or sequences present in mature RNA transcripts and/or in precursor RNA transcripts, but not including protein coding sequences.

In a particular embodiment of the invention there is provided a strategy for gene suppression targeted towards the non-coding regions of a gene and using a characteristic of one of the alleles of a gene, for example, the allele carrying a disease mutation. Suppressors are targeted to non-coding regions of a gene and to a characteristic of one allele of a gene such that suppression in specific or partially specific to one allele of the gene. The invention further provides for replacement nucleic acids containing altered non-coding sequences such that replacement nucleic acids cannot be recognized by suppressors which are targeted towards the non-coding regions of a gene. Replacement nucleic acids provide the wild type or an equivalent gene product but are protected completely or in part from suppression effectors targeted to non-coding regions.

In a further embodiment of the invention there is provided replacement nucleic acids with altered non-coding sequences such that replacement nucleic acids cannot be recognized by naturally occurring endogenous suppressors present in one or more individuals, animals or plants. Replacement nucleic acids with altered non-coding sequences provide the wild type or equivalent gene product but are completely or partially protected from suppression by naturally occurring endogenous suppression effectors.

In an additional embodiment of the invention there is provided replacement nucleic acids with altered non-coding sequences such that replacement nucleic acids provide a wild type or equivalent gene product or gene product with beneficial characteristics. For example, the 3' non-coding sequences of the replacement nucleic acids could be altered to modify the stability and turn over the RNA expressed from the replacement nucleic acids thereby sometimes affecting levels of resulting gene product.

The invention further provides the use of a vector or vectors containing suppression effectors in the form of nucleic acids, said nucleic acids being directed towards untranslated regions or control sequences of the target gene and vector(s) containing genomic DNA or cDNA encoding a replacement gene sequence to which nucleic acids for suppression are unable to bind, in the preparation of a combined medicament for the treatment of an autosomal dominant disease. Nucleic acids for suppression or replacement gene nucleic acids may be provided in the same vector or in separate vectors. Nucleic acids for suppression or replacement gene nucleic acids may be provided as a combination of nucleic acids alone or in vectors. The vector may contain antisense nucleic acid with or without, ribozymes.

The invention further provides a method of treatment for a disease caused by an endogenous mutant gene, said method comprising sequential or concomitant introduction of (a) antisense nucleic acids to the non-coding regions of a gene to be suppressed, to the 5' and/or 3' untranslated regions of a gene or intronic regions or to the non-control regions of a gene to be suppressed, (b) replacement gene sequence with control sequences which allow it to be expressed.

The nucleic acid for gene suppression can be administered before, after, or at the same time the replacement gene is administered.

The invention further provides a kit for use in the treatment of a disease caused by an endogenous mutation in a gene, the kit comprising nucleic acids for suppression able to bind to the 5' and/or 3' untranslated regions or intronic regions or control regions of the gene to be suppressed and (preferably packaged separately thereto) a replacement nucleic acid to replace the mutant gene having a control sequence to allow it to be expressed.

Nucleotides can be administered as naked DNA or RNA, with or without ribozymes and/or with dendrimers. Dendrimers (for example dendrimers of methylmethacrylate) can be utilized. It is believed the dendrimers mimic histones and as such are capable of transporting nucleic acids into cells. Oligonucleotides can be synthesized, purified and modified with phosphorothioate linkages and 2'0-allyl groups to render them resistant to cellular nucleases while still supporting RNase H medicated degradation of RNA. Also, nucleic acids can be mixed with lipids to increase efficiency of delivery to somatic tissues.

Nucleotides can be delivered in vectors. Naked nucleic acids or nucleic acids in vectors can be delivered with lipids or other derivatives which aid gene delivery. Nucleotides may be modified to render them more stable, for example, resistant to cellular nucleases while still supporting Rnase H mediated degradation of RNA or with increased binding efficiencies as discussed earlier.

Suppression effectors and replacement sequences can be injected sub-sectionally, or may be administered systemically.

DETAILED DESCRIPTION OF THE INVENTION

There is now an armament with which to obtain gene suppression. This, in conjunction with a better understanding of the molecular etiology of disease, results in an ever increasing number of disease targets for therapies based on suppression. In many cases, complete (100%) suppression of gene expression has been difficult to achieve. Possibly a combined approach using a number of suppression effectors may be required. For some disorders it may be necessary to block expression of a disease allele completely to prevent disease symptoms whereas for others low levels of mutant protein may be tolerated. In parallel with an increased knowledge of the molecular defects causing disease has been the realization that many disorders are genetically heterogeneous. Examples in which multiple genes and/or multiple mutations within a gene can give rise to a similar disease phenotype include osteogenesis imperfecta, familial hypercholesteremia, retinitis pigmentosa, and many others.

The invention addresses some shortcomings of the prior art and aims to provide a novel approach to the design of suppression effectors directed to target mutant genes. Suppression of every mutation giving rise to a disease phenotype may be costly, problematic and sometimes impossible. Disease mutations are often single nucleotide changes. As a result, differentiating between the disease and normal alleles may be difficult. Furthermore, some suppression effectors require specific sequence targets. For example, ribozymes can only cleave at NUX sites and hence will not be able to target some mutations. Notably, the wide spectrum of mutations observed in many diseases adds an additional layer of complexity in the development of therapeutic strategies for such disorders. A further problem associated with suppression is the high level of homology present in coding sequences between members of some gene families. This can limit the range of target sites for suppression which will enable specific suppression of a single member of such a gene family.

The strategy described herein has applications for alleviating autosomal dominant diseases. Complete silencing of a disease allele may be difficult to achieve using antisense, ribozyme and triple helix approaches or any combination of these. However small quantities of mutant product may be tolerated in some autosomal dominant disorders. In others a significant reduction in the proportion of mutant to normal product may result in an amelioration of disease symptoms. Hence this strategy may be applied to any autosomal dominantly inherited disease in man where the molecular basis of the disease has been established. This strategy will enable the same therapy to be used to treat a wide range of different disease mutations within the same gene. The development of strategies will be important to future gene therapies for some autosomal dominant diseases, the key to a general strategy being that it circumvents the need for a specific therapy for every dominant mutation in a given disease-causing gene. This is particularly relevant in some disorders, for example, rhodopsin linked autosomal dominant RP (adRP), in which to date about 100 different mutations in the rhodopsin gene have been observed in adRP patients. The costs of developing designer therapies for each individual mutation which may be present in some cases in a single patient are prohibitive at present. Hence strategies such as this using a more universally applicable approach for therapy will be required.

This strategy may be applied in gene therapy approaches for biologically important polygenic disorders affecting large proportions of the world's populations such as age related macular degeneration (ARMD), glaucoma, manic depression, cancers having a familial component and indeed many others. Polygenic diseases require the inheritance of more than one mutation (component) to give rise to the disease phenotype. Notably an amelioration in disease symptoms may require reduction in the presence of only one of these components, that is, suppression of one of the genotypes which, together with others, leads to the disease phenotype, may be sufficient to prevent or ameliorate symptoms of the disease. In some cases the suppression of more than one component giving rise to the disease pathology may be required to obtain an amelioration in disease symptoms. The strategy described here may be applied broadly to possible future interventive therapies in common polygenic diseases to suppress a particular genotype(s) and thereby suppress the disease phenotype.

In the present invention suppression effectors are designed specifically to target the non-coding regions of genes, for example, the 5' and 3' UTRs. This provides sequence specificity for gene suppression. In addition it provides greater flexibility in the choice of target sequence for suppression in contrast to suppression strategies directed towards single disease mutations. Furthermore it allows suppression effectors to target non-coding sequences 5' or 3' of the coding region thereby allowing the possibility of including the ATG start site in the target site for suppression and hence presenting an opportunity for suppression at the level of translation or inducing instability in RNA by, for example, cleavage of the RNA before the polyA tail. Notably the invention has the advantage that the same suppression strategy when directed to the 5' and 3' non-coding sequences could be used to suppress, in principle, any mutation in a given gene. This is particularly relevant when large numbers of mutations within a single gene cause a disease pathology. Suppression targeted to non-coding sequences allows, when necessary, the introduction of a replacement gene(s) with the same or similar coding sequences to provide the normal gene product. The replacement gene can be designed to have altered non-coding sequences and hence can escape suppression as it does not contain the target site(s) for suppression. The same replacement gene could in principle be used in conjunction with the suppression of any disease mutation in a given gene. In the case of suppression of an individual member of a gene family, the non-coding regions typically show lower levels of homology between family members thereby providing more flexibility and specificity in the choice of target sites for suppression. In relation to this aspect of the invention, the use of intronic sequences for suppression of an individual member of a family of genes has been described in a previous invention (REF: WO 92/07071). However the use of 5' and 3' non-coding sequences as targets for suppression holds the advantage that these sequences are present not only in precursor messenger RNAs but also in mature messenger RNAs, thereby enabling suppressors to target all forms of RNA. In contrast, intronic sequences are spliced out of mature RNAs.

In summary the invention can involve gene suppression and replacement such that the replacement gene cannot be suppressed. Both the same suppression and replacement steps can be used for many and in some cases all of the disease mutations identified in a given gene. Therefore the invention enables the same approach to be used to suppress a wide range of mutations within the same gene. Suppression and replacement can be undertaken in conjunction with each other or separately.

EXAMPLES

The present invention is exemplified using four different genes: human rhodopsin, human peripherin, mouse rhodopsin and mouse peripherin. While all four genes are retina-specific, there is no reason why the present invention could not be deployed in the suppression of other genes. Notably the 5'UTR and part of the coding sequence of the COL1A2 gene has been cloned together with a ribozyme to target the 5'UTR of the gene emphasizing the broad utility of the invention in gene suppression. The 5'UTR and part of the coding sequence of the COL1A2 gene in which there are many mutations have previously been identified which give rise to autosomal dominant osteogenesis imperfecta, has begun but was not completed at the time of submission. Many examples of mutant genes which give rise to disease phenotypes are available from the prior art—these all represent disease targets for this invention. The present invention is exemplified using ribozymes with antisense arms to elicit RNA cleavage. There is no reason why other suppression effectors directed towards the non-coding regions of genes could not be used to achieve gene suppression. Many examples from the prior art detailing the use of suppression effectors inter alia antisense RNA/DNA, triple helix, PNAs, peptides to achieve suppression of gene expression are reported as discussed earlier. The present invention is exemplified using ribozymes with antisense arms to elicit cleavage of template RNA transcribed from one vector and non-cleavage of replacement RNAs with altered untranslated region sequences transcribed from a second vector. There is no reason why both the suppression and replacement steps could not be in the same vector. In addition there is no reason why ribozymes could not be used to combine both the suppression and replacement steps, that is, to cleave the target RNA and to ligate to the cleavage product, a replacement RNA with an altered sequence, to prevent subsequent cleavage by ribozymes which are frequently autocatalytic as discussed. The present invention is exemplified using suppression effectors directed to target the 5' untranslated region of the above named genes. There is no reason why other non-coding regions of a gene inter alia the 3' untranslated region or the regions involved in the control of gene expression such as promoter regions or any combination of non-coding regions could not be used to achieve gene suppression. Suppression targeted to any non-coding region of a gene would allow the expression of a replacement gene with altered sequences in the non-coding region of the gene to which the suppression effector(s) was targeted.

MATERIALS AND METHODS

Cloning vectors cDNA templates, cDNA hybrids with altered non-coding sequences, ribozymes and antisense DNA fragments were cloned into commercial expression vectors (pcDNA3, pZeoSV or pBluescript) which enable expression in a test tube from T7, T3 or SP6 promoters or expression in cells from CMV or SV40 promoters. Inserts were placed into the multiple cloning site (MCS) of these vectors typically at or near the terminal ends of the MCS to delete most of the MCS and thereby prevent any possible problems with efficiency of expression subsequent to cloning.

Sequencing Protocols

Clones containing template cDNAs, hybrid cDNAs with altered non-coding sequences, ribozymes and antisense were sequenced by ABI automated sequencing machinery using standard protocols.

Expression of RNAs

RNA was obtained from clones in vitro using a commercially available Ribomax expression system (Promega) and standard protocols. RNA purifications were undertaken using the Bio-101 RNA purification kit or a solution of 0.3M sodium acetate and 0.2% SDS. Cleavage reactions were performed using standard protocols with varying $MgCl_2$ concentrations (0–15 mM) at 37°C. typically for 3 hours. Time points were performed at the predetermined optimal $MgCl_2$ concentrations for up to 5 hours. Radioactively labeled RNA products were obtained by incorporating $\alpha$-$P^{32}$ rUTP (Amersham) in the expression reactions (Gaughan et al. 1995). Labeled RNA products were run on polyacrylamide gels before cleavage reactions were undertaken for the purposes of RNA purification and subsequent to cleavage reactions to establish if RNA cleavage had been achieved.

The exact base at which transcription starts has not been defined fully for some promoters (pcDNA3 Invitrogen) hence the sizes of the RNA products may vary slightly from those predicted in Table 1. In addition multiple rounds of cloning of a cDNA results in inserts carrying extra portions of MCS again, sometimes altering marginally the size of expressed RNA products. Typically 4–8% polyacrylamide gels were run to resolve RNA products.

RNA Secondary Structures

Predictions of the secondary structures of human rhodopsin, mouse rhodopsin, human peripherin, mouse peripherin and human type I Collagen COLIA2 mRNAs where obtained using the RNAPlotFold program. Ribozyme and antisense was designed to target areas of the RNA that were predicted to be accessible to suppression effectors and which were composed of non-coding sequence. The integrity of open loop structures was evaluated from the 15 most probable RNA structures. Additionally RNA structures for truncated RNA products were generated and the integrity of open loops between full length and truncated RNAs compared.

TEMPLATE/HYBRID/RIBOZYME AND ANTISENSE CONSTRUCTS

EXAMPLES

Various products of the examples are illustrated in FIGS. 1 to 20 and are explained in the results sections.

Mouse Rhodopsin

Template cDNA

A full length mouse rhodopsin cDNA was generated from a partial cDNA clone missing the sequence coding for the first 20 amino acids of the protein and a partial genomic clone, which enabled the production of a full length cDNA (kindly donated by Dr. Wolfgang Baehr). The full length cDNA was cloned into the EcoRI site of pcDNA3 in a 5' to 3' orientation allowing subsequent expression of RNA from the T7 or CMV promoters in the vector. The full length 5'UTR sequence was present in this clone. In addition to the full length 5' UTR sequence the clone contains additional 5' upstream sequence of the mouse rhodopsin gene as the clone was generated using the EcoRI site present at position 1120 (Accession number: M55171). (SEQ ID NO:1)

Hybrid cDNAs with Altered Non-coding Regions

Hybrid 1

The mouse rhodopsin hybrid cDNA sequence was altered in the non-coding sequences by PCR primer directed mutagenesis and cloned into the HindIII and EcoRI sites of pcDNA3 in a 5' to 3' orientation allowing subsequent expression of RNA from the T7 or CMV promoters in the vector. PCR mutagenesis was undertaken using a HindIII (in the MCS of pcDNA3) to Eco47111 (in Exon 2 of the gene) DNA fragment. The 5'UTR was altered significantly—the mouse rhodopsin 5'UTR was completely replaced by the 5'UTR of the human peripherin gene, that is, by 5'UTR sequence from a different gene (peripherin) and from a different species (human) but from a gene expressed in the same tissue as mouse rhodopsin, i.e., photoreceptor cells (SEQ ID NO: 2 (forward) and SEQ ID NO: 19 (reverse)). The sequence of the mouse rhodopsin cDNA is present in the clone from the ATG start onwards.

Hybrid 2

The mouse rhodopsin hybrid cDNA sequence was altered in the non-coding sequences to eliminate the GUC ribozyme binding site targeted in the 5'UTR of mouse rhodopsin. The U of the target was changed to G, that is, GUC→GGC (nucleotides 340–342 of SEQ ID NO:3). Again PCR mutagenesis was primer driven and was undertaken using a HindIII (in pcDNA3) to Eco47111 (in the coding sequence of the mouse rhodopsin cDNA) DNA fragment. (SEQ ID NO: 3 (forward) and SEQ ID NO: 20 (reverse)).

Ribozyme constructs

A hammerhead ribozyme (termed Rib3) designed to target an open loop structure in the RNA in the 5' non-coding region of the gene was cloned into the HindIII and XbaI sites of pcDNA3 again allowing subsequent expression of RNA from the T7 or CMV promoters in the vector (SEQ ID NO:4). The target site was GUC at position 1393–1395 of the mouse rhodopsin sequence (Accession number: M55171). Antisense flanks are underlined.

Rib3: <u>CUUCGUA</u>CUGAUGAGUCCGUGAGGACGAA<u>ACAGAGAC</u> (SEQ ID NO:21, corresponding to nucleotides 95–131 of SEQ ID NO:4)

Human Rhodopsin

Template cDNA

The human rhodopsin cDNA was cloned into the HindIII and EcoRI sites of the MCS of pcDNA3 in a 5' to 3' orientation allowing subsequent expression of RNA from the T7 or CMV promoters in the vector. The full length 5'UTR sequence was inserted into this clone using primer driven PCR mutagenesis and a HindIII (in pcDNA3) to BstEII (in the coding sequence of the human rhodopsin cDNA) DNA fragment (SEQ ID NO:5)

Hybrid cDNAs with altered non-coding regions

The human rhodopsin hybrid cDNA with altered non-coding sequences was cloned into the EcoRI site of pcDNA3 in a 5' to 3' orientation allowing subsequent expression of RNA from the T7 or CMV promoters in the vector. The 5'UTR of this clone included only the first 21 bases of the non-coding region of human rhodopsin before the ATG start site (SEQ ID NO:6).

Ribozyme constructs

A hammerhead ribozyme (termed Rib15) designed to target an open loop structure in the RNA from the non-coding regions of the gene was cloned subsequent to synthesis and annealing into the HindIII and XbaI sites of pcDNA3 again allowing subsequent expression of RNA from the T7 or CMV promoters in the vector (SEQ ID NO:7). The target site was AUU (the NUX rule) at position 249–251 of the human rhodopsin sequence (Accession number: K02281). Antisense flanks are underlined.

Rib15: ACCCAAGCUGAUGAGUCCGUGAGGACGAA AUGCUGC (SEQ ID NO:22, corresponding to nucleotides 104–139 of SEQ ID NO:7)

Mouse Peripherin

Template cDNA

A mouse peripherin cDNA was cloned into the HindIII and EcoRV sites of pcDNA3. The clone is in a 5' to 3' orientation allowing subsequent expression of RNA from the T7 or CMV promoters in the vector (SEQ ID NO:8). The clone contains the complete 5'UTR sequence together with 27 bases of additional sequence 5' of this UTR sequence left probably from other cloning vectors.

Hybrid cDNAs with altered non-coding regions

The mouse peripherin hybrid cDNA was altered in the 5'non-coding region. Using primer driven PCR mutagenesis the mouse peripherin 5'UTR sequence was replaced by the sequence of the mouse rhodopsin 5'UTR (SEQ ID NO:9). The PCR mutagenesis was achieved using a HindIII (in pcDNA3) to SacII (in the coding sequence of the mouse peripherin cDNA) DNA fragment.

Ribozyme constructs

A hammerhead ribozyme (termed Rib17) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:10). The target site was AUU at position 162–164 of the mouse peripherin sequence (Accession number: X14770). Antisense flanks are underlined.

Rib17: CACUCCUCUGAUGAGUCCGUGAGGACGAA AUCCGAGU (SEQ ID NO:23, corresponding to nucleotides 99–136 of SEQ ID NO:10)

Antisense constructs

Antisense and sense constructs were PCR amplified and cloned into pcDNA3 and pZEOSV for expression in vitro and in vivo. For example, a 127 bp fragment from the 5'UTR sequence of mouse peripherin was cloned in both orientations into the above stated vectors. The effectiveness of antisense at suppression is under evaluation. The altered hybrid cDNA clones are being used to establish if RNAs expressed from these altered clones are protected from antisense suppression effects (SEQ ID NOS:17 and 18).

Human Peripherin

Template cDNA

A human peripherin cDNA cloned into the EcoRI site of the commercially available vector pBluescript was kindly provided by Dr. Gabriel Travis. The clone is in a 5' to 3' orientation allowing subsequent expression of RNA from the T7 promoter in the vector. The full length 5'UTR sequence is present in this clone (SEQ ID NO:11).

Hybrid cDNAs with altered non-coding regions

The hybrid clone with altered non-coding sequences was generated as follows. The hybrid clone contains human peripherin 5'UTR sequences until the BamHI site in the human peripherin 5'UTR sequence. From this site the clone runs into mouse peripherin 5'UTR sequence until the ATG start site where it returns to human peripherin sequence (SEQ ID NO:12). The clone was generated using primer driven PCR mutagenesis of a BamHI (in the 5'UTR sequence) to BglI (in the coding sequence of the human peripherin cDNA) DNA fragment.

Ribozyme constructs

Hammerhead ribozymes (termed Rib8 and Rib9) designed to target open loop structures in the RNA from the non-coding regions of the gene were cloned into the HindIII and XbaI sites of pcDNA3 which again allows subsequent expression of RNA from the T7 or CMV promoters in the vector (SEQ ID NOS:13 and 14). The target sites were CUA and GUU at positions 234–236 and 190–192 respectively of the human peripherin sequence (Accession number: M62958). Antisense flanks are underlined.

Rib8: CCAAGUGCUGAUGAGUCCGUGAGGACGAA AGUCCGG (SEQ ID NO:24, corresponding to nucleotides 93–128 of SEQ ID NO:13)

Rib9: CAAACCUUCUGAUGAGUCCGUGAGGACGAA ACGAGCC (SEQ ID NO:25, corresponding to nucleotides 94–130 of SEQ ID NO:14)

Human Type I Collagen—COL1A2

Template cDNA

A partial human type I collagen 1A2 cDNA sequence including the 5'UTR sequence and exon 1 was cloned after PCR amplification into the HindIII and XbaI sites of pcDNA3. The clone is in a 5' to 3' orientation allowing subsequent expression of RNA from the T7 and or CMV promoters in the vector (SEQ ID NO:15). The clone contains the complete 5'UTR sequence together with Exon I of COL1A2.

Ribozyme constructs

A hammerhead ribozyme (termed Rib18) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:16). The target site was GUC at position 448–450 of the human type I collagen 1A2 sequence (Accession number: J03464; M18057; X02488). Antisense flanks are underlined.

Rib18: AGACAUGCCUGAUGAGUCCGUGAGGACGAA ACUCCUU (SEQ ID NO:26, corresponding to nucleotides 85–121 of SEQ ID NO:16)

RESULTS

Human and mouse rhodopsin and peripherin cDNAs were expressed in vitro. Likewise human and mouse rhodopsin and peripherin cDNAs with altered 5'non-coding sequences were expressed in vitro. Ribozymes targeting the 5'UTRs of these retinal cDNAs were also expressed in vitro. cDNA clones were cut with various restriction enzymes resulting in the production of differently sized RNAs after expression. This aided in differentiating between RNAs expressed from the original cDNAs or from altered hybrid cDNAs. The sites used to cut each clone, the predicted sizes of the resulting RNAs and the predicted sizes of cleavage products after cleavage by target ribozymes are given below in Table 1.

TABLE 1

|  | Restriction Enzyme | RNA Size | Cleavage Products |
|---|---|---|---|
| Example 1 | | | |
| Mouse rhodopsin | Eco47111 | 778 bases | 336 + 442 bases |
| Mouse rhodopsin hybrid 1 | Eco47111 | 643 bases | |
| Mouse rhodopsin hybrid 2 | Fsp 1 | 577 bases | |
| Rib 3 (See Table 1; SEQ ID Nos: 1–4; FIGS. 1–7) | Xho 1 | 60 bases | |
| Example 2 | | | |
| Human rhodopsin | BstEII | 8511 bases | 61 + 790 bases |
|  | Acy 1 | 1183 bases | 61 + 1122 bases |
| Human rhodopsin hybrid | BstEII | 841 bases | |
|  | Acy 1 | 1173 bases | |
|  | Fspl | 300 bases | |
| Rib 15 (See Table 1; SEQ ID Nos: 5–7; FIGS. 8–12) | Xbal | 55 bases | |
| Example 3 | | | |
| Mouse peripherin | BglI | 488 bases | 201 + 287 bases |
| Mouse peripherin hybrid | BglI | 344 bases | |
| Rib 17 (See Table 1; SEQ ID Nos: 8–10; FIGS. 13–16) | Xbal | 60 bases | |
| Example 4 | | | |
| Human peripherin | BglI | 489 bases | 238 + 251 (Rib 8) |
|  |  |  | 194 + 295 (Rib 9) |
| Human peripherin hybrid | AvrII | 331 bases | |
| Rib 8 | Xbal | 55 bases | |
| Rib 9 (see Table 1; SEQ ID Nos: 11–14; FIGS. 17–20) | Xbal | 55 bases | |
| Example 5 | | | |
| Collagen 1A2 | XhoI | | |
| Rib 18 (See Table 1; SEQ ID Nos: 15 and 16) | Xbal | | |
| Example 6 | | | |
| Antisense constructs (See Table 1; SEQ ID Nos: 17 and 18) | | | |

The examples of the invention are illustrated in the accompanying figures wherein:

FIG. 1: pBR322 was cut with MspI, radioactively labeled and run on a polyacrylamide gel to enable separation of the resulting DNA fragments. The sizes of these fragments are given in FIG. 1. This DNA ladder was then used on subsequent polyacrylamide gels to provide an estimate of the size of the RNA products run on the gels.

Figure 2A:
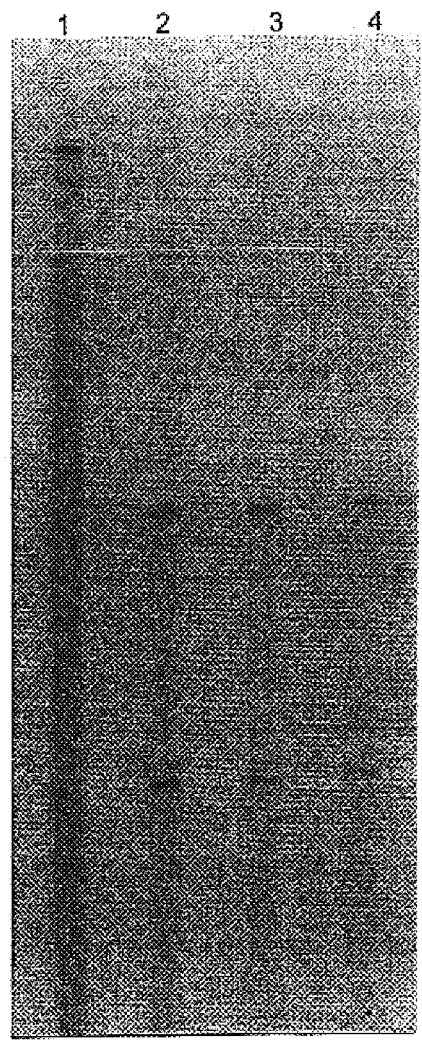
Figure 2B:
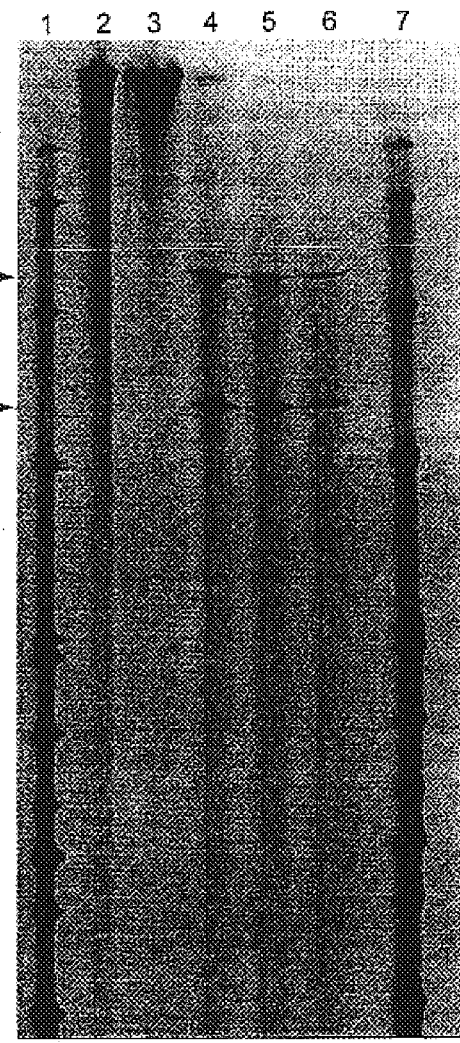

FIG. 2: Mouse rhodopsin cDNA was expressed from the T7 promoter to the Eco47III site in the coding sequence. The RNA was mixed with Rib3 RNA with varying concentrations of magnesium chloride. Lane 1–4: Rhodopsin RNA and Rib3 RNA after incubation for 3 hours at 37° C. with 0 mM, 5 mM, 10 mM and 15 mM magnesium chloride. The sizes of the expressed RNAs and cleavage products are as expected (Table 1). Complete cleavage of mouse rhodopsin RNA was obtained with a small residual amount of intact RNA present at 5 mM magnesium chloride. Note at 0mM magnesium chloride before activation of Rib3 RNA no cleavage products were observed.

B: Mouse rhodopsin cDNA was expressed from the T7 promoter to the Eco47III site in the coding sequence. Resulting RNA was mixed with Rib3 RNA with varying concentrations of magnesium chloride. Lane 1: DNA ladder as in FIG. 1. Lane 2: intact mouse rhodopsin RNA. Lane 3–6: Rhodopsin RNA and Rib3 RNA after incubation for 3 hours at 37° C. with 0 mM, 5 mM, 10 mM and 15 mM magnesium chloride. Again complete cleavage of mouse rhodopsin RNA was obtained with a small residual amount of intact RNA present at 5 mM magnesium chloride. Lane 7: DNA ladder as in FIG. 1.

Figure 3:
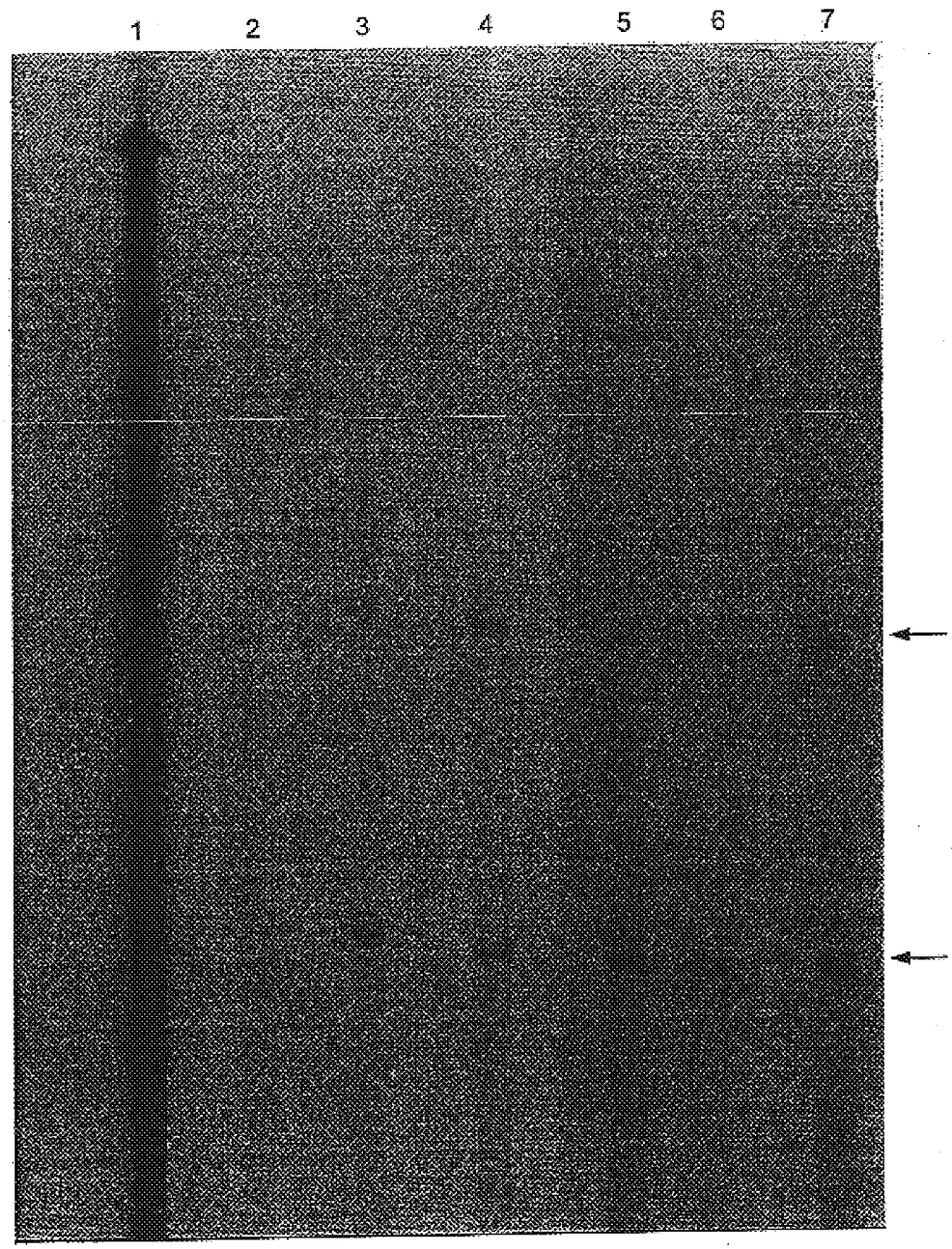

FIG. 3: Mouse rhodopsin cDNA was expressed from the T7 promoter to the Eco47III site in the coding sequence. Lane 1: intact mouse rhodopsin RNA. Lanes 2–7: Mouse rhodopsin RNA was mixed with Rib3 RNA with 15 mM magnesium chloride and incubated at 37° C. for 0, 30, 60, 90, 120 and 180 minutes. The sizes of the expressed RNAs and cleavage products are as expected (Table 1). Complete cleavage of mouse rhodopsin RNA was obtained. Notably cleavage was observed immediately after the addition of the divalent ions which activated Rib3 RNA (see Lane 2: 0 minutes).

Figure 4:
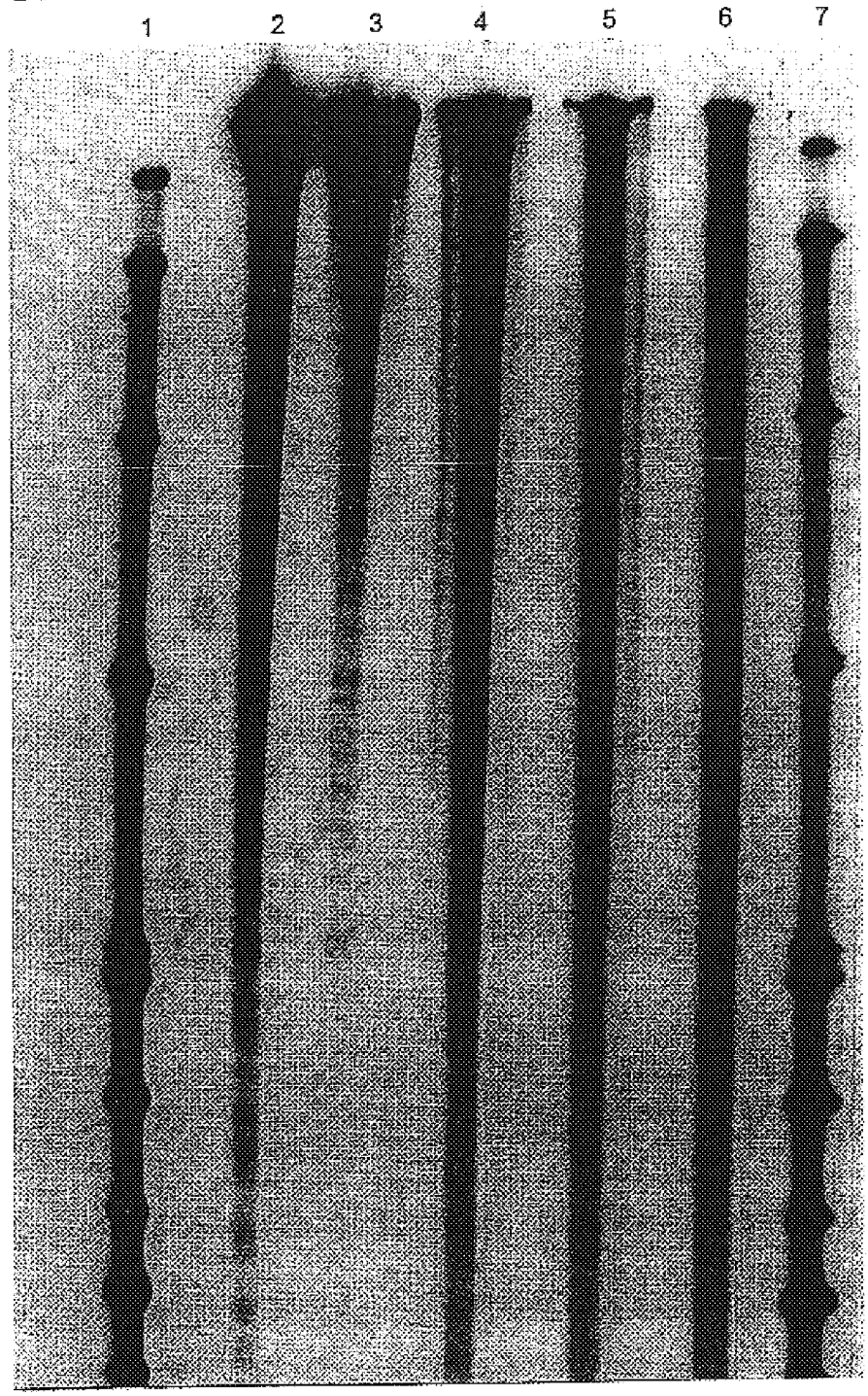

FIG. 4: Mouse rhodopsin cDNA with altered 5'UTR sequence was expressed from the T7 promoter to the Eco47III site in the coding sequence. The resulting RNA was mixed with Rib3 RNA using varying concentrations of magnesium chloride. Lane 1: DNA ladder as in FIG. 1. Lane 2: intact altered mouse rhodopsin RNA. Lane 3 6: altered mouse rhodopsin RNA and Rib3 RNA after incubation for 3 hours at 37° C. with 0 mM, 5 mM, 10 mM and 15 mM magnesium chloride. No cleavage of the altered hybrid RNA occurred.

Figure 5:
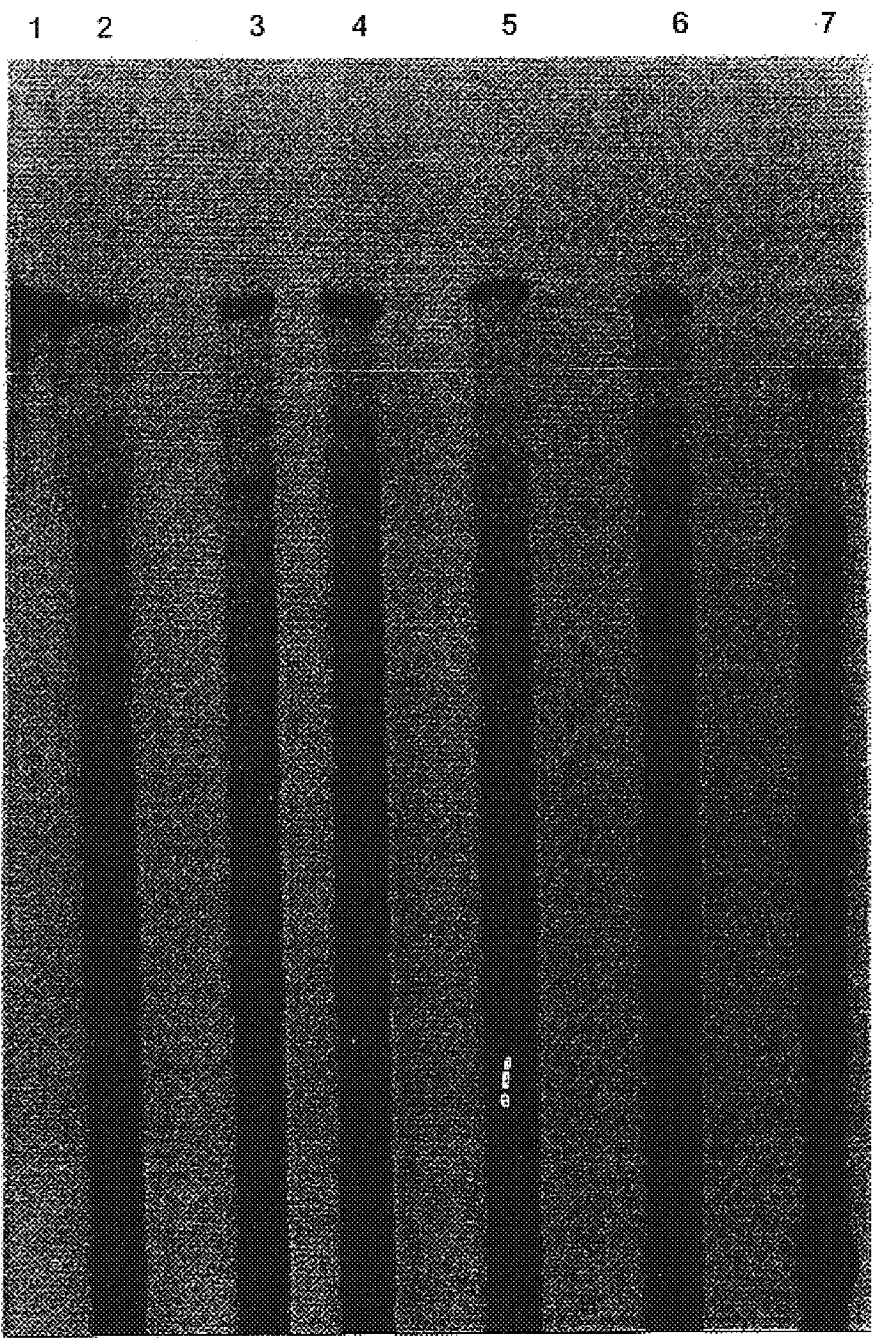

FIG. 5: Mouse rhodopsin cDNA with altered 5'UTR sequence was expressed from the T7 promoter to the Eco47III site in the coding sequence. The resulting RNA was mixed with Rib3 RNA with 10 mM magnesium chloride and incubated at 37° C. Lane 1: intact altered mouse rhodopsin RNAs. Lane 2–6: altered mouse rhodopsin RNA and Rib3 RNA after incubation for 0, 30, 60,120, 180 minutes. No cleavage of the hybrid RNA was obtained. Notably after 3 hours incubation with Rib3 RNA the adapted mouse rhodopsin RNA was as intense as at 0 minutes. Lane 7: DNA ladder as in FIG. 1.

Figure 6A:
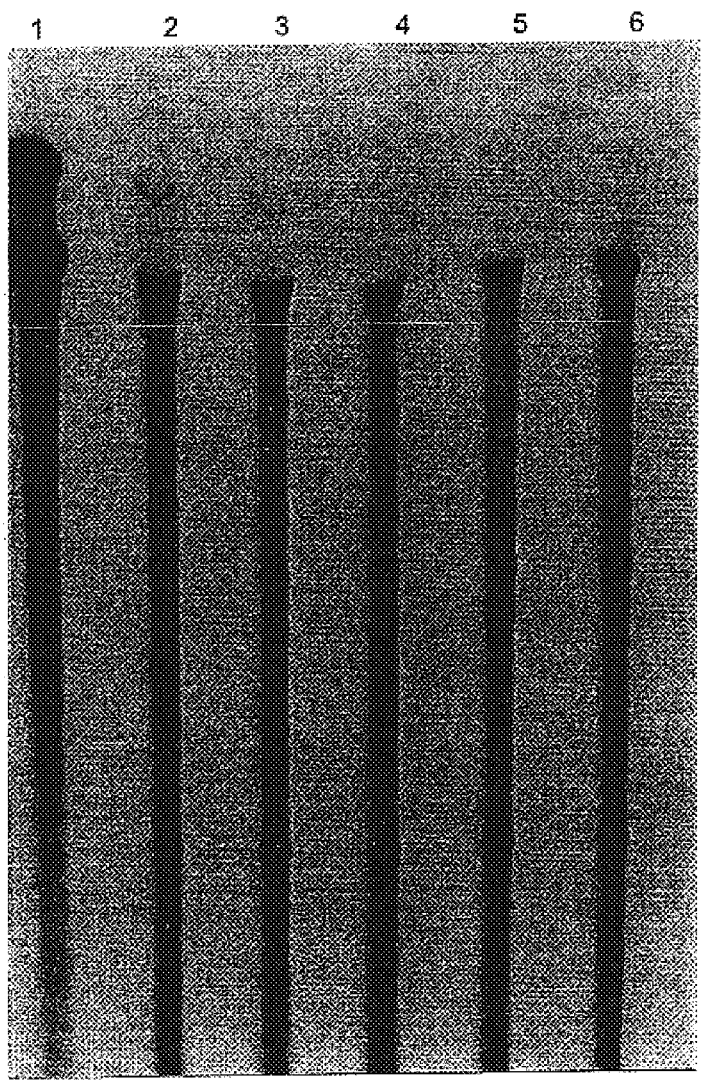
Figure 6B:
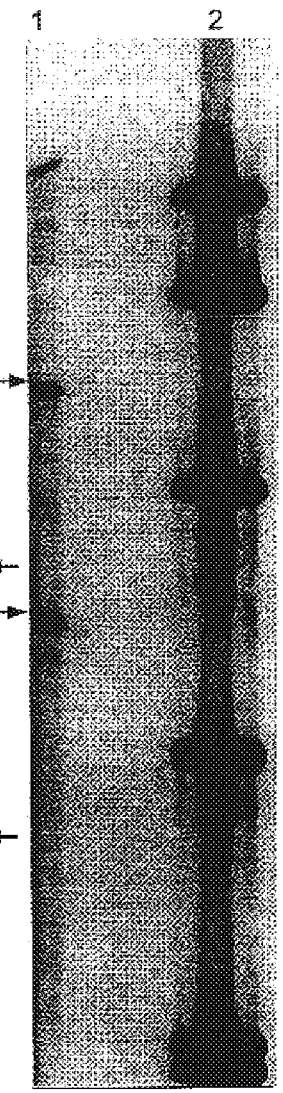

FIG. 6: A: The unadapted mouse rhodopsin cDNA and the mouse rhodopsin cDNA with altered 5'UTR sequence were expressed from the T7 promoter to the Eco47III site in the coding sequence. The resulting RNAs were mixed together with Rib3 RNA and 10 mM magnesium chloride. Lane 1: intact unadapted and altered mouse rhodopsin RNAs which can clearly be differentiated by size as predicted (Table 1). Lane 2–6: unadapted and altered mouse rhodopsin RNAs and Rib3 RNA after incubation for 0, 30, 60,120,180 minutes with 10 mM magnesium chloride at 37° C. No cleavage of the altered hybrid RNA was obtained. The hybrid was of equal intensity after 3 hours as it was at 0 minutes. Notably the majority of the unadapted mouse rhodopsin RNA is cleaved immediately by Rib3 RNA even in the presence of the altered mouse rhodopsin RNA. The cleavage products are highlighted with arrows. The background is due to a small amount of RNA degradation. B: In a separate experiment the three RNAs (unadapted, altered mouse rhodopsin RNAs and Rib3 RNA), were incubated at 15 mM magnesium chloride for 5 hours. The altered hybrid RNA remains intact but the unadapted mouse rhodopsin RNA has been cleaved completely.

Figure 7:
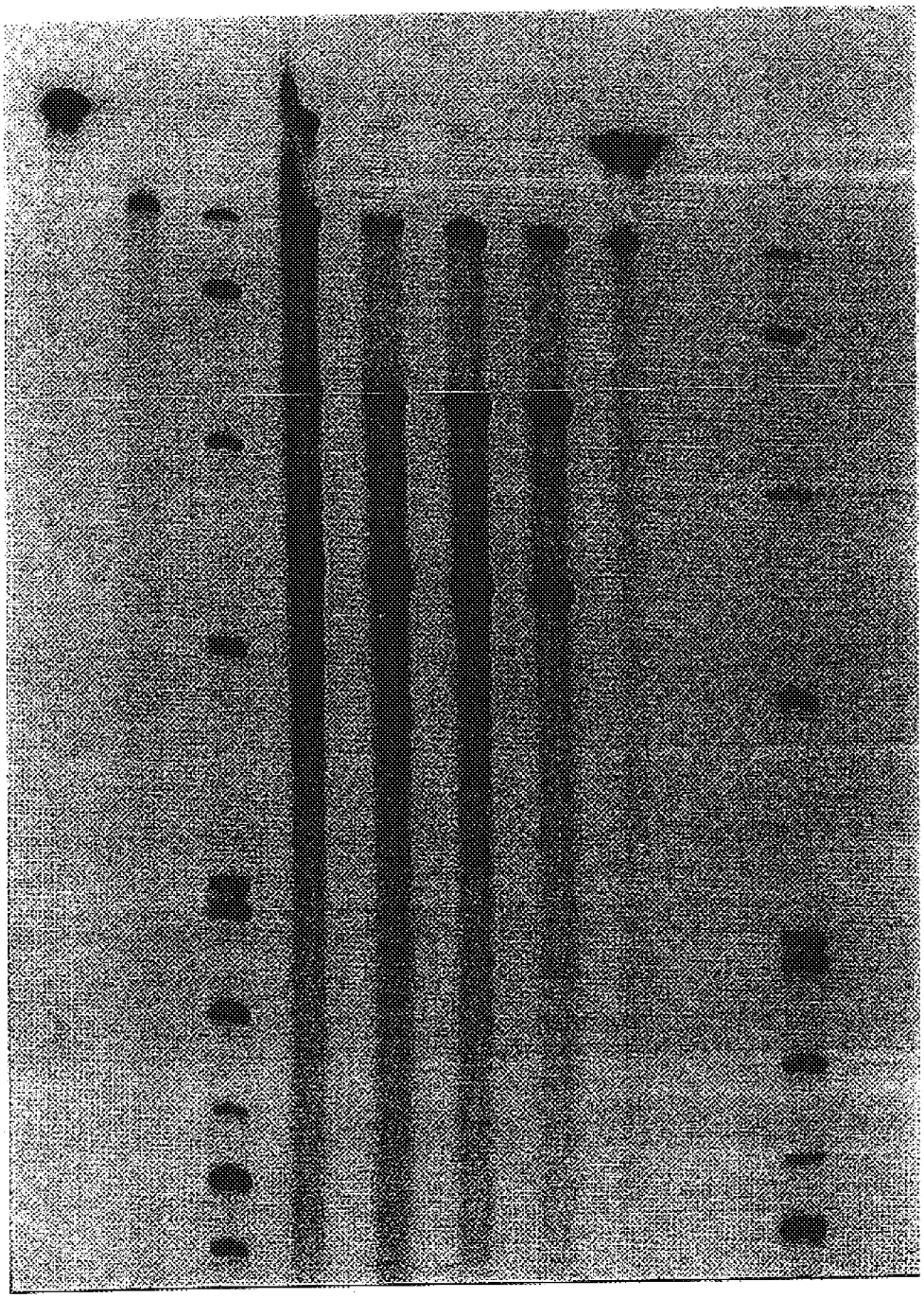

FIG. 7: A second altered mouse rhodopsin cDNA involving a single base change at the ribozyme cleavage site was generated. This adapted mouse rhodopsin cDNA was expressed from the T7 promoter to the FspI site in the coding sequence. Likewise the unadapted mouse rhodopsin cDNA was expressed from the T7 promoter to the Eco47III site in the coding sequence. These two RNAs were mixed with Rib3 RNA and incubated at 37° C. with 15 mM magnesium chloride. Lane 1: Intact mouse rhodopsin RNA. Lane 2: Intact altered mouse rhodopsin RNA (2nd alteration). Lane 3: DNA ladder as in FIG. 1. Lanes 4–7: Unadapted and altered mouse rhodopsin RNAs and Rib3 RNA after incubation for 0, 60, 120 and 180 minutes with 15 mM magnesium chloride at 37° C. Note the reduction of the unadapted RNA product over time in the presence of the altered RNA (Lanes 4 and 5). The adapted RNA remains intact and maintains equal intensity at each time point indicating that it is resistant to cleavage by Rib3 RNA. Again, as with all other altered RNAs, no additional cleavage products were observed. Lane 8: The unadapted and adapted mouse rhodopsin RNA without ribozyme. Lane 9: DNA ladder as in FIG. 1.

Figure 8:
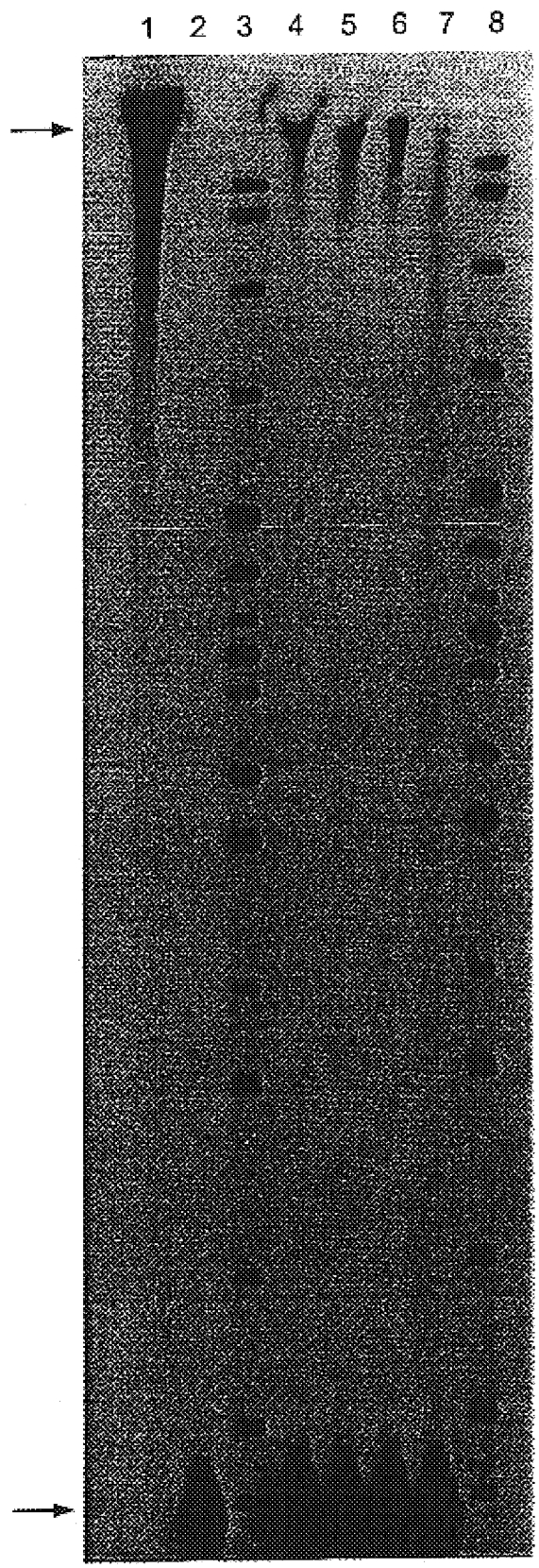

FIG. 8: Human rhodopsin was expressed from the T7 promoter to the BstEII site in Exon IV. The resulting RNA was mixed with Rib15 RNA with varying concentrations of magnesium chloride. Lane 1: intact rhodopsin RNA alone. Lane 2: Rib15 alone. Lane 3: DNA ladder as in FIG. 1. Lanes 4–7: Rhodopsin RNA and Ri15 RNA after incubation for 3 hours at 37° C. with the 0 mM, 5 mM, 10 mM and 15 mM magnesium chloride. Predicted cleavage products are 61 and 790 bases (Table 1). Lane 8: DNA ladder. Partial cleavage of the RNA was obtained—a doublet representing the intact RNA and the larger cleavage product is present (most clearly in lane 5). The gel was run a shorter distance than the gel presented in FIGS. 9–12 to show the presence of Rib15 RNA at the bottom of the gel and to demonstrate that one of the cleavage products cannot be visualized due to the presence of the labeled ribozyme which runs at approximately the same size. Subsequent gels were run further to achieve better separation of these two RNA fragments.

Figure 9:
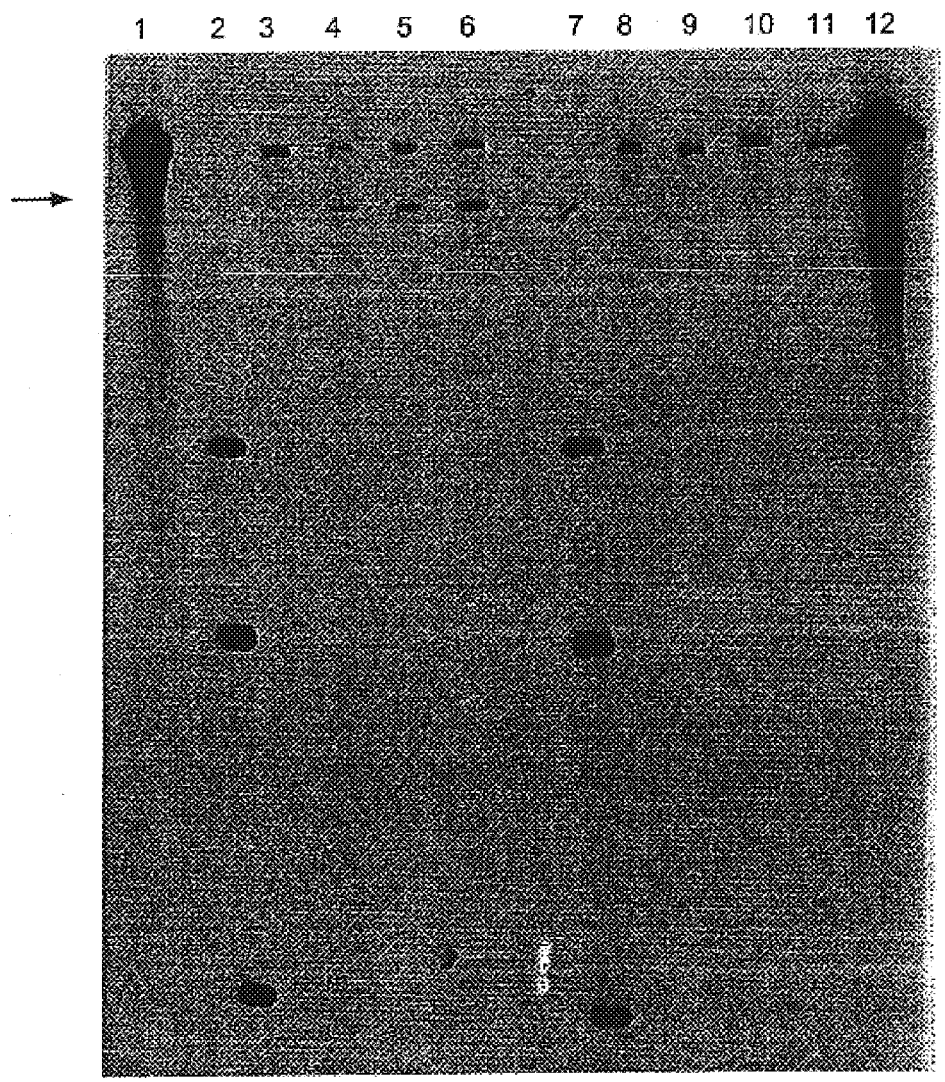

FIG. 9: Both the unadapted human rhodopsin cDNA and the altered cDNA were expressed from the T7 promoter to the BstEII site in Exon IV. The resulting RNA was mixed with Rib15 RNA with varying concentrations of magnesium chloride. Lane 1: intact human rhodopsin RNA alone. Lane 2: DNA ladder as in FIG. 1. Lane 3–6: Rhodopsin RNA and Rib15 RNA after incubation together for 3 hours at 37° C. with O mM, 5 mM, 10 mM and 15 mM magnesium chloride. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodopsin RNA with altered 5'UTR sequence alone. The predicted cleavage products for human rhodopsin are 61 and 790 bases (Table 1)—the larger cleavage product is clearly visible when the ribozyme becomes active after the addition of magnesium chloride (Lanes 4–6). This larger cleavage product is highlighted by an arrow.

Figure 10:
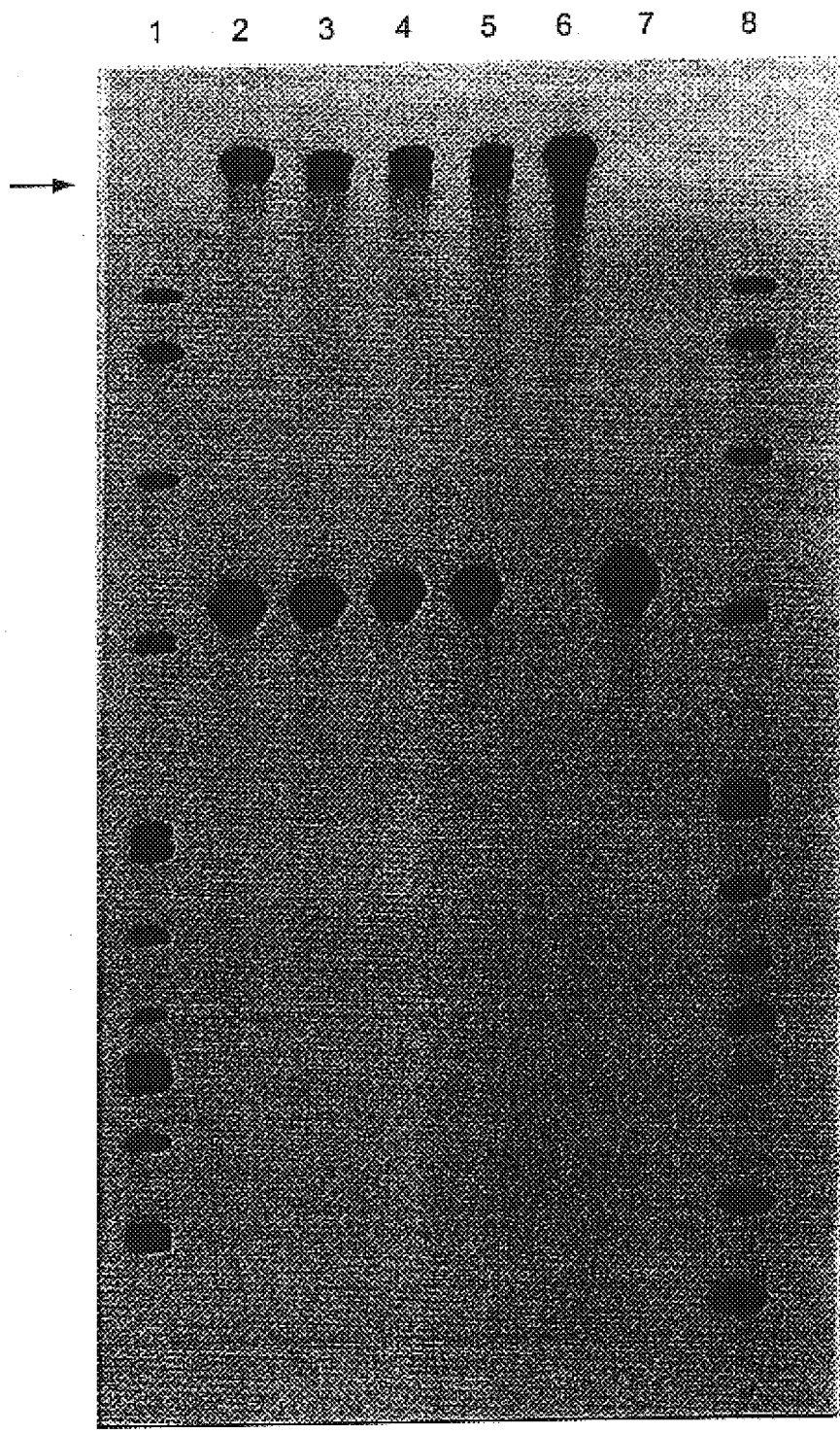

FIG. 10: Human rhodopsin cDNA was expressed from the T7 promoter to the BstEII site in Exon IV. Likewise the altered human rhodopsin cDNA was expressed from the T7 promoter to the FspI site in Exon 1. Both resulting RNAs were mixed together with Rib15 RNA with varying concentrations of magnesium chloride. Lane 1: DNA ladder as in FIG. 1. Lanes 2–5: Rhodopsin RNA, altered rhodopsin RNA and Rib15 RNA after incubation for 3 hours at 37° C. with 0 mM, 5 mM, 10 mM and 15 mM magnesium chloride. The sizes of the expressed RNAs and cleavage products are as expected (Table 1). Partial cleavage of the unadapted RNA was obtained after magnesium was added to the reaction. The altered human rhodopsin RNA was protected from cleavage in all reactions. If cleavage of the altered human rhodopsin RNA had occurred the products rationally would most likely be of a different size than those observed with the unadapted RNA. Notably no additional cleavage products were observed. Moreover there was no change in intensity of the altered RNA when the ribozyme was active (in the presence of magnesium chloride) or inactive (at OmM magnesium chloride). In contrast the unadapted human rhodopsin RNA is less intense in lanes 3–5 after cleavage than in lane 2 before the addition of magnesium to activate Rib15. Lane 6: intact human rhodopsin RNA. Lane 7: intact human rhodopsin RNA with altered 5'UTR sequence. Lane 8: DNA ladder.

Figure 11:
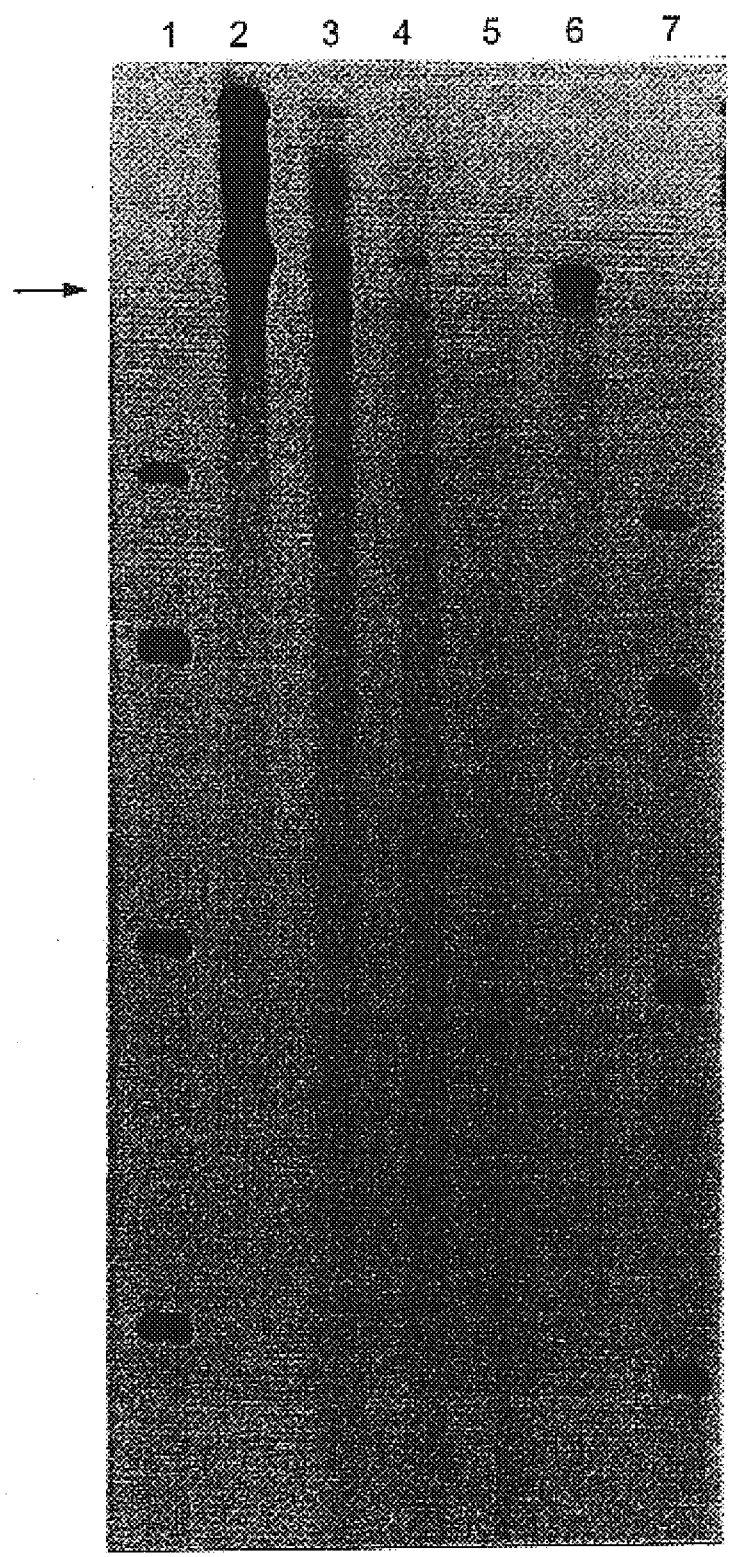

FIG. 11: Human rhodopsin cDNA was expressed from the T7 promoter to the BstEII site in Exon IV. Likewise the altered human rhodopsin cDNA was expressed from the T7 promoter to the AcyI in the 3'rhodopsin sequence after the stop codon. Both resulting RNAs were mixed together with Rib15 RNA with varying concentrations of magnesium chloride. Lane 1: DNA ladder as in FIG. 1. Lanes 2–5: Rhodopsin RNA, altered rhodopsin RNA and Rib15 RNA after incubation for 3 hours at 37° C. with 0 mM, 5 mM, 10 mM and 15 mM magnesium chloride. Lane 6: Intact human rhodopsin RNA. Lane 7: DNA ladder as in FIG. 1. Note that neither RNAs or cleavage products are present in Lane 5 as too little sample may have been loaded in this lane.

Figure 12:
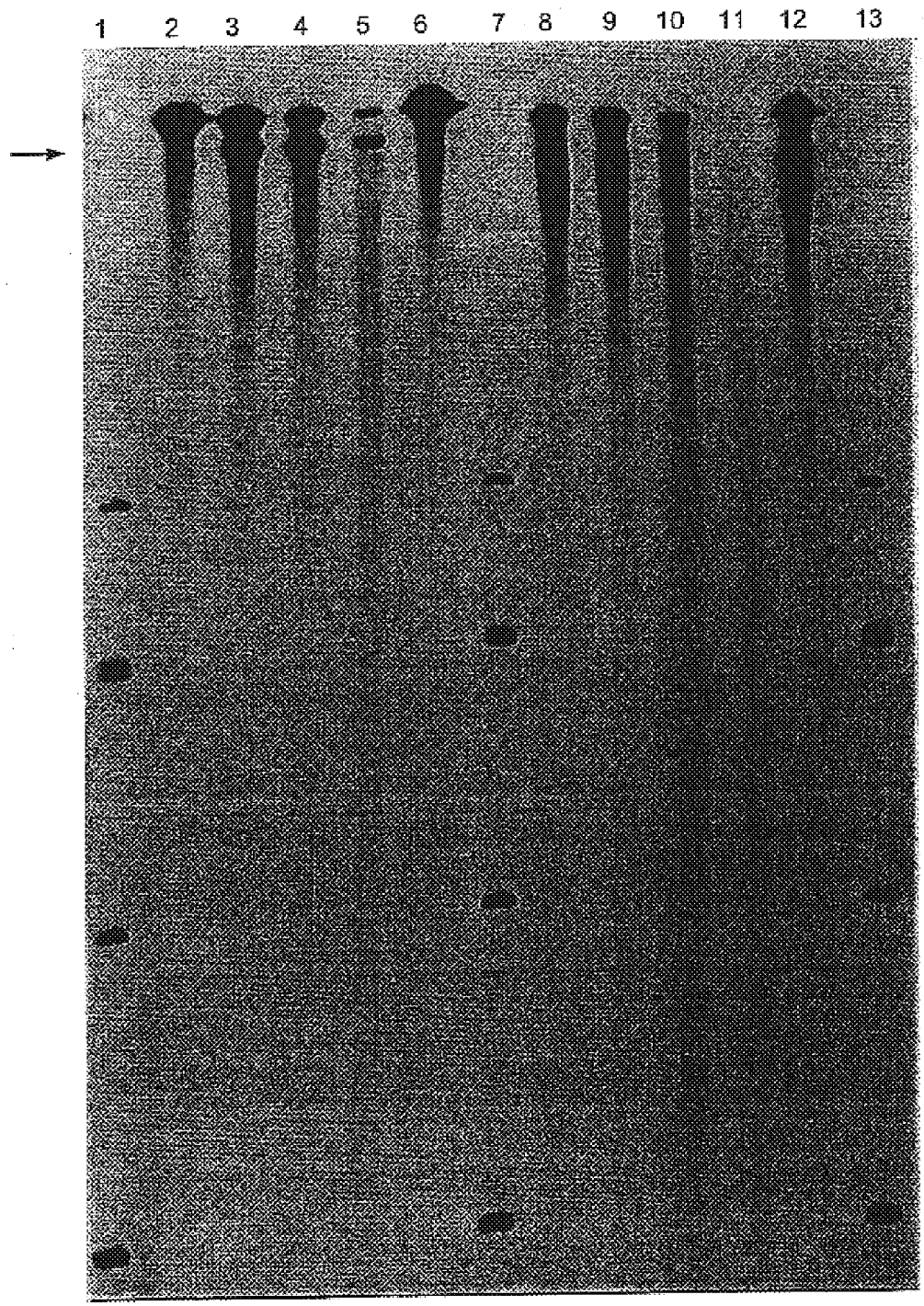

FIG. 12: Human rhodopsin cDNA and the cDNA with altered 5'sequence were expressed from the T7 promoter to the AcyI site after the coding sequence of human rhodopsin. The resulting RNA was mixed with Rib15 RNA with varying concentrations of magnesium chloride. Lane 1: DNA ladder as in FIG. 1. Lane 2–5: Human rhodopsin RNA and Rib15 RNA after incubation together for 3 hours at 37° C. with OmM, 5 mM, 10 mM and 15 mM magnesium chloride. Lane 6: Intact human rhodopsin RNA. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodopsin RNA with altered 5'UTR sequence alone. Lane 13: DNA ladder as in FIG. 1. The larger of the predicted cleavage products is present in lanes 3–5 and is highlighted by an arrow. The adapted human rhodopsin RNA again was protected from cleavage by Rib15 RNA. Note that in Lane 12 too little sample may have been loaded.

Figure 13:
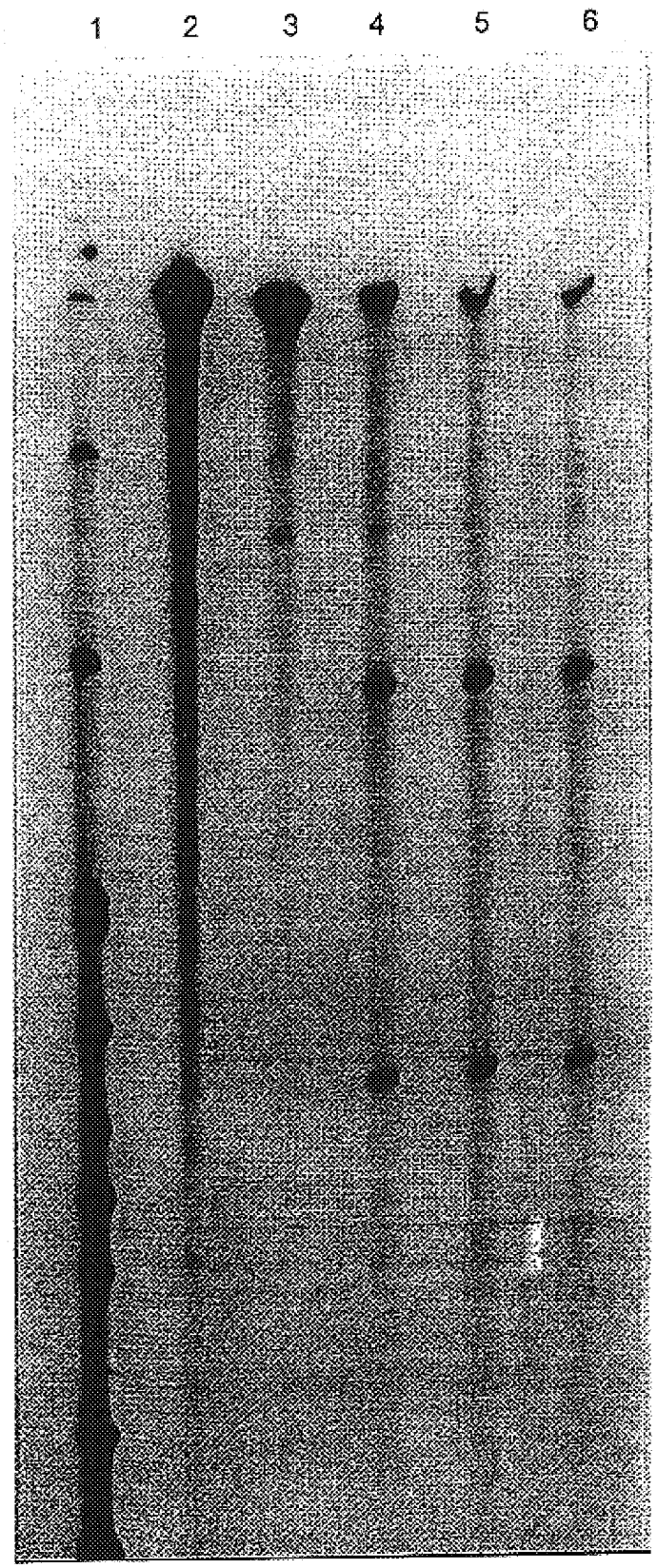

FIG. 13: Mouse peripherin cDNA was expressed from the T7 promoter to the BglIII site in the coding sequence. The RNA was mixed with Rib17 RNA with varying concentrations of magnesium chloride. Lane 1: DNA ladder as in FIG. 1. Lane 2: intact mouse peripherin RNA. Lanes 3–6: Mouse peripherin RNA and Rib17 RNA after incubation for 3 hours at 37° C. with 0 mM, 5 mM, 10 mM and 15 mM magnesium chloride. The sizes of the expressed RNAs and cleavage products are as expected (Table 1). Partial cleavage of mouse rhodopsin RNA was obtained once Rib17 RNA was activated with magnesium chloride. Possibly some of the RNA was in a conformation that was inaccessible to Rib17 RNA. It should be noted that in the absence of magnesium chloride the ribozyme was inactive and no cleavage products were observed.

Figure 14:
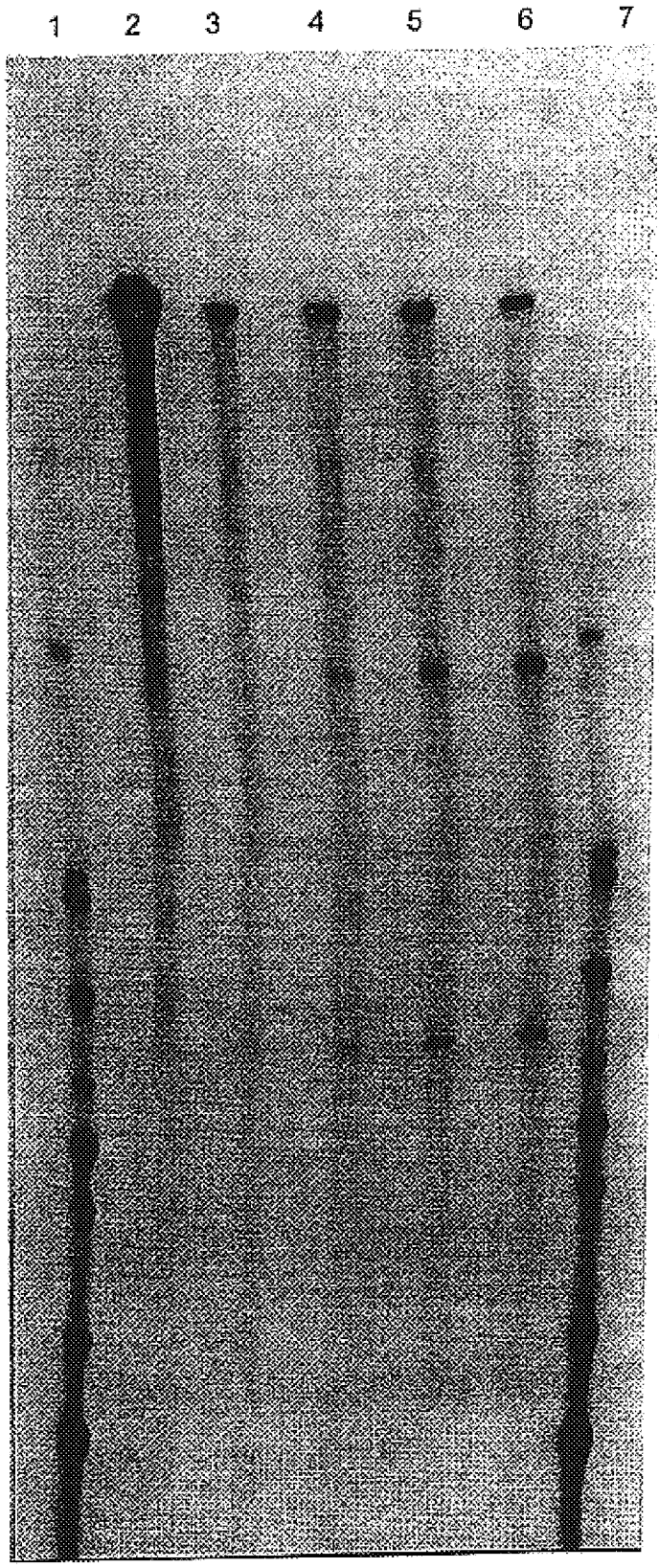

FIG. 14: Mouse peripherin cDNA was expressed from the T7 promoter to the BglII site in the coding sequence. The resulting RNA was mixed with Rib17 RNA with 15 mM magnesium chloride and incubated at 37° C. for varying times. Lane 1: DNA ladder as in FIG. 1. Lane 2: intact mouse peripherin RNA. Lanes 3–6: Mouse peripherin RNA and Rib17 RNA after incubation together with 15 mM magnesium chloride at 37° C. for 0,1, 2 and 3 hours respectively. The sizes of the expressed RNAs and cleavage products are as expected (Table 1). Partial cleavage of mouse rhodopsin RNA was obtained with Rib17 after 1 hour. The proportion of the RNA cleaved increased over time. The intensity of the mouse rhodopsin RNA band decreased visibly on the gel by 3 hours and similarly the cleavage products visibly increased in intensity. It is possible that further cleavage might be obtained over longer time periods. Lane 7: DNA ladder as in FIG. 1.

Figure 15:
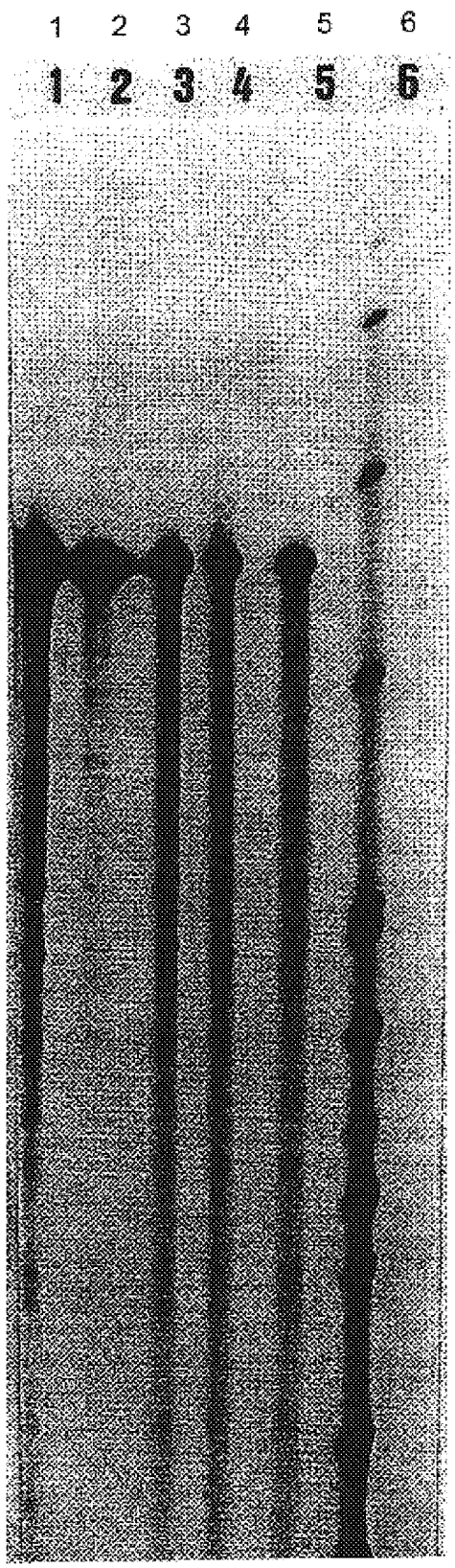

FIG. 15: Mouse peripherin cDNA with altered 5'sequences was expressed from the T7 promoter to the BglII site in the coding sequence. The resulting RNA was mixed with Rib17 RNA with varying concentrations of magnesium chloride. Lane 1: intact altered mouse peripherin RNA with no ribozyme. Lanes 2–5: Mouse peripherin RNA with altered 5'sequence and Rib17 RNA after incubation for 3 hours at 37° C. with 0 mM, 5 mM, 10 mM and 15 mM magnesium chloride. The sizes of the expressed RNAs are as expected (Table 1). No cleavage of the adapted mouse rhodopsin RNA was obtained before or after Rib17 RNA was activated with magnesium chloride. Lane 6: DNA ladder as in FIG. 1.

Figure 16:
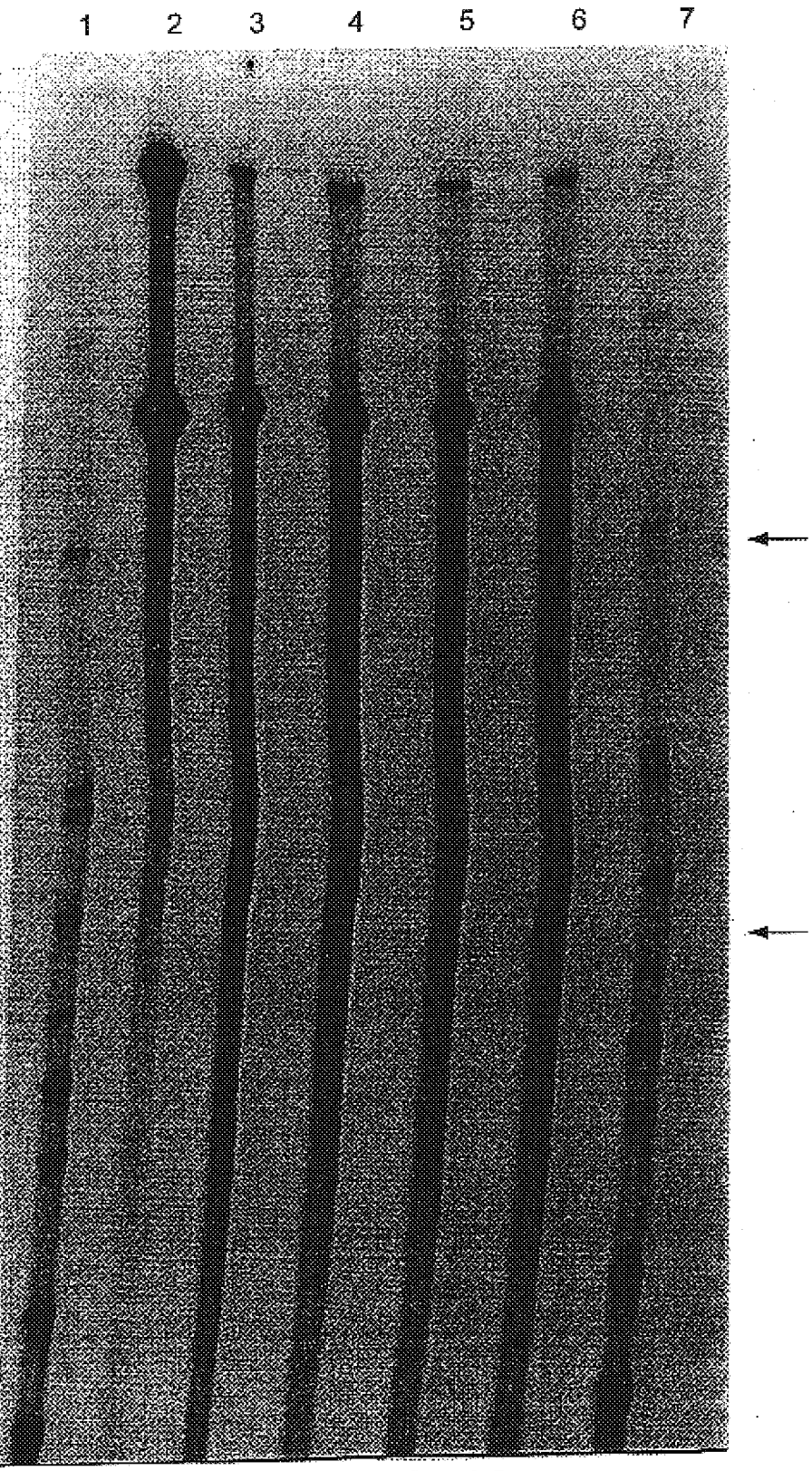

FIG. 16: Both the unadapted and adapted mouse peripherin cDNAs were expressed from the T7 promoter to the BglII site in the coding sequence. The resulting RNAs were mixed together with Rib17 RNA with 15 mM magnesium chloride and incubated at 37° C. for varying times. Lane 1: DNA ladder as in FIG. 1. Lane 2: intact unadapted and altered mouse peripherin RNA. Lanes 3–6: Unadapted mouse peripherin RNA, altered mouse peripherin RNA and Rib17 RNA after incubation together with 15 mM magnesium chloride at 37° C. for 0, 30, 90 and 180 minutes respectively. The sizes of the expressed RNAs and cleavage products are as expected (Table 1). Partial cleavage of the unadapted mouse peripherin RNA was obtained with Rib17 RNA after 1 hour. The intensity of the larger unadapted mouse peripherin RNA product decreases slightly over time. In contrast the cleavage products increase in intensity. The intensity of the smaller altered mouse peripherin RNA product remains constant over time indicating that the RNA is not cleaved by Rib17 RNA. Lane 7: DNA ladder as in FIG. 1.

Figure 17:
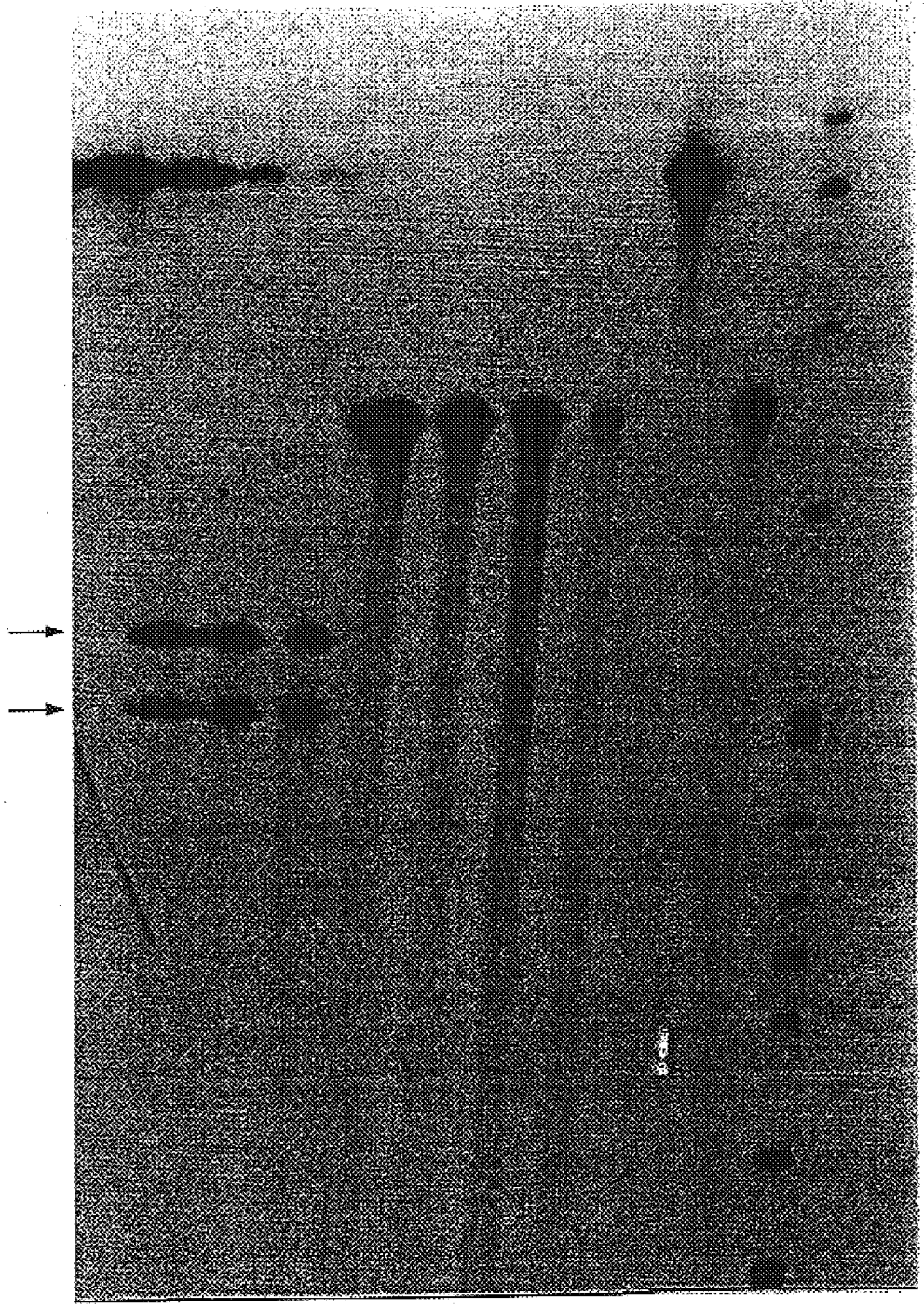

FIG. 17: Both the unadapted and adapted human peripherin cDNAs were expressed from the T7 promoter to the BglII site in the coding sequence. The resulting RNAs were mixed together with Rib8 RNA with varying concentrations of magnesium chloride and incubated at 37° C. for 3 hours. Lane 1: Unadapted human peripherin without ribozyme. Lanes 2–5: Unadapted human peripherin RNA and Rib8 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib8 RNA after 3 hours. The intensity of the larger unadapted human peripherin RNA product decreases over time. Lanes 6–9: Altered human peripherin RNA and Rib8 RNA after incubation together with 0, 5,10, 15 mM magnesium chloride respectively at 37° C. for 3 hours. The sizes of the expressed RNAs are as expected (Table 1). No cleavage of the altered human peripherin RNA was obtained with Rib8 RNA even after 3 hours. The intensity of the smaller altered mouse peripherin RNA product remains constant (with the exception of lane 9 in which less sample may have been loaded) indicating that the RNA is not cleaved by Rib8 RNA. In addition no cleavage products were observed. Lane 10: Intact unadapted human peripherin RNA alone. Lane 11: Intact altered human peripherin RNA alone. Lane 12: DNA ladder as in FIG. 1.

Figure 18:
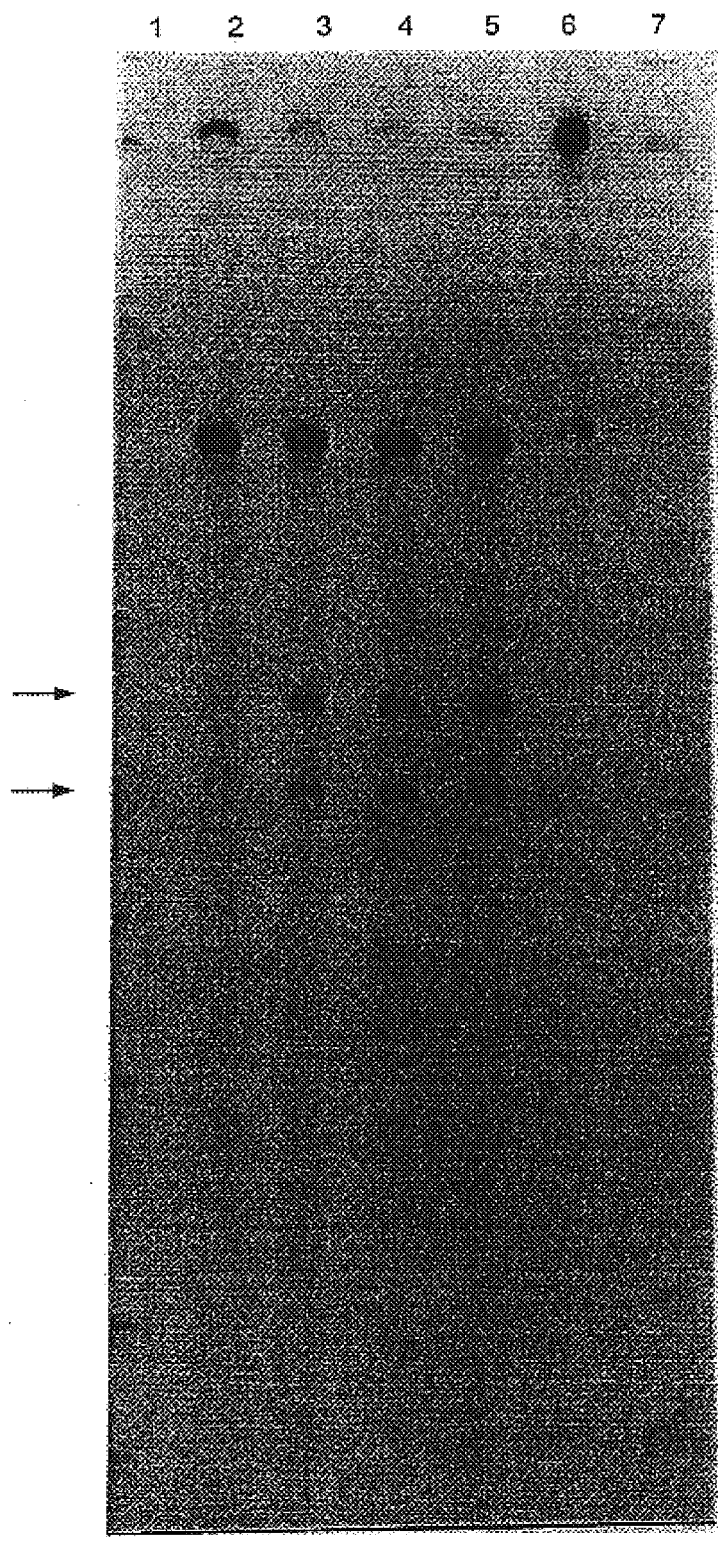

FIG. 18: The unadapted and altered human peripherin cDNAs were expressed from the T7 promoter to the BglII site in the coding sequence. The resulting RNAs were mixed together with Rib8 RNA for varying times with 15 mM magnesium chloride and incubated at 37° C. Lane 1: DNA ladder as in FIG. 1. Lane 2–5: Unadapted and altered human peripherin RNAs and Rib8 RNA after incubation together for 0,1, 2 and 3 hours respectively at 37° C. with 15 mM magnesium chloride. The sizes of the expressed RNAs and cleavage products are as expected (Table 1). Almost complete cleavage of the larger unadapted human peripherin RNA was obtained with Rib8 RNA after 3 hours. The intensity of the larger unadapted human peripherin RNA product decreases over time. Altered human peripherin RNA was not cleaved by Rib8 RNA even after 3 hours. The intensity of the smaller altered mouse peripherin RNA product remains constant over time indicating that the RNA is not cleaved by Rib8 RNA. In addition no additional cleavage products were observed. Lane 6: Intact unadapted and altered human peripherin RNA together without ribozyme. Lane 7: DNA ladder as in FIG. 1.

Figure 19:
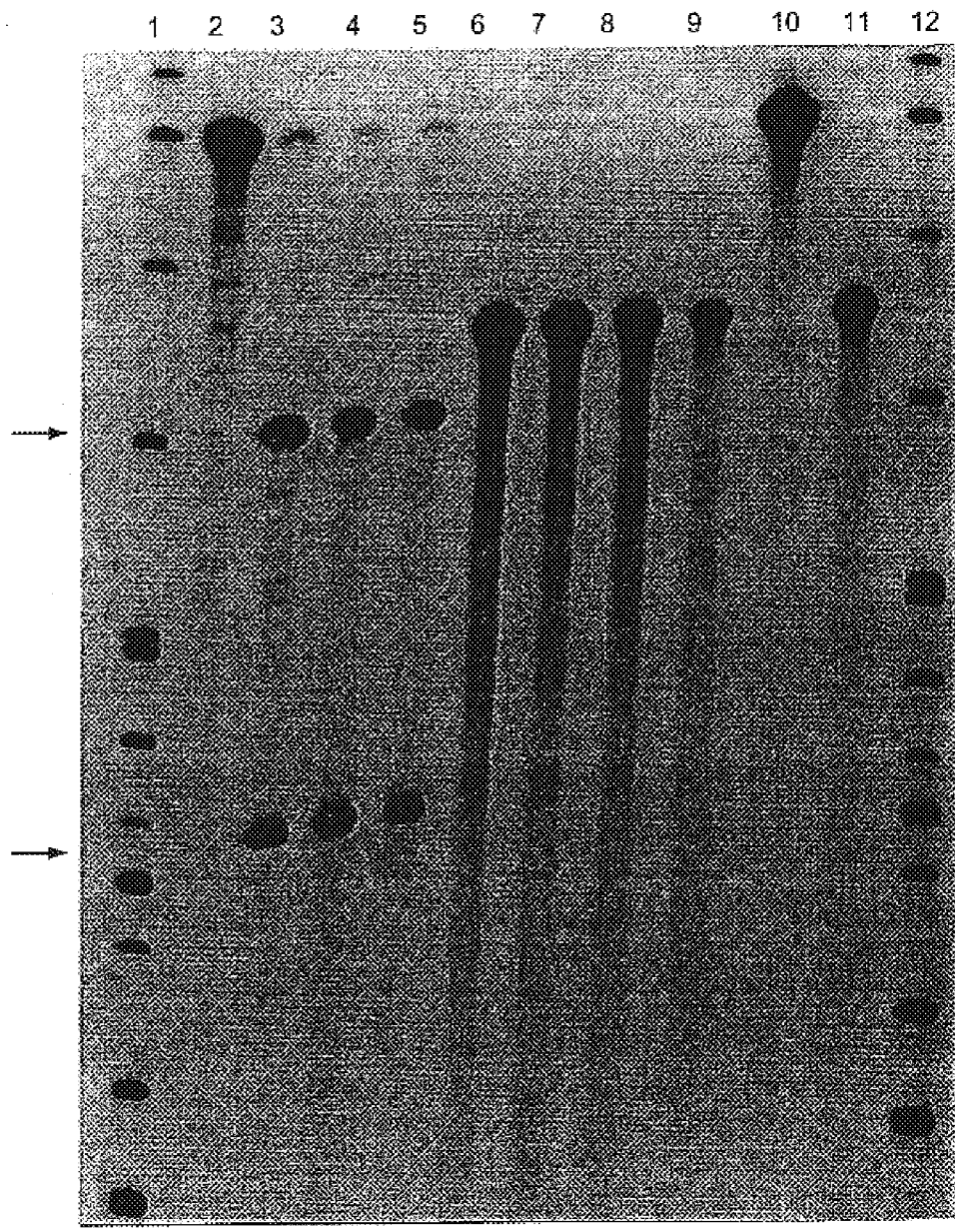

FIG. 19: Both the unadapted and adapted human peripherin cDNAs were expressed from the T7 promoter to the BglII site in the coding sequence. The resulting RNAs were mixed together with Rib9 RNA with varying concentrations of magnesium chloride and incubated at 37° C. for 3 hours. Lane 1: DNA ladder as in FIG. 1. Lanes 2–5: Unadapted human peripherin RNA and Rib9 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib9 RNA. The intensity of the larger unadapted human peripherin RNA product decreases greatly. Lanes 6–9: Altered human peripherin RNA and Rib9 RNA after incubation together with 0, 5, 10, 15 mM magnesium chloride respectively at 37° C. for 3 hours. The sizes of the expressed RNAs are as expected (Table 1). No cleavage of the altered human peripherin RNA was obtained with Rib17 RNA even after 3 hours. The intensity of the smaller altered mouse peripherin RNA was observed—the product remains constant over time indicating that the RNA is not cleaved by Rib9 RNA. Lane 10: Intact unadapted human peripherin RNA alone. Lane 11: Intact altered human peripherin RNA alone. Lane 12: DNA ladder as in FIG. 1. Rib9 RNA was designed to target a different loop structure in the 5'sequence of human peripherin. It may result in slightly more efficient cleavage of RNA than Rib8 RNA.

Figure 20:
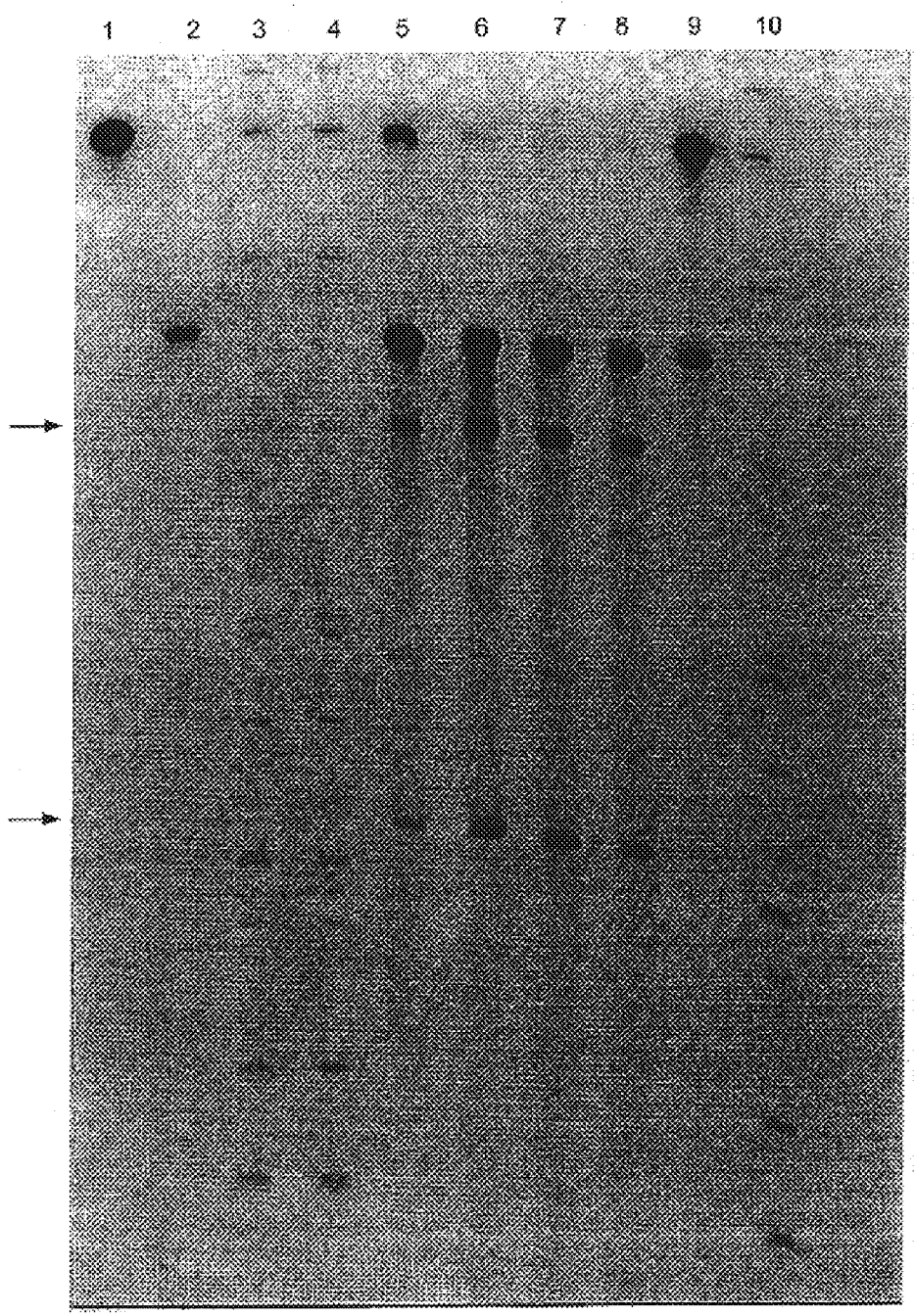
Figure 21A:
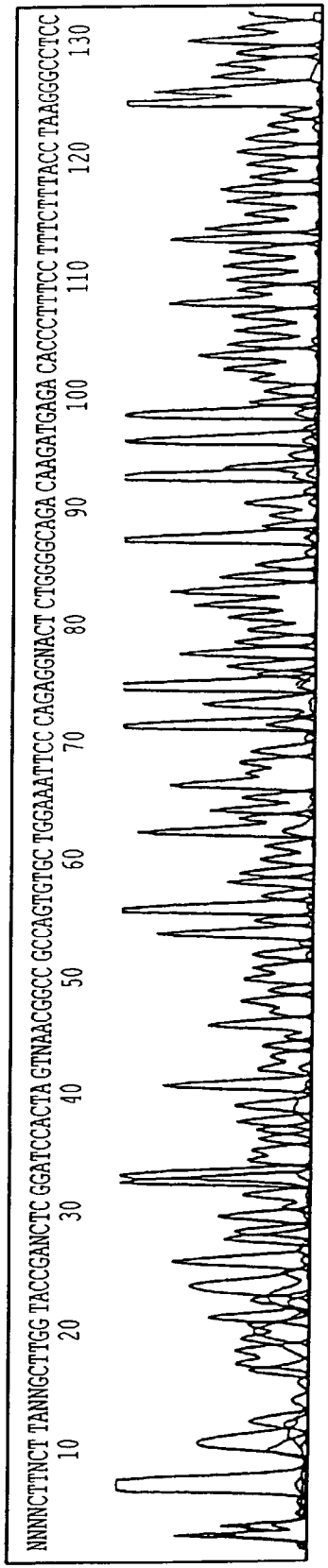
Figure 21B:
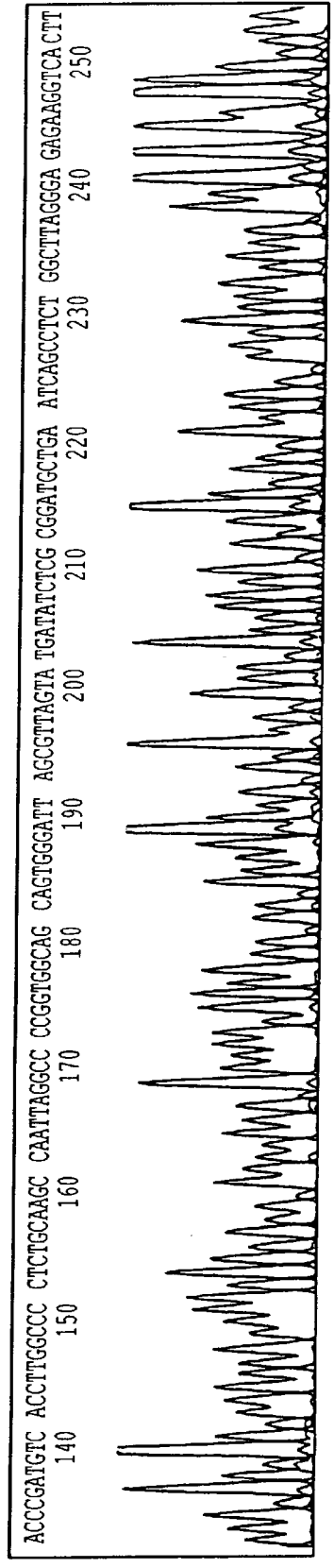
Figure 21C:
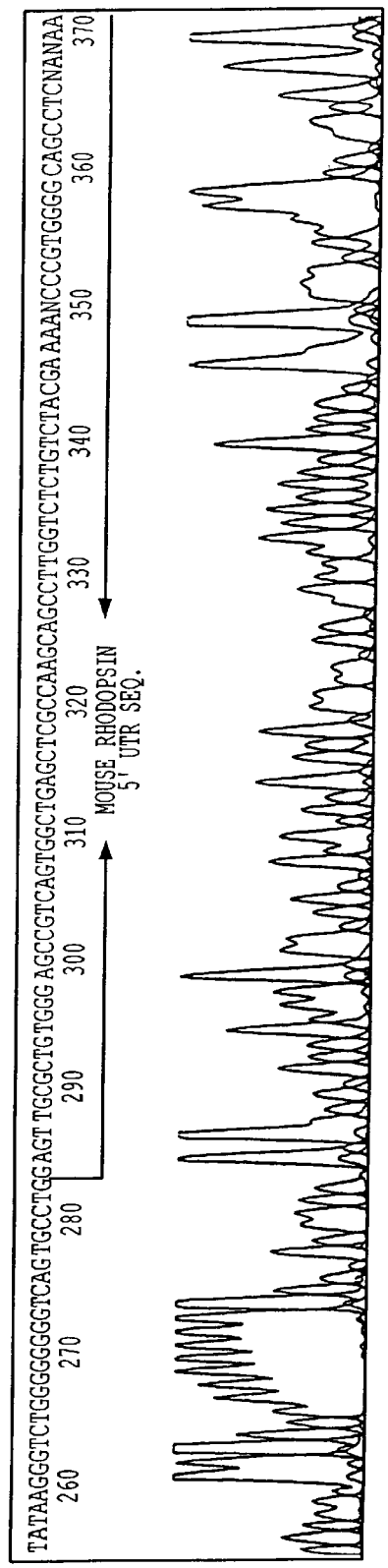
Figure 21D:
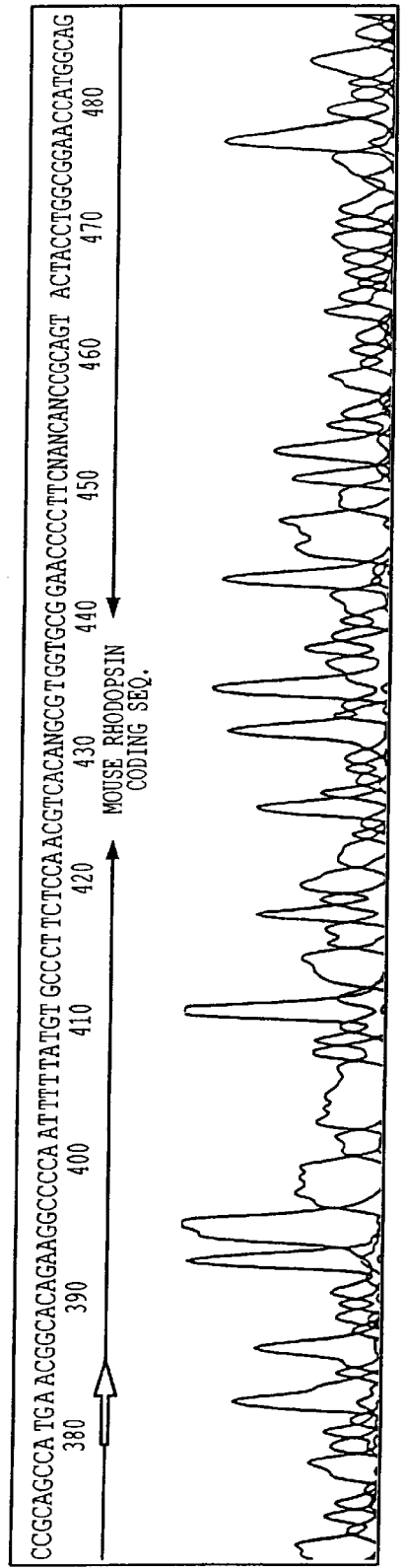
Figure 21E:
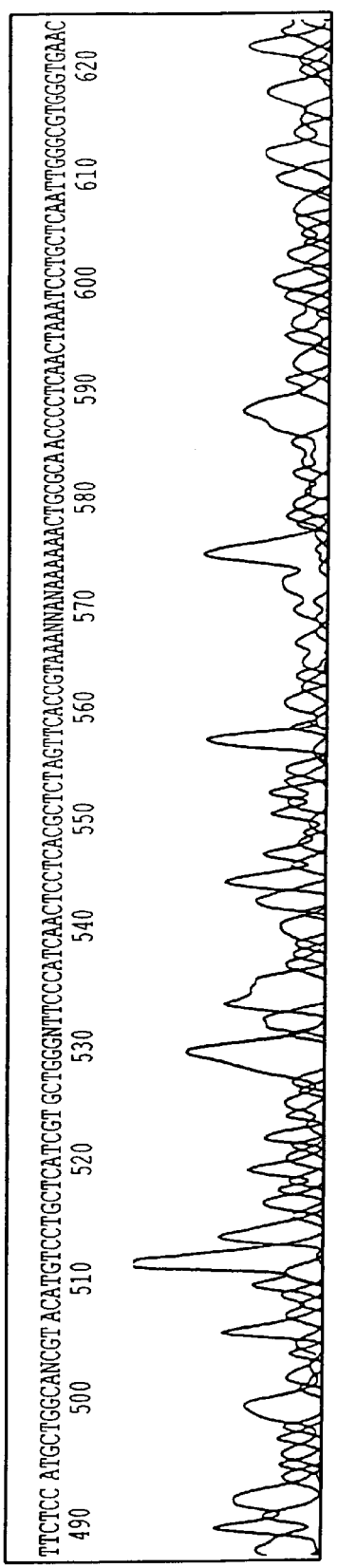
Figure 22A:
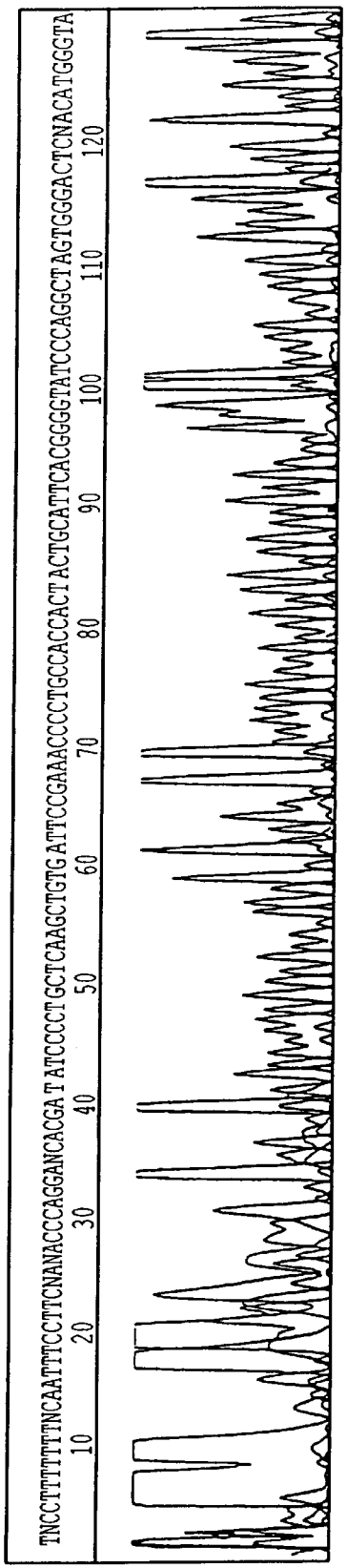
Figure 22B:
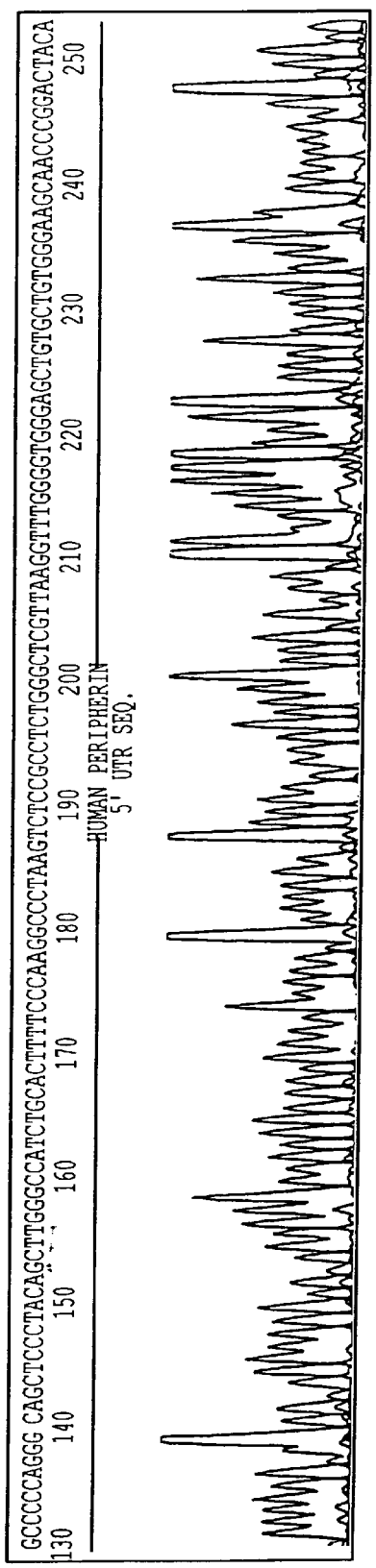
Figure 22C:
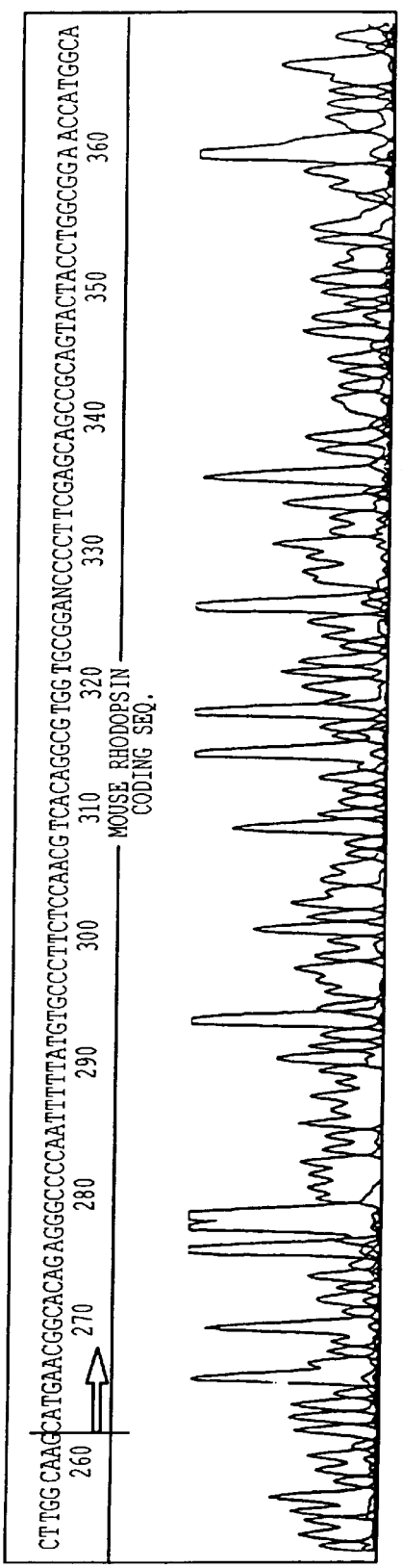
Figure 22D:
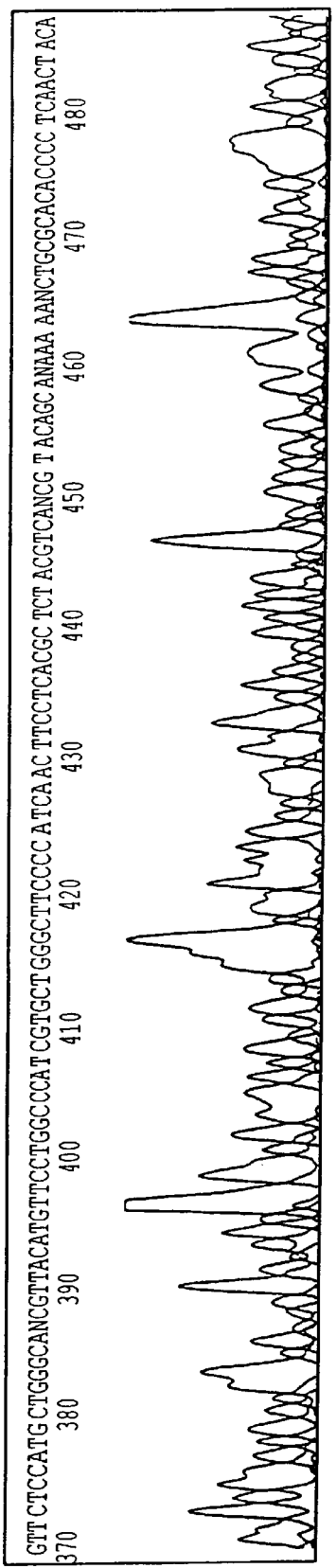
Figure 22E:
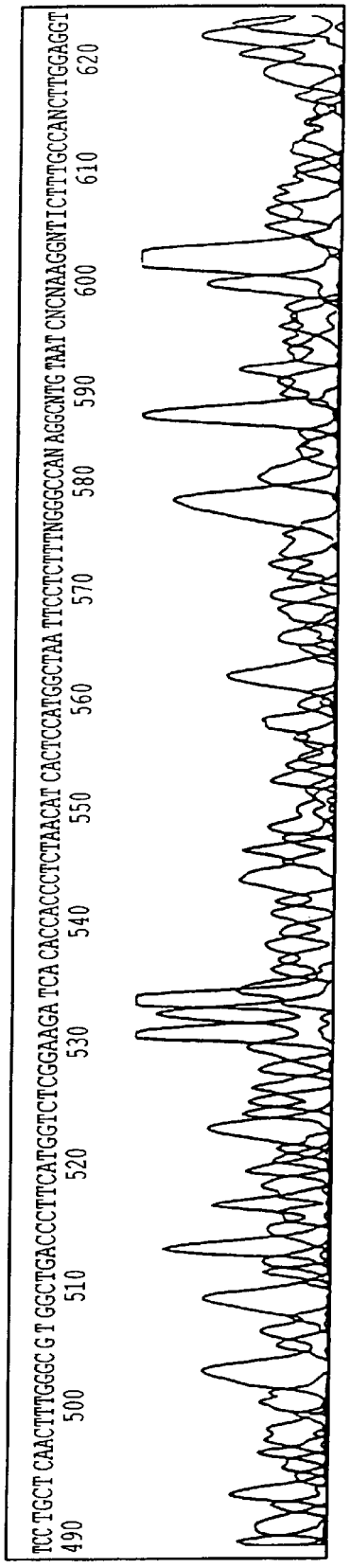
Figure 23A:
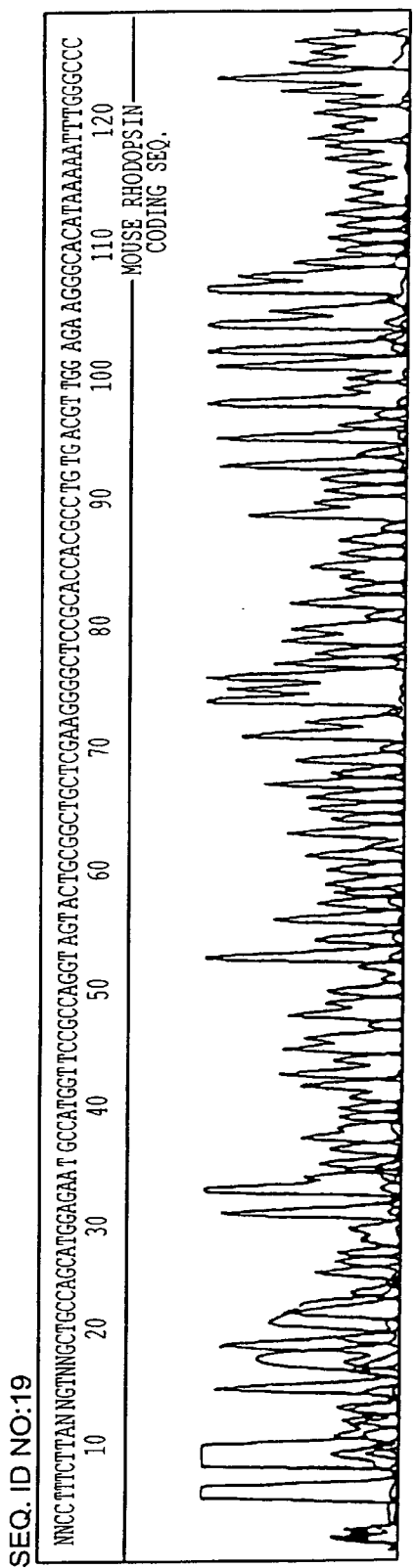
Figure 23B:
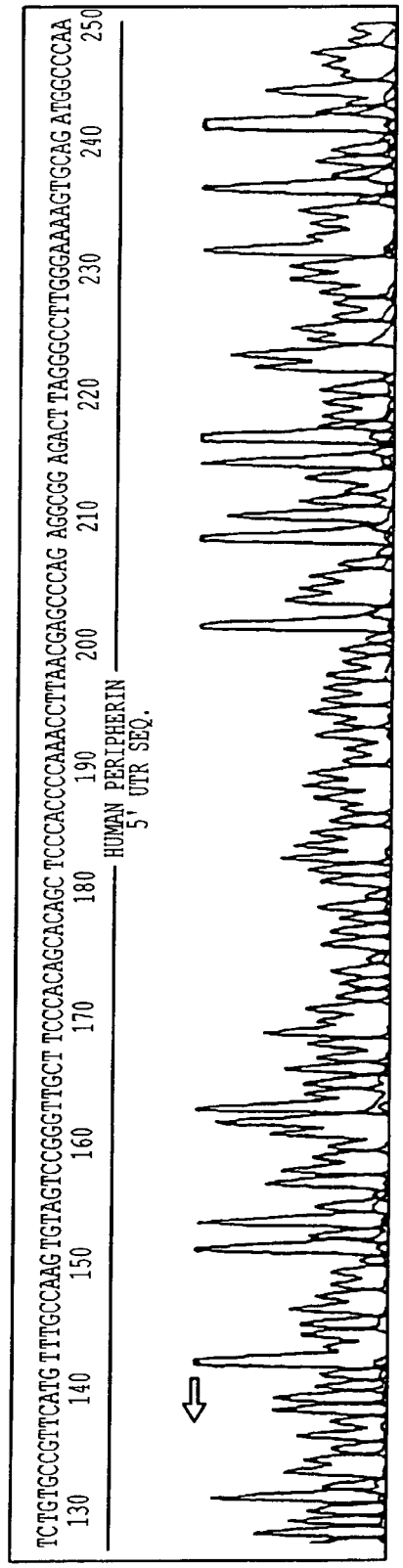
Figure 23C:
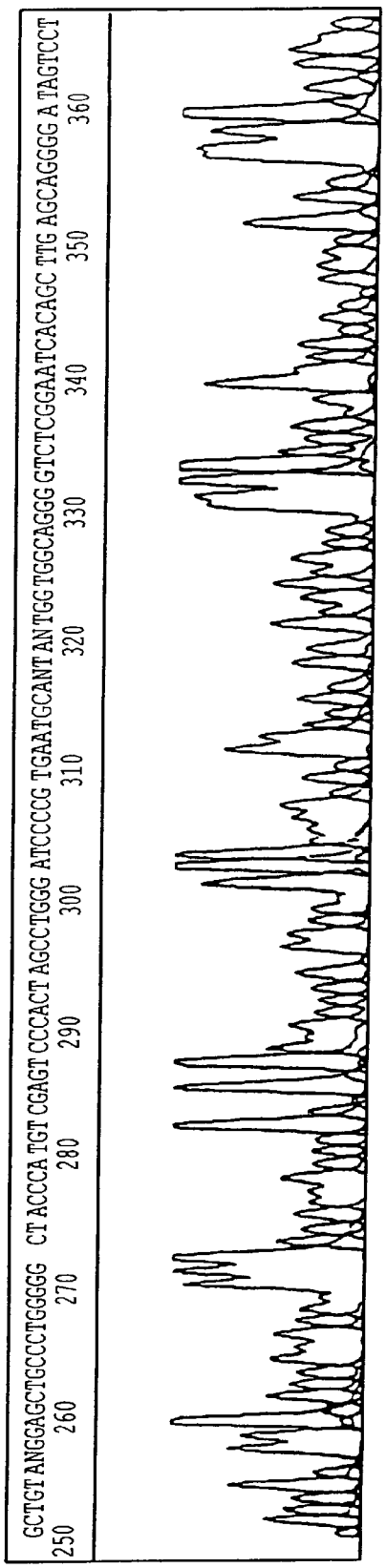
Figure 23D:
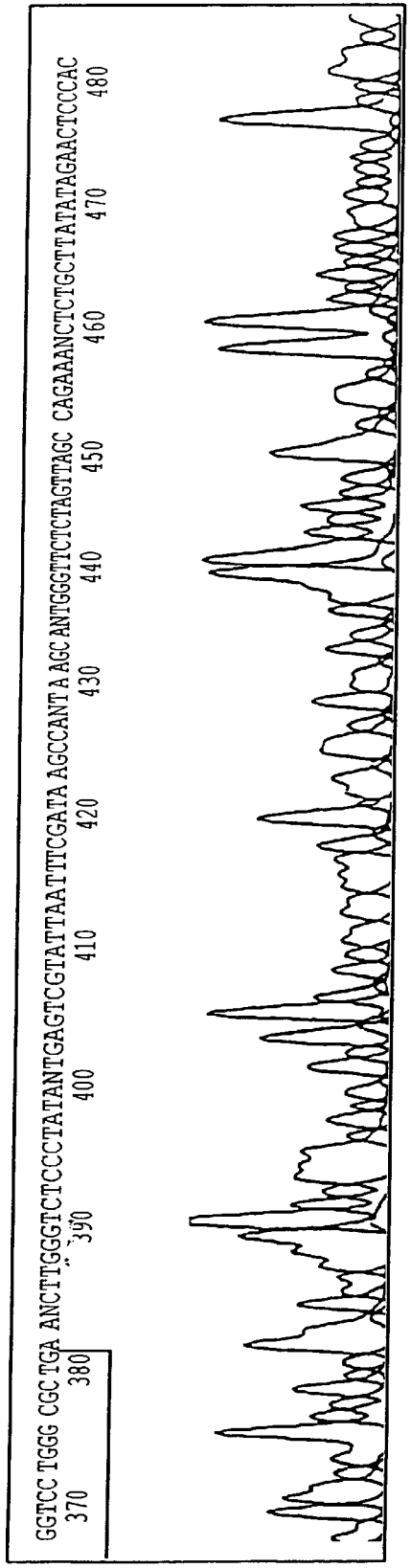
Figure 23E:
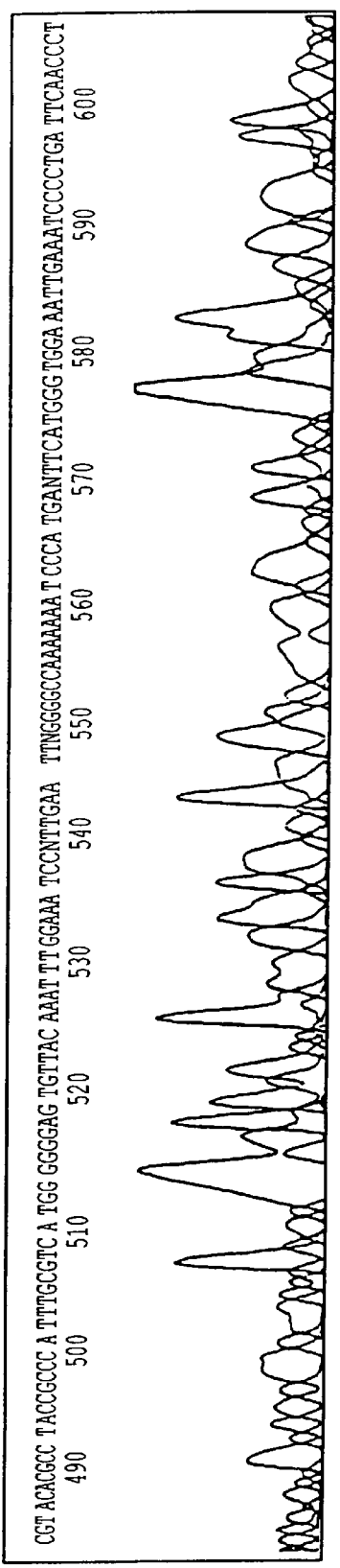
Figure 24A:
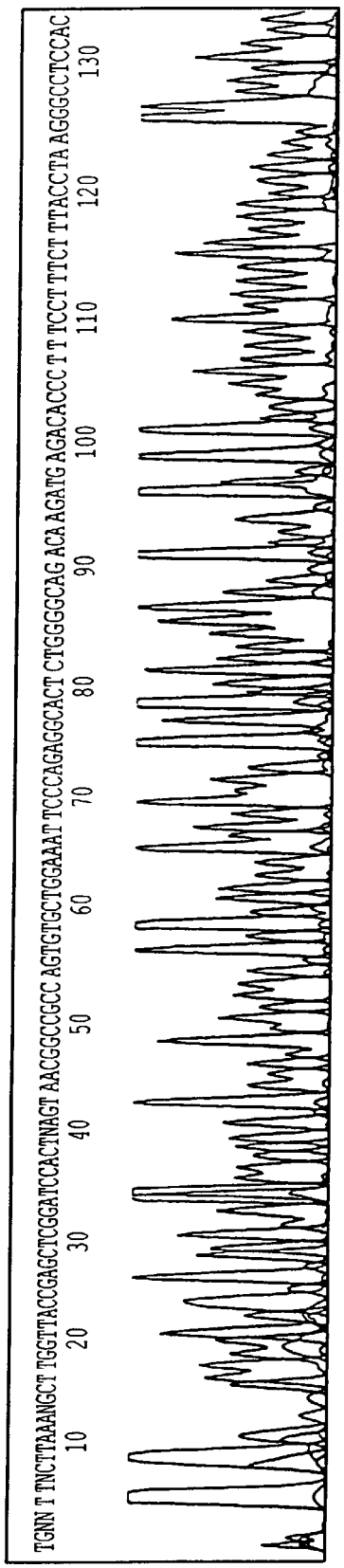
Figure 24B:
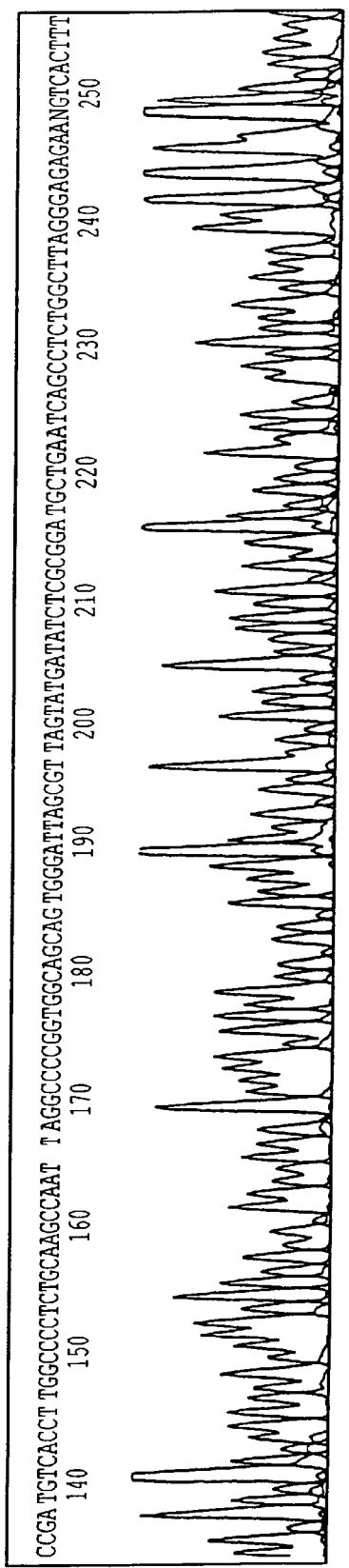
Figure 24C:
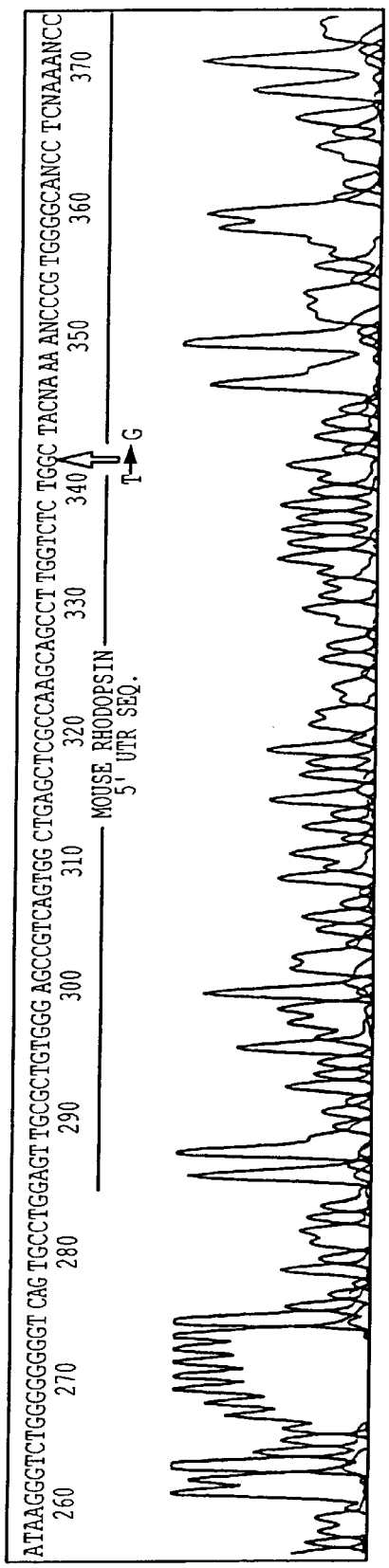
Figure 24D:
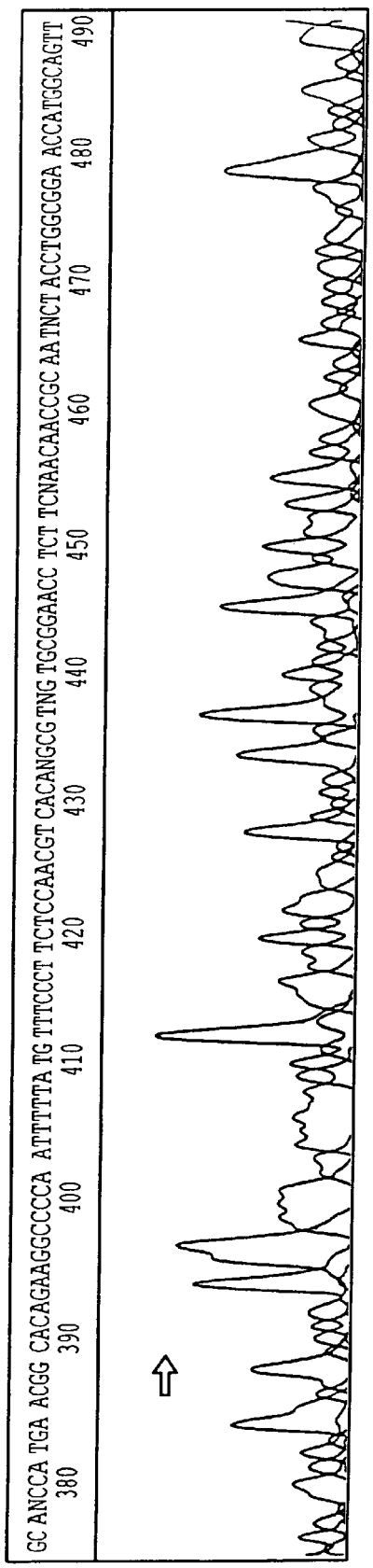
Figure 24E:
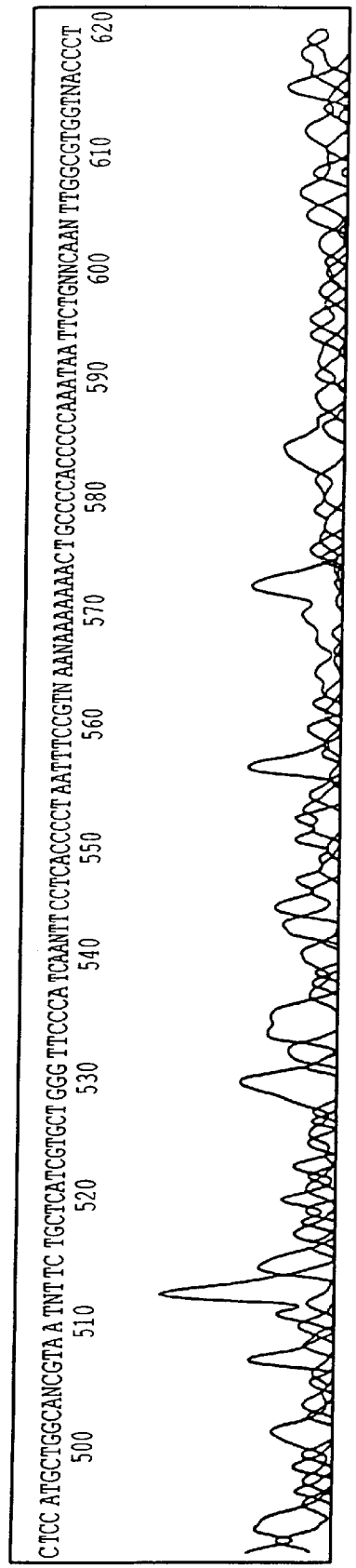
Figure 25A:
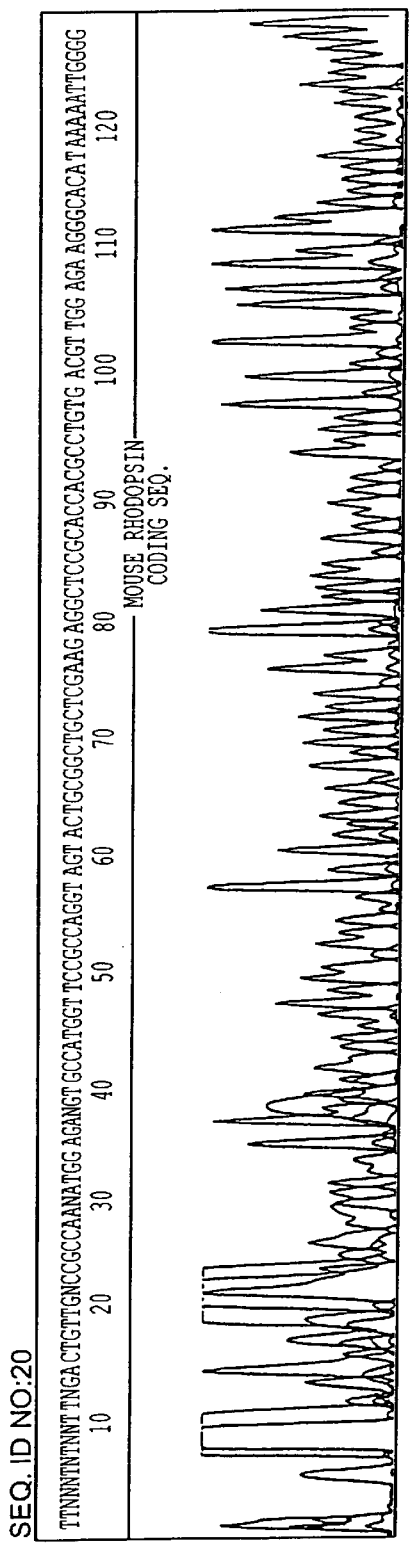
Figure 25B:
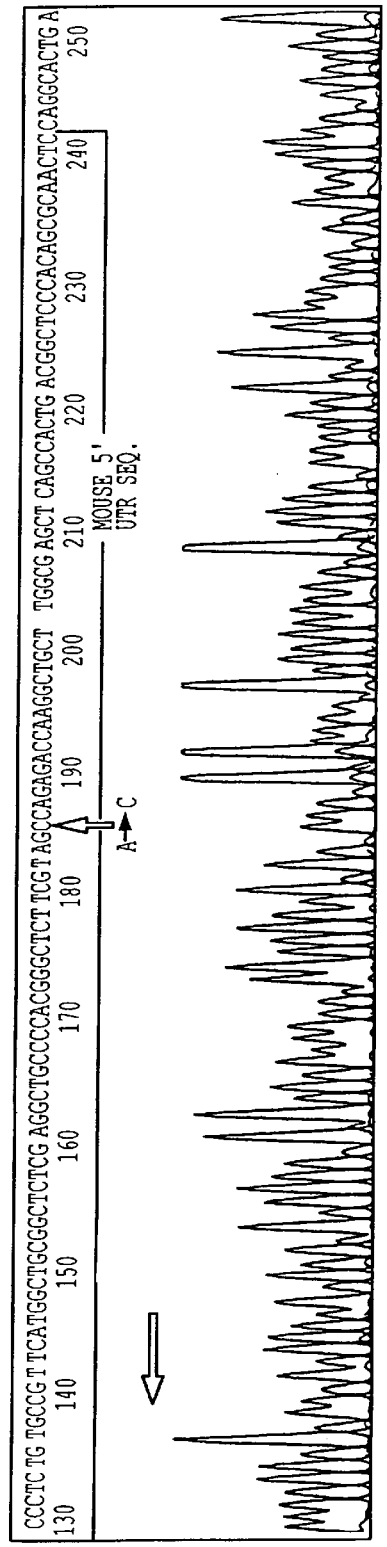
Figure 25C:
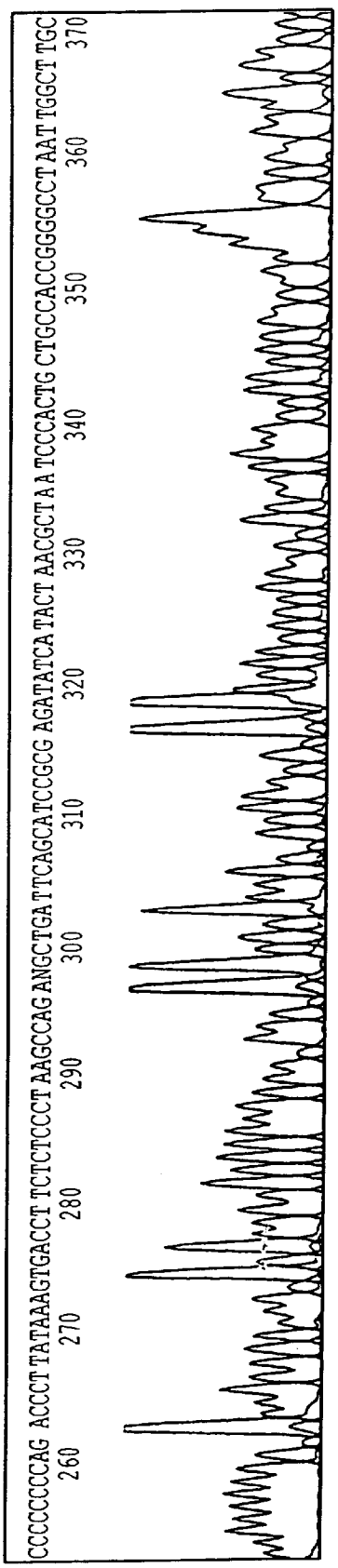
Figure 25D:
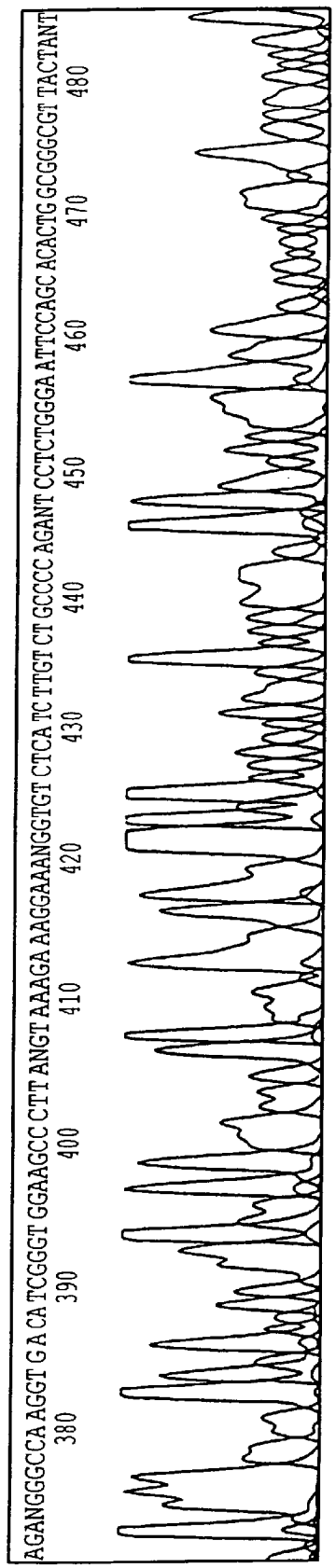
Figure 25E:
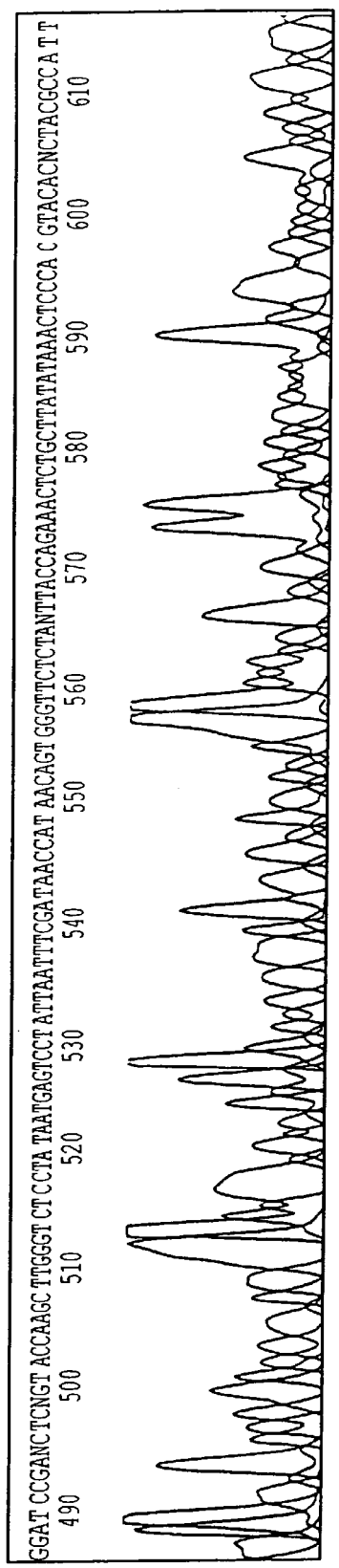
Figure 26A:
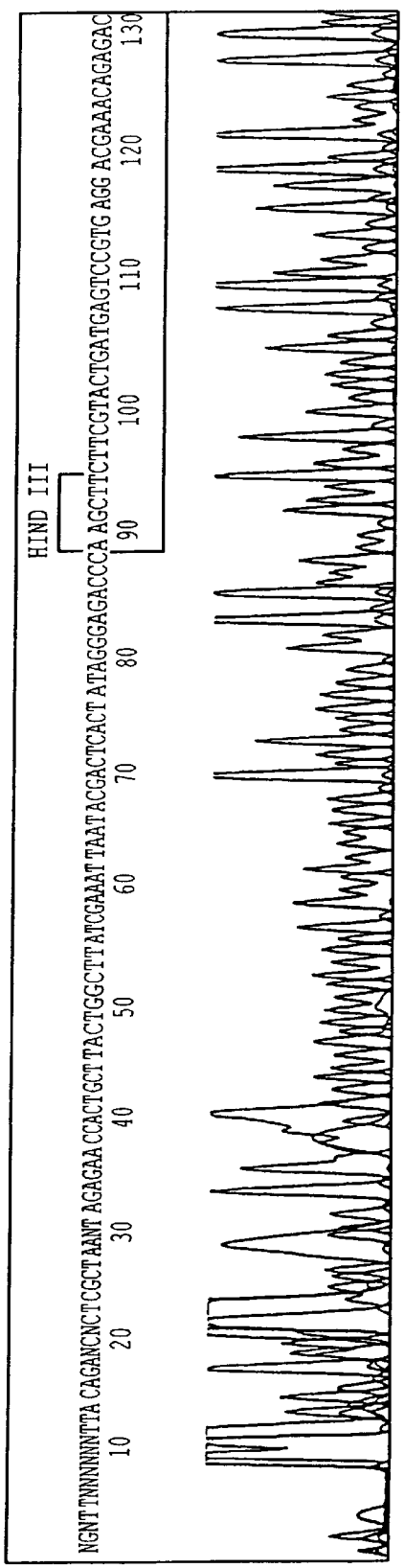
Figure 26B:
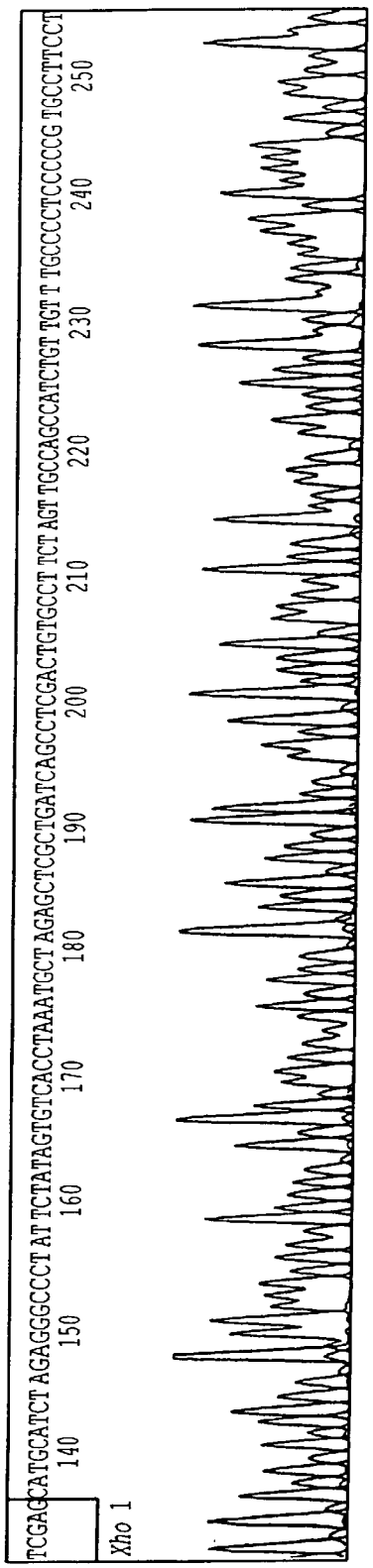
Figure 26C:
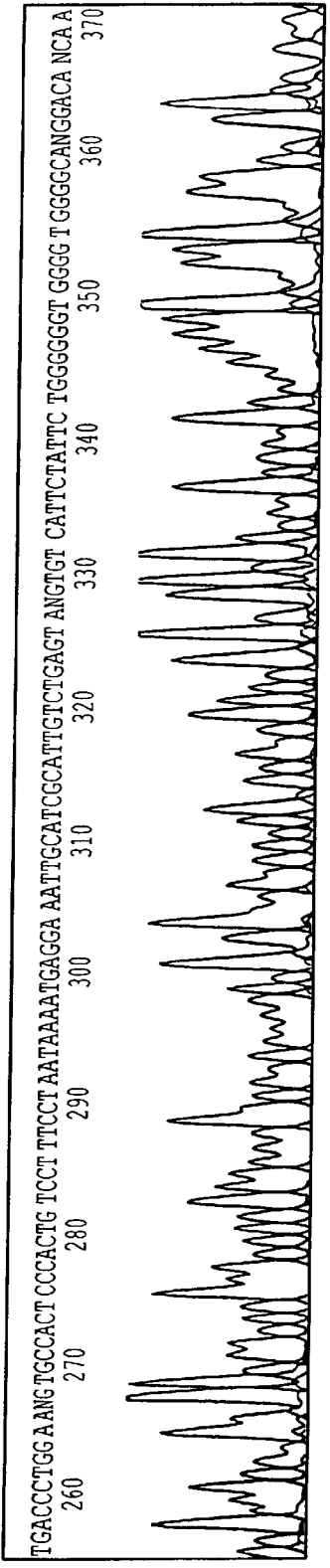
Figure 26D:
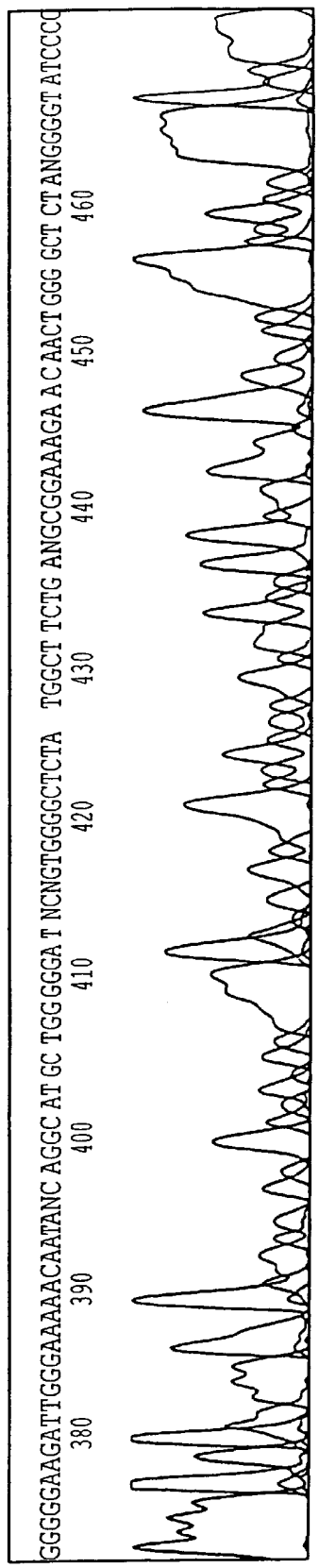
Figure 26E:
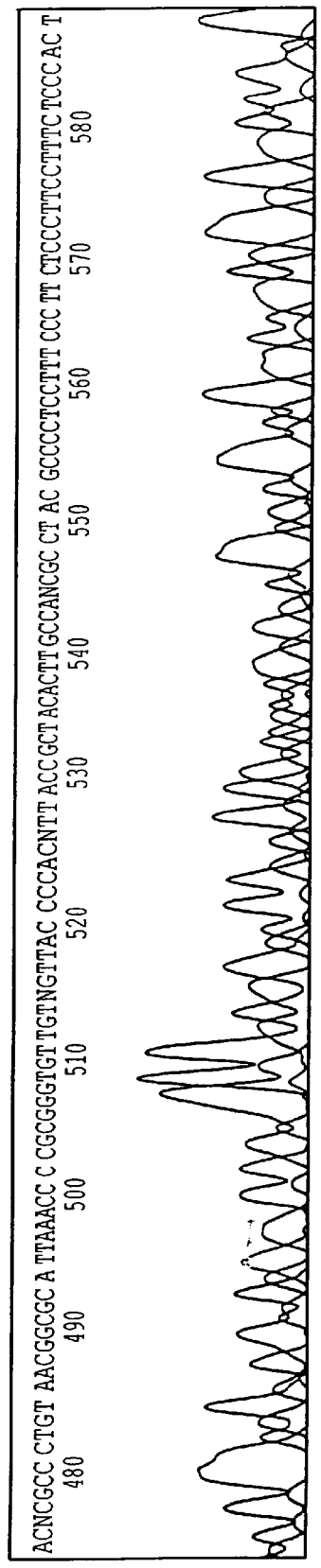
Figure 27A:
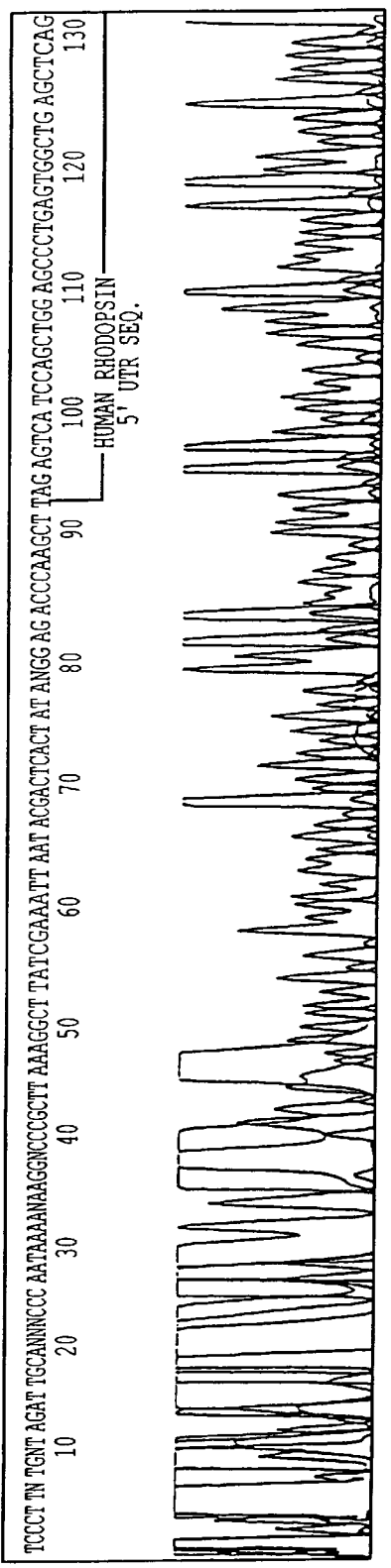
Figure 27B:
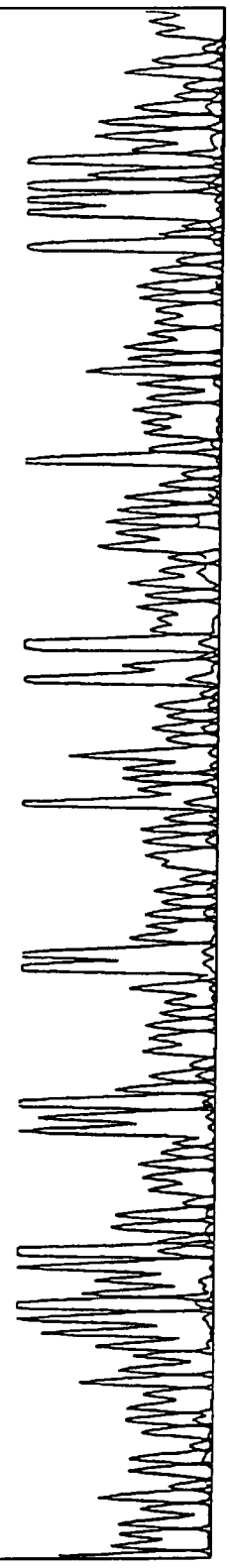
Figure 27C:
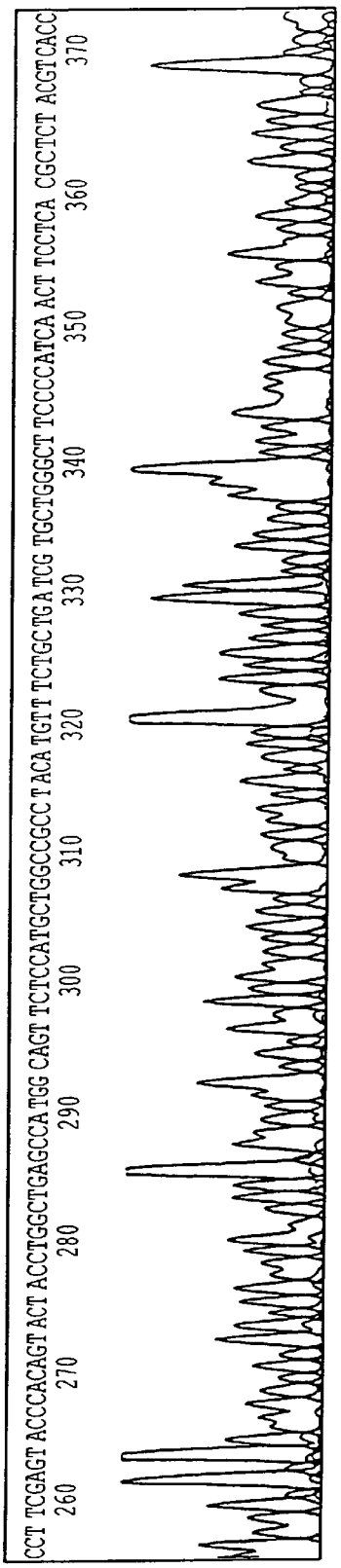
Figure 27D:
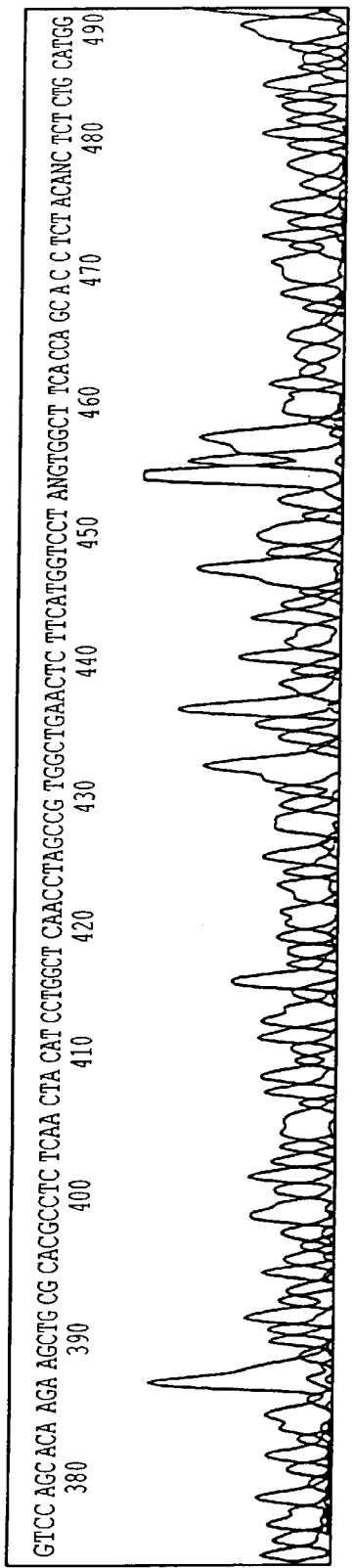
Figure 27E:
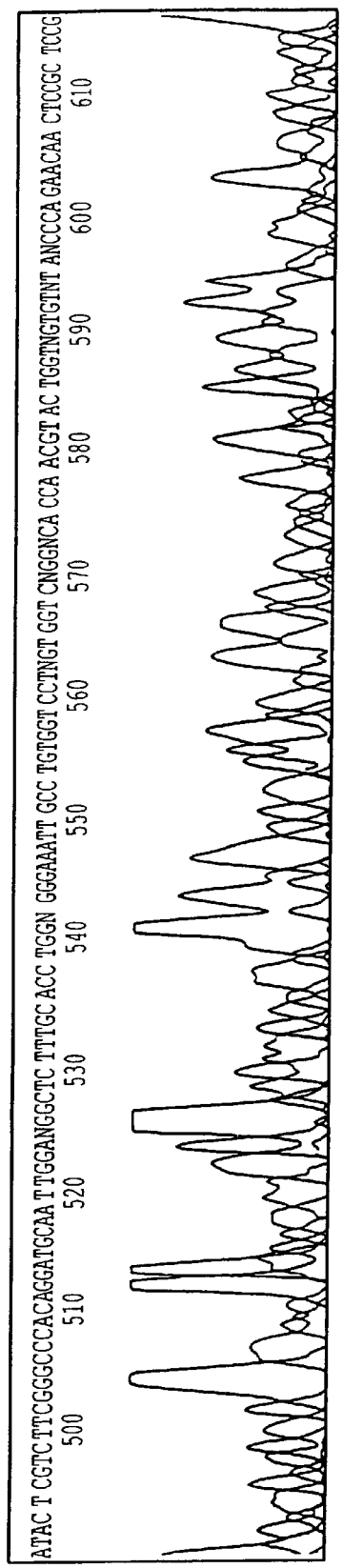
Figure 28A:
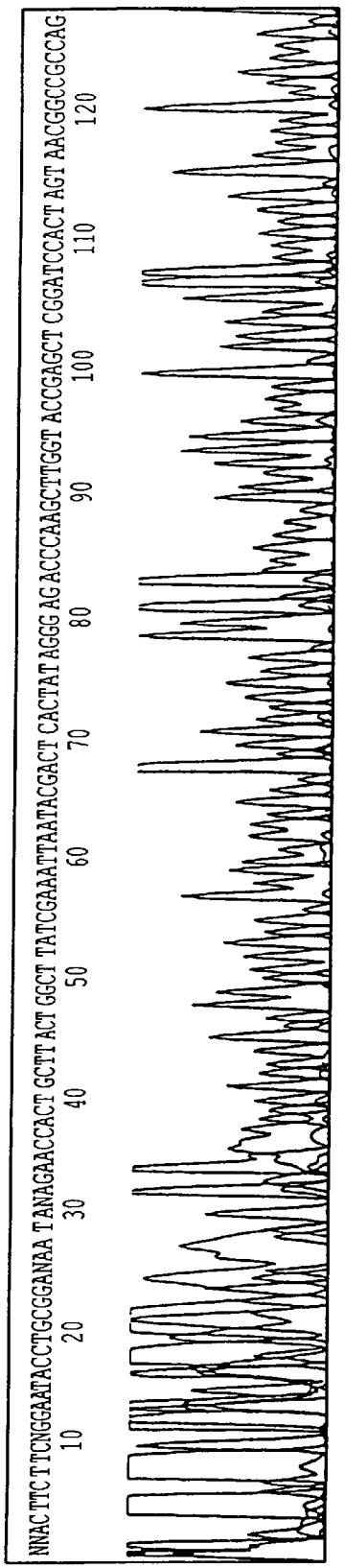
Figure 28B:
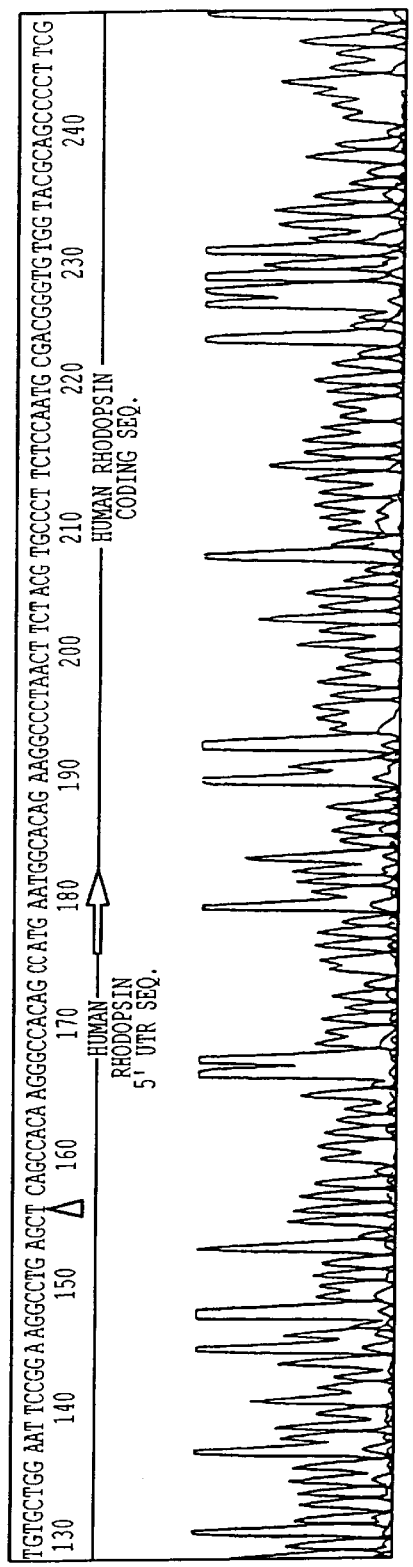
Figure 28C:
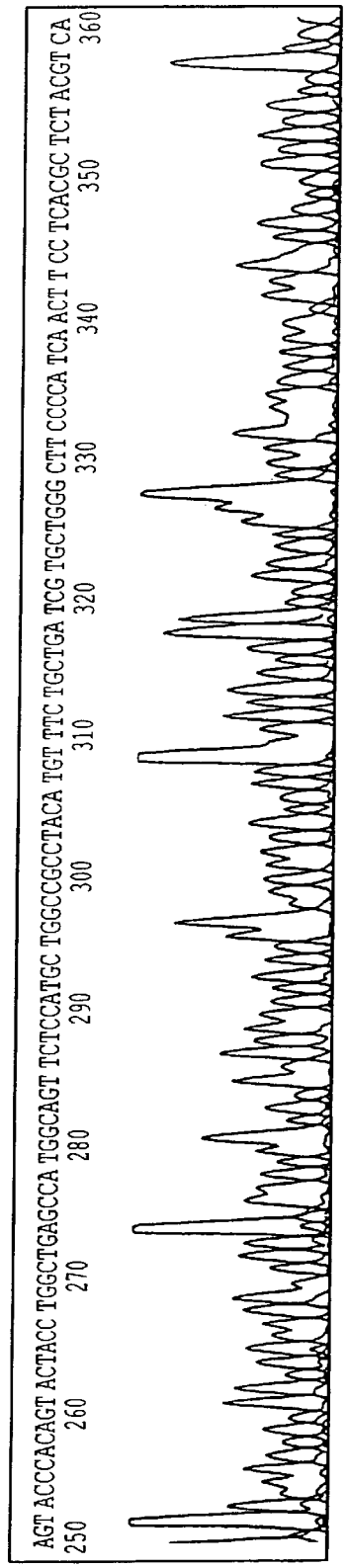
Figure 28D:
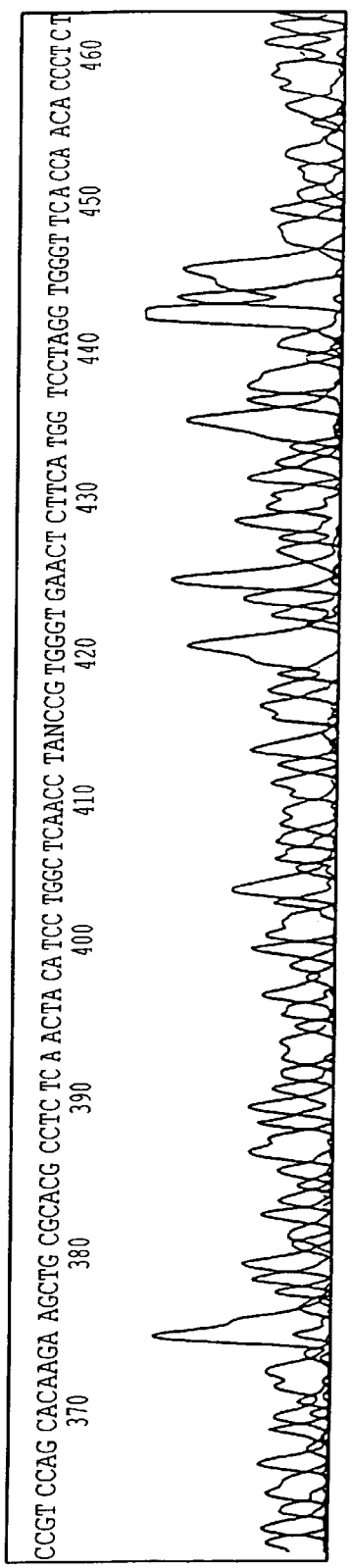
Figure 28E:
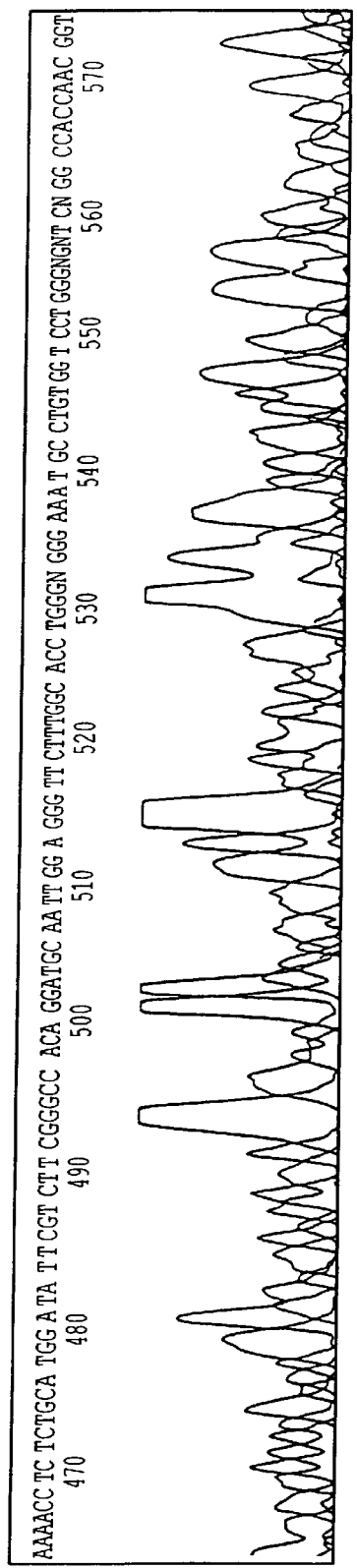
Figure 29A:
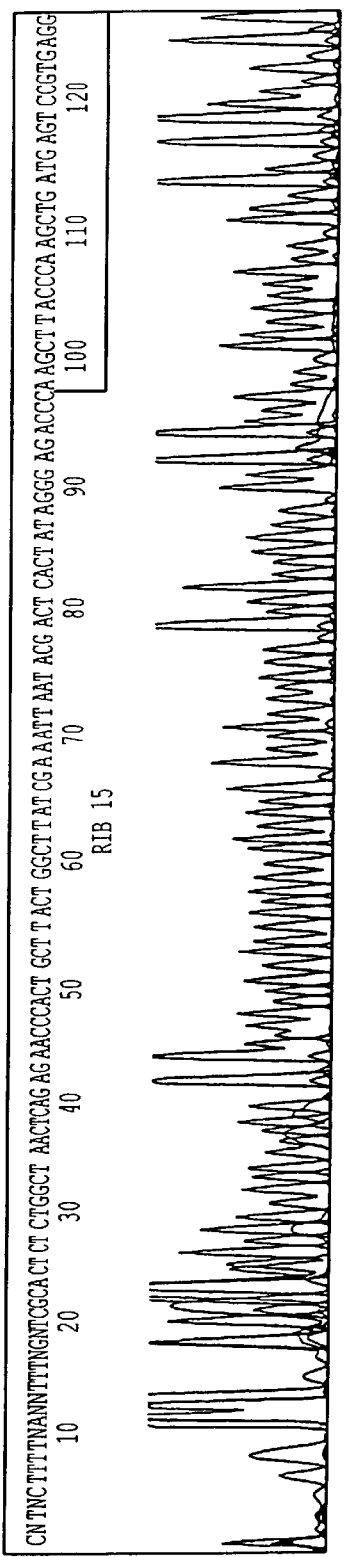
Figure 29B:
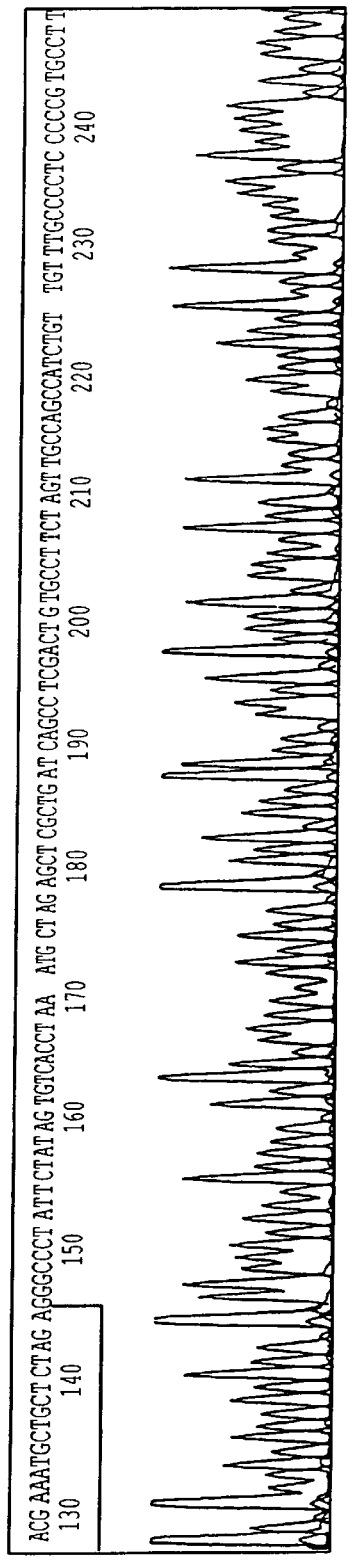
Figure 29C:
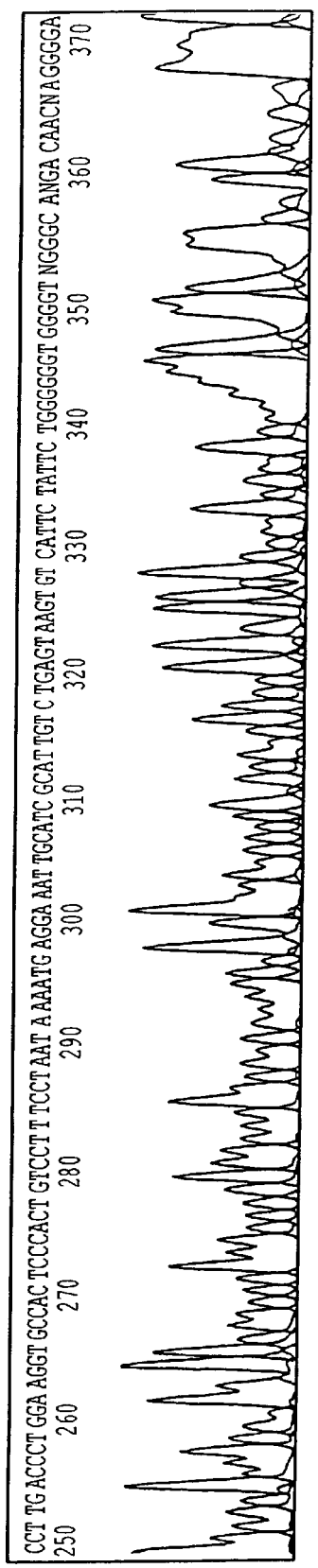
Figure 29D:
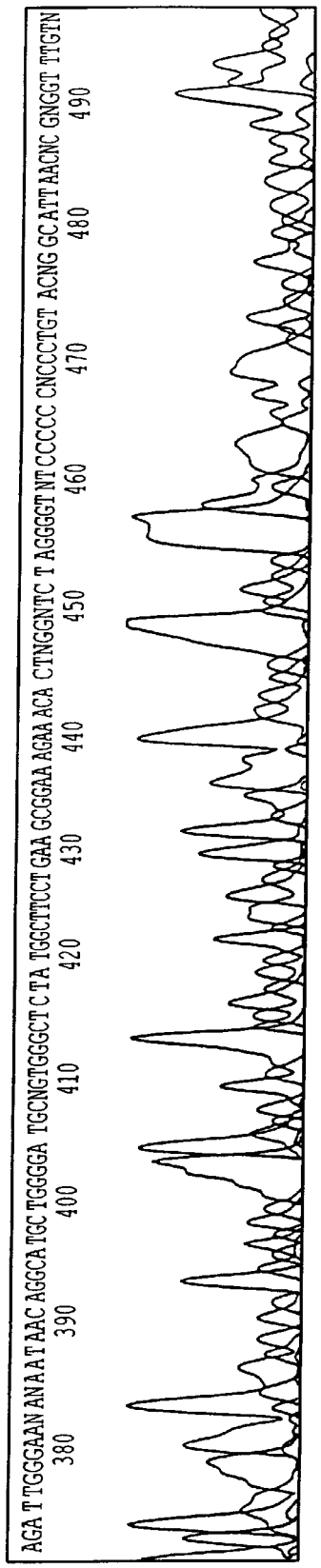
Figure 29E:
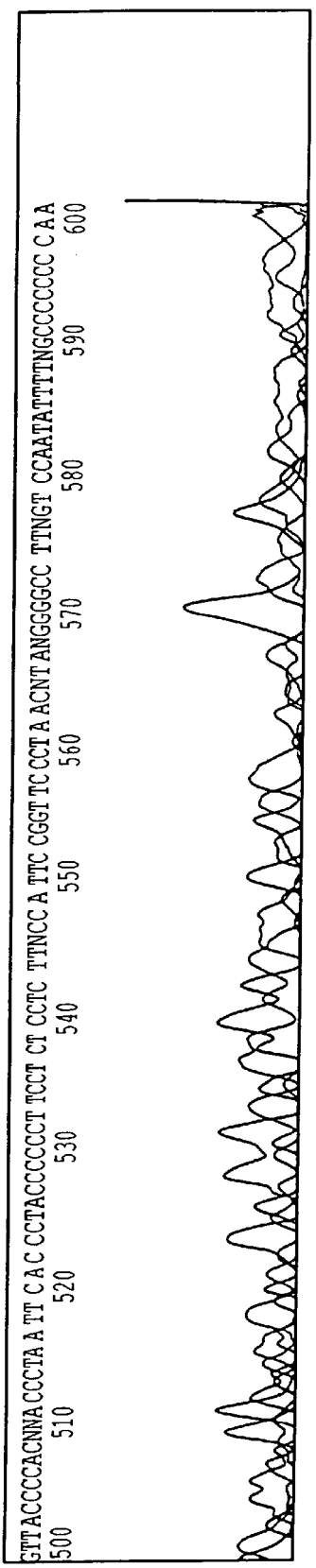
Figure 30A:
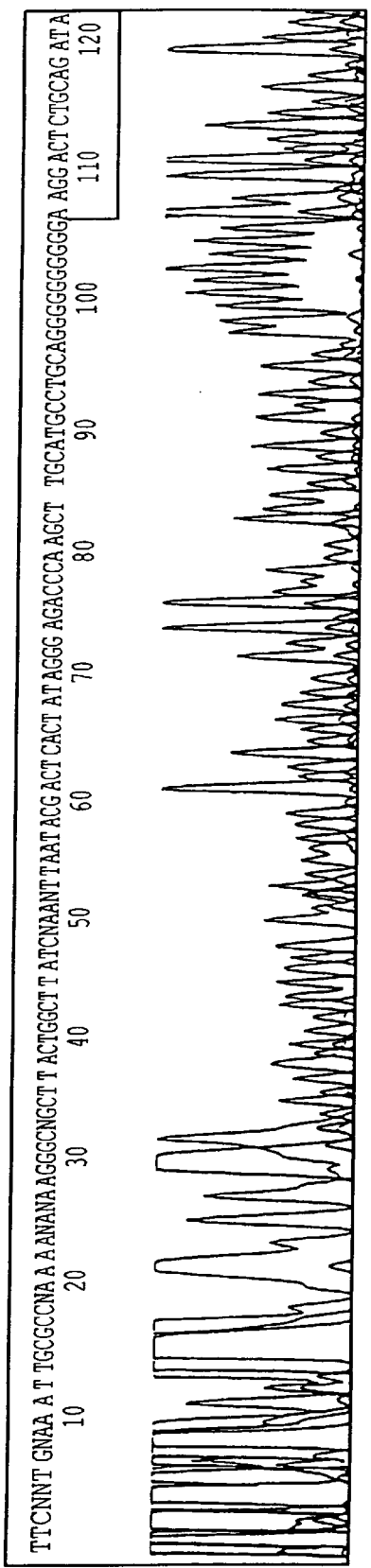
Figure 30B:
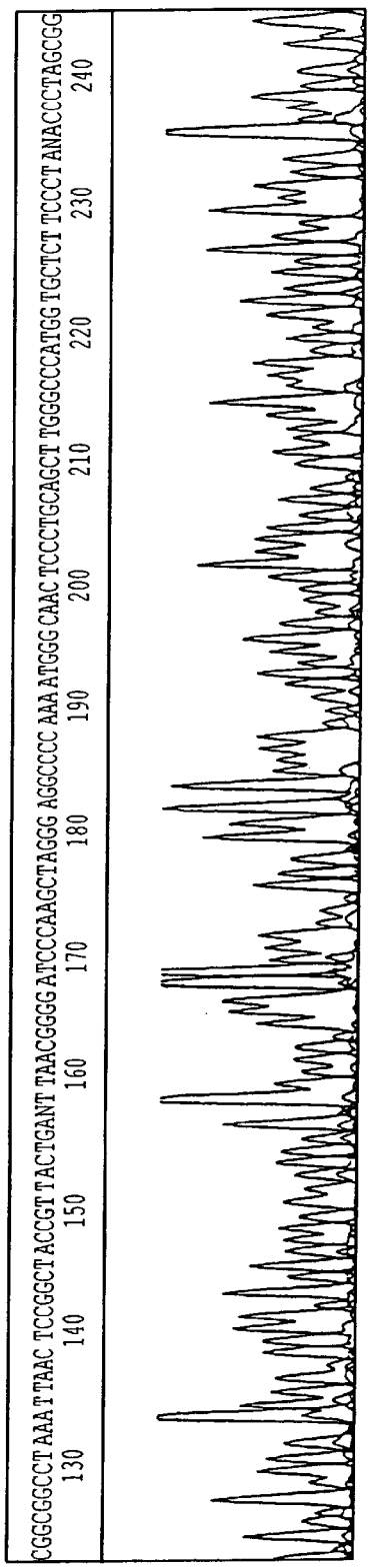
Figure 30C:
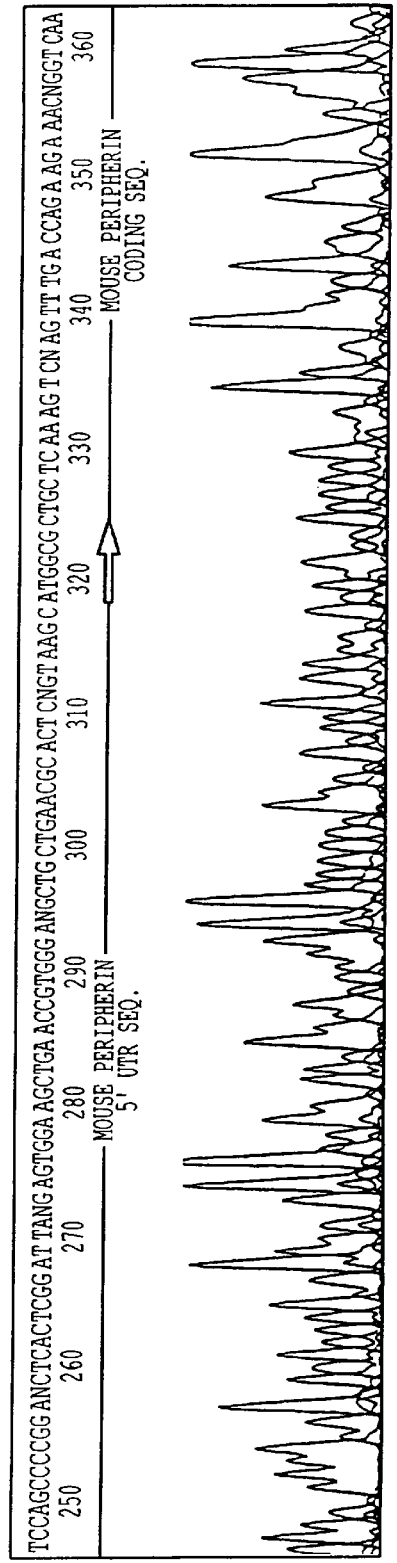
Figure 30D:
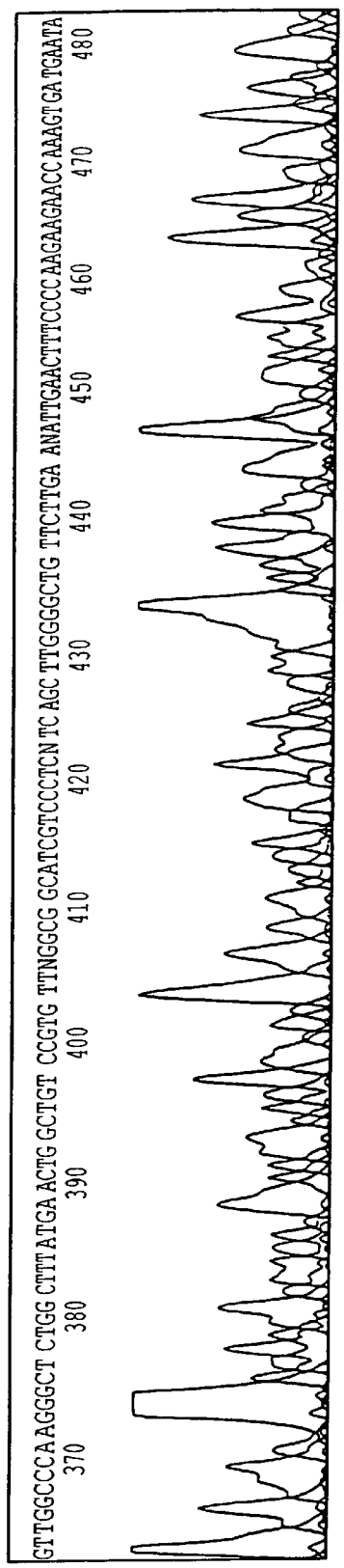
Figure 30E:
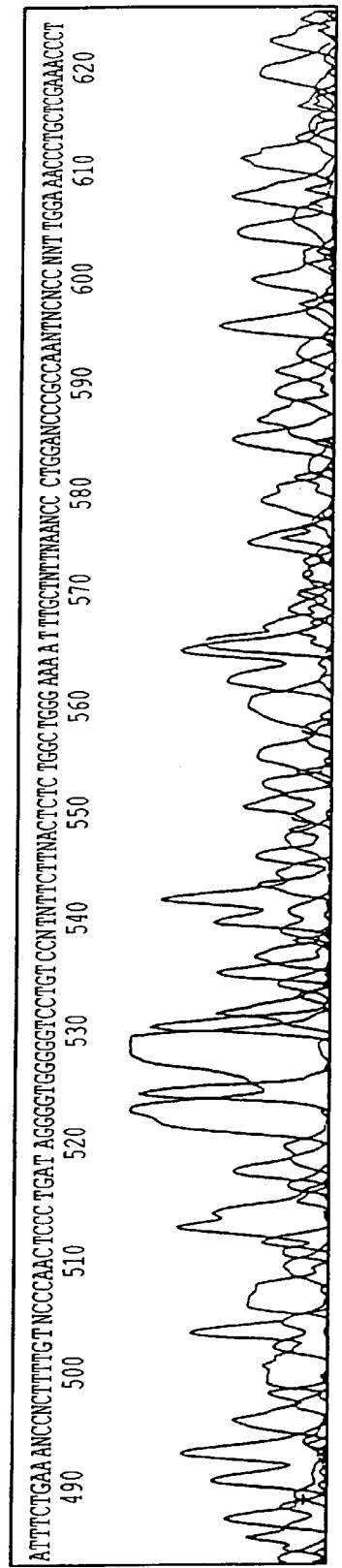
Figure 31A:
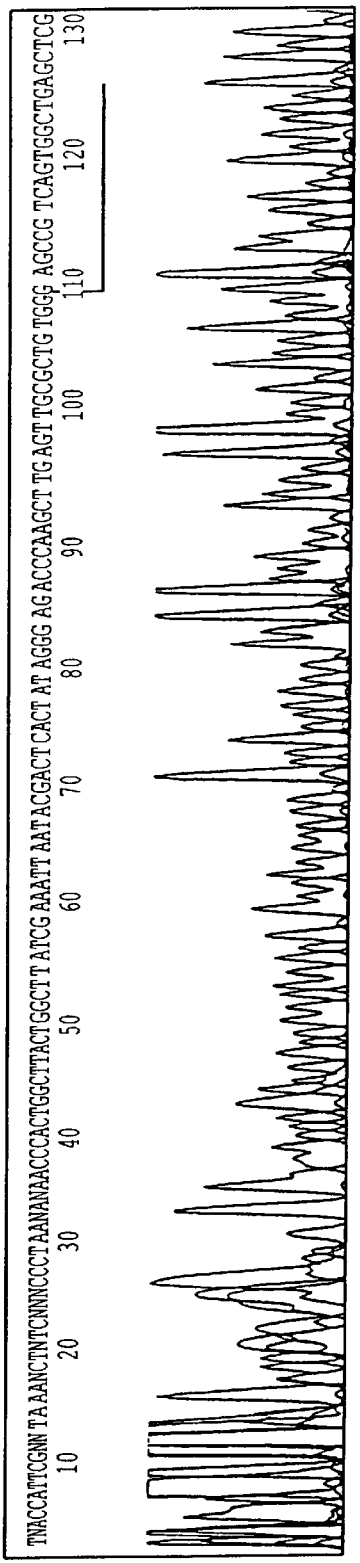
Figure 31B:
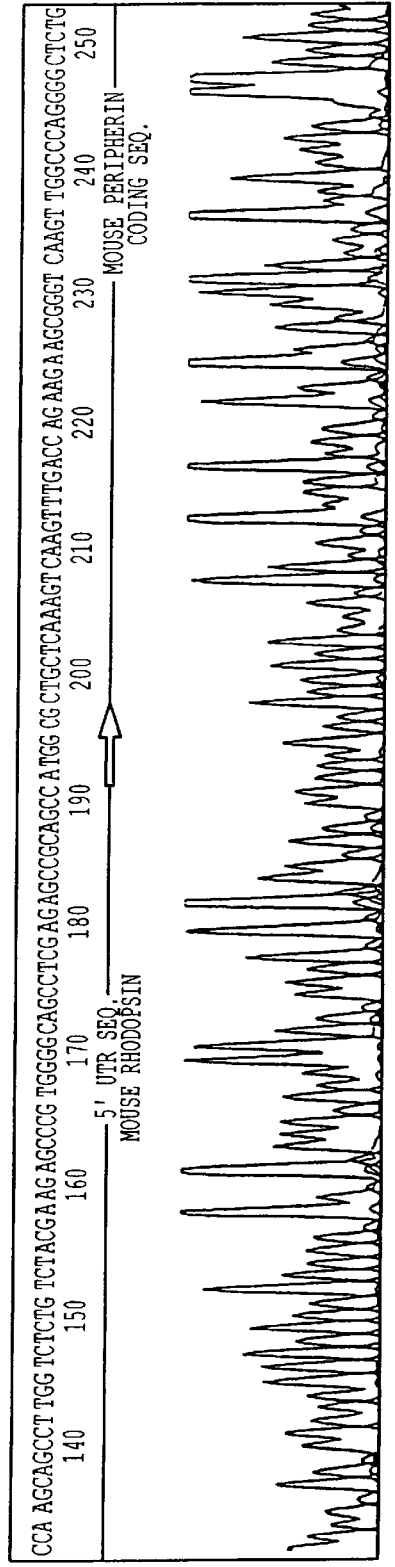
Figure 31C:
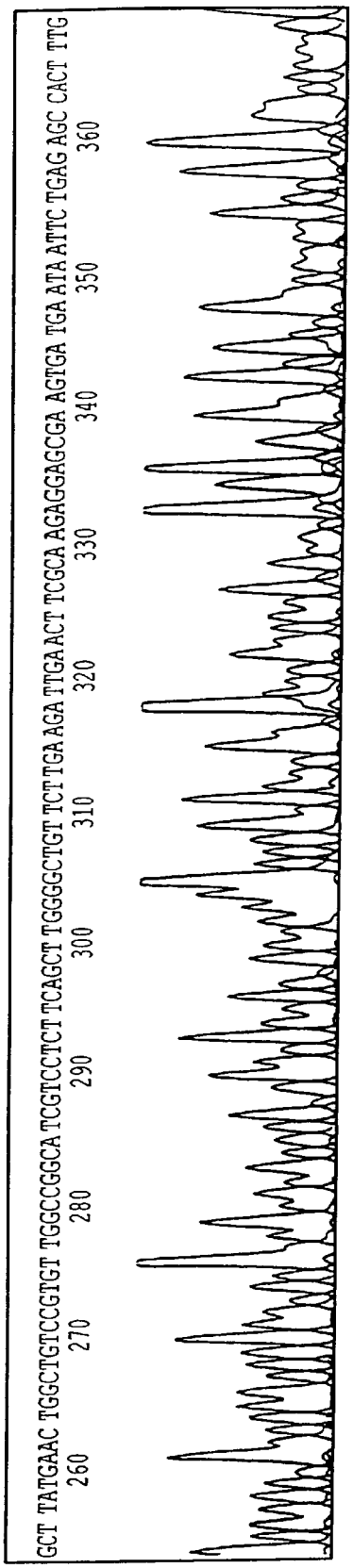
Figure 31D:
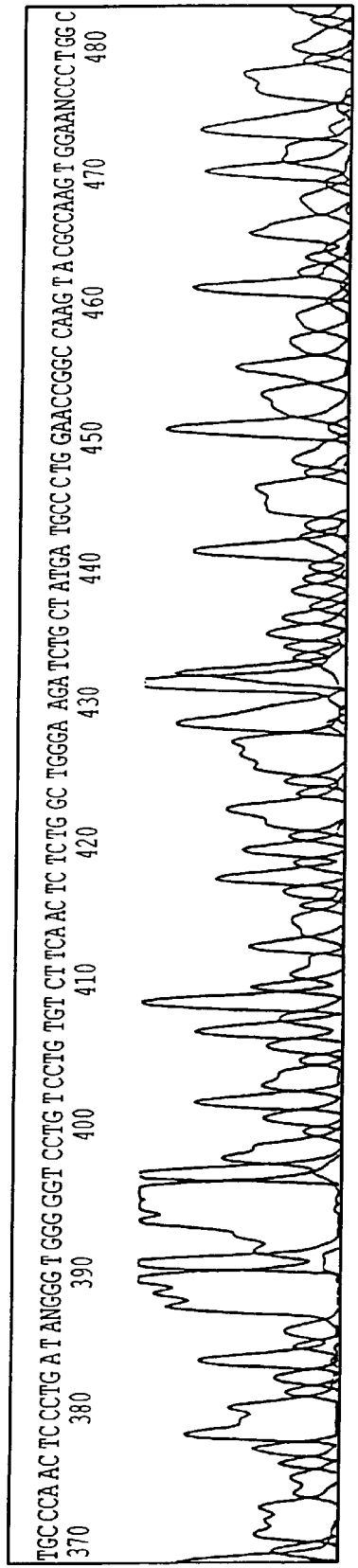
Figure 31E:
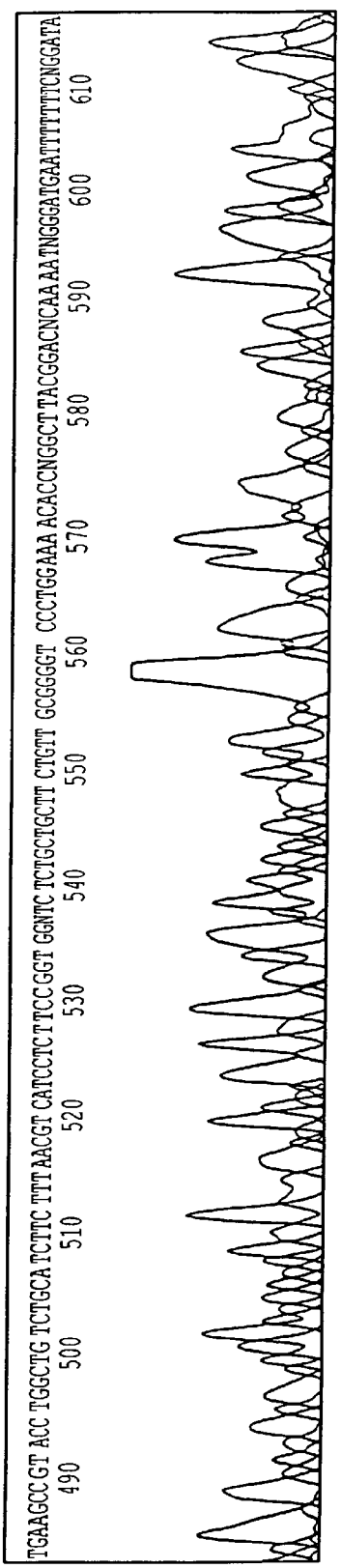
Figure 32A:
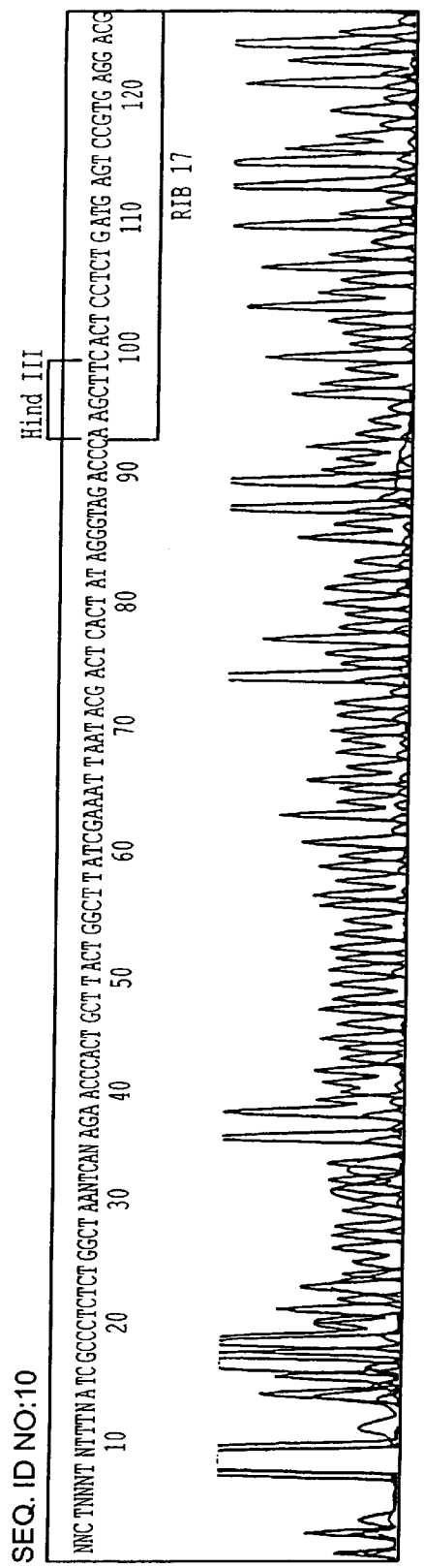
Figure 32B:
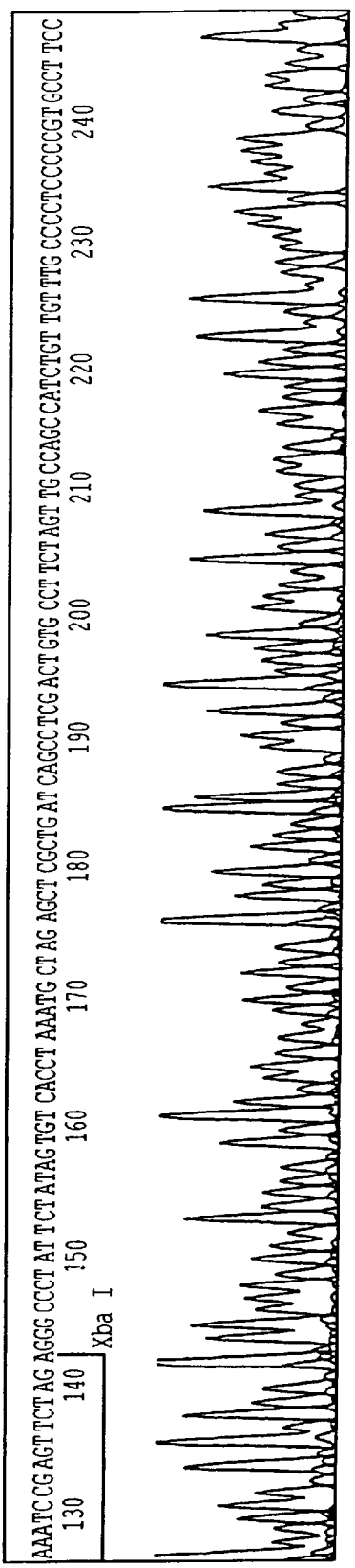
Figure 32C:
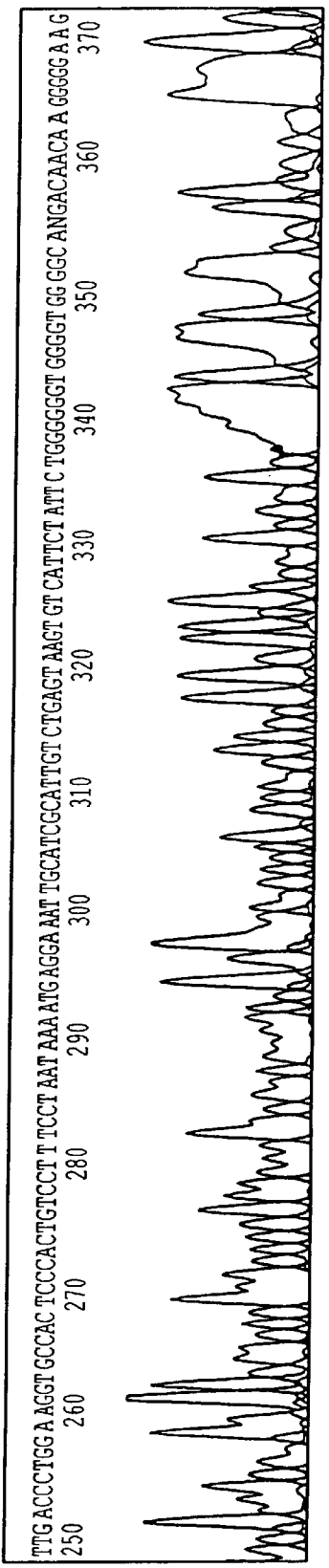
Figure 32D:
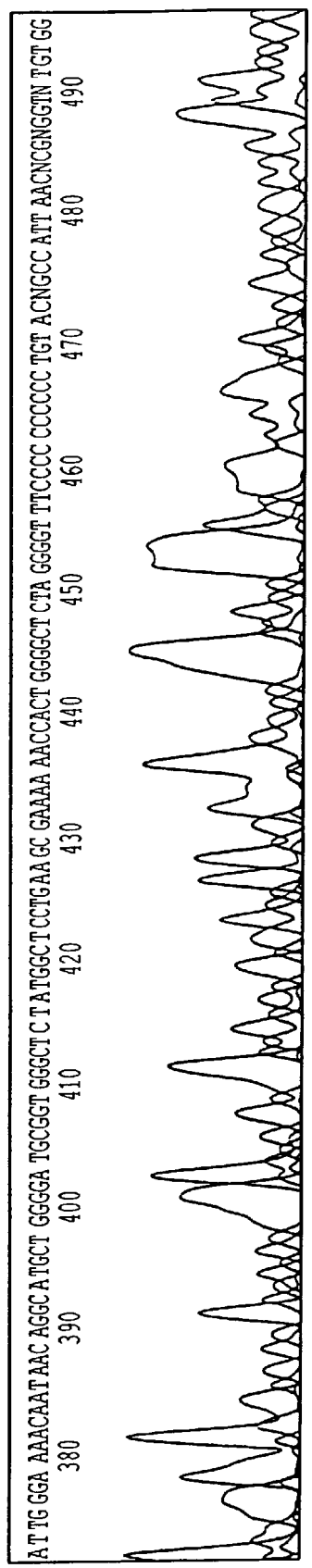
Figure 32E:
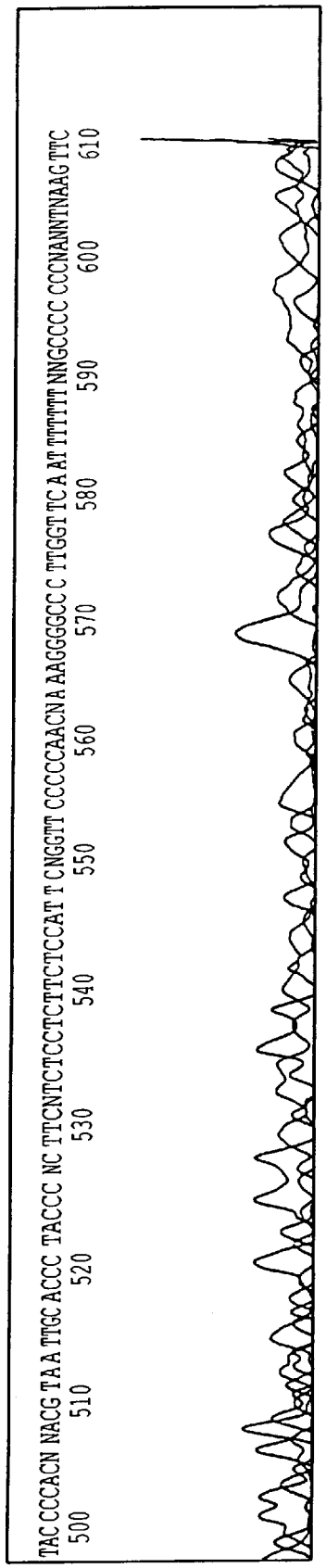
Figure 33A:
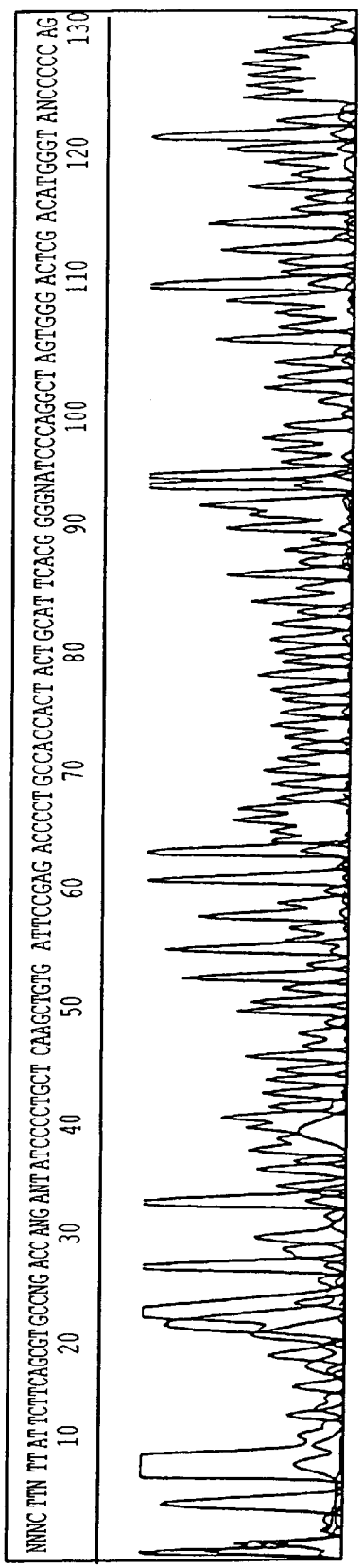
Figure 33B:
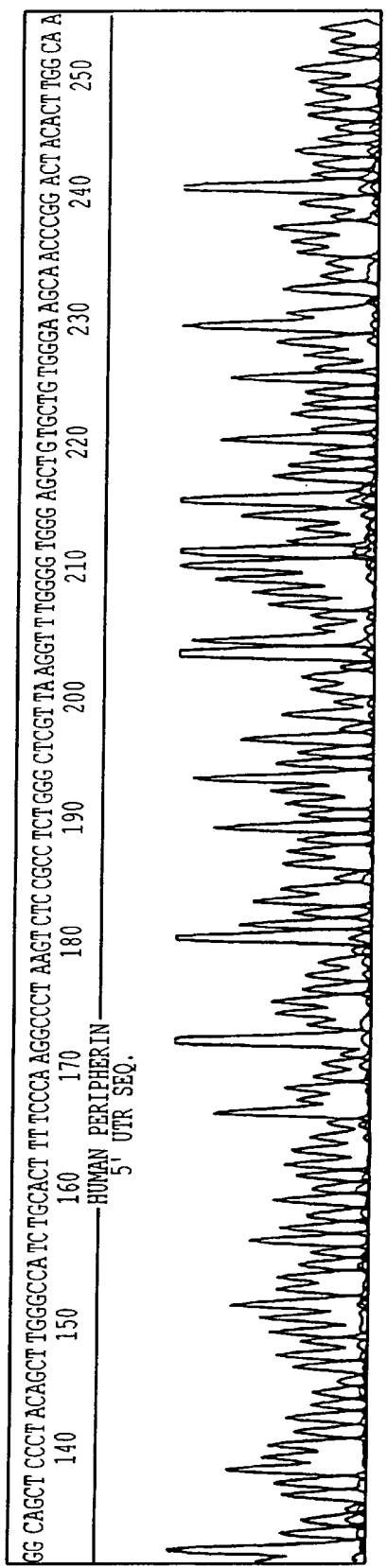
Figure 33C:
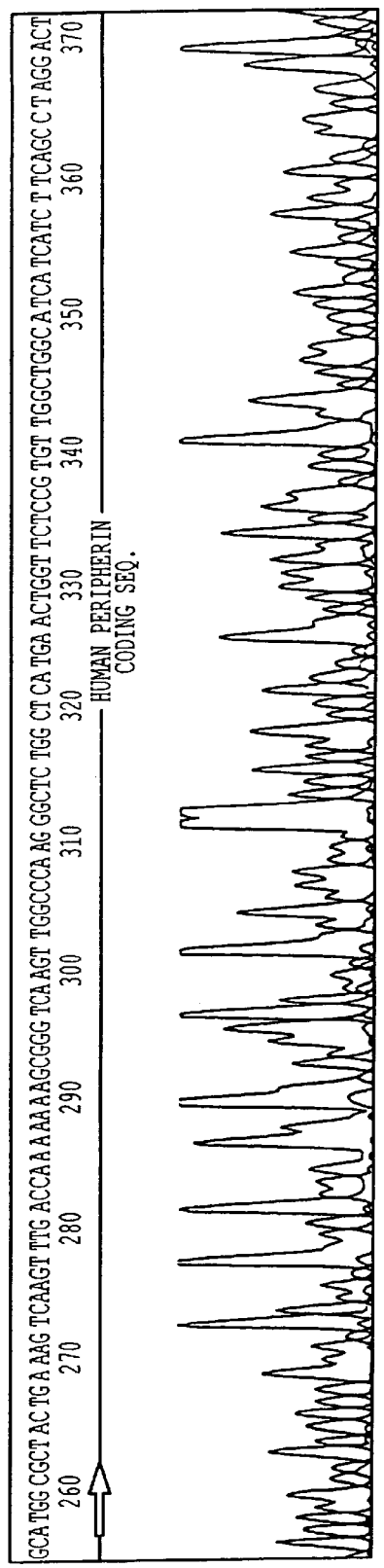
Figure 33D:
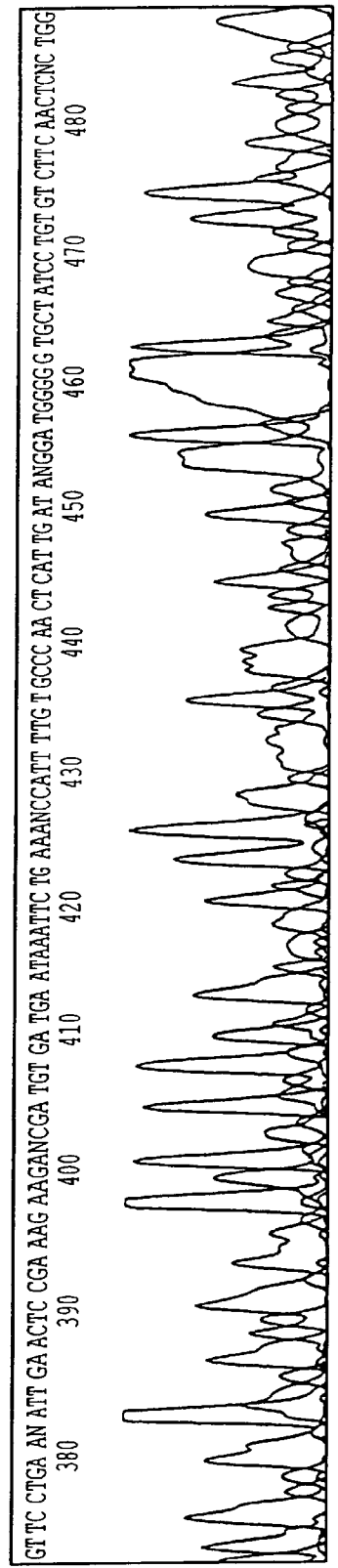
Figure 33E:
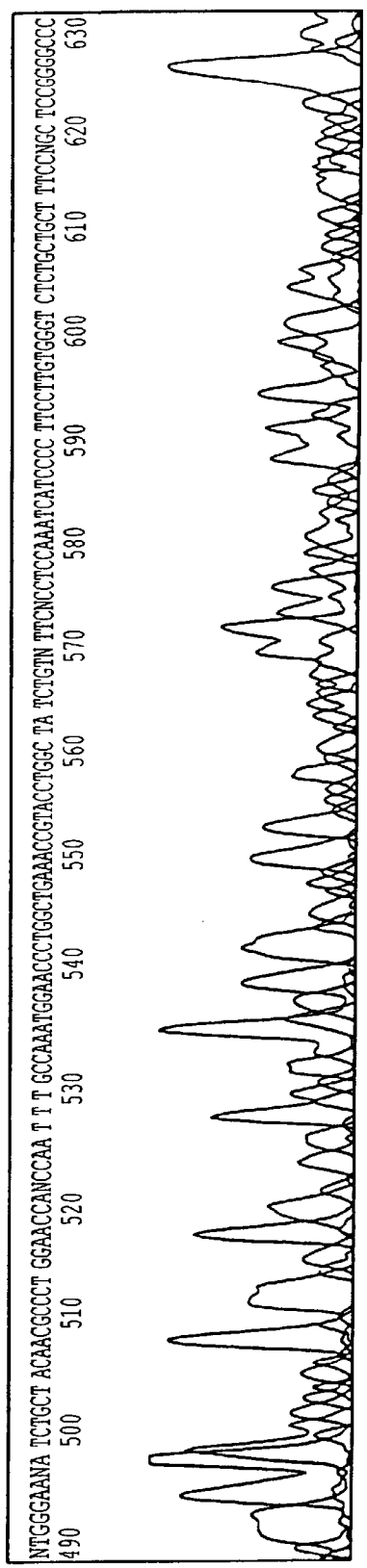
Figure 34A:
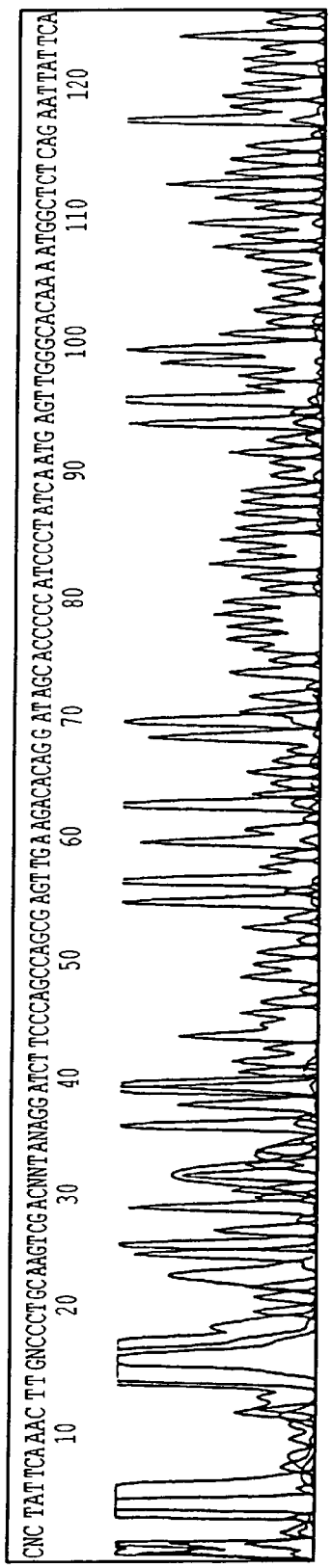
Figure 34B:
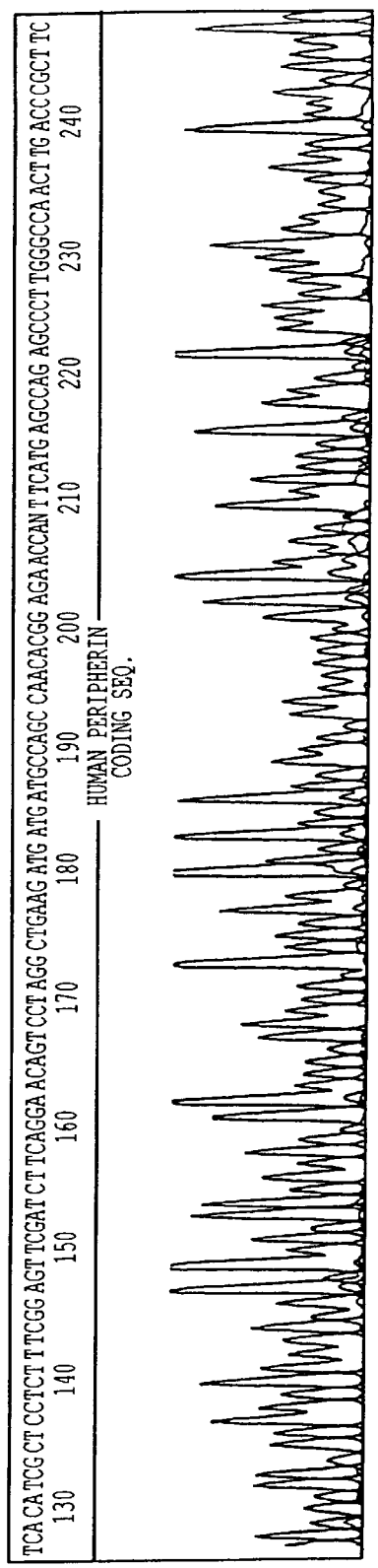
Figure 34C:
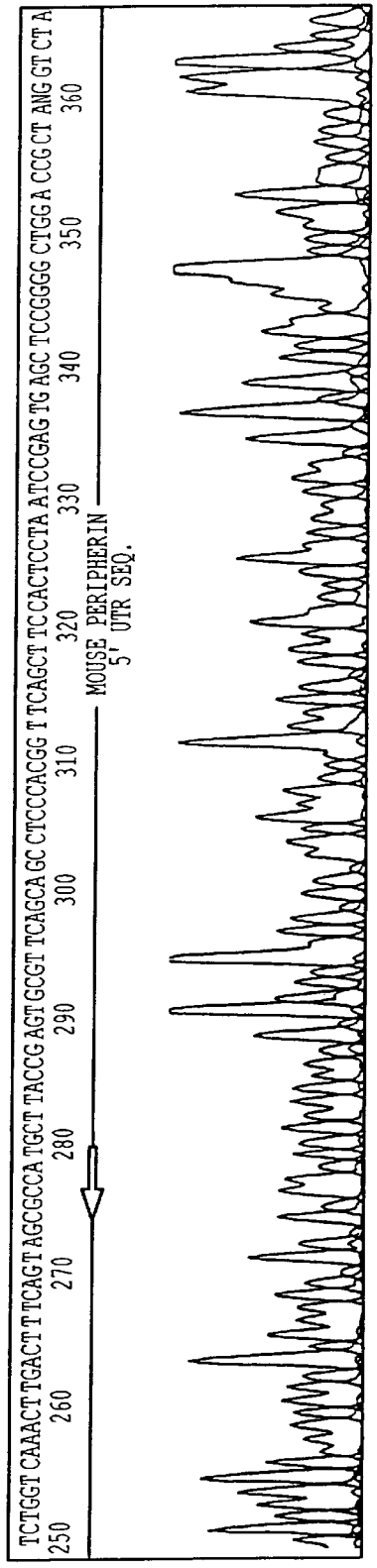
Figure 34D:
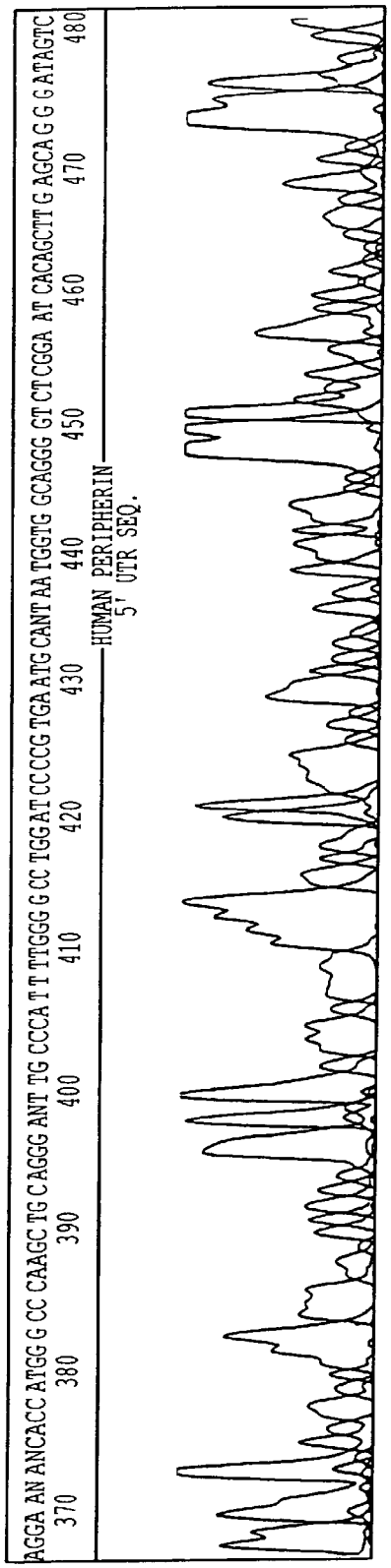
Figure 34E:
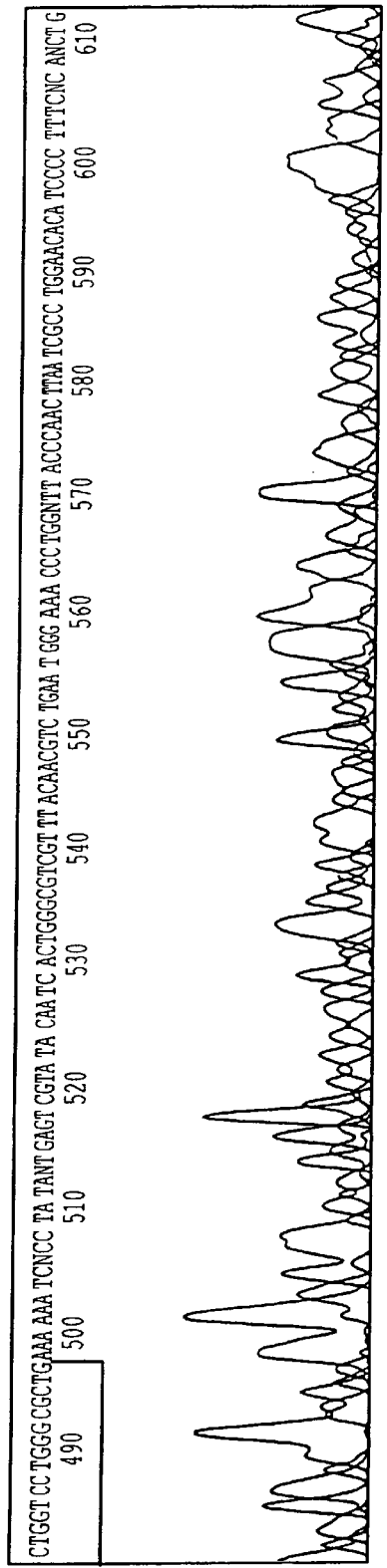
Figure 35A:
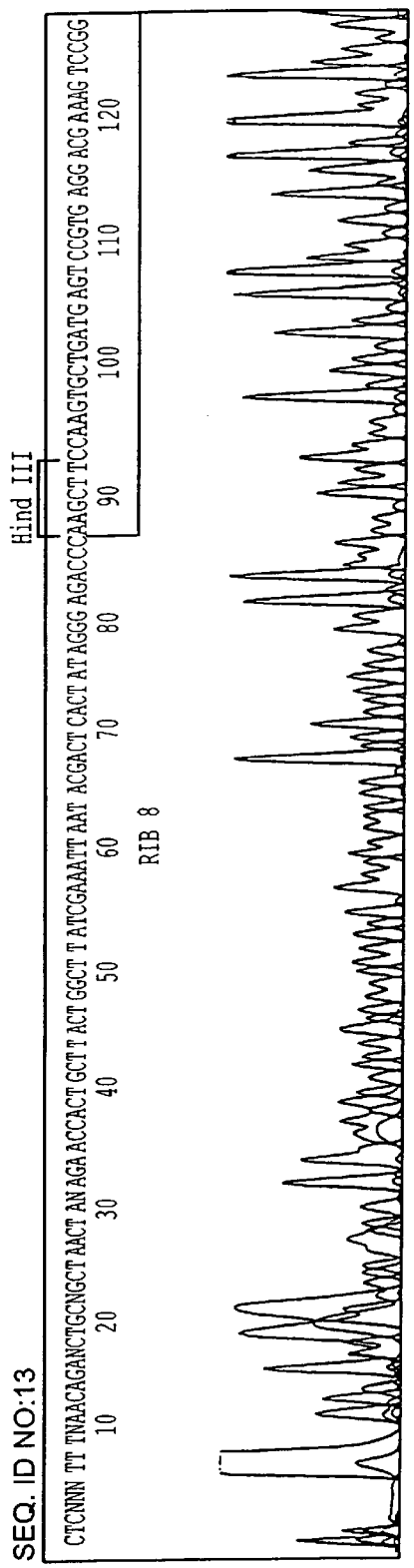
Figure 35B:
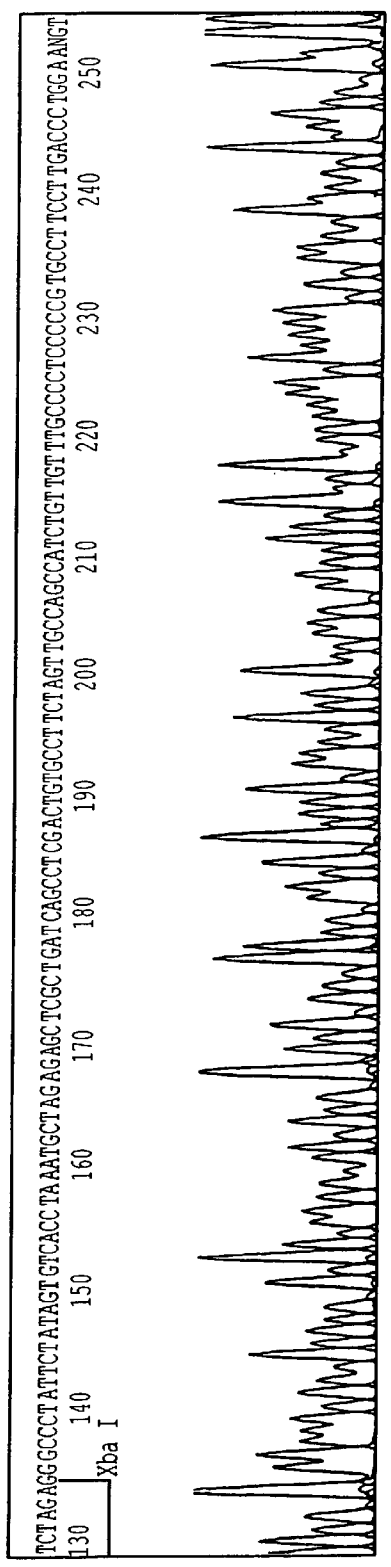
Figure 35C:
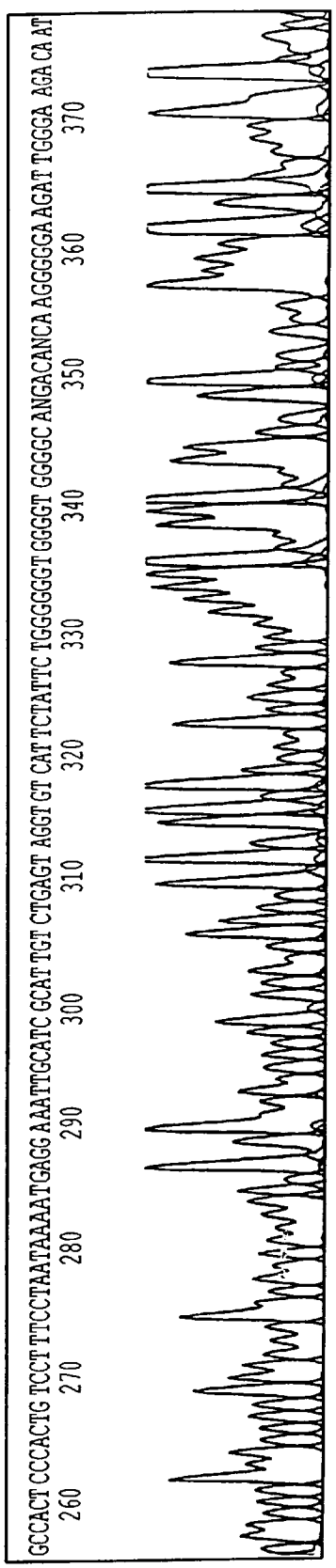
Figure 35D:
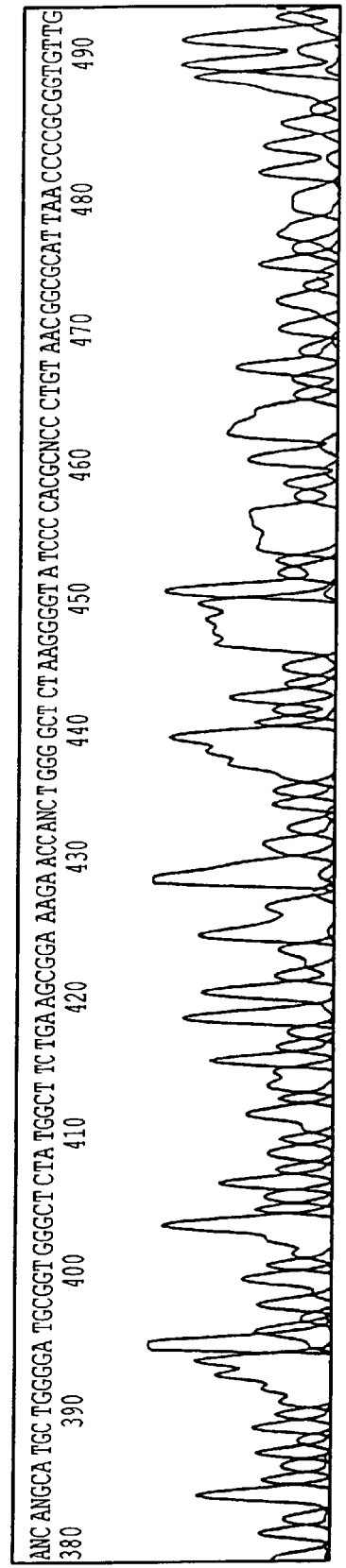
Figure 35E:
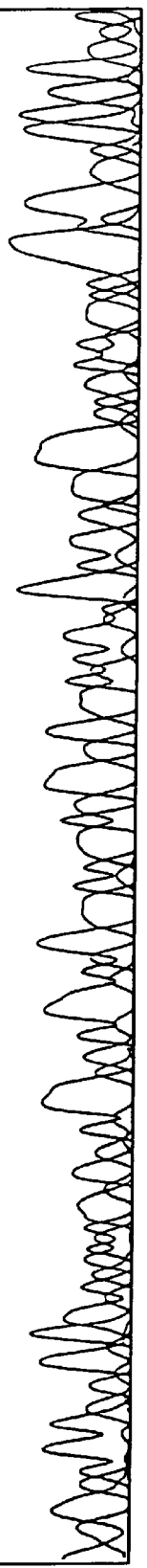
Figure 36A:
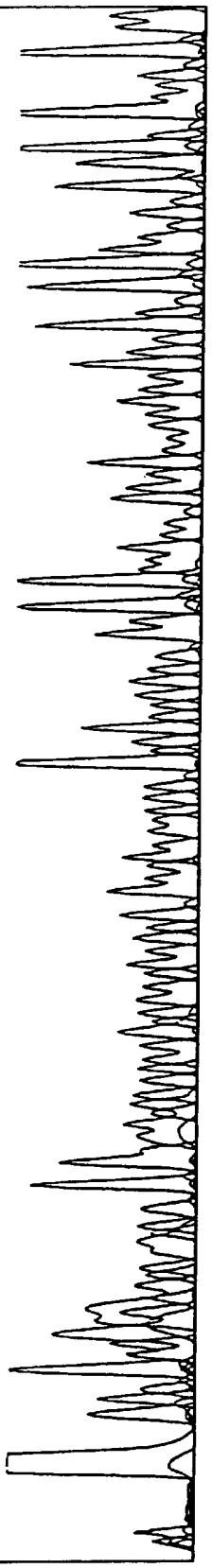
Figure 36B:
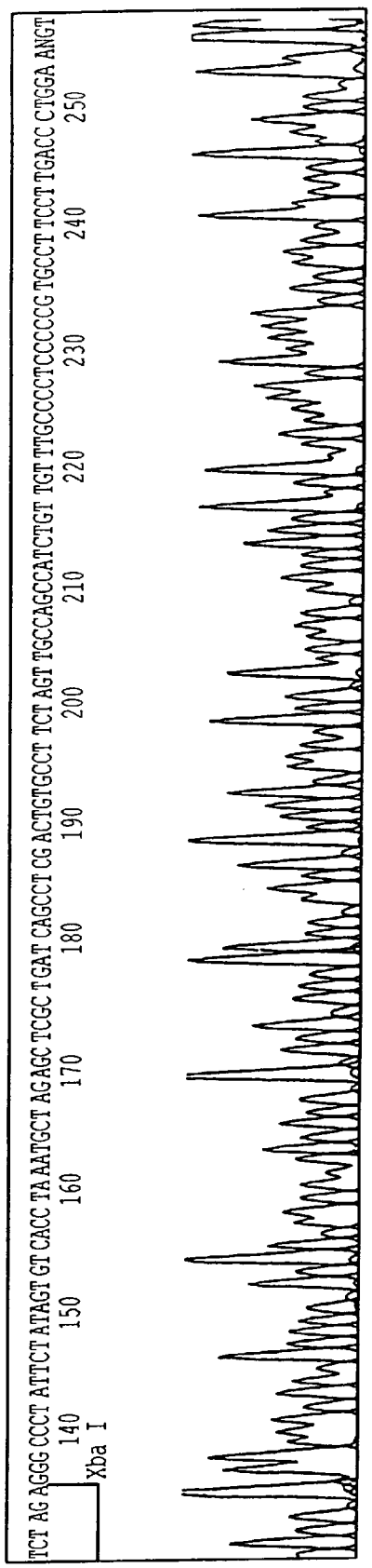
Figure 36C:
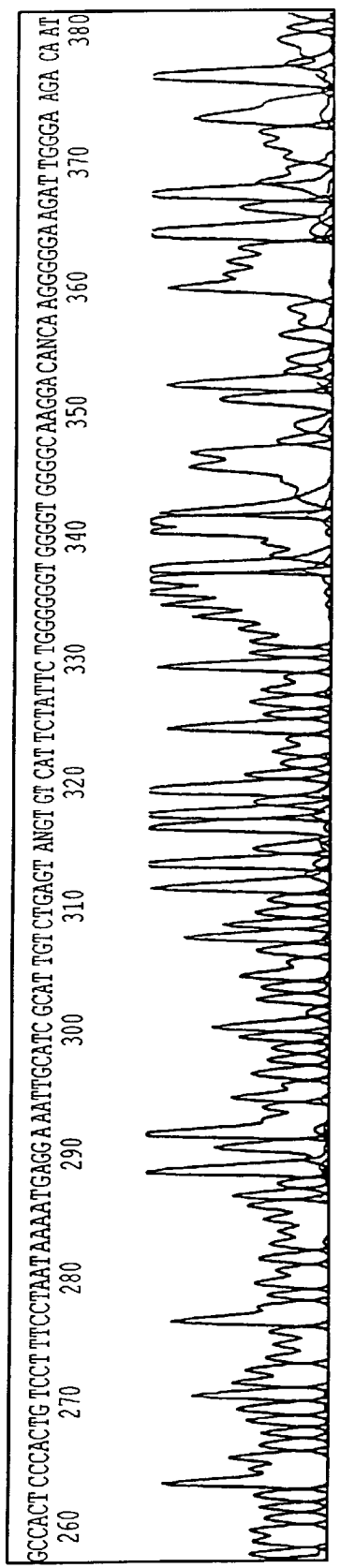
Figure 36D:
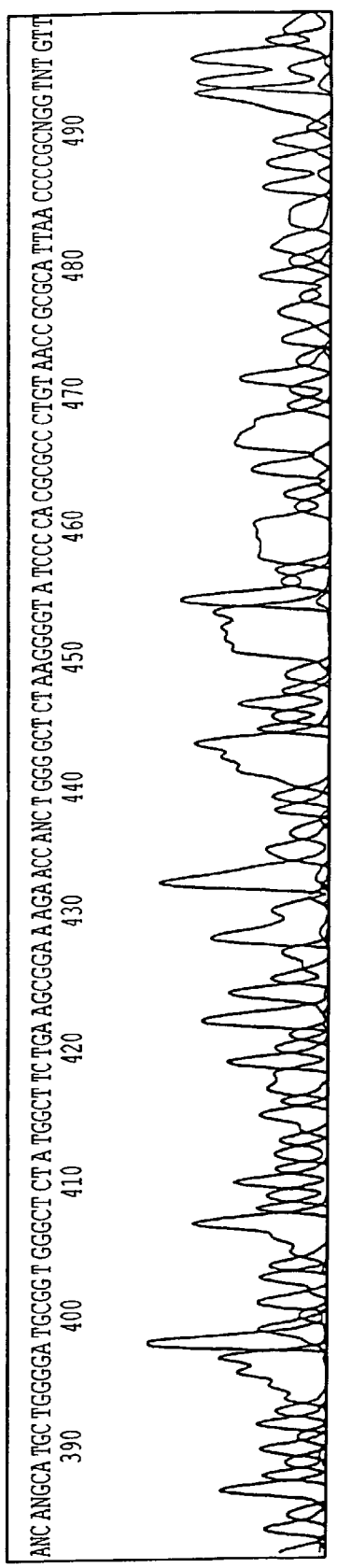
Figure 36E:
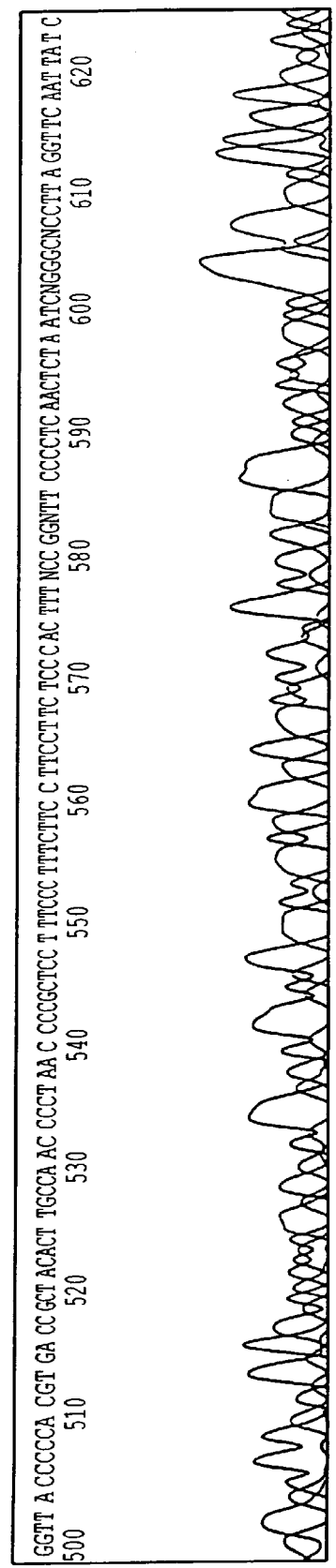
Figure 37A:
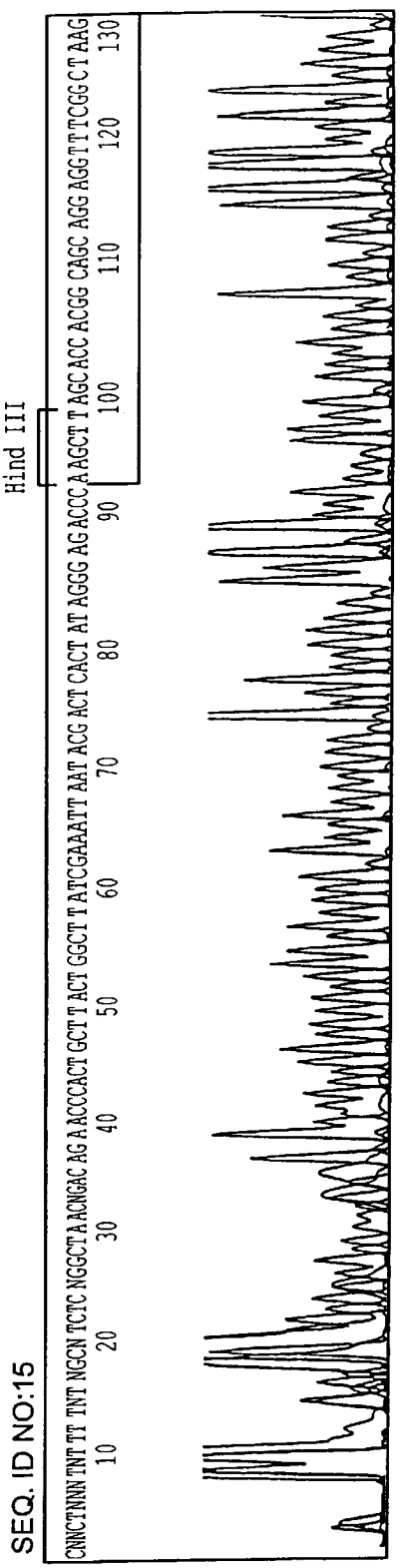
Figure 37B:
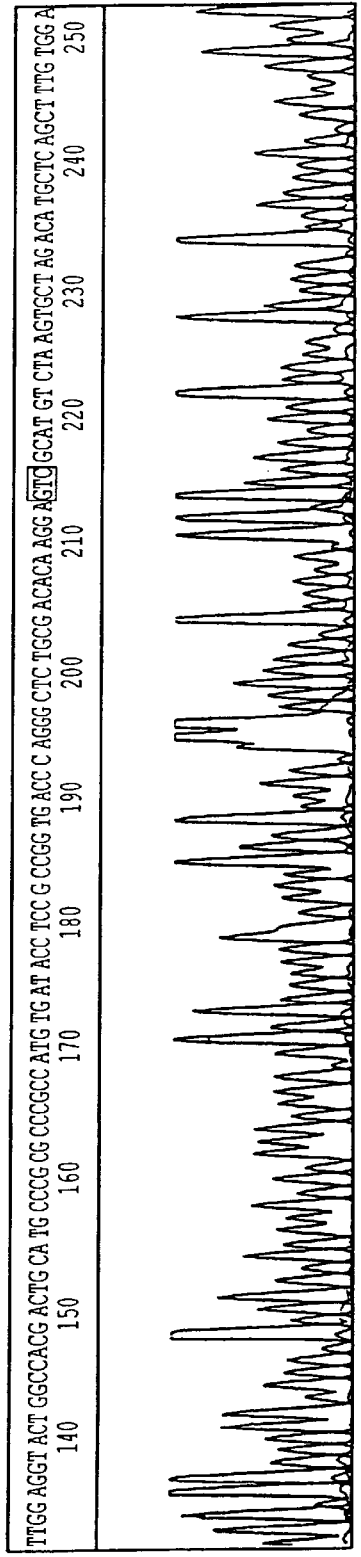
Figure 37C:
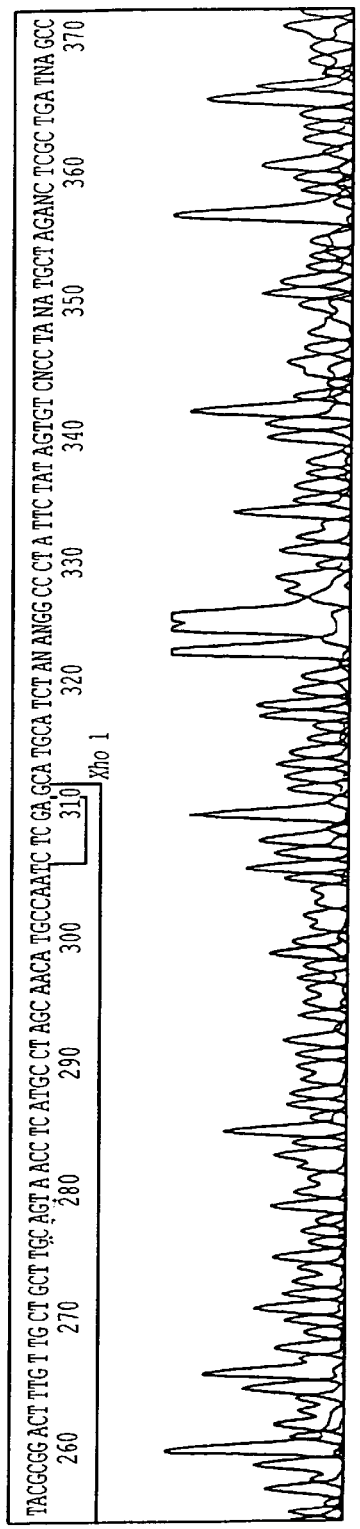
Figure 37D:
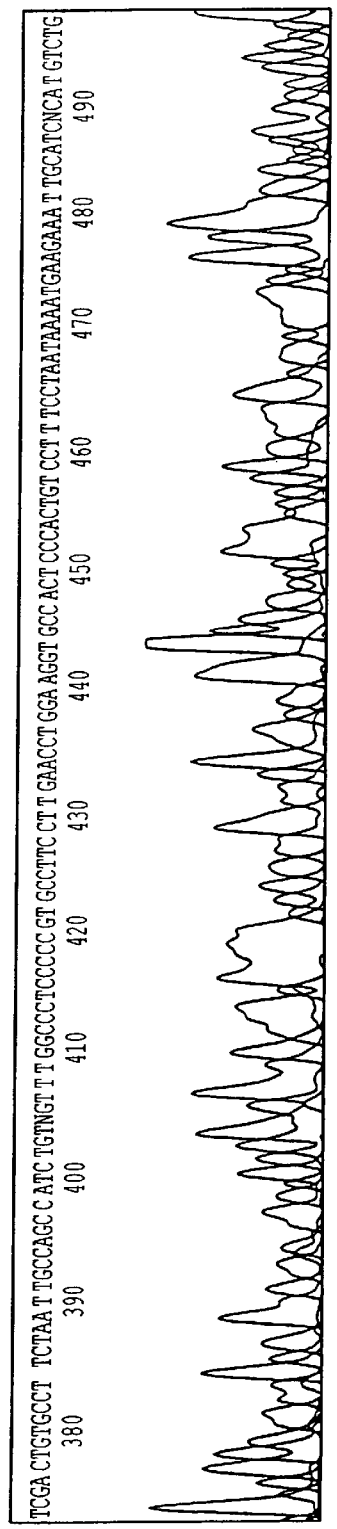
Figure 37E:
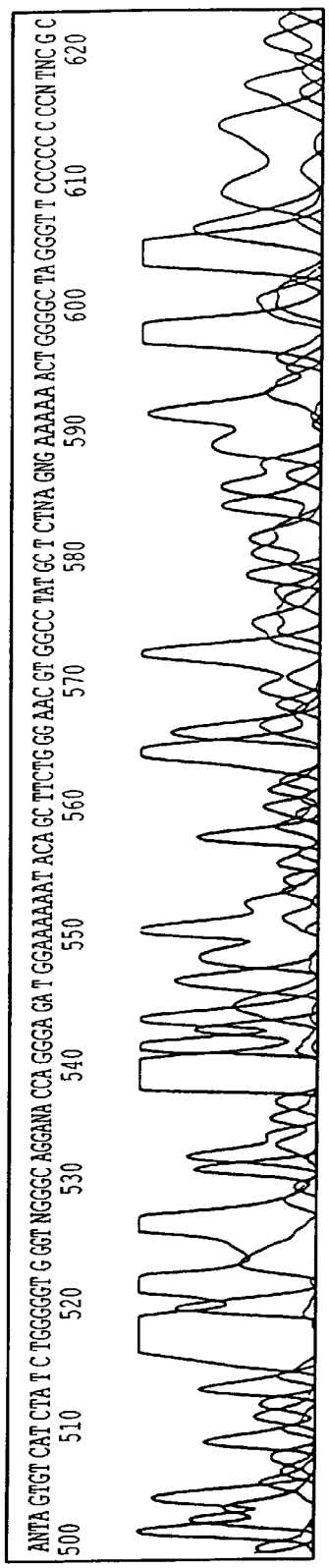
Figure 38A:
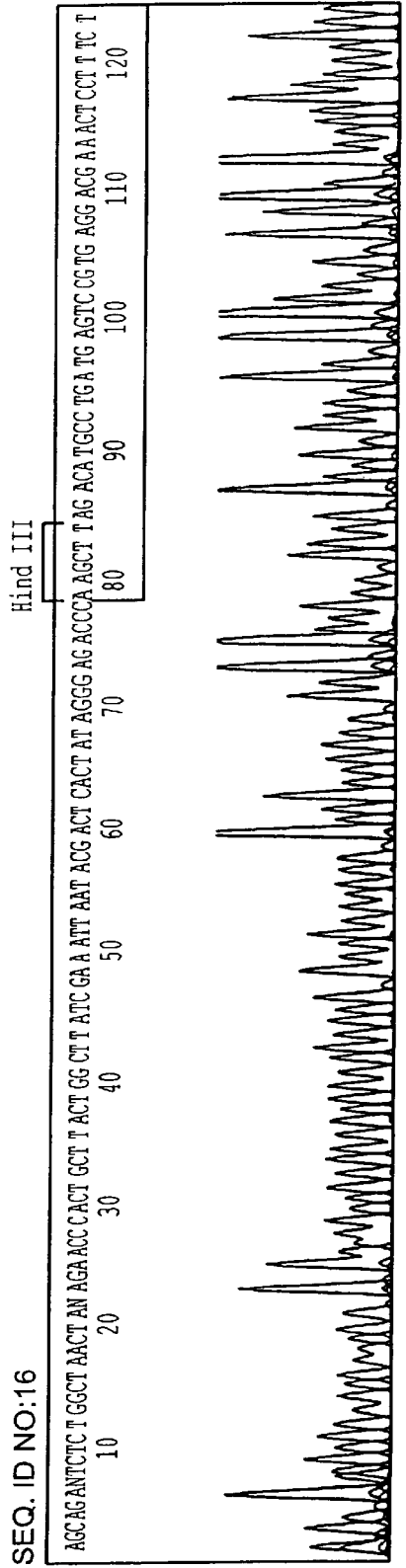
Figure 38B:
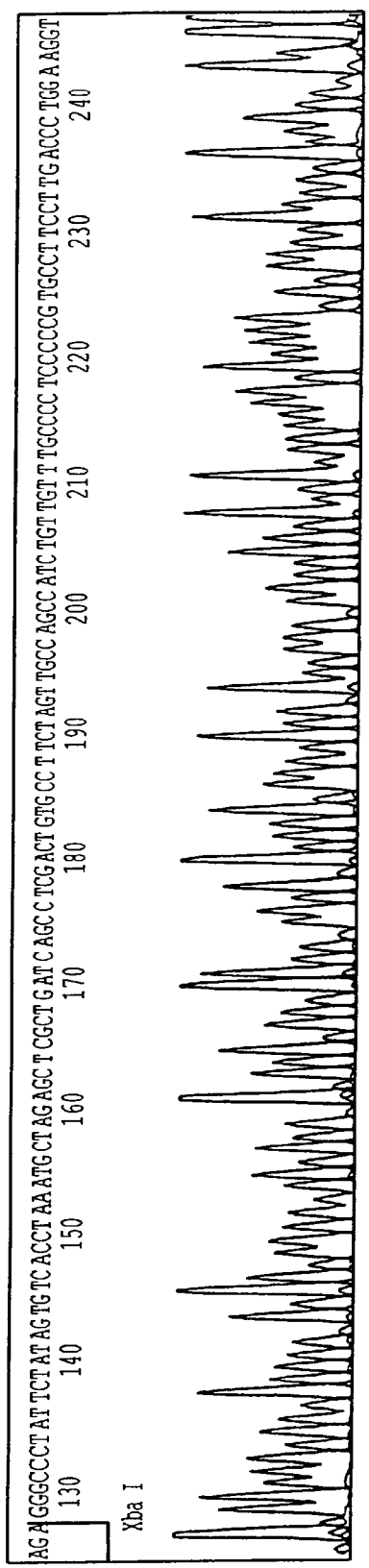
Figure 38C:
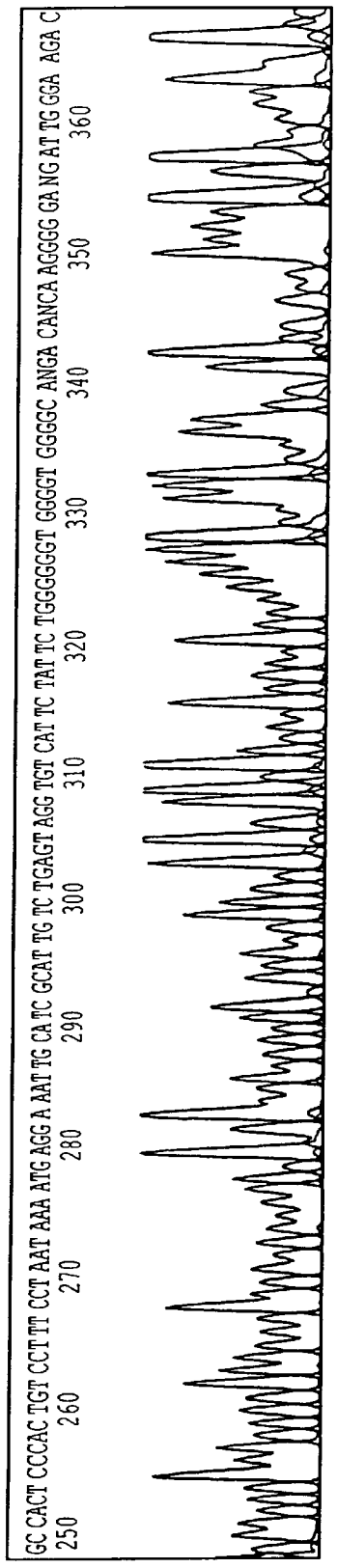
Figure 38D:
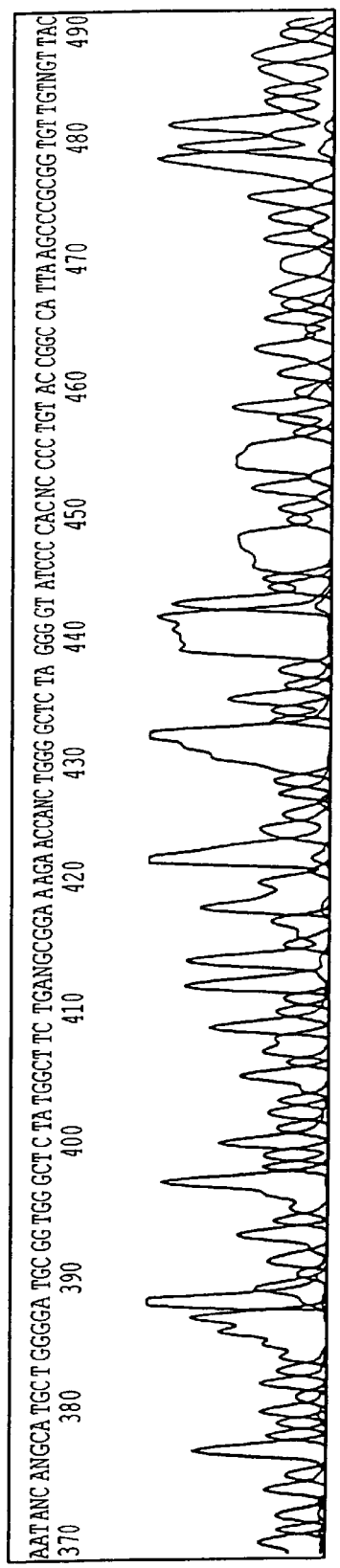
Figure 38E:
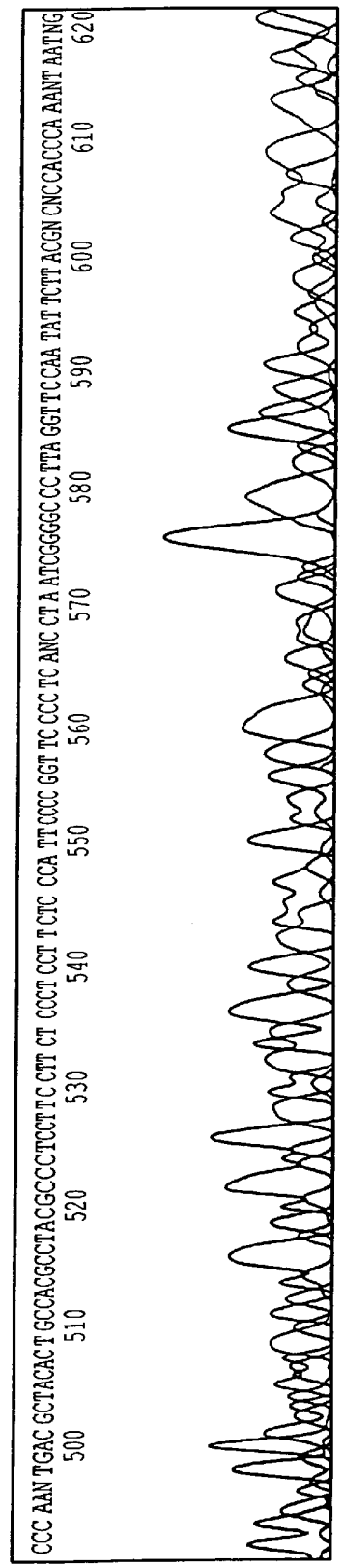
Figure 39A:
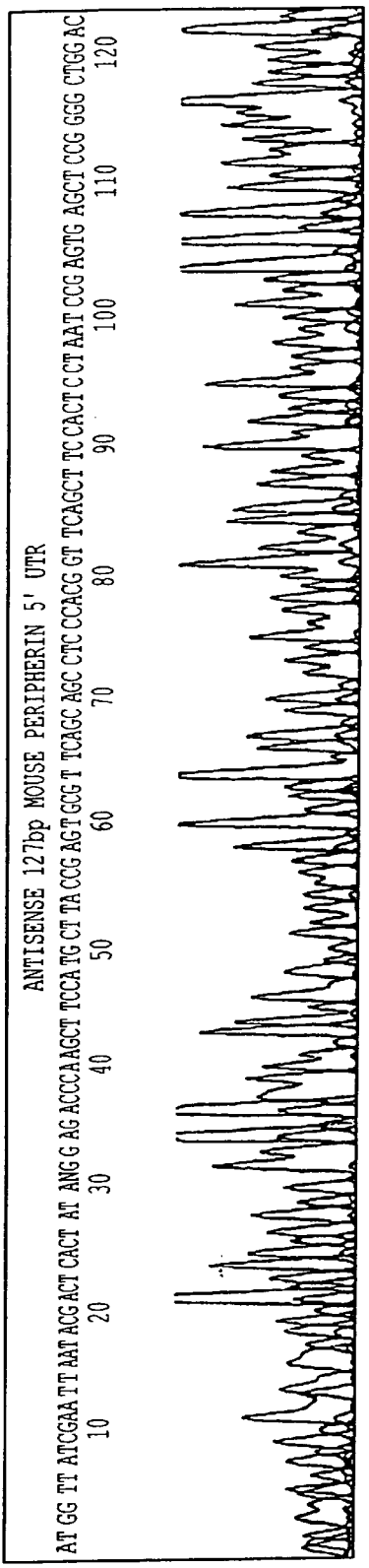
Figure 39B:
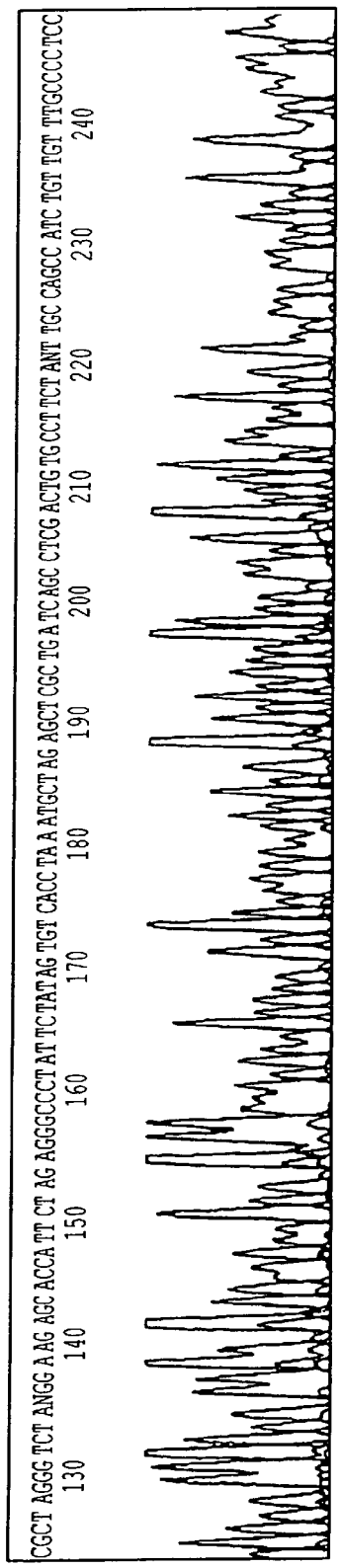
Figure 39C:
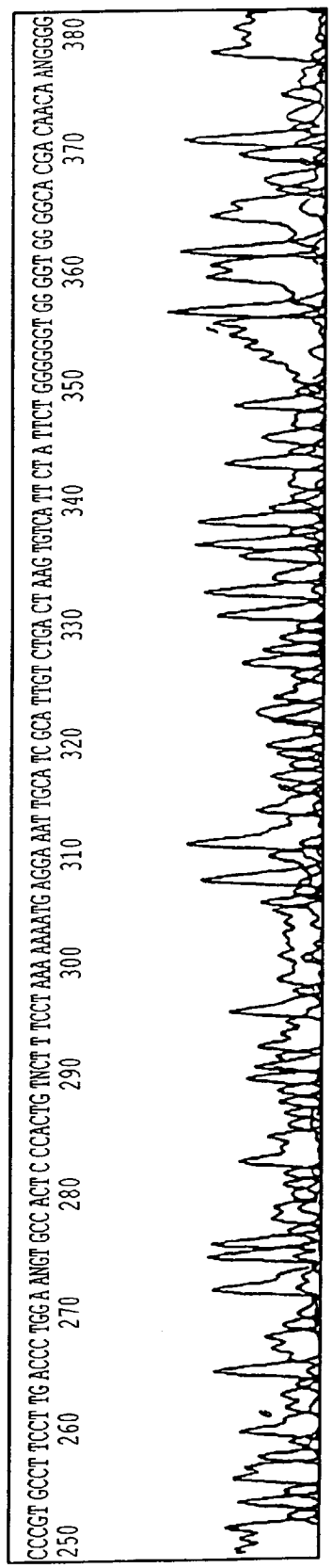
Figure 39D:
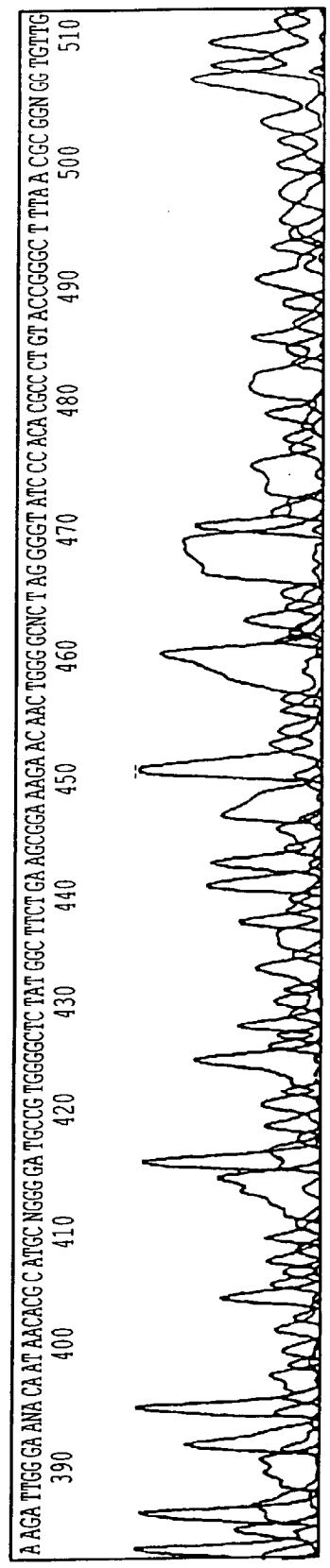
Figure 39E:
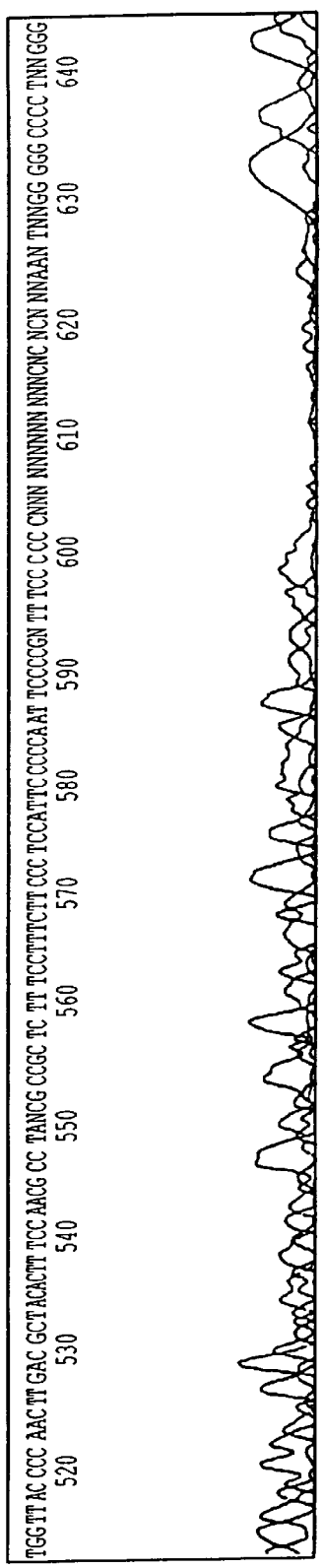
Figure 40A:
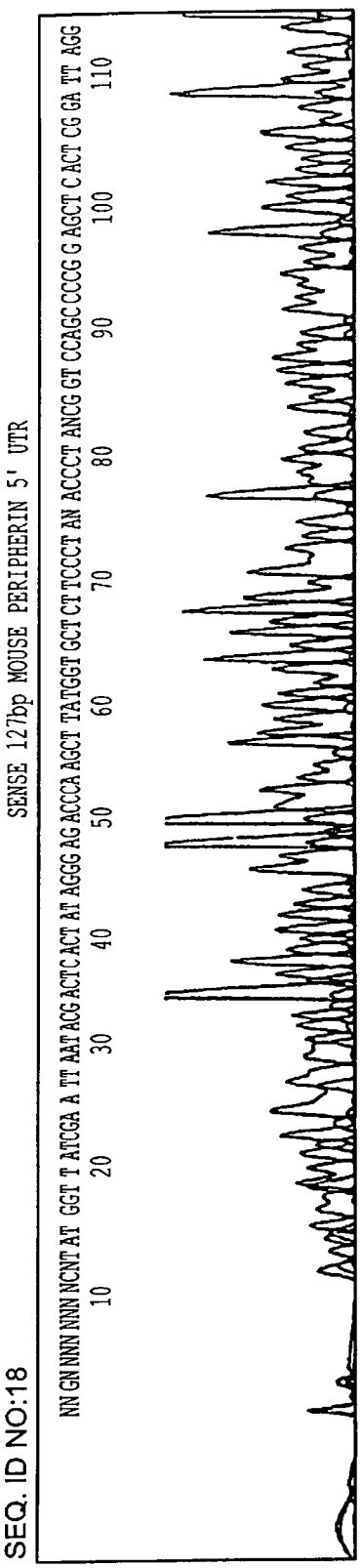
Figure 40B:
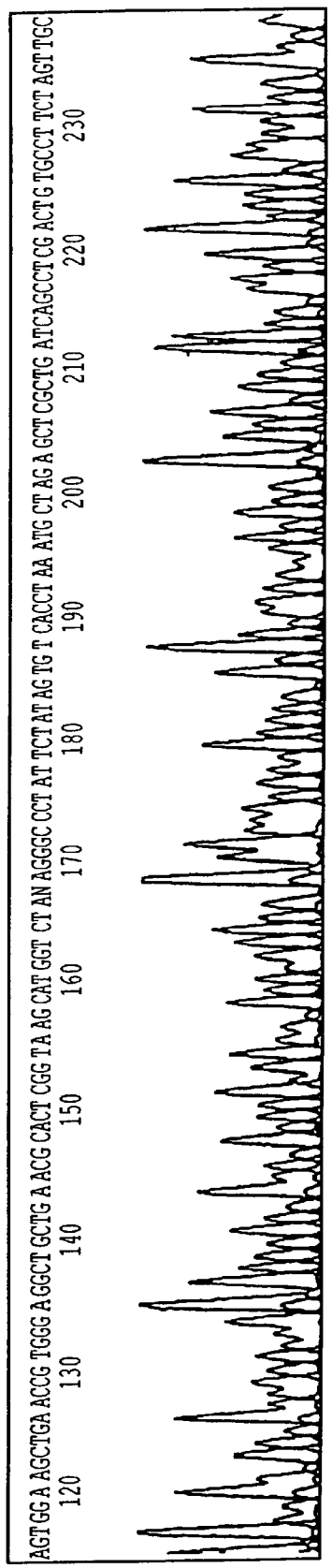
Figure 40C:
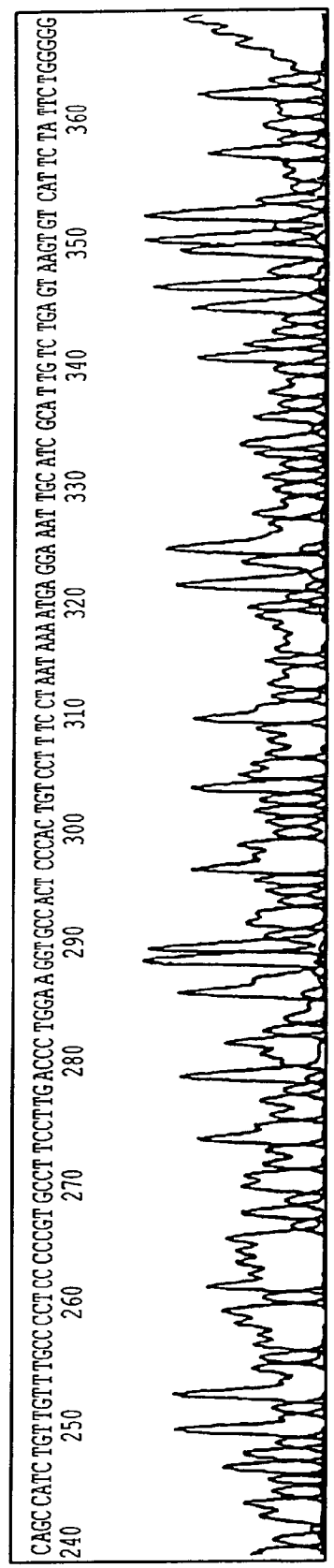
Figure 40D:
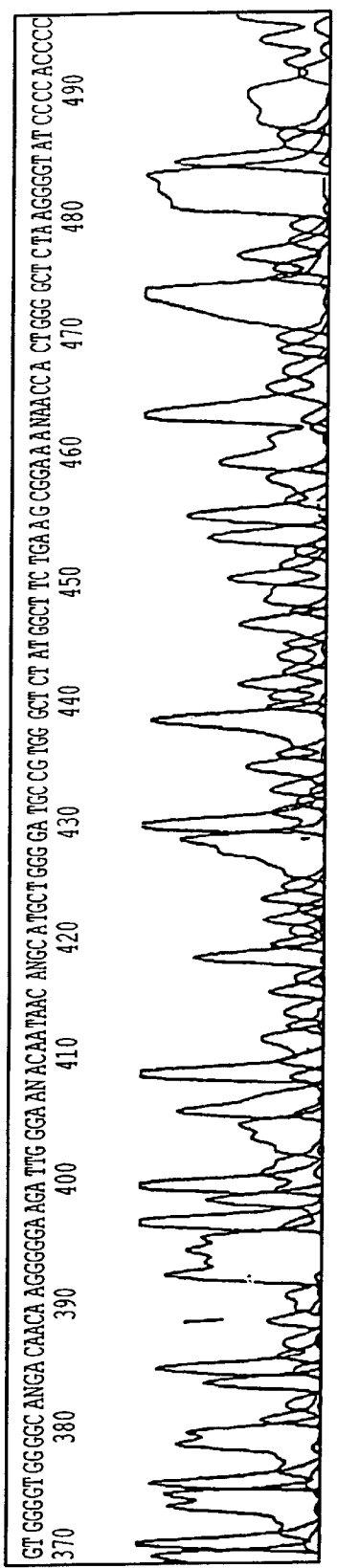
Figure 40E:
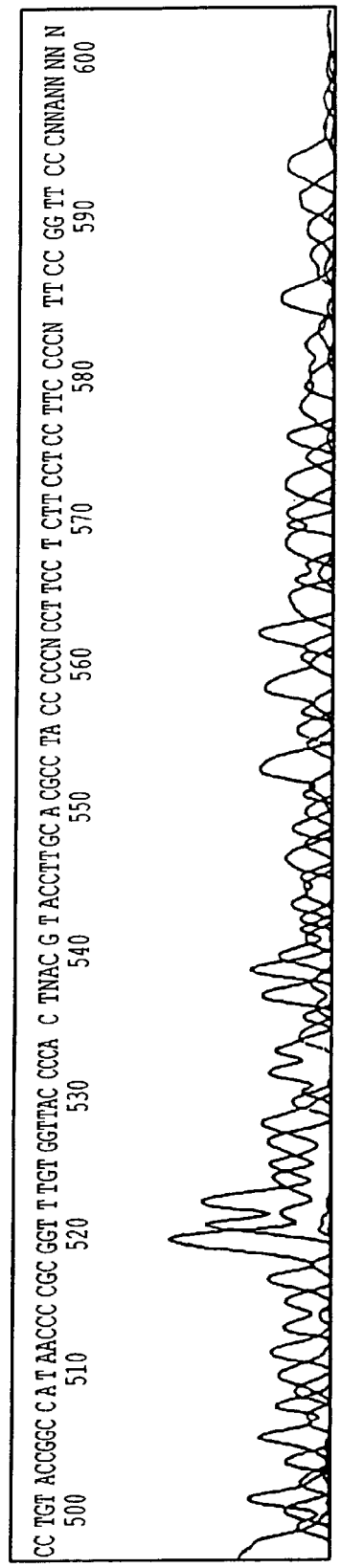

FIG. 20: The unadapted and altered human peripherin cDNAs were expressed from the T7 promoter to the BglII site in the coding sequence. The resulting RNAs were mixed together with Rib9 RNA for varying times with 15 mM magnesium chloride and incubated at 37° C. Lane 1: Intact unadapted human peripherin RNA without ribozyme. Lane 2: Intact altered human peripherin RNA without ribozyme. Lanes 3 and 4: DNA ladder as in FIG. 1. Lane 5–8: Unadapted and altered human peripherin RNAs and Rib9 RNA after incubation together for 0,1, 2 and 3 hours, respectively, at 37° C. with 15 mM magnesium chloride. The sizes of the expressed RNAs and cleavage products are as expected (Table 1). Cleavage products were observed at time zero. Almost complete cleavage of the larger unadapted human peripherin RNA was obtained with Rib9 RNA after 1 hour. The intensity of the larger unadapted human peripherin RNA product decreased quickly over time. The altered human peripherin RNA was not cleaved by Rib9 RNA even after 3 hours. The intensity of the smaller altered human peripherin RNA product remains constant over time indicating that the RNA is not cleaved by Rib9 RNA. In addition, no additional cleavage products were observed. Lane 9: Intact unadapted and altered human peripherin RNA together without ribozyme. Lane 10: DNA ladder as in FIG. 1.

FIGS. 21–40: In each case the most relevant sequences have been underlined. The position of the ATG start in each sequence is highlighted by an arrow.

FIG. 21: Mouse Rhodopsin cDNA sequences mouse rhodopsin 5'UTR sequences/the ATG start site/mouse rhodopsin coding sequences are shown. (SEQ ID NO: 1).

FIG. 22: Forward mouse Rhodopsin cDNA with altered non-coding sequences mouse rhodopsin 5'UTR sequences with a 1 base change/the ATG start site/mouse rhodopsin coding sequences are shown. (SEQ ID NO: 2).

FIG. 23: Reverse Mouse Rhodopsin cDNA with altered non-coding sequences mouse rhodopsin 5'UTR sequences with a 1 base change/the ATG start site/mouse rhodopsin coding sequences are shown. (SEQ ID NO: 19).

FIG. 24: Forward Mouse Rhodopsin cDNA with altered non-coding sequences mouse rhodopsin 5'UTR sequences with a 1 base change/the ATG start site/mouse rhodopsin coding sequences are shown. (SEQ ID NO: 3).

FIG. 25: Reverse Mouse Rhodopsin cDNA with altered non-coding sequences mouse rhodopsin 5'UTR sequences with a 1 base change/the ATG start site/mouse rhodopsin coding sequences are shown. (SEQ ID NO: 20).

FIG. 26: Ribozyme 3. (SEQ ID NO: 4).

FIG. 27: Human Rhodopsin cDNA sequence human rhodopsin 5'UTR sequences/the ATG start site/human rhodopsin coding sequences are shown. (SEQ ID NO: 5).

FIG. 28: Human Rhodopsin cDNA with altered non-coding sequences human rhodopsin 5'UTR sequences (shorter UTR)/the ATG start site/human rhodopsin coding sequences are shown. (SEQ ID NO: 6).

FIG. 29: Ribozyme 15. (SEQ ID NO: 7).

FIG. 30: Mouse peripherin cDNA sequences mouse peripherin 5'UTR sequences/the ATG start site/mouse peripherin coding sequences are shown. (SEQ ID NO: 8).

FIG. 31: Mouse peripherin cDNA with altered non-coding sequences mouse rhodopsin 5'UTR sequences/the ATG start site/mouse peripherin coding sequences are shown. (SEQ ID NO: 9).

FIG. 32: Ribozyme 17. (SEQ ID NO: 10).

FIG. 33: Human peripherin cDNA sequences human peripherin 5'UTR sequences/the ATG start site/human peripherin coding sequences are shown. (SEQ ID NO: 11).

FIG. 34: Human peripherin cDNA with altered non-coding sequences. Partial human and mouse peripherin 5'UTR sequences/the ATG start site/human peripherin coding sequences are shown. (SEQ ID NO: 12).

FIG. 35: Ribozyme 8. (SEQ ID NO: 13).

FIG. 36: Ribozyme 9. (SEQ ID NO: 14).

FIG. 37: Human type I collagen (COL1A2) sequence—5'UTR and exon 1 sequence. (SEQ ID NO: 15).

FIG. 38: Ribozyme 18. (SEQ ID NO: 16).

FIG. 39: Antisense construct containing 127 bp of antisense sequence targeting the 5'UTR of the mouse peripherin gene. (SEQ ID NO: 17).

FIG. 40: Sense construct containing 127 bp of sense sequence from the 5'UTR of the mouse peripherin gene. (SEQ ID NO: 18).

EXAMPLE 1

Mouse Rhodopsin

Rib3 RNA targeting the mouse rhodopsin 5'non-coding sequence was cut with Xho I and expressed in vitro. The mouse rhodopsin cDNA and hybrid cDNA with altered 5'non-coding sequence (with the human peripherin 5'UTR sequence in place of the mouse rhodopsin 5'UTR sequence) were cut with Eco47111, expressed and both RNAs mixed separately and together with Rib3 RNA to test for cleavage. RNAs were mixed with varying concentrations of $MgCl_2$ and for varying amounts of time to optimize cleavage of RNA by Rib3 RNA (FIGS. 2–7). Likewise, a second hybrid with a small modification of the 5'UTR sequence was cut with FspI, expressed and tested for cleavage with Rib3 RNA alone and together with the original unadapted mouse rhodopsin RNA. This alteration is a single base change at the ribozyme cleavage site involving a U→G, that is, altering the ribozyme cleavage site from GUC to GGC thereby removing the target site. In all cases the expressed RNA was the correct size. In all cases cleavage of the larger unadapted mouse rhodopsin RNA product was achieved. In some cases cleavage was complete and all cleavage products were of the predicted size. Notably hybrid mouse rhodopsin RNAs with altered 5'UTR sequences were not cleaved by Rib3 RNA either when mixed alone with Rib3 RNA or when combined with Rib3 RNA and the unadapted mouse rhodopsin RNA (FIGS. 2–7). This highlights the sequence specificity of the Rib3 RNA target in that small sequence alterations may be all that is required to prevent cleavage. Likewise small modifications in the targets for the antisense arms of ribozymes or more generally for any antisense may result in the inability of a suppression effector to attack the modified RNA. The first hybrid described above could be used to prevent ribozyme cleavage or antisense binding of many ribozymes or antisense suppression effectors and therefore would be particularly useful if more than one suppression effector was required to achieve suppression.

Example 2

Human Rhodopsin

The human rhodopsin cDNA clone (with a full length 5'UTR) and the human rhodopsin hybrid cDNA clone with altered 5'non-coding sequence (shorter 5'UTR) were cut with BstEII and expressed in vitro. The Rib15 clone was cut with XbaI and expressed in vitro. The resulting ribozyme and human rhodopsin RNAs were mixed with varying concentrations of $MgCl_2$ to optimize cleavage of the template RNA by Rib15 RNA. (FIGS. 8–12). The human rhodopsin cDNA and hybrid cDNA with altered 5'non-coding sequence were cut with AcyI, expressed and both RNAs mixed separately (due to their similar sizes) with Rib15 RNA to test for cleavage (FIGS. 8–12). The human rhodopsin cDNA was cut with BstEII and the hybrid cDNA with altered 5'non-coding sequence cut with FspI, expressed and mixed separately and together with Rib15 RNA to test for cleavage (FIGS. 8–12). In all cases the expressed RNA was the correct size. Similarly in all cases the unadapted RNA template was cut into cleavage products of the predicted sizes. The cleavage of the unadapted RNA template was incomplete with some residual uncleaved RNA remaining. This may be due, for example, to the inability of the ribozyme to access RNA in some conformations. In all cases RNA expressed from the altered hybrid human rhodopsin cDNA with a shorter 5'UTR remained intact, that is, it was not cleaved by Rib15 RNA. It is worth noting that AcyI enzyme cuts after the stop codon of the coding region of the gene and therefore the resulting RNA includes all of the coding sequence that gives rise to the protein. The RNA from the original unadapted human rhodopsin cDNA clone cut with AcyI is cleaved by Rib15 RNA. In contrast, RNA from the hybrid clone with an altered 5'UTR sequence is not cleaved by Rib15 RNA. (FIGS. 8–12). The sequence of the ribozyme target site and of the antisense flanks are not present in the altered human rhodopsin RNA. Clearly, altering the sequence in non-coding regions masks the resulting altered gene from being suppressed by antisense or ribozymes targeting sites in non-coding regions.

Example 3

Mouse Peripherin

Rib17 targeting mouse peripherin 5'non-coding sequence was cut with XbaI and expressed in vitro. The mouse peripherin cDNA and mouse peripherin hybrid cDNA with an altered 5'non-coding sequence (in which the mouse peripherin 5'UTR sequence has been replaced by mouse rhodopsin 5'UTR sequence) were cut with BglII, expressed in vitro and both RNAs mixed separately and together with Rib17 RNA to test for cleavage. RNAs were mixed with varying concentrations of $MgCl_2$ and for varying times to optimize cleavage of RNAs by Rib17 RNA (FIGS. 13–16). Partial cleavage of the unadapted mouse peripherin RNA by Rib17 RNA was obtained—all RNAs expressed and all cleavage products were the predicted sizes. Partial cleavage may be due to the inaccessibility of some RNA conformations to antisense binding and/or ribozyme cleavage. In contrast the adapted hybrid mouse peripherin RNA containing mouse rhodopsin non-coding sequences remained intact (FIGS. 13–16). This again highlights that RNAs can be designed so that they code for a correct protein, in this case, mouse peripherin and such that they are masked from a suppression effector(s), in this case, a ribozyme with antisense flanks.

Example 4

Human Peripherin

Rib8 and Rib9 clones targeting human peripherin 5'non-coding sequence were cut with XbaI and expressed in vitro. The human peripherin cDNA and human peripherin hybrid cDNA with altered 5'non-coding sequence (with part of the human peripherin 5'UTR sequence replaced by mouse peripherin 5'UTR sequence) were cut with BglII and AvrII respectively, expressed in vitro and both RNAs mixed separately and together with Rib9 RNA to test for cleavage. RNAs were mixed with varying concentrations of $MgCl_2$ to optimize cleavage of RNAs by Rib9 RNA (FIGS. 17–20). Notably the majority of the larger unadapted RNA product was cleaved while the adapted RNA product with altered noncoding sequence remained intact (FIGS. 17–20). Similar results were obtained with Rib8 RNA which targets a different open loop than Rib9 RNA in the non-coding sequence of human peripherin. However, in the case of Rib8 RNA, the extent of the cleavage was significantly less than Rib9 RNA (FIGS. 17–20) suggesting the important role of RNA structure in antisense binding and RNA cleavage.

Example 5

Human COL1A2

Rib18 which has been cloned into pcDNA3 (SEQ ID NO:16) targets the 5'UTR sequence of the human type I collagen COL1A2 gene, multiple mutations in which can cause autosomal dominantly inherited osteogenesis imperfecta involving bone fragility, amongst other symptoms. A clone containing the 5'UTR sequence together with exon I of the human COL1A2 gene has also been generated (SEQ ID NO:15) to apply suppression and replacement strategies to this human gene.

Antisense constructs

A number of constructs have been generated in pcDNA3 and pZEOSV containing tracks of sense and antisense sequence from the non-coding regions of the mouse rhodopsin and peripherin genes. An example of these sequences is given in SEQ ID NOS:17 and 18. Antisense effects are under evaluation.

DISCUSSION

In the first four examples outlined above, RNA was expressed from cDNAs coding for four different proteins: mouse and human rhodopsin and mouse and human peripherin. All four RNAs have been significantly attacked in vitro using suppression effectors directed towards the non-coding regions of the RNA. In all four examples the ribozymes directed to 5'UTR sequences were successful in cleaving target RNAs in the predicted manner. Antisense targeting non-coding sequences was used successfully to elicit binding and cleavage of target RNAs in a sequence specific manner.

In some cases it is possible that cleavage of the RNA at the 5'UTR would not effect the functioning of the resulting RNA cleavage products in generating protein. Moreover although lowering RNA levels may often lead to a parallel lowering of protein levels this is not always the case. In some situations mechanisms may prevent a significant decrease in protein levels despite a substantial decrease in levels of RNA. However in many instances suppression at the RNA level has been shown to be effective. In some cases it is thought that ribozymes elicit suppression not only by cleavage of RNA but also by an antisense effect due to the antisense arms in the ribozyme. Notably we have demonstrated sequence specific attack of target RNAs in non-coding regions, which is an important stage in gene suppression.

In the four examples provided ribozymes were designed to target 5'UTR sequences, however, they could be readily designed to target any non-coding sequences. Suppression could be achieved using antisense or ribozymes targeting for example, the 3'UTR sequences or any combination of non-coding sequences.

Additionally, in all four examples, cDNAs with altered sequences in the non-coding regions targeted by ribozymes were generated. RNAs expressed from altered cDNAs were protected entirely from cleavage due the absence of the ribozyme target by each of the ribozymes tested. Alterations involved replacement of UTR sequence with UTR sequence from another gene expressed in the same tissue or UTR sequence from the same gene but from a different mammalian species (e.g., mouse peripherin, human peripherin, mouse rhodopsin). In one case the target site was deleted (human rhodopsin). Of particular interest is the second mouse rhodopsin hybrid cDNA for Rib3 which contains a single base change thereby preventing RNA cleavage. In some cases the non-coding sequences of a gene may be essential to the overall efficient expression and functioning of the gene. Therefore it may be useful to alter replacement genes in subtle ways to prevent ribozyme cleavage or nucleic acid binding. Changing a few nucleotides in many instances may be sufficient to prevent nucleolytic attack.

As highlighted before in this text using this invention the same method of suppression (targeting non-coding sequences) and gene replacement (using a gene with altered non-coding sequences) may be used as a therapeutic approach for any mutation within a given gene.

REFERENCES

Carter G and Lemoine N R. (1993) Cancer Res. 67: 869–876.

Cazenave et al. (1989) Nucl. Acid Res. 17: 42554273.

Dosaka-Akita H et al. (1995) Cancer Res. 55: 1559–1564.

Dryja T P et al. (1990) Nature 343: 364–366.

Duval-Valentin et al. (1992) Proc. Natl. Acad. Sci. USA 89: 504–508.

Ellis and Rodgers (1993) Nucl. Acid Res. 21: 5171–5178.

Farrar G J et al. (1991) Nature 354: 478–480.

Farrar G J et al. (1991) Genomics 14: 805–807.

Farrar G J et al. (1995) Invest. Ophthamol. Vis. Sci. (ARVO) 36: (4).

Feng M, Cabrera G, Deshane J, Scanlon K and Curiel D T. (1995) Cancer Res. 55: 2024–2028.

Gaughan D J, Steel D M, and Whitehead S A. (1995) FEBS Letters 374: 241–245.

Hanvey J C et al. (1992) Science 258:1481–1485.

Hardenbol P and Van Dyke M W. (1996) Proc. Natl. Acad. Sci. USA 93: 2811–2816.

Herschlag D, Khosla M, Tsuchihashi Z and Karpel R L. (1994) EMBO 13: (12) 29132924.

Herskowitz et al. (1987) Nature 329: 219–222.

Jankowsky E and Schwenzer B. (1996) Nucl. Acid Res. 24: (3) 423 429.

Jones J T, Lee S-W and Sullenger B A. (1996) Nature Medicine 2: 643–648.

Jordan S A et al. (1993) Nature Genetics 4: 54–58.

Quattrone A, Fibbi G, Anichini E, Pucci M et al. (1995) Cancer Res. 55: 90–95.

Kajiwara et al. (1991) Nature 354: 480–483.

Knudsen H and Nielsen P E. (1996) Nucl. Acid Res. 24: (3) 494–500.

Lange W et al. (1993) Leukemia 7: 1786–1794.

Mansergh F et al. (1995) J. Med. Genet. 32: 855–858.

Mashhour B et al. (1994) Gene Therapy 1:122–126.

McKay R A, Cummins L L, Graham M J, Lesnik E A et al. (1996) Nuc Acid Res 24: (3) 411–417.

McWilliam P et al. (1989) Genomics 5: 612–619.

Ohta Y, Kijima H, Ohkawa T, Kashani-Sabet M and Scanlon K J. (1996) Nucl. Acid. Res. 24: (5) 938–942.

Ott J et al. (1989) Proc. Natl. Acad. Sci. 87: 701–704.

Oyama T et al. (1995) Pathol. Int. 45: 45–50.

Postel et al. (1991) Proc. Natl. Acad. Sci. USA 88: 8227–8231.

Porumb H, Gousset, Letellier R, Salle V, et al. (1996) Cancer Res. 56: 515–522.

Rimsky et al. (1989) Nature 341: 453–456.

Sullenger B A and Cech T R. (1994) Nature 371: 619–622.

Sun J S et al. (1989) Proc. Natl. Acad. Sci. USA 86: 9198–9202.

Trauger J W, Baird E E and Dervan P B. (1996) Nature 382: 559–561.

Valera A et al. (1994) J. Biol. Chem. 269: 28543–28546.

Van Soest S et al. (1994) Genomics 22: 499–504.

Wei Z, Tung C-H, Zhu T, Dickerhof WA et al. (1996) Nucl. Acid Res. 24: (4) 655–661.

---

SEQUENCE LISTING

<160> NUMBER OF SEQ ID NOS: 26

<210> SEQ ID NO 1
<211> LENGTH: 624
<212> TYPE: DNA
<213> ORGANISM: Artificial Sequence
<220> FEATURE:
<223> OTHER INFORMATION: Mouse Rhodopsin cDNA sequences mouse rhodopsin
    5'UTR sequences/the ATG start site/mouse rhodopsin coding
    sequences are included.
<220> FEATURE:
<221> NAME/KEY: n
<222> LOCATION: (1)..(624)
<223> OTHER INFORMATION: any

<400> SEQUENCE: 1
nnnncttnct tanngcttgg taccganctc ggatccacta gtnaacggcc gccagtgtgc    60
tggaaattcc cagaggnact ctggggcaga caagatgaga caccctttcc tttctttacc    120
taaggncctc cacccgatgt caccttggcc cctctgcaag ccaattaggc cccggtggca    180

-continued

```
gcagtgggat tagcgttagt atgatatctc gcggatgctg aatcagcctc tggcttaggg      240
agagaaggtc actttataag ggtctggggg gggtcagtgc ctggagttgc gctgtgggag      300
ccgtcagtgg ctgagctcgc caagcagcct tggtctctgt ctacgaaaan cccgtggggc      360
agcctcnana accgcagcca tgaacggcac agaaggcccc aattttatg tgcccttctc       420 caacgtcaca ngcgtggtgc ggaaccccct cnancanccg cagtactacc tggcggaacc      480
atggcagttc tccatgctgg cancgtacat gtcctgctca tcgtgctggg nttcccatca      540
actcctcacg ctctagttca ccgtaaanna naaaaaactg cgcaaccccct caactaaatc     600 ctgctcaatt gggcgtgggt gaac                                             624
```

<210> SEQ ID NO 2
<211> LENGTH: 624
<212> TYPE: DNA
<213> ORGANISM: Artificial Sequence
<220> FEATURE:
<223> OTHER INFORMATION: Forward mouse Rhodopsin cDNA with altered
      non-coding sequences mouse rhodopsin 5'UTR sequences with a 1 base
      change/the ATG start site/mouse rhodopsin coding sequences are
      included.
<220> FEATURE:
<221> NAME/KEY: n
<222> LOCATION: (1)..(624)
<223> OTHER INFORMATION: any

<400> SEQUENCE: 2

```
tnccttttt tncaatttcc ttcnanaccc aggancacga tatccccctgc tcaagctgtg       60 attccgaaac ccctgccacc actactgcat tcacggggta tcccaggcta gtgggactcn      120
acatgggtag ccccagggc agctccctac agcttgggcc atctgcactt ttcccaaggc       180
cctaagtctc cgcctctggg ctcgttaagg tttggggtgg gagctgtgct gtgggaagca      240
acccggacta cacttggcaa gcatgaacgg cacagagggc cccaattttt atgtgccctt      300
ctccaacgtc acaggcgtgg tgcggancc cttcgagcag ccgcagtact acctggcgga      360
accatggcag ttctccatgc tgggcancgt tacatgttcc tggcccatcg tgctgggctt      420
ccccatcaac ttcctcacgc tctacgtcan cgtacagcan aaaaanctgc gcacacccct     480
caactacatc ctgctcaact ttgggcgtgg ctgacccttc atggtctcgg aagatcacac      540
caccctctaa catcactcca tggctaattc ctctttnggg ccanaggcnt gtaatcncna      600
aggnttcttt gccancttgg aggt                                             624
```

<210> SEQ ID NO 3
<211> LENGTH: 620
<212> TYPE: DNA
<213> ORGANISM: Artificial Sequence
<220> FEATURE:
<223> OTHER INFORMATION: Forward Mouse Rhodopsin cDNA with altered
      non-coding sequences mouse rhodopsin 5'UTR sequences with a 1 base
      change/the ATG start site/mouse rhodopsin coding sequences are
      included.
<220> FEATURE:
<221> NAME/KEY: n
<222> LOCATION: (1)..(620)
<223> OTHER INFORMATION: any

<400> SEQUENCE: 3

```
tgnnttnctt aaangcttgg ttaccgagct cggatccact nagtaacggc cgccagtgtg       60
ctggaaattc ccagaggcac tctggggcag acaagatgag acacccttc ctttctttac      120 ctaagggcct ccacccgatg tcaccttggc ccctctgcaa gccaattagg ccccggtggc      180
agcagtggga ttagcgttag tatgatatct cgcggatgct gaatcagcct ctggcttagg     240
```

```
gagagaangt cactttataa gggtctgggg ggggtcagtg cctggagttg cgctgtggga    300
gccgtcagtg gctgagctcg ccaagcagcc ttggtctctg gctacnaaaa ncccgtgggg    360
cancctcnaa anccgcancc atgaacggca cagaaggccc caatttttat gtttccctte    420 tccaacgtca cangcgtngt gcggaacctc ttcnaacaac cgcaatncta cctggcggaa    480
ccatggcagt tctccatgct ggcancgtaa tnttctgctc atcgtgctgg gttcccatca    540
anttcctcac ccctaatttc cgtnaanaaa aaaactgccc caccccaaa taattctgnn     600 caanttggcg tggtnaccct                                                620

<210> SEQ ID NO 4
<211> LENGTH: 705
<212> TYPE: DNA
<213> ORGANISM: Artificial Sequence
<220> FEATURE:
<223> OTHER INFORMATION: Ribozyme 3 cloned in pcDNA3.
<220> FEATURE:
<221> NAME/KEY: n
<222> LOCATION: (1)..(705)
<223> OTHER INFORMATION: any

<400> SEQUENCE: 4
ngnttnnnnn nttacaganc nctcgctaan tagagaacca ctgcttactg gcttatcgaa     60
attaatacga ctcactatag ggagacccaa gcttcttcgt actgatgagt ccgtgaggac    120
gaaacagaga ctcgagcatg catctagagg gccctattct atagtgtcac ctaaatgcta    180
gagctcgctg atcagcctcg actgtgcctt ctagttgcca gccatctgtt gtttgcccct    240
cccccgtgcc ttccttgacc ctggaangtg ccactcccac tgtcctttcc taataaaatg    300
aggaaattgc atcgcattgt ctgagtangt gtcattctat tctgggggt ggggtgggc     360 anggacanca aggggaaga ttgggaaaaa caatancagg catgctgggg gatncngtgg    420
ggctctatgg cttctgangc ggaaagaaca actggggctc tanggggtat cccacncgc    480 cctgtaacgg cgcattaaac cccgcgggtg ttgtngttac cccacnttac cgctacactt    540
gccancgcct acgcccctcc tttcccttct cccttccttt ctcccacttc ccgcttccc    600 ctcaactcta atcgggccc cttaggttcc attaattctt acggnccca ccccaaaact    660 nataggtang gtcccttntt ggccnccct anaanggttt tccct                    705

<210> SEQ ID NO 5
<211> LENGTH: 617
<212> TYPE: DNA
<213> ORGANISM: Artificial Sequence
<220> FEATURE:
<223> OTHER INFORMATION: Human Rhodopsin cDNA sequence human rhodopsin
      5'UTR sequences/the ATG start site/human rhodopsin coding
      sequences are included.
<220> FEATURE:
<221> NAME/KEY: n
<222> LOCATION: (1)..(617)
<223> OTHER INFORMATION: any

<400> SEQUENCE: 5
tcccttntgn tagattgcan nncccaataa aanaaggncc cgcttaaagg cttatcgaaa     60
ttaatacgac tcactatang gagacccaag cttagagtca tccagctgga gccctgagtg    120
gctgagctca ggccttcgca gcattcttgg gtgggagcag ccacgggtca gccacaaggg    180
ccacagccat gaatggcaca gaaggcccta acttctacgt gccttctcc aatgcgacgg    240 gtgtggtacg cagcccnttc gagtacccac agtactacct ggctgagcca nggcagntcn    300
```

| | |
|---|---|
| ccatgctggc cgcctacatg tttctgctga tcgtgctggg cttccccatc aacttcctca | 360 |
| cgctctacgt caccgtccag cacaagaagc tgcgcacgcc tctcaactac atcctggctc | 420 |
| aacctagccg tggctgaact cttcatggtc ctangtggct tcaccagcac ctctacanct | 480 |
| ctctgcatgg atactcgtct tcgggcccac aggatgcaat tgganggctc tttgcacctg | 540 |
| gngggaaatt gcctgtggtc ctngtggtcn ggncaccaac gtactggtng tgtntanccc | 600 |
| agaacaactc cgctccg | 617 |

<210> SEQ ID NO 6
<211> LENGTH: 574
<212> TYPE: DNA
<213> ORGANISM: Artificial Sequence
<220> FEATURE:
<223> OTHER INFORMATION: Human Rhodopsin cDNA with altered non-coding
      sequences human rhod opsin 5'UTR sequences (shorter UTR)/the AT
      G start site/human rhodopsin coding sequences are included.
<220> FEATURE:
<221> NAME/KEY: n
<222> LOCATION: (1)..(574)
<223> OTHER INFORMATION: any

<400> SEQUENCE: 6

| | |
|---|---|
| nnacttcttc ngganatacct gcgganaata nagaaccact gcttactggc ttatcgaaat | 60 |
| taatacgact cactataggg agacccaagc ttggtaccga gctcggatcc actagtaacg | 120 |
| gccgccagtg tgctggaatt ccggaaggcc tgagctcagc acaagggcc acagccatga | 180 |
| atggcacaga aggccctaac ttctacgtgc ccttctccaa tgcgacgggt gtggtacgca | 240 |
| gccccttcga gtacccacag tactacctgg ctgagccatg gcagttctcc atgctggccg | 300 |
| cctacatgtt tctgctgatc gtgctgggct tccccatcaa cttcctcacg ctctacgtca | 360 |
| ccgtccagca caagaagctg cgcacgcctc tcaactacat cctggctcaa cctanccgtg | 420 |
| ggtgaactct tcatggtcct aggtgggttc accaacaccc tctaaaacct ctctgcatgg | 480 |
| atattcgtct tcgggccaca ggatgcaatt ggagggttct ttggcacctg ggngggaaat | 540 |
| gcctgtggtc ctgggngntc nggccaccaa cggt | 574 |

<210> SEQ ID NO 7
<211> LENGTH: 601
<212> TYPE: DNA
<213> ORGANISM: Artificial Sequence
<220> FEATURE:
<223> OTHER INFORMATION: Ribozyme 15 cloned in pcDNA3.
<220> FEATURE:
<221> NAME/KEY: n
<222> LOCATION: (1)..(601)
<223> OTHER INFORMATION: any

<400> SEQUENCE: 7

| | |
|---|---|
| cntncttttn anntttngnt cgcactctct ggctaactca gagaaccac tgcttactgg | 60 |
| cttatcgaaa ttaatacgac tcactatagg gagacccaag cttacccaag ctgatgagtc | 120 |
| cgtgaggacg aaatgctgct ctagagggcc ctattctata gtgtcaccta aatgctagag | 180 |
| ctcgctgatc agcctcgact gtgccttcta gttgccagcc atctgttgtt tgcccctccc | 240 |
| ccgtgccttc cttgaccctg gaaggtgcca ctcccactgt cctttcctaa taaaatgagg | 300 |
| aaattgcatc gcattgtctg agtaagtgtc attctattct gggggtggg gtngggcang | 360 |
| acaacnaggg gaagattggg aananaataa caggcatgct gggggatgcng tgggctctat | 420 |
| ggcttcctga agcggaaaga aacactnggn tctagggggtn tccccccncc ctgtacnggc | 480 |
| attaacncgn ggtttgtngt tacccacnn anctaattc accctancccc cctt stn tc | 540 |

```
ctcttnccat tccggttccc taacntangg ggccttngtc caatattttn gcccccccca    600
a                                                                    601
```

```
<210> SEQ ID NO 8
<211> LENGTH: 626
<212> TYPE: DNA
<213> ORGANISM: Artificial Sequence
<220> FEATURE:
<223> OTHER INFORMATION: Mouse peripherin cDNA sequences mouse
      peripherin 5'UTR sequences/ the ATG start site/mouse peripherin
      coding sequences are included.
<220> FEATURE:
<221> NAME/KEY: n
<222> LOCATION: (1)..(626)
<223> OTHER INFORMATION: any

<400> SEQUENCE: 8
ttcnntgnaa attgcgccna aaananaagg gcngcttact ggcttatcna anttaatacg     60
actcactata gggagaccca agcttgcatg cctgcagggg ggggggaagg actctgcaga   120
tacggcggcc taaattaact ccggctaccg ttactgantt aacggggatc ccaagctagg   180
gaggcccaa aatgggcaac tccctgcagc ttgggcccat ggtgctcttc cctanaccct    240
agcggtccag ccccgganct cactcggatt angagtggaa gctgaaccgt gggangctgc   300
tgaacgcact cngtaagcat ggcgctgctc aaagtcnagt ttgaccagaa gaaacnggtc   360
aagttggccc aagggctctg gctttatgaa ctggctgtcc gtgttnggcg gcatcgtccc   420
tcntcagctt ggggctgttc ttgaanattg aactttcccc aagaagaacc aaagtgatga   480
ataatttctg aaanccnctt ttgtncccaa ctccctgata ggggtggggg tcctgtccnt   540
nttcttnact ctctggctgg gaaaatttgc tnttnaancc ctgganccccg ccaantncnc   600
cnnttggaaa ccctgctcga aaccct                                        626
```

```
<210> SEQ ID NO 9
<211> LENGTH: 617
<212> TYPE: DNA
<213> ORGANISM: Artificial Sequence
<220> FEATURE:
<223> OTHER INFORMATION: Mouse peripherin cDNA with altered non-coding
      sequences mouse rhodopsin 5'UTR sequences/the ATG start site/mouse
      peripherin coding sequences are included.
<220> FEATURE:
<221> NAME/KEY: n
<222> LOCATION: (1)..(617)
<223> OTHER INFORMATION: any

<400> SEQUENCE: 9
tnaccattcg nntaaanctn tcnnnccta ananaaccca ctggcttact ggcttatcga      60
aattaatacg actcactata gggagaccca agcttgagtt gcgctgtggg agccgtcagt   120
ggctgagctc gccaagcagc cttggtctct gtctacgaag agcccgtggg gcagcctcga   180
gagccgcagc catggcgctg ctcaaagtca gtttgaccaa gaagaagcgg gtcaagttgg   240
cccagggggct ctggcttatg aactggctgt ccgtgttggc cggcatcgtc ctcttcagct   300
tgggctgtt cttgaagatt gaacttcgca agaggagcga agtgatgaat aattctgaga   360
gccactttgt gcccaactcc ctgatanggg tggggtcct gtcctgtgtc ttcaactctc   420
tggctgggaa gatctgctat gatgccctgg aaccggccaa gtacgccaag tggaaccct    480
ggctgaagcc gtacctggct gtctgcatct tctttaacgt catcctcttc cggtggntct   540
ctgctgcttc tgttgcgggg tccctggaaa acaccnggct tacggacnca aaatngggat   600
```

```
gaattttttt cnggata                                                   617

<210> SEQ ID NO 10
<211> LENGTH: 610
<212> TYPE: DNA
<213> ORGANISM: Artificial Sequence
<220> FEATURE:
<223> OTHER INFORMATION: Ribozyme 17 sequence is included.
<220> FEATURE:
<221> NAME/KEY: n
<222> LOCATION: (1)..(610)
<223> OTHER INFORMATION: any

<400> SEQUENCE: 10
nnctnnntnt ttnatcgccc tctctggcta antcanagaa cccactgctt actggcttat    60
cgaaattaat acgactcact atagggtaga cccaagcttc actcctctga tgagtccgtg  120
aggacgaaat ccgagttcta gagggccta ttctatagtg tcacctaaat gctagagctc   180
gctgatcagc ctcgactgtg ccttctagtt gccagccatc tgttgtttgc ccctcccccg  240
tgccttcctt gaccctggaa ggtgccactc ccactgtcct ttcctaataa aatgaggaaa  300
ttgcatcgca ttgtctgagt aagtgtcatt ctattctggg gggtggggtg gggcangaca  360
acaaggggga agattgggaa aacaataaca ggcatgctgg ggatgcggtg ggctctatgg  420
ctcctgaagc gaaaaaacca ctgggctct agggggttcc ccccccctg tacngccatt    480 aacncgnggt ntgtggtacc ccacnnacgt aattgcaccc taccncttc ntctcctctt   540 ctccattcng gttcccccaa cnaaggggc ccttggttca atttttttnn gccccccna    600 nntnaagttc                                                          610

<210> SEQ ID NO 11
<211> LENGTH: 630
<212> TYPE: DNA
<213> ORGANISM: Artificial Sequence
<220> FEATURE:
<223> OTHER INFORMATION: Human peripherin cDNA sequences human
      peripherin 5'UTR sequences/ the ATG start site/human
      peripherin coding sequences are included.
<220> FEATURE:
<221> NAME/KEY: n
<222> LOCATION: (1)..(630)
<223> OTHER INFORMATION: any

<400> SEQUENCE: 11
nnncttntta ttcttcagcg tgccngacca ngantatccc ctgctcaagc tgtgattccg    60
agacccctgc caccactact gcattcacgg ggnatcccag gctagtggga ctcgacatgg   120 gtancccca gggcagctcc ctacagcttg ggccatctgc acttttccca aggccctaag    180
tctccgcctc tgggctcgtt aaggtttggg gtgggagctg tgctgtggga agcaacccgg   240
actacacttg gcaagcatgg cgctactgaa agtcaagttt gaccaaaaaa agcgggtcaa   300
gttggcccaa gggctctggc tcatgaactg gttctccgtg ttggctggca tcatcatctt   360
cagcctagga ctgttcctga anattgaact ccgaaagaag ancgatgtga tgaataaatt   420
ctgaaancca ttttgtgccc aactcattga tanggatggg ggtgctatcc tgtgtcttca   480
actcnctggn tgggaanatc tgctacaacg ccctggaacc anccaatttg ccaaatggaa   540
ccctggctga aaccgtacct ggctatctgt nttcncctcc aaatcatccc cttccttgtg   600
ggtctctgct gctttccngc tccggggccc                                    630

<210> SEQ ID NO 12
<211> LENGTH: 612
```

<212> TYPE: DNA
<213> ORGANISM: Artificial Sequence
<220> FEATURE:
<223> OTHER INFORMATION: Human peripherin cDNA with altered non-coding sequences. Partial human and mouse peripherin 5'UTR sequences/the ATG start site/human peripherin coding sequences are included.
<220> FEATURE:
<221> NAME/KEY: n
<222> LOCATION: (1)..(612)
<223> OTHER INFORMATION: any

<400> SEQUENCE: 12

```
cnctattcaa acttgnccct gcaagtcgac nntanaggat cttcccagcc agcgagttga      60
agacacagga tagcacccccc atccctatca atgagttggg cacaaaatgg ctctcagaat    120
tattcatcac atcgctcctc tttcggagtt cgatcttcag gaacagtcct aggctgaaga    180
tgatgatgcc agccaacacg gagaaccant tcatgagcca gagcccttgg gccaacttga    240
cccgcttctt ctggtcaaac ttgactttca gtagcgccat gcttaccgag tgcgttcagc    300
agcctcccac ggttcagctt ccactcctaa tccgagtgag ctccggggct ggaccgctan    360
ggtctaagga anancaccat gggcccaagc tgcagggant tgcccatttt ggggcctgga    420
tccccgtgaa tgcantaatg gtggcagggg tctcggaatc acagcttgag cagggatagt    480
cctggtcctg ggcgctgaaa aaatcnccta tantgagtcg tatacaatca ctgggcgtcg    540
tttacaacgt ctgaatggga aaccctggnt tacccaactt aatcgcctgg aacacatccc    600
ctttcncanc tg                                                         612
```

<210> SEQ ID NO 13
<211> LENGTH: 619
<212> TYPE: DNA
<213> ORGANISM: Artificial Sequence
<220> FEATURE:
<223> OTHER INFORMATION: Ribozyme 8 sequence cloned in pcDNA3.
<220> FEATURE:
<221> NAME/KEY: n
<222> LOCATION: (1)..(619)
<223> OTHER INFORMATION: any

<400> SEQUENCE: 13

```
ctcnnntttn aacaganctg cngctaacta nagaaccact gcttactggc ttatcgaaat      60
taatacgact cactataggg agacccaagc ttccaagtgc tgatgagtcc gtgaggacga    120
aagtccggtc tagagggccc tattctatag tgtcacctaa atgctagagc tcgctgatca    180
gcctcgactg tgccttctag ttgccagcca tctgttgttt gccccctccc cgtgccttcc    240
ttgaccctgg aangtgccac tcccactgtc ctttcctaat aaaatgagga aattgcatcg    300
cattgtctga gtaggtgtca ttctattctg gggggtgggg tggggcanga cancaagggg    360
gaagattggg aagacaatan cangcatgct ggggatgcgg tgggctctat ggcttctgaa    420
gcggaaagaa ccanctgggg ctctaagggg tatccccacg cnccctgtaa cggcgcatta    480
accccgcggt gttgttgtta cccccaacnt gaccgctaca cttgccaacc cctaaccccg    540
ctcctttcct ttcttccttc cttctcncac tttcccngct tcccntcaac tctaatcggg    600
gccccttagg ttcaattat                                                  619
```

<210> SEQ ID NO 14
<211> LENGTH: 760
<212> TYPE: DNA
<213> ORGANISM: Artificial Sequence
<220> FEATURE:
<223> OTHER INFORMATION: Ribozyme 9 sequence cloned in pcDNA3.
<220> FEATURE:

```
<221> NAME/KEY: n
<222> LOCATION: (1)..(760)
<223> OTHER INFORMATION: any

<400> SEQUENCE: 14
nnnnnntttt naacaganct ccggctaact anagaaccac tgcttactgg cttatcgaaa      60
ttaatacgac tcactatagg gagacccaag cttcaaacct tctgatgagt ccgtgaggac     120
gaaacgagcc tctagagggc cctattctat agtgtcacct aaatgctaga gctcgctgat     180
cagcctcgac tgtgccttct agttgccagc catctgttgt ttgcccctcc cccgtgcctt     240
ccttgaccct ggaangtgcc actcccactg tcctttccta ataaaatgag gaaattgcat     300
cgcattgtct gagtangtgt cattctattc tggggggtgg ggtggggcaa ggacancaag     360
ggggaagatt gggaagacaa tancangcat gctggggatg cggtgggctc tatggcttct     420
gaagcggaaa gaaccanctg gggctctaag gggtatcccc acgcgccctg taaccgcgca     480
ttaaccccgc nggtntgttg gttaccccca cgtgaccgct acacttgcca accccctaacc    540 ccgctccttt ccctttcttc cttccttctc ccactttncc ggnttcccct caactctaat     600
cngggcncct taggttcaat tatcttacgn cncanccaaa atgataggta angtcntttt     660
ggccncccta aaaaggtttc ccttnattga tcccttctta natgancttt ccaatgaaaa    720
ccaccnncgt cttcttaata angattgcat cgccttgtaa                           760

<210> SEQ ID NO 15
<211> LENGTH: 620
<212> TYPE: DNA
<213> ORGANISM: Artificial Sequence
<220> FEATURE:
<223> OTHER INFORMATION: Human type I collagen (COL1A2) sequence - 5'UTR
      and exon 1 sequence are included.
<220> FEATURE:
<221> NAME/KEY: n
<222> LOCATION: (1)..(620)
<223> OTHER INFORMATION: any

<400> SEQUENCE: 15
cnnctnnntn ttttntngcn tctcnggcta acngacagaa cccactgctt actggcttat      60
cgaaattaat acgactcact atagggagac ccaagcttag caccacggca gcaggaggtt    120
tcggctaagt tggaggtact ggccacgact gcatgcccgc gcccgccatg tgatacctcc    180
gccggtgacc cagggctctg cgacacaagg agtcgcatgt ctaagtgcta gacatgctca    240
gctttgtgga tacgcggact ttgttgctgc ttgcagtaac ctcatgccta gcaacatgcc    300
aatctcgagc atgcatctan anggccctat tctatagtgt cncctanatg ctaganctcg    360
ctgatnagcc tcgactgtgc cttctaattg ccagccatct gtngtttggc cctcccccgt    420
gccttccttg aacctggaag gtgccactcc cactgtcctt tcctaataaa atgaagaaat    480
tgcatcncat gtctgantag tgtcatctat ctgggggtgg gtngggcagg anaccaggga    540
gatggaaaaa atacagcttc tgggaacgtg gcctatgctc tnagngaaaa aactggggct    600
agggttcccc ccccntncgc                                                 620

<210> SEQ ID NO 16
<211> LENGTH: 621
<212> TYPE: DNA
<213> ORGANISM: Artificial Sequence
<220> FEATURE:
<223> OTHER INFORMATION: Ribozyme 18 sequence cloned in pcDNA3.
<220> FEATURE:
<221> NAME/KEY: n
<222> LOCATION: (1)..(621)
```

<223> OTHER INFORMATION: any

<400> SEQUENCE: 16

```
agcagantct ctggctaact anagaaccca ctgcttactg gcttatcgaa attaatacga      60
ctcactatag ggagacccaa gcttagacat gcctgatgag tccgtgagga cgaaactcct     120
ttctagaggg ccctattcta tagtgtcacc taaatgctag agctcgctga tcagcctcga     180
ctgtgccttc tagttgccag ccatctgttg tttgcccctc ccccgtgcct tccttgaccc     240
tggaaggtgc cactcccact gtcctttcct aataaaatga ggaaattgca tcgcattgtc     300
tgagtaggtg tcattctatt ctgggggtg gggtggggca ngacancaag ggggangatt      360
gggaagacaa tancangcat gctggggatg cggtgggctc tatggcttct gangcggaaa     420
gaaccanctg gggctctagg ggtatcccca cnccoctgta ccggccatta agcccgcggt     480
gttgtngtta ccccaantga cgctacactg ccacgcctac gccctccttc cttctccctc     540
cttctcccat tccccggttc ccctcancct aatcggggcc cttaggttcc aatattctta     600
cgncnccacc caaantaatn g                                               621
```

<210> SEQ ID NO 17
<211> LENGTH: 644
<212> TYPE: DNA
<213> ORGANISM: Artificial Sequence
<220> FEATURE:
<223> OTHER INFORMATION: Antisense construct containing 127 bp of antisense sequence targeting the 5'UTR of the mouse peripherin gene.
<220> FEATURE:
<221> NAME/KEY: n
<222> LOCATION: (1)..(644)
<223> OTHER INFORMATION: any

<400> SEQUENCE: 17

```
atggttatcg aattaatacg actcactata ngGagaccca agcttccatg cttaccgagt      60
gcgttcagca gcctcccacg gttcagcttc cactcctaat ccgagtgagc tccggggctg     120
gaccgctagg gtctanggaa gagcaccatt ctagagggcc ctattctata gtgtcaccta     180
aatgctagag ctcgctgatc agcctcgact gtgccttcta nttgccagcc atctgttgtt     240
tgcccctccc ccgtgccttc cttgaccctg gaangtgcca ctcccactgt nctttcctaa     300
aaaaatgagg aaattgcatc gcattgtctg actaagtgtc attctattct gggggtggg      360
gtggggcacg acaacaangg ggaagattgg qaanacaata acacgcatgc ngggatgcc      420
gtggggctct atggcttctg aagcggaaag aacaactggg gcnctagggg tatcccacac     480
gccctgtacc gggctttaac gcggnggtgt tgtggttacc ccaacttgac gctacacttt     540
ccaacgccta ncgccgctct ttcctttctt ccctccattc ccccaattcc ccgntttccc     600
cccnnnnnnn nnnnncncnc nnnaantnng ggggccctn nggg                       644
```

<210> SEQ ID NO 18
<211> LENGTH: 603
<212> TYPE: DNA
<213> ORGANISM: Artificial Sequence
<220> FEATURE:
<223> OTHER INFORMATION: Sense construct containing 127 bp of sense sequence from the 5'UTR of the mouse peripherin gene.
<220> FEATURE:
<221> NAME/KEY: n
<222> LOCATION: (1)..(603)
<223> OTHER INFORMATION: any

<400> SEQUENCE: 18

```
nngnnnnnnn ncntatggtt atcgaattaa tacgactcac tatagggaga cccaagctta      60
tggtgctctt ccctanaccc tancggtcca gccccggagc tcactcggat taggagtgga     120
agctgaaccg tgggaggctg ctgaacgcac tcggtaagca tggtctanag ggccctattc     180
tatagtgtca cctaaatgct agagctcgct gatcagcctc gactgtgcct tctagttgcc     240
agccatctgt tgtttgcccc tccccgtgc cttccttgac cctggaaggt gccactccca      300
ctgtcctttc ctaataaaat gaggaaattg catcgcattg tctgagtaag tgtcattcta     360
ttctgggggg tggggtgggg cangacaaca agggggaaga ttgggaanac aataacangc     420
atgctgggga tgccgtgggc tctatggctt ctgaagcgga aanaaccact ggggctctaa     480
ggggtatccc caccccctg taccggccat aacccgcgg tttgtggtta ccccactnac      540
gtaccttgca cgcctacccc cnccttcctc ttcctccttc cccnttccgg ttcccnnann     600
nnn                                                                  603

<210> SEQ ID NO 19
<211> LENGTH: 607
<212> TYPE: DNA
<213> ORGANISM: Artificial Sequence
<220> FEATURE:
<223> OTHER INFORMATION: Reverse Mouse Rhodopsin cDNA with altered
      non-coding sequences mouse rhodopsin 5'UTR sequences with a 1
      base change/the ATG start site/mouse rhodopsin coding sequences
      are included.
<220> FEATURE:
<221> NAME/KEY: n
<222> LOCATION: (1)..(607)
<223> OTHER INFORMATION: any

<400> SEQUENCE: 19 nnccttctt anngtnngct gccagcatgg agaatgccat ggttccgcca ggtagtactg       60
cggctgctcg aagggctcc gcaccacgcc tgtgacgttg gagaagggca cataaaatt       120
tgggccctct gtgccgttca tgtttgccaa gtgtagtccg ggttgcttcc cacagcacag    180
ctcccacccc aaaccttaac gagcccagag gcggagactt agggccttgg gaaaagtgca    240
gatggcccaa gctgtangga gctgcccctgg gggctaccca tgtcgagtcc cactagcctg   300
ggatccccgt gaatgcanta ntggtggcag gggtctcgga atcacagctt gagcagggga   360
tagtcctggt cctgggcgct gaancttggg tctccctata ntgagtcgta ttaatttcga   420
taagccanta agcantgggt tctctagtta gccagaaanc tctgcttata tagaactccc   480
accgtacacg cctaccgccc atttgcgtca tggggggagt gttacaaatt tggaaatccn   540
ttgaattngg ggccaaaaaa atcccatgan ttcatgggtg gaaattgaaa tccctgatt    600
caaccct                                                             607

<210> SEQ ID NO 20
<211> LENGTH: 615
<212> TYPE: DNA
<213> ORGANISM: Artificial Sequence
<220> FEATURE:
<223> OTHER INFORMATION: Reverse Mouse Rhodopsin cDNA with altered
      non-coding sequences mouse rhodopsin 5'UTR sequences with a 1
      base change/the ATG start site/mouse rhodopsin coding sequences
      are included.
<220> FEATURE:
<221> NAME/KEY: n
<222> LOCATION: (1)..(615)
<223> OTHER INFORMATION: any

<400> SEQUENCE: 20
ttnnntntnn ttngactgtt gnccgccaan atggaganqt gccatggttc cgccaggtag     60
```

-continued

```
tactgcggct gctcgaagag gctccgcacc acgcctgtga cgttggagaa gggcacataa      120
aaattggggc cctctgtgcc gttcatggct gcggctctcg aggctgcccc acgggctctt      180
cgtagccaga gaccaaggct gcttggcgag ctcagccact gacggctccc acagcgcaac      240
tccaggcact gacccccccc agacccttat aaagtgacct tctctccctc agccagangc      300
tgattcagca tccgcgagat atcatactaa cgctaatccc actgctgcca ccggggccta      360
attggcttgc agangggcca aggtgacatc gggtggaagc ccttangtaa agaaaggaaa      420
nggtgtctca tcttgtctgc cccagantcc tctgggaatt ccagcacact ggcgggcgtt      480
actantggat ccganctcng taccaagctt gggtctccta taatgagtcc tattaatttc      540
gataaccata acagtgggtt ctctanttac cagaaactct gcttatataa actcccacgt      600
acacnctacg ccatt                                                       615
```

<210> SEQ ID NO 21
<211> LENGTH: 37
<212> TYPE: RNA
<213> ORGANISM: Artificial Sequence
<220> FEATURE:
<223> OTHER INFORMATION: Rib3

<400> SEQUENCE: 21
cuucguacug augaguccgu gaggacgaaa cagagac                               37

<210> SEQ ID NO 22
<211> LENGTH: 36
<212> TYPE: RNA
<213> ORGANISM: Artificial Sequence
<220> FEATURE:
<223> OTHER INFORMATION: Rib15

<400> SEQUENCE: 22
acccaagcug augaguccgu gaggacgaaa ugcugc                                36

<210> SEQ ID NO 23
<211> LENGTH: 37
<212> TYPE: RNA
<213> ORGANISM: Artificial Sequence
<220> FEATURE:
<223> OTHER INFORMATION: Rib17

<400> SEQUENCE: 23
cacuccucug augaguccgu gaggacgaaa uccgagu                               37

<210> SEQ ID NO 24
<211> LENGTH: 36
<212> TYPE: RNA
<213> ORGANISM: Artificial Sequence
<220> FEATURE:
<223> OTHER INFORMATION: Rib8

<400> SEQUENCE: 24
ccaagugcug augaguccgu gaggacgaaa guccgg                                36

<210> SEQ ID NO 25
<211> LENGTH: 37
<212> TYPE: RNA
<213> ORGANISM: Artificial Sequence
<220> FEATURE:
<223> OTHER INFORMATION: Rib9

<400> SEQUENCE: 25

```
caaaccuucu gaugaguccg ugaggacgaa acgagcc                              37
```

<210> SEQ ID NO 26
<211> LENGTH: 37
<212> TYPE: RNA
<213> ORGANISM: Artificial Sequence
<220> FEATURE:
<223> OTHER INFORMATION: Rib18

<400> SEQUENCE: 26

```
agacaugccu gaugaguccg ugaggacgaa acuccuu                              37
```

What is claimed is:

1. A therapeutic composition for treating a genetic disease, the composition comprising:
   a) a suppression effector that binds to an untranslated region of a mature RNA encoding a mutant allele, wherein said suppression effector inhibits the expression of the mutant allele; and
   b) a replacement nucleic acid that encodes a wild-type or non-disease causing allele and that is not inhibited by the suppression effector.

2. The composition of claim 1, wherein the suppression effector is a nucleic acid or peptide nucleic acid (PNA).

3. The composition of claim 1, wherein the suppression effector is a peptide.

4. The composition of claim 1, wherein the suppression effector is an antisense nucleic acid.

5. The composition of claim 1, wherein the suppression effector cleaves or degrades mRNA.

6. The composition of claim 1, wherein the suppression effector is a ribozyme.

7. The composition of claim 1, wherein the suppression effector is a nucleic acid that forms a triple helix with a portion of the untranslated region of the mutant allele.

8. The composition of claim 1, wherein the suppression effector is specific for mammalian rhodopsin RNA.

9. The composition of claim 1, wherein the suppression effector is specific for mammalian peripherin RNA.

10. The composition of claim 1, wherein the suppression effector is specific for mammalian collagen RNA.

11. The composition of claim 1, wherein the replacement nucleic acid does not hybridize with, or is only partially suppressed by, the suppression effector.

12. The composition of claim 1, wherein the replacement nucleic acid encodes a protein selected from the group consisting of mammalian rhodopsin, collagen 1A2 and peripherin.

13. The composition of claim 1, wherein the suppression effector comprises a nucleic acid sequence selected from the group consisting of SEQ ID NOS: 7, 13, 14 and 16.

14. The composition of claim 1, wherein suppression effector is operatively linked to an expression vector.

15. The composition of claim 1, wherein the replacement nucleic acid is operatively linked to an expression vector.

16. The composition of claim 1, wherein the suppression effector and the replacement nucleic acid are operatively linked to the same expression vector.

17. The composition of claim 1, wherein the untranslated region is essentially a 5' untranslated region.

18. The composition of claim 1, wherein the untranslated region is essentially a 3' untranslated region.

19. The composition of claim 17 or 18, wherein the suppression effector binds to said untranslated region and to a portion of the coding sequence.

20. The composition of claim 1, wherein the genetic disease is an autosomal dominant disease or a polygenic disease.

21. The composition of claim 1, wherein the genetic disease is osteogenesis imperfecta, retinitis pigmentosa, age-related macular degeneration, glaucoma, manic depression or cancer.

22. A therapeutic composition for suppressing the expression of a mutant allele of a protein, the composition comprising:
   a) a ribozyme that targets an untranslated region of a mature RNA encoding a mutant allele; and
   b) a replacement nucleic acid that encodes a wild-type or non-disease causing allele and that is not targeted by the ribozyme.

23. The composition of claim 22, wherein the ribozyme cleavage site is an NUX site.

24. The composition of claim 22, wherein the ribozyme is specific for mammalian rhodopsin RNA.

25. The composition of claim 22, wherein the ribozyme is specific for mammalian peripherin RNA.

26. The composition claim 22, wherein the ribozyme is specific for mammalian collagen RNA.

27. The composition of claim 22, wherein the replacement nucleic acid does not hybridize with, or is only partially suppressed by, the ribozyme.

28. The composition of claim 22, wherein the replacement nucleic acid encodes a protein selected from the group consisting of mammalian rhodopsin, collagen 1A2 and peripherin.

29. The composition of claim 22, wherein the suppression effector comprises a nucleic acid sequence selected from the group consisting of SEQ ID NOS: 7, 13, 14 and 16.

30. The composition of claim 22, wherein the ribozyme is operatively linked to an expression vector.

31. The composition of claim 22, wherein the replacement nucleic acid is operatively linked to an expression vector.

32. The composition of claim 22, wherein the ribozyme and the replacement nucleic acid are operatively linked to the same expression vector.

33. The composition of claim 22, wherein the untranslated region is essentially a 5' untranslated region.

34. The composition of claim 22, wherein the untranslated region is essentially a 3' untranslated region.

35. The composition of claim 33 or 34, wherein the ribozyme binds to said untranslated region and to a portion of the coding sequence.

UNITED STATES PATENT AND TRADEMARK OFFICE
CERTIFICATE OF CORRECTION

PATENT NO. : 6,713,457 B2
DATED : March 30, 2004
INVENTOR(S) : Farrar et al.

It is certified that error appears in the above-identified patent and that said Letters Patent is hereby corrected as shown below:

Columns 1-42 should be deleted and replaced with the attached pages consisting of columns 1-46.

Signed and Sealed this

Thirtieth Day of May, 2006

JON W. DUDAS
*Director of the United States Patent and Trademark Office*

STRATEGY FOR SUPPRESSING THE EXPRESSION OF AN ENDOGENEOUS GENE BY USING COMPOUNDS THAT ARE ABLE TO BIND TO THE NON-CODING REGIONS OF THE GENE TO BE SUPPRESSED

REFERENCE TO RELATED APPLICATIONS

This application was filed under 35 U.S.C. §371 for, and claims priority to, PCT/GB96/02357, filed Sep. 23, 1996, which claims priority to GB9519299.3, filed Sep. 21, 1995, the disclosures of which are incorporated by reference herein.

FIELD OF THE INVENTION

The present invention relates to a strategy and medicaments for suppressing a gene. In particular the invention relates to the suppression of mutated genes which give rise to a dominant or deleterious effect either monogenically or polygenically. The invention relates to a strategy for suppressing a gene or disease allele such that (if required) a replacement gene, gene product or alternative gene therapy can be introduced.

The invention also relates to a medicament or medicaments for use in suppressing a gene or disease allele which is present in a genome of one or more individuals or animals. The said medicament(s) may also introduce the replacement gene sequence, product or alternative therapy.

Generally the strategy of the present invention will be useful where the gene, which is naturally present in the genome of a patient, contributes to a disease state. Generally, the gene in question will be mutated, that is, will possess alterations in its nucleotide sequence that affect the function or level of the gene product. For example, the alteration may result in an altered protein product from the wild type gene or altered control of transcription and processing. Inheritance or the somatic acquisition of such a mutation can give rise to a disease phenotype or can predispose an individual to a disease phenotype. However the gene of interest could also be of wild type phenotype, but contribute to a disease state in another way such that the suppression of the gene would alleviate or improve the disease state.

BACKGROUND OF THE INVENTION

Studies of degenerative hereditary ocular conditions, including Retinitis Pigmentosa (RP) and various macular dystrophies have resulted in a substantial elucidation of the molecular basis of these debilitating human eye disorders. In a collaborative study, applying the approach of genetic linkage, two x-linked RP genes were localized to the short arm of the X chromosome (Ott et al. 1990). In autosomal dominant forms of RP (adRP) three genes have been localized. The first adRP gene mapped on 3q close to the gene encoding the photoreceptor specific protein rhodopsin (Mcwilliam et al. 1989; Dryja et al. 1990). Similarly, an adRP gene was placed on 6p close to the gene encoding the photoreceptor specific protein peripherin/RDS (Farrar et al. 1991a,b; Kajiwara et al. 1991). A third adRP gene mapped to 7q (Jordan et al. 1993); no known candidate genes for RP reside in this region of 7q. In addition, the disease gene segregating in a Best's macular dystrophy family was placed on 11q close to the region previously shown to be involved in some forms of this dystrophy (Mansergh et al. 1995). Recently, an autosomal recessive RP gene was placed on 1q (Van Soest et al. 1994). Genetic linkage, in combination with techniques for rapid mutational screening of candidate genes, enabled subsequent identification of causative mutations in the genes encoding rhodopsin and peripherin/RDS proteins. Globally about 100 rhodopsin mutations have now been found in patients with RP or congenital stationary night blindness. Similarly about 40 mutations have been characterised in the peripherin/RDS gene in patients with RP or with various macular dystrophies.

Knowledge of the molecular etiology of some forms of human inherited retinopathies has stimulated the establishment of methodologies to generate animal models for these diseases and to explore methods of therapeutic intervention; the goal being the development of treatments for human retinal diseases (Farrar et al. 1995). Surgical procedures enabling the injection of sub-microliter volumes of fluid intravitreally or sub-retinally into mouse eyes have been developed by Dr. Paul Kenna. In conjunction with the generation of animal models, optimal systems for delivery of gene therapies to retinal tissues using viral (inter alia Adenovirus, Adeno Associated Virus, Herpes Simplex Type 1 Virus) and non-viral (inter alia liposomes, dendrimers) vectors alone or in association with derivatives to aid gene transfer are being investigated.

Generally, gene therapies utilizing both viral and non-viral delivery systems have been applied in the treatment of a number of inherited disorders; of cancers and of some infectious disorders. The majority of this work has been undertaken on animal models, although, some human gene therapies have been approved. Many studies have focused on recessively inherited disorders, the rationale being, that the introduction and efficient expression of the wild type gene may be sufficient to result in a prevention/amelioration of disease phenotype. In contrast gene therapy for dominant disorders will require the suppression of the dominant disease allele. Notably the majority of characterised mutations that cause inherited retinal degenerations such as RP are inherited in an autosomal dominant fashion. Indeed there are over 1,000 autosomal dominantly inherited disorders in man. In addition there are many polygenic disorders due to the co-inheritance of a number of genetic components which together give rise to a disease phenotype. Effective gene therapy in dominant or polygenic disease will require suppression of the disease allele while in many cases still maintaining the function of the normal allele.

Strategies to differentiate between normal and disease alleles and to selectively switch off the disease allele using suppression effectors inter alia antisense DNA/RNA, ribozymes or triple helix DNA, targeted towards the disease mutation may be difficult in many cases and impossible in others—frequently the disease and normal alleles may differ by only a single nucleotide. For example, the disease mutation may not occur at a ribozyme cleavage site. Similarly the disease allele may be difficult to target specifically by antisense DNA/RNA or triple helix DNA if there are only small sequence differences between the disease and normal alleles. A further difficulty inhibiting the development of gene therapies is the heterogeneous nature of some dominant disorders—many different mutations in the same gene give rise to a similar disease phenotype. The development of specific gene therapies for each of these would be extremely costly. To circumvent the dual difficulties associated with specifically targeting the disease mutation and the genetic heterogeneity present in some inherited disorders, the present invention aims to provide a novel strategy for gene suppression and replacement exploiting the noncoding and control regions of a gene.

Suppression effectors have been used previously to achieve specific suppression of gene expression. Antisense DNA and RNA has been used to inhibit gene expression in many instances. Many modifications, such as phosphorothioates, have been made to antisense oligonucleotides to increase resistance to nuclease degradation, binding affinity and uptake (Cazenave et al. 1989; Sun et al. 1989; McKay et al. 1996; Wei et al. 1996). In some instances, using antisense and ribozyme suppression strategies has led to the reversal of the tumor phenotype by greatly reducing the expression of a gene product or by cleaving a mutant transcript at the site of the mutation (Carter and Lemoine 1993; Lange et al. 1993; Valera et al. 1994; Dosaka-Akita et al. 1995; Feng et al. 1995; Quattrone et al. 1995; Ohta et al. 1996). For example, neoplastic reversion was obtained using a ribozyme targeted to the codon 12 H-ras mutation in bladder carcinoma cells (Feng et al. 1995). Ribozymes have also been proposed as a means of both inhibiting gene expression of a mutant gene and of correcting the mutant by targeted trans-splicing (Sullenger and Cech 1994; Jones et al. 1996). Ribozymes can be designed to elicit autocatalytic cleavage of RNA targets. However the inhibitory effect of some ribozymes may be due in part to an antisense effect of the variable antisense sequences flanking the catalytic core which specify the target site (Ellis and Rodgers 1993; Jankowsky and Schwenzer 1996). Ribozyme activity may be augmented by the use of non-specific nucleic acid binding proteins or facilitator oligonucleotides (Herschlag et al. 1994; Jankowsky and Schwenzer 1996). Triple helix approaches have also been investigated for sequence specific gene suppression—triplex forming oligonucleotides have been found in some cases to bind in a sequence specific manner (Postel et al. 1991; Duval-Valentin et al. 1992; Hardenbol and Van Dyke 1996; Porumb et al. 1996). Similarly peptide nucleic acids have been shown in some instances to inhibit gene expression (Hanvey et al. 1992; Knudson and Nielsen 1996). Minor groove binding polyamides have been shown to bind in a sequence specific manner to DNA targets and hence may represent useful small molecules for future suppression at the DNA level (Trauger et al. 1996). In addition, suppression has been obtained by interference at the protein level using dominant negative mutant peptides and antibodies (Herskowitz 1987; Rimsky et al. 1989; Wright et al. 1989). In some cases suppression strategies have lead to a reduction in RNA levels without a concomitant reduction in proteins, whereas in others, reductions in RNA levels have been mirrored by reductions in protein levels.

SUMMARY OF THE INVENTION

The present invention aims to circumvent the shortcomings in the prior art by using a two step approach for suppression and replacement.

According to the present invention there is provided a strategy for suppressing expression of an endogenous gene, wherein said strategy comprises providing suppression effectors able to bind to the non-coding regions of a gene to be suppressed, to prevent the functional expression thereof. Preferably the suppression effectors are antisense nucleic acids. Preferably the targeted non-coding regions include the transcribed but non-translated regions of a gene.

Generally the term suppression effectors includes nucleic acids, peptide nucleic acids (PNAs) or peptides which can be used to silence or reduce gene expression in a sequence specific manner.

The antisense nucleic acids can be DNA or RNA, can be directed to 5' and/or 3' untranslated regions and/or to introns and/or to control regions or to any combination of such untranslated regions. However targeted the binding of the antisense nucleic acid prevents or lowers the functional expression of the endogenous gene. Chimeric antisense nucleic acids including a small proportion of translated regions of a gene can be used in some cases to help to optimize suppression. Likewise chimeric antisense nucleic acids including a small proportion of promoter regions of a gene can be used in some cases to help to optimize suppression.

Generally the term 'functional expression' means the expression of a gene product able to function in a manner equivalent to or better than a wild type product. In the case of a mutant gene 'functional expression' means the expression of a gene product whose presence gives rise to a deleterious effect.

In a particular embodiment of the invention the strategy further employs ribozymes. These can be designed to elicit cleavage of target RNAs.

The strategy further employs nucleotides which form triple helix DNA.

Nucleic acids for antisense, ribozymes and triple helix may be modified to increase stability, binding efficiencies and uptake as discussed earlier. Nucleic acids can be incorporated into a vector. Vectors include DNA plasmid vectors, RNA or DNA virus vectors. These can be combined with lipids, polymers or other derivatives to aid gene delivery and expression.

The invention further provides the use of antisense nucleotides, ribozymes, triple helix nucleotides or other suppression effectors alone or in a vector or vectors, wherein the nucleic acids are able to bind specifically to untranslated regions of a gene such as the 5' and 3' UTRs to prevent the functional expression thereof, in the preparation of a medicament for the treatment of an autosomal dominant disease.

In a further embodiment the non-coding regions of the gene can include promoter regions which are untranslated.

According to the present invention there is provided a strategy for suppressing an endogenous gene and introducing a replacement gene, said strategy comprising the steps of:

1. providing antisense nucleic acid able to bind to at least one non-coding or untranslated region of a gene to be suppressed and
2. providing genomic DNA or cDNA encoding a replacement gene sequence, wherein the antisense nucleic acid is unable to bind to equivalent non-coding or untranslated regions in the genomic DNA or cDNA to prevent expression of the replacement gene sequence.

The replacement nucleic acids will not be recognized by the suppression nucleic acid. The control sequences of the replacement nucleic acid may belong to a different mammalian species, may belong to a different human gene or may be similar but altered from those in the gene to be suppressed and may thus permit translation of the part of the replacement nucleic acid to be initiated.

By control sequences is meant sequences which are involved in the control of gene expression or in the control of processing and/or sequences present in mature RNA transcripts and/or in precursor RNA transcripts, but not including protein coding sequences.

In a particular embodiment of the invention there is provided a strategy for gene suppression targeted towards the non-coding regions of a gene and using a characteristic of one of the alleles of a gene, for example, the allele carrying a disease mutation. Suppressors are targeted to non-coding regions of a gene and to a characteristic of one allele of a gene such that suppression in specific or partially specific to one allele of the gene. The invention further provides for replacement nucleic acids containing altered non-coding sequences such that replacement nucleic acids cannot be recognized by suppressors which are targeted towards the non-coding regions of a gene. Replacement nucleic acids provide the wild type or an equivalent gene product but are protected completely or in part from suppression effectors targeted to non-coding regions.

In a further embodiment of the invention there is provided replacement nucleic acids with altered non-coding sequences such that replacement nucleic acids cannot be recognized by naturally occurring endogenous suppressors present in one or more individuals, animals or plants. Replacement nucleic acids with altered non-coding sequences provide the wild type or equivalent gene product but are completely or partially protected from suppression by naturally occurring endogenous suppression effectors.

In an additional embodiment of the invention there is provided replacement nucleic acids with altered non-coding sequences such that replacement nucleic acids provide a wild type or equivalent gene product or gene product with beneficial characteristics. For example, the 3' non-coding sequences of the replacement nucleic acids could be altered to modify the stability and turn over the RNA expressed from the replacement nucleic acids thereby sometimes affecting levels of resulting gene product.

The invention further provides the use of a vector or vectors containing suppression effectors in the form of nucleic acids, said nucleic acids being directed towards untranslated regions or control sequences of the target gene and vector(s) containing genomic DNA or cDNA encoding a replacement gene sequence to which nucleic acids for suppression are unable to bind, in the preparation of a combined medicament for the treatment of an autosomal dominant disease. Nucleic acids for suppression or replacement gene nucleic acids may be provided in the same vector or in separate vectors. Nucleic acids for suppression or replacement gene nucleic acids may be provided as a combination of nucleic acids alone or in vectors. The vector may contain antisense nucleic acid with or without, ribozymes.

The invention further provides a method of treatment for a disease caused by an endogenous mutant gene, said method comprising sequential or concomitant introduction of (a) antisense nucleic acids to the non-coding regions of a gene to be suppressed, to the 5' and/or 3' untranslated regions of a gene or intronic regions or to the non-control regions of a gene to be suppressed, (b) replacement gene sequence with control sequences which allow it to be expressed.

The nucleic acid for gene suppression can be administered before, after, or at the same time the replacement gene is administered.

The invention further provides a kit for use in the treatment of a disease caused by an endogenous mutation in a gene, the kit comprising nucleic acids for suppression able to bind to the 5' and/or 3' untranslated regions or intronic regions or control regions of the gene to be suppressed and (preferably packaged separately thereto) a replacement nucleic acid to replace the mutant gene having a control sequence to allow it to be expressed.

Nucleotides can be administered as naked DNA or RNA, with or without ribozymes and/or with dendrimers. Dendrimers (for example dendrimers of methylmethacrylate) can be utilized. It is believed the dendrimers mimic histones and as such are capable of transporting nucleic acids into cells. Oligonucleotides can be synthesized, purified and modified with phosphorothioate linkages and 2'0-allyl groups to render them resistant to cellular nucleases while still supporting RNase H medicated degradation of RNA. Also, nucleic acids can be mixed with lipids to increase efficiency of delivery to somatic tissues.

Nucleotides can be delivered in vectors. Naked nucleic acids or nucleic acids in vectors can be delivered with lipids or other derivatives which aid gene delivery. Nucleotides may be modified to render them more stable, for example, resistant to cellular nucleases while still supporting Rnase H mediated degradation of RNA or with increased binding efficiencies as discussed earlier.

Suppression effectors and replacement sequences can be injected sub-sectionally, or may be administered systemically.

DETAILED DESCRIPTION OF THE INVENTION

There is now an armament with which to obtain gene suppression. This, in conjunction with a better understanding of the molecular etiology of disease, results in an ever increasing number of disease targets for therapies based on suppression. In many cases, complete (100%) suppression of gene expression has been difficult to achieve. Possibly a combined approach using a number of suppression effectors may be required. For some disorders it may be necessary to block expression of a disease allele completely to prevent disease symptoms whereas for others low levels of mutant protein may be tolerated. In parallel with an increased knowledge of the molecular defects causing disease has been the realization that many disorders are genetically heterogeneous. Examples in which multiple genes and/or multiple mutations within a gene can give rise to a similar disease phenotype include osteogenesis imperfecta, familial hypercholesteremia, retinitis pigmentosa, and many others.

The invention addresses some shortcomings of the prior art and aims to provide a novel approach to the design of suppression effectors directed to target mutant genes. Suppression of every mutation giving rise to a disease phenotype may be costly, problematic and sometimes impossible. Disease mutations are often single nucleotide changes. As a result, differentiating between the disease and normal alleles may be difficult. Furthermore, some suppression effectors require specific sequence targets. For example, ribozymes can only cleave at NUX sites and hence will not be able to target some mutations. Notably, the wide spectrum of mutations observed in many diseases adds an additional layer of complexity in the development of therapeutic strategies for such disorders. A further problem associated with suppression is the high level of homology present in coding sequences between members of some gene families. This can limit the range of target sites for suppression which will enable specific suppression of a single member of such a gene family.

The strategy described herein has applications for alleviating autosomal dominant diseases. Complete silencing of a disease allele may be difficult to achieve using antisense, ribozyme and triple helix approaches or any combination of these. However small quantities of mutant product may be tolerated in some autosomal dominant disorders. In others a significant reduction in the proportion of mutant to normal product may result in an amelioration of disease symptoms. Hence this strategy may be applied to any autosomal dominantly inherited disease in man where the molecular basis of the disease has been established. This strategy will enable the same therapy to be used to treat a wide range of different disease mutations within the same gene. The development of strategies will be important to future gene therapies for some autosomal dominant diseases, the key to a general strategy being that it circumvents the need for a specific therapy for every dominant mutation in a given disease-causing gene. This is particularly relevant in some disorders, for example, rhodopsin linked autosomal dominant RP (adRP), in which to date about 100 different mutations in the rhodopsin gene have been observed in adRP patients. The costs of developing designer therapies for each individual mutation which may be present in some cases in a single patient are prohibitive at present. Hence strategies such as this using a more universally applicable approach for therapy will be required.

This strategy may be applied in gene therapy approaches for biologically important polygenic disorders affecting large proportions of the world's populations such as age related macular degeneration (ARMD), glaucoma, manic depression, cancers having a familial component and indeed many others. Polygenic diseases require the inheritance of more than one mutation (component) to give rise to the disease phenotype. Notably an amelioration in disease symptoms may require reduction in the presence of only one of these components, that is, suppression of one of the genotypes which, together with others, leads to the disease phenotype, may be sufficient to prevent or ameliorate symptoms of the disease. In some cases the suppression of more than one component giving rise to the disease pathology may be required to obtain an amelioration in disease symptoms. The strategy described here may be applied broadly to possible future interventive therapies in common polygenic diseases to suppress a particular genotype(s) and thereby suppress the disease phenotype.

In the present invention suppression effectors are designed specifically to target the non-coding regions of genes, for example, the 5' and 3' UTRs. This provides sequence specificity for gene suppression. In addition it provides greater flexibility in the choice of target sequence for suppression in contrast to suppression strategies directed towards single disease mutations. Furthermore it allows suppression effectors to target non-coding sequences 5' or 3' of the coding region thereby allowing the possibility of including the ATG start site in the target site for suppression and hence presenting an opportunity for suppression at the level of translation or inducing instability in RNA by, for example, cleavage of the RNA before the polyA tail. Notably the invention has the advantage that the same suppression strategy when directed to the 5' and 3' non-coding sequences could be used to suppress, in principle, any mutation in a given gene. This is particularly relevant when large numbers of mutations within a single gene cause a disease pathology. Suppression targeted to non-coding sequences allows, when necessary, the introduction of a replacement gene(s) with the same or similar coding sequences to provide the normal gene product. The replacement gene can be designed to have altered non-coding sequences and hence can escape suppression as it does not contain the target site(s) for suppression. The same replacement gene could in principle be used in conjunction with the suppression of any disease mutation in a given gene. In the case of suppression of an individual member of a gene family, the non-coding regions typically show lower levels of homology between family members thereby providing more flexibility and specificity in the choice of target sites for suppression. In relation to this aspect of the invention, the use of intronic sequences for suppression of an individual member of a family of genes has been described in a previous invention (REF: WO 92/07071). However the use of 5' and 3' non-coding sequences as targets for suppression holds the advantage that these sequences are present not only in precursor messenger RNAs but also in mature messenger RNAs, thereby enabling suppressors to target all forms of RNA. In contrast, intronic sequences are spliced out of mature RNAs.

In summary the invention can involve gene suppression and replacement such that the replacement gene cannot be suppressed. Both the same suppression and replacement steps can be used for many and in some cases all of the disease mutations identified in a given gene. Therefore the invention enables the same approach to be used to suppress a wide range of mutations within the same gene. Suppression and replacement can be undertaken in conjunction with each other or separately.

EXAMPLES

The present invention is exemplified using four different genes: human rhodopsin, human peripherin, mouse rhodopsin and mouse peripherin. While all four genes are retina-specific, there is no reason why the present invention could not be deployed in the suppression of other genes. Notably the 5'UTR and part of the coding sequence of the COL1A2 gene has been cloned together with a ribozyme to target the 5'UTR of the gene emphasizing the broad utility of the invention in gene suppression. The 5'UTR and part of the coding sequence of the COL1A2 gene in which there are many mutations have previously been identified which give rise to autosomal dominant osteogenesis imperfecta, has begun but was not completed at the time of submission. Many examples of mutant genes which give rise to disease phenotypes are available from the prior art—these all represent disease targets for this invention. The present invention is exemplified using ribozymes with antisense arms to elicit RNA cleavage. There is no reason why other suppression effectors directed towards the non-coding regions of genes could not be used to achieve gene suppression. Many examples from the prior art detailing the use of suppression effectors inter alia antisense RNA/DNA, triple helix, PNAs, peptides to achieve suppression of gene expression are reported as discussed earlier. The present invention is exemplified using ribozymes with antisense arms to elicit cleavage of template RNA transcribed from one vector and non-cleavage of replacement RNAs with altered untranslated region sequences transcribed from a second vector. There is no reason why both the suppression and replacement steps could not be in the same vector. In addition there is no reason why ribozymes could not be used to combine both the suppression and replacement steps, that is, to cleave the target RNA and to ligate to the cleavage product, a replacement RNA with an altered sequence, to prevent subsequent cleavage by ribozymes which are frequently autocatalytic as discussed. The present invention is exemplified using suppression effectors directed to target the 5' untranslated region of the above named genes. There is no reason why other non-coding regions of a gene inter alia the 3' untranslated region or the regions involved in the control of gene expression such as promoter regions or any combination of non-coding regions could not be used to achieve gene suppression. Suppression targeted to any non-coding region of a gene would allow the expression of a replacement gene with altered sequences in the non-coding region of the gene to which the suppression effector(s) was targeted.

MATERIALS AND METHODS

Cloning vectors cDNA templates, cDNA hybrids with altered non-coding sequences, ribozymes and antisense DNA fragments were cloned into commercial expression vectors (pcDNA3, pZeoSV or pBluescript) which enable expression in a test tube from T7, T3 or SP6 promoters or expression in cells from CMV or SV40 promoters. Inserts were placed into the multiple cloning site (MCS) of these vectors typically at or near the terminal ends of the MCS to delete most of the MCS and thereby prevent any possible problems with efficiency of expression subsequent to cloning.

Sequencing Protocols

Clones containing template cDNAs, hybrid cDNAs with altered non-coding sequences, ribozymes and antisense were sequenced by ABI automated sequencing machinery using standard protocols.

Expression of RNAs

RNA was obtained from clones in vitro using a commercially available Ribomax expression system (Promega) and standard protocols. RNA purifications were undertaken using the Bio-101 RNA purification kit or a solution of 0.3M sodium acetate and 0.2% SDS. Cleavage reactions were performed using standard protocols with varying $MgCl_2$ concentrations (0–15 mM) at 37°C. typically for 3 hours. Time points were performed at the predetermined optimal $MgCl_2$ concentrations for up to 5 hours. Radioactively labeled RNA products were obtained by incorporating $\alpha$-$P^{32}$ rUTP (Amersham) in the expression reactions (Gaughan et al. 1995). Labeled RNA products were run on polyacrylamide gels before cleavage reactions were undertaken for the purposes of RNA purification and subsequent to cleavage reactions to establish if RNA cleavage had been achieved.

The exact base at which transcription starts has not been defined fully for some promoters (pcDNA3 Invitrogen) hence the sizes of the RNA products may vary slightly from those predicted in Table 1. In addition multiple rounds of cloning of a cDNA results in inserts carrying extra portions of MCS again, sometimes altering marginally the size of expressed RNA products. Typically 4–8% polyacrylamide gels were run to resolve RNA products.

RNA Secondary Structures

Predictions of the secondary structures of human rhodopsin, mouse rhodopsin, human peripherin, mouse peripherin and human type I Collagen COLIA2 mRNAs where obtained using the RNAPlotFold program. Ribozyme and antisense was designed to target areas of the RNA that were predicted to be accessible to suppression effectors and which were composed of non-coding sequence. The integrity of open loop structures was evaluated from the 15 most probable RNA structures. Additionally RNA structures for truncated RNA products were generated and the integrity of open loops between full length and truncated RNAs compared.

TEMPLATE/HYBRID/RIBOZYME AND ANTISENSE CONSTRUCTS

EXAMPLES

Various products of the examples are illustrated in FIGS. 1 to 20 and are explained in the results sections.

Mouse Rhodopsin

Template cDNA

A full length mouse rhodopsin cDNA was generated from a partial cDNA clone missing the sequence coding for the first 20 amino acids of the protein and a partial genomic clone, which enabled the production of a full length cDNA (kindly donated by Dr. Wolfgang Baehr). The full length cDNA was cloned into the EcoRI site of pcDNA3 in a 5' to 3' orientation allowing subsequent expression of RNA from the T7 or CMV promoters in the vector. The full length 5'UTR sequence was present in this clone. In addition to the full length 5' UTR sequence the clone contains additional 5' upstream sequence of the mouse rhodopsin gene as the clone was generated using the EcoRI site present at position 1120 (Accession number: M55171). (SEQ ID NO:1)

Hybrid cDNAs with Altered Non-coding Regions

Hybrid I

The mouse rhodopsin hybrid cDNA sequence was altered in the non-coding sequences by PCR primer directed mutagenesis and cloned into the HindIII and EcoRI sites of pcDNA3 in a 5' to 3' orientation allowing subsequent expression of RNA from the T7 or CMV promoters in the vector. PCR mutagenesis was undertaken using a HindIII (in the MCS of pcDNA3) to Eco47111 (in Exon 2 of the gene) DNA fragment. The 5'UTR was altered significantly—the mouse rhodopsin 5'UTR was completely replaced by the 5'UTR of the human peripherin gene, that is, by 5'UTR sequence from a different gene (peripherin) and from a different species (human) but from a gene expressed in the same tissue as mouse rhodopsin, i.e., photoreceptor cells (SEQ ID NO: 2 (forward) and SEQ ID NO: 19 (reverse)). The sequence of the mouse rhodopsin cDNA is present in the clone from the ATG start onwards.

Hybrid 2

The mouse rhodopsin hybrid cDNA sequence was altered in the non-coding sequences to eliminate the GUC ribozyme binding site targeted in the 5'UTR of mouse rhodopsin. The U of the target was changed to G, that is, GUC→GGC (nucleotides 340–342 of SEQ ID NO:3). Again PCR mutagenesis was primer driven and was undertaken using a HindIII (in pcDNA3) to Eco47111 (in the coding sequence of the mouse rhodopsin cDNA) DNA fragment. (SEQ ID NO: 3 (forward) and SEQ ID NO: 20 (reverse)).

Ribozyme constructs

A hammerhead ribozyme (termed Rib3) designed to target an open loop structure in the RNA in the 5' non-coding region of the gene was cloned into the HindIII and XbaI sites of pcDNA3 again allowing subsequent expression of RNA from the T7 or CMV promoters in the vector (SEQ ID NO:4). The target site was GUC at position 1393–1395 of the mouse rhodopsin sequence (Accession number: M55171). Antisense flanks are underlined.

Rib3: <u>CUUCGUA</u>CUGAUGAGUCCGUGAGGACGAA<u>ACAGAGAC</u> (SEQ ID NO:21, corresponding to nucleotides 95–131 of SEQ ID NO:4)

Human Rhodopsin

Template cDNA

The human rhodopsin cDNA was cloned into the HindIII and EcoRI sites of the MCS of pcDNA3 in a 5' to 3' orientation allowing subsequent expression of RNA from the T7 or CMV promoters in the vector. The full length 5'UTR sequence was inserted into this clone using primer driven PCR mutagenesis and a HindIII (in pcDNA3) to BstEII (in the coding sequence of the human rhodopsin cDNA) DNA fragment (SEQ ID NO:5)

Hybrid cDNAs with altered non-coding regions

The human rhodopsin hybrid cDNA with altered non-coding sequences was cloned into the EcoRI site of pcDNA3 in a 5' to 3' orientation allowing subsequent expression of RNA from the T7 or CMV promoters in the vector. The 5'UTR of this clone included only the first 21 bases of the non-coding region of human rhodopsin before the ATG start site (SEQ ID NO:6).

Ribozyme constructs

A hammerhead ribozyme (termed Rib15) designed to target an open loop structure in the RNA from the non-coding regions of the gene was cloned subsequent to synthesis and annealing into the HindIII and XbaI sites of pcDNA3 again allowing subsequent expression of RNA from the T7 or CMV promoters in the vector (SEQ ID NO:7). The target site was AUU (the NUX rule) at position 249-251 of the human rhodopsin sequence (Accession number: K02281). Antisense flanks are underlined.

Rib15: ACCCAAGCUGAUGAGUCCGUGAGGACGAA AUGCUGC (SEQ ID NO:22, corresponding to nucleotides 104-139 of SEQ ID NO:7)

Mouse Peripherin

Template cDNA

A mouse peripherin cDNA was cloned into the HindIII and EcoRV sites of pcDNA3. The clone is in a 5' to 3' orientation allowing subsequent expression of RNA from the T7 or CMV promoters in the vector (SEQ ID NO:8). The clone contains the complete 5'UTR sequence together with 27 bases of additional sequence 5' of this UTR sequence left probably from other cloning vectors.

Hybrid cDNAs with altered non-coding regions

The mouse peripherin hybrid cDNA was altered in the 5'non-coding region. Using primer driven PCR mutagenesis the mouse peripherin 5'UTR sequence was replaced by the sequence of the mouse rhodopsin 5'UTR (SEQ ID NO:9). The PCR mutagenesis was achieved using a HindIII (in pcDNA3) to SacII (in the coding sequence of the mouse peripherin cDNA) DNA fragment.

Ribozyme constructs

A hammerhead ribozyme (termed Rib17) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:10). The target site was AUU at position 162-164 of the mouse peripherin sequence (Accession number: X14770). Antisense flanks are underlined.

Rib17: CACUCCUCUGAUGAGUCCGUGAGGACGAA AUCCGAGU (SEQ ID NO:23, corresponding to nucleotides 99-136 of SEQ ID NO:10)

Antisense constructs

Antisense and sense constructs were PCR amplified and cloned into pcDNA3 and pZEOSV for expression in vitro and in vivo. For example, a 127 bp fragment from the 5'UTR sequence of mouse peripherin was cloned in both orientations into the above stated vectors. The effectiveness of antisense at suppression is under evaluation. The altered hybrid cDNA clones are being used to establish if RNAs expressed from these altered clones are protected from antisense suppression effects (SEQ ID NOS:17 and 18).

Human Peripherin

Template cDNA

A human peripherin cDNA cloned into the EcoRI site of the commercially available vector pBluescript was kindly provided by Dr. Gabriel Travis. The clone is in a 5' to 3' orientation allowing subsequent expression of RNA from the T7 promoter in the vector. The full length 5'UTR sequence is present in this clone (SEQ ID NO:11).

Hybrid cDNAs with altered non-coding regions

The hybrid clone with altered non-coding sequences was generated as follows. The hybrid clone contains human peripherin 5'UTR sequences until the BamHI site in the human peripherin 5'UTR sequence. From this site the clone runs into mouse peripherin 5'UTR sequence until the ATG start site where it returns to human peripherin sequence (SEQ ID NO:12). The clone was generated using primer driven PCR mutagenesis of a BamHI (in the 5'UTR sequence) to BglI (in the coding sequence of the human peripherin cDNA) DNA fragment.

Ribozyme constructs

Hammerhead ribozymes (termed Rib8 and Rib9) designed to target open loop structures in the RNA from the non-coding regions of the gene were cloned into the HindIII and XbaI sites of pcDNA3 which again allows subsequent expression of RNA from the T7 or CMV promoters in the vector (SEQ ID NOS:13 and 14). The target sites were CUA and GUU at positions 234-236 and 190-192 respectively of the human peripherin sequence (Accession number: M62958). Antisense flanks are underlined.

Rib8: CCAAGUGCUGAUGAGUCCGUGAGGACGAA AGUCCGG (SEQ ID NO:24, corresponding to nucleotides 93-128 of SEQ ID NO:13)

Rib9: CAAACCUUCUGAUGAGUCCGUGAGGACGAA ACGAGCC (SEQ ID NO:25, corresponding to nucleotides 94-130 of SEQ ID NO:14)

Human Type I Collagen—COL1A2

Template cDNA

A partial human type I collagen 1A2 cDNA sequence including the 5'UTR sequence and exon 1 was cloned after PCR amplification into the HindIII and XbaI sites of pcDNA3. The clone is in a 5' to 3' orientation allowing subsequent expression of RNA from the T7 and or CMV promoters in the vector (SEQ ID NO:15). The clone contains the complete 5'UTR sequence together with Exon I of COL1A2.

Ribozyme constructs

A hammerhead ribozyme (termed Rib18) designed to target an open loop structure in the RNA from the non-coding regions of the gene was cloned into the HindIII and XbaI sites of pcDNA3 again allowing subsequent expression of RNA from the T7 or CMV promoters in the vector (SEQ ID NO:16). The target site was GUC at position 448-450 of the human type I collagen 1A2 sequence (Accession number: J03464; M18057; X02488). Antisense flanks are underlined.

Rib18: AGACAUGCCUGAUGAGUCCGUGAGGACGAA ACUCCUU (SEQ ID NO:26, corresponding to nucleotides 85-121 of SEQ ID NO:16)

RESULTS

Human and mouse rhodopsin and peripherin cDNAs were expressed in vitro. Likewise human and mouse rhodopsin and peripherin cDNAs with altered 5'non-coding sequences were expressed in vitro. Ribozymes targeting the 5'UTRs of these retinal cDNAs were also expressed in vitro. cDNA clones were cut with various restriction enzymes resulting in the production of differently sized RNAs after expression. This aided in differentiating between RNAs expressed from the original cDNAs or from altered hybrid cDNAs. The sites used to cut each clone, the predicted sizes of the resulting RNAs and the predicted sizes of cleavage products after cleavage by target ribozymes are given below in Table 1.

TABLE 1

| | Restriction Enzyme | RNA Size | Cleavage Products |
|---|---|---|---|
| Example 1 | | | |
| Mouse rhodopsin | Eco47111 | 778 bases | 336 + 442 bases |
| Mouse rhodopsin hybrid 1 | Eco47111 | 643 bases | |
| Mouse rhodopsin hybrid 2 | Fsp 1 | 577 bases | |
| Rib 3 (See Table 1; SEQ ID Nos: 1-4; FIGS. 1-7) | Xho 1 | 60 bases | |
| Example 2 | | | |
| Human rhodopsin | BstEll | 8511 bases | 61 + 790 bases |
| | Acy 1 | 1183 bases | 61 + 1122 bases |
| Human rhodopsin hybrid | BstEll | 841 bases | |
| | Acy 1 | 1173 bases | |
| | Fspl | 300 bases | |
| Rib 15 (See Table 1; SEQ ID Nos: 5-7; FIGS. 8-12) | Xbal | 55 bases | |
| Example 3 | | | |
| Mouse peripherin | Bgll | 488 bases | 201 + 287 bases |
| Mouse peripherin hybrid | Bgll | 344 bases | |
| Rib 17 (See Table 1; SEQ ID Nos: 8-10; FIGS. 13-16) | Xbal | 60 bases | |
| Example 4 | | | |
| Human peripherin | Bgll | 489 bases | 238 + 251 (Rib 8) 194 + 295 (Rib 9) |
| Human peripherin hybrid | Avrll | 331 bases | |
| Rib 8 | Xbal | 55 bases | |
| Rib 9 (see Table 1; SEQ ID Nos: 11-14; FIGS. 17-20) | Xbal | 55 bases | |
| Example 5 | | | |
| Collagen 1A2 | Xhol | | |
| Rib 18 (See Table 1; SEQ ID Nos: 15 and 16) | Xbal | | |
| Example 6 | | | |
| Antisense constructs (See Table 1; SEQ ID Nos; 17 and 18) | | | |

The examples of the invention are illustrated in the accompanying figures wherein:

FIG. 1: pBR322 was cut with MspI, radioactively labeled and run on a polyacrylamide gel to enable separation of the resulting DNA fragments. The sizes of these fragments are given in FIG. 1. This DNA ladder was then used on subsequent polyacrylamide gels to provide an estimate of the size of the RNA products run on the gels.

FIG. 2: Mouse rhodopsin cDNA was expressed from the T7 promoter to the Eco47III site in the coding sequence. The RNA was mixed with Rib3 RNA with varying concentrations of magnesium chloride. Lane 1-4: Rhodopsin RNA and Rib3 RNA after incubation for 3 hours at 37° C. with 0 mM, 5 mM, 10 mM and 15 mM magnesium chloride. The sizes of the expressed RNAs and cleavage products are as expected (Table 1). Complete cleavage of mouse rhodopsin RNA was obtained with a small residual amount of intact RNA present at 5 mM magnesium chloride. Note at OmM magnesium chloride before activation of Rib3 RNA no cleavage products were observed.

B: Mouse rhodopsin cDNA was expressed from the T7 promoter to the Eco47III site in the coding sequence. Resulting RNA was mixed with Rib3 RNA with varying concentrations of magnesium chloride. Lane 1: DNA ladder as in FIG. 1. Lane 2: intact mouse rhodopsin RNA. Lane 3-6: Rhodopsin RNA and Rib3 RNA after incubation for 3 hours at 37° C. with 0 mM, 5 mM, 10 mM and 15 mM magnesium chloride. Again complete cleavage of mouse rhodopsin RNA was obtained with a small residual amount of intact RNA present at 5 mM magnesium chloride. Lane 7: DNA ladder as in FIG. 1.

FIG. 3: Mouse rhodopsin cDNA was expressed from the T7 promoter to the Eco47III site in the coding sequence. Lane 1: intact mouse rhodopsin RNA. Lanes 2-7: Mouse rhodopsin RNA was mixed with Rib3 RNA with 15 mM magnesium chloride and incubated at 37° C. for 0, 30, 60, 90, 120 and 180 minutes. The sizes of the expressed RNAs and cleavage products are as expected (Table 1). Complete cleavage of mouse rhodopsin RNA was obtained. Notably cleavage was observed immediately after the addition of the divalent ions which activated Rib3 RNA (see Lane 2: 0 minutes).

FIG. 4: Mouse rhodopsin cDNA with altered 5'UTR sequence was expressed from the T7 promoter to the Eco47III site in the coding sequence. The resulting RNA was mixed with Rib3 RNA using varying concentrations of magnesium chloride. Lane 1: DNA ladder as in FIG. 1. Lane 2: intact altered mouse rhodopsin RNA. Lane 3 6: altered mouse rhodopsin RNA and Rib3 RNA after incubation for 3 hours at 37° C. with 0 mM, 5 mM, 10 mM and 15 mM magnesium chloride. No cleavage of the altered hybrid RNA occurred.

FIG. 5: Mouse rhodopsin cDNA with altered 5'UTR sequence was expressed from the T7 promoter to the Eco47III site in the coding sequence. The resulting RNA was mixed with Rib3 RNA with 10 mM magnesium chloride and incubated at 37° C. Lane 1: intact altered mouse rhodopsin RNAs. Lane 2-6: altered mouse rhodopsin RNA and Rib3 RNA after incubation for 0, 30, 60,120, 180 minutes. No cleavage of the hybrid RNA was obtained. Notably after 3 hours incubation with Rib3 RNA the adapted mouse rhodopsin RNA was as intense as at 0 minutes. Lane 7: DNA ladder as in FIG. 1.

FIG. 6: A: The unadapted mouse rhodopsin cDNA and the mouse rhodopsin cDNA with altered 5'UTR sequence were expressed from the T7 promoter to the Eco47III site in the coding sequence. The resulting RNAs were mixed together with Rib3 RNA and 10 mM magnesium chloride. Lane 1: intact unadapted and altered mouse rhodopsin RNAs which can clearly be differentiated by size as predicted (Table 1). Lane 2-6: unadapted and altered mouse rhodopsin RNAs and Rib3 RNA after incubation for 0, 30, 60,120,180 minutes with 10 mM magnesium chloride at 37° C. No cleavage of the altered hybrid RNA was obtained. The hybrid was of equal intensity after 3 hours as it was at 0 minutes. Notably the majority of the unadapted mouse rhodopsin RNA is cleaved immediately by Rib3 RNA even in the presence of the altered mouse rhodopsin RNA. The cleavage products are highlighted with arrows. The background is due to a small amount of RNA degradation. B: In a separate experiment the three RNAs (unadapted, altered mouse rhodopsin RNAs and Rib3 RNA), were incubated at 15 mM magnesium chloride for 5 hours. The altered hybrid RNA remains intact but the unadapted mouse rhodopsin RNA has been cleaved completely.

FIG. 7: A second altered mouse rhodopsin cDNA involving a single base change at the ribozyme cleavage site was generated. This adapted mouse rhodopsin cDNA was expressed from the T7 promoter to the FspI site in the coding sequence. Likewise the unadapted mouse rhodopsin cDNA was expressed from the T7 promoter to the Eco47III site in the coding sequence. These two RNAs were mixed with Rib3 RNA and incubated at 37° C. with 15 mM magnesium chloride. Lane 1: Intact mouse rhodopsin RNA. Lane 2: Intact altered mouse rhodopsin RNA (2nd alteration). Lane 3: DNA ladder as in FIG. 1. Lanes 4–7: Unadapted and altered mouse rhodopsin RNAs and Rib3 RNA after incubation for 0, 60, 120 and 180 minutes with 15 mM magnesium chloride at 37° C. Note the reduction of the unadapted RNA product over time in the presence of the altered RNA (Lanes 4 and 5). The adapted RNA remains intact and maintains equal intensity at each time point indicating that it is resistant to cleavage by Rib3 RNA. Again, as with all other altered RNAs, no additional cleavage products were observed. Lane 8: The unadapted and adapted mouse rhodopsin RNA without ribozyme. Lane 9: DNA ladder as in FIG. 1.

FIG. 8: Human rhodopsin was expressed from the T7 promoter to the BstEII site in Exon IV. The resulting RNA was mixed with Rib15 RNA with varying concentrations of magnesium chloride. Lane 1: intact rhodopsin RNA alone. Lane 2: Rib15 alone. Lane 3: DNA ladder as in FIG. 1. Lanes 4–7: Rhodopsin RNA and Ril5 RNA after incubation for 3 hours at 37° C. with the 0 mM, 5 mM, 10 mM and 15 mM magnesium chloride. Predicted cleavage products are 61 and 790 bases (Table 1). Lane 8: DNA ladder. Partial cleavage of the RNA was obtained—a doublet representing the intact RNA and the larger cleavage product is present (most clearly in lane 5). The gel was run a shorter distance than the gel presented in FIGS. 9–12 to show the presence of Rib15 RNA at the bottom of the gel and to demonstrate that one of the cleavage products cannot be visualized due to the presence of the labeled ribozyme which runs at approximately the same size. Subsequent gels were run further to achieve better separation of these two RNA fragments.

FIG. 9: Both the unadapted human rhodopsin cDNA and the altered cDNA were expressed from the T7 promoter to the BstEII site in Exon IV. The resulting RNA was mixed with Rib15 RNA with varying concentrations of magnesium chloride. Lane 1: intact human rhodopsin RNA alone. Lane 2: DNA ladder as in FIG. 1. Lane 3–6: Rhodopsin RNA and Rib15 RNA after incubation together for 3 hours at 37° C. with O mM, 5 mM, 10 mM and 15 mM magnesium chloride. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodopsin RNA with altered 5'UTR sequence alone. The predicted cleavage products for human rhodopsin are 61 and 790 bases (Table 1)—the larger cleavage product is clearly visible when the ribozyme becomes active after the addition of magnesium chloride (Lanes 4–6). This larger cleavage product is highlighted by an arrow.

FIG. 10: Human rhodopsin cDNA was expressed from the T7 promoter to the BstEII site in Exon IV. Likewise the altered human rhodopsin cDNA was expressed from the T7 promoter to the FspI site in Exon 1. Both resulting RNAs were mixed together with Rib15 RNA with varying concentrations of magnesium chloride. Lane 1: DNA ladder as in FIG. 1. Lanes 2–5: Rhodopsin RNA, altered rhodopsin RNA and Rib15 RNA after incubation for 3 hours at 37° C. with 0 mM, 5 mM, 10 mM and 15 mM magnesium chloride. The sizes of the expressed RNAs and cleavage products are as expected (Table 1). Partial cleavage of the unadapted RNA was obtained after magnesium was added to the reaction. The altered human rhodopsin RNA was protected from cleavage in all reactions. If cleavage of the altered human rhodopsin RNA had occurred the products rationally would most likely be of a different size than those observed with the unadapted RNA. Notably no additional cleavage products were observed. Moreover there was no change in intensity of the altered RNA when the ribozyme was active (in the presence of magnesium chloride) or inactive (at OmM magnesium chloride). In contrast the unadapted human rhodopsin RNA is less intense in lanes 3–5 after cleavage than in lane 2 before the addition of magnesium to activate Rib15. Lane 6: intact human rhodopsin RNA. Lane 7: intact human rhodopsin RNA with altered 5'UTR sequence. Lane 8: DNA ladder.

FIG. 11: Human rhodopsin cDNA was expressed from the T7 promoter to the BstEII site in Exon IV. Likewise the altered human rhodopsin cDNA was expressed from the T7 promoter to the AcyI in the 3'rhodopsin sequence after the stop codon. Both resulting RNAs were mixed together with Rib15 RNA with varying concentrations of magnesium chloride. Lane 1: DNA ladder as in FIG. 1. Lanes 2–5: Rhodopsin RNA, altered rhodopsin RNA and Rib15 RNA after incubation for 3 hours at 37° C. with 0 mM, 5 mM, 10 mM and 15 mM magnesium chloride. Lane 6: Intact human rhodopsin RNA. Lane 7: DNA ladder as in FIG. 1. Note that neither RNAs or cleavage products are present in Lane 5 as too little sample may have been loaded in this lane.

FIG. 12: Human rhodopsin cDNA and the cDNA with altered 5'sequence were expressed from the T7 promoter to the AcyI site after the coding sequence of human rhodopsin. The resulting RNA was mixed with Rib15 RNA with varying concentrations of magnesium chloride. Lane 1: DNA ladder as in FIG. 1. Lane 2–5: Human rhodopsin RNA and Rib15 RNA after incubation together for 3 hours at 37° C. with OmM, 5 mM, 10 mM and 15 mM magnesium chloride. Lane 6: Intact human rhodopsin RNA. Lane 7: DNA ladder as in FIG. 1. Lane 8–11: Human rhodopsin RNA with altered 5'UTR sequence and Rib15 RNA after incubation together for 3 hours at 37° C. with 0 mM, 5 mM, 10 mM and 15 mM magnesium chloride. Lane 12: intact human rhodopsin RNA with altered 5'UTR sequence alone. Lane 13: DNA ladder as in FIG. 1. The larger of the predicted cleavage products is present in lanes 3–5 and is highlighted by an arrow. The adapted human rhodopsin RNA again was protected from cleavage by Rib15 RNA. Note that in Lane 12 too little sample may have been loaded.

FIG. 13: Mouse peripherin cDNA was expressed from the T7 promoter to the BglIII site in the coding sequence. The RNA was mixed with Rib17 RNA with varying concentrations of magnesium chloride. Lane 1: DNA ladder as in FIG. 1. Lane 2: intact mouse peripherin RNA. Lanes 3–6: Mouse peripherin RNA and Rib17 RNA after incubation for 3 hours at 37° C. with 0 mM, 5 mM, 10 mM and 15 mM magnesium chloride. The sizes of the expressed RNAs and cleavage products are as expected (Table 1). Partial cleavage of mouse rhodopsin RNA was obtained once Rib17 RNA was activated with magnesium chloride. Possibly some of the RNA was in a conformation that was inaccessible to Rib17 RNA. It should be noted that in the absence of magnesium chloride the ribozyme was inactive and no cleavage products were observed.

FIG. 14: Mouse peripherin cDNA was expressed from the T7 promoter to the BglII site in the coding sequence. The resulting RNA was mixed with Rib17 RNA with 15 mM magnesium chloride and incubated at 37° C. for varying times. Lane 1: DNA ladder as in FIG. 1. Lane 2: intact mouse peripherin RNA. Lanes 3–6: Mouse peripherin RNA and Rib17 RNA after incubation together with 15 mM magnesium chloride at 37° C. for 0,1, 2 and 3 hours respectively. The sizes of the expressed RNAs and cleavage products are as expected (Table 1). Partial cleavage of mouse rhodopsin RNA was obtained with Rib17 after 1 hour. The proportion of the RNA cleaved increased over time. The intensity of the mouse rhodopsin RNA band decreased visibly on the gel by 3 hours and similarly the cleavage products visibly increased in intensity. It is possible that further cleavage might be obtained over longer time periods. Lane 7: DNA ladder as in FIG. 1.

FIG. 15: Mouse peripherin cDNA with altered 5'sequences was expressed from the T7 promoter to the BglII site in the coding sequence. The resulting RNA was mixed with Rib17 RNA with varying concentrations of magnesium chloride. Lane 1: intact altered mouse peripherin RNA with no ribozyme. Lanes 2–5: Mouse peripherin RNA with altered 5'sequence and Rib17 RNA after incubation for 3 hours at 37° C. with 0 mM, 5 mM, 10 mM and 15 mM magnesium chloride. The sizes of the expressed RNAs are as expected (Table 1). No cleavage of the adapted mouse rhodopsin RNA was obtained before or after Rib17 RNA was activated with magnesium chloride. Lane 6: DNA ladder as in FIG. 1.

FIG. 16: Both the unadapted and adapted mouse peripherin cDNAs were expressed from the T7 promoter to the BglII site in the coding sequence. The resulting RNAs were mixed together with Rib17 RNA with 15 mM magnesium chloride and incubated at 37° C. for varying times. Lane 1: DNA ladder as in FIG. 1. Lane 2: intact unadapted and altered mouse peripherin RNA. Lanes 3–6: Unadapted mouse peripherin RNA, altered mouse peripherin RNA and Rib17 RNA after incubation together with 15 mM magnesium chloride at 37° C. for 0, 30, 90 and 180 minutes respectively. The sizes of the expressed RNAs and cleavage products are as expected (Table 1). Partial cleavage of the unadapted mouse peripherin RNA was obtained with Rib17 RNA after 1 hour. The intensity of the larger unadapted mouse peripherin RNA product decreases slightly over time. In contrast the cleavage products increase in intensity. The intensity of the smaller altered mouse peripherin RNA product remains constant over time indicating that the RNA is not cleaved by Rib17 RNA. Lane 7: DNA ladder as in FIG. 1.

FIG. 17: Both the unadapted and adapted human peripherin cDNAs were expressed from the T7 promoter to the BglII site in the coding sequence. The resulting RNAs were mixed together with Rib8 RNA with varying concentrations of magnesium chloride and incubated at 37° C. for 3 hours. Lane 1: Unadapted human peripherin without ribozyme. Lanes 2–5: Unadapted human peripherin RNA and Rib8 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib8 RNA after 3 hours. The intensity of the larger unadapted human peripherin RNA product decreases over time. Lanes 6–9: Altered human peripherin RNA and Rib8 RNA after incubation together with 0, 5,10, 15 mM magnesium chloride respectively at 37° C. for 3 hours. The sizes of the expressed RNAs are as expected (Table 1). No cleavage of the altered human peripherin RNA was obtained with Rib8 RNA even after 3 hours. The intensity of the smaller altered mouse peripherin RNA product remains constant (with the exception of lane 9 in which less sample may have been loaded) indicating that the RNA is not cleaved by Rib8 RNA. In addition no cleavage products were observed. Lane 10: Intact unadapted human peripherin RNA alone. Lane 11: Intact altered human peripherin RNA alone. Lane 12: DNA ladder as in FIG. 1.

FIG. 18: The unadapted and altered human peripherin cDNAs were expressed from the T7 promoter to the BglII site in the coding sequence. The resulting RNAs were mixed together with Rib8 RNA for varying times with 15 mM magnesium chloride and incubated at 37° C. Lane 1: DNA ladder as in FIG. 1. Lane 2–5: Unadapted and altered human peripherin RNAs and Rib8 RNA after incubation together for 0,1, 2 and 3 hours respectively at 37° C. with 15 mM magnesium chloride. The sizes of the expressed RNAs and cleavage products are as expected (Table 1). Almost complete cleavage of the larger unadapted human peripherin RNA was obtained with Rib8 RNA after 3 hours. The intensity of the larger unadapted human peripherin RNA product decreases over time. Altered human peripherin RNA was not cleaved by Rib8 RNA even after 3 hours. The intensity of the smaller altered mouse peripherin RNA product remains constant over time indicating that the RNA is not cleaved by Rib8 RNA. In addition no additional cleavage products were observed. Lane 6: Intact unadapted and altered human peripherin RNA together without ribozyme. Lane 7: DNA ladder as in FIG. 1.

FIG. 19: Both the unadapted and adapted human peripherin cDNAs were expressed from the T7 promoter to the BglII site in the coding sequence. The resulting RNAs were mixed together with Rib9 RNA with varying concentrations of magnesium chloride and incubated at 37° C. for 3 hours. Lane 1: DNA ladder as in FIG. 1. Lanes 2–5: Unadapted human peripherin RNA and Rib9 RNA after incubation together with 0, 5, 10, 15 mM magnesium chloride respectively at 37° C. for 3 hours. The sizes of the expressed RNAs and cleavage products are as expected (Table 1). Almost complete cleavage of the unadapted human peripherin RNA was obtained with Rib9 RNA. The intensity of the larger unadapted human peripherin RNA product decreases greatly. Lanes 6–9: Altered human peripherin RNA and Rib9 RNA after incubation together with 0, 5, 10, 15 mM magnesium chloride respectively at 37° C. for 3 hours. The sizes of the expressed RNAs are as expected (Table 1). No cleavage of the altered human peripherin RNA was obtained with Rib17 RNA even after 3 hours. The intensity of the smaller altered mouse peripherin RNA was observed—the product remains constant over time indicating that the RNA is not cleaved by Rib9 RNA. Lane 10: Intact unadapted human peripherin RNA alone. Lane 11: Intact altered human peripherin RNA alone. Lane 12: DNA ladder as in FIG. 1. Rib9 RNA was designed to target a different loop structure in the 5'sequence of human peripherin. It may result in slightly more efficient cleavage of RNA than Rib8 RNA.

FIG. 20: The unadapted and altered human peripherin cDNAs were expressed from the T7 promoter to the BglII site in the coding sequence. The resulting RNAs were mixed together with Rib9 RNA for varying times with 15 mM magnesium chloride and incubated at 37° C. Lane 1: Intact unadapted human peripherin RNA without ribozyme. Lane 2: Intact altered human peripherin RNA without ribozyme. Lanes 3 and 4: DNA ladder as in FIG. 1. Lane 5–8: Unadapted and altered human peripherin RNAs and Rib9 RNA after incubation together for 0,1, 2 and 3 hours, respectively, at 37° C. with 15 mM magnesium chloride. The sizes of the expressed RNAs and cleavage products are as expected (Table 1). Cleavage products were observed at time zero. Almost complete cleavage of the larger unadapted human peripherin RNA was obtained with Rib9 RNA after 1 hour. The intensity of the larger unadapted human peripherin RNA product decreased quickly over time. The altered human peripherin RNA was not cleaved by Rib9 RNA even after 3 hours. The intensity of the smaller altered human peripherin RNA product remains constant over time indicating that the RNA is not cleaved by Rib9 RNA. In addition, no additional cleavage products were observed. Lane 9: Intact unadapted and altered human peripherin RNA together without ribozyme. Lane 10: DNA ladder as in FIG. 1.

FIGS. 21–40: In each case the most relevant sequences have been underlined. The position of the ATG start in each sequence is highlighted by an arrow.

FIG. 21: Mouse Rhodopsin cDNA sequences mouse rhodopsin 5'UTR sequences/the ATG start site/mouse rhodopsin coding sequences are shown. (SEQ ID NO: 1).

FIG. 22: Forward mouse Rhodopsin cDNA with altered non-coding sequences mouse rhodopsin 5'UTR sequences with a 1 base change/the ATG start site/mouse rhodopsin coding sequences are shown. (SEQ ID NO: 2).

FIG. 23: Reverse Mouse Rhodopsin cDNA with altered non-coding sequences mouse rhodopsin 5'UTR sequences with a 1 base change/the ATG start site/mouse rhodopsin coding sequences are shown. (SEQ ID NO: 19).

FIG. 24: Forward Mouse Rhodopsin cDNA with altered non-coding sequences mouse rhodopsin 5'UTR sequences with a 1 base change/the ATG start site/mouse rhodopsin coding sequences are shown. (SEQ ID NO: 3).

FIG. 25: Reverse Mouse Rhodopsin cDNA with altered non-coding sequences mouse rhodopsin 5'UTR sequences with a 1 base change/the ATG start site/mouse rhodopsin coding sequences are shown. (SEQ ID NO: 20).

FIG. 26: Ribozyme 3. (SEQ ID NO: 4).

FIG. 27: Human Rhodopsin cDNA sequence human rhodopsin 5'UTR sequences/the ATG start site/human rhodopsin coding sequences are shown. (SEQ ID NO: 5).

FIG. 28: Human Rhodopsin cDNA with altered non-coding sequences human rhodopsin 5'UTR sequences (shorter UTR)/the ATG start site/human rhodopsin coding sequences are shown. (SEQ ID NO: 6).

FIG. 29: Ribozyme 15. (SEQ ID NO: 7).

FIG. 30: Mouse peripherin cDNA sequences mouse peripherin 5'UTR sequences/the ATG start site/mouse peripherin coding sequences are shown. (SEQ ID NO: 8).

FIG. 31: Mouse peripherin cDNA with altered non-coding sequences mouse rhodopsin 5'UTR sequences/the ATG start site/mouse peripherin coding sequences are shown. (SEQ ID NO: 9).

FIG. 32: Ribozyme 17. (SEQ ID NO: 10).

FIG. 33: Human peripherin cDNA sequences human peripherin 5'UTR sequences/the ATG start site/human peripherin coding sequences are shown. (SEQ ID NO: 11).

FIG. 34: Human peripherin cDNA with altered non-coding sequences. Partial human and mouse peripherin 5'UTR sequences/the ATG start site/human peripherin coding sequences are shown. (SEQ ID NO: 12).

FIG. 35: Ribozyme 8. (SEQ ID NO: 13).

FIG. 36: Ribozyme 9. (SEQ ID NO: 14).

FIG. 37: Human type I collagen (COL1A2) sequence—5'UTR and exon 1 sequence. (SEQ ID NO: 15).

FIG. 38: Ribozyme 18. (SEQ ID NO: 16).

FIG. 39: Antisense construct containing 127 bp of antisense sequence targeting the 5'UTR of the mouse peripherin gene. (SEQ ID NO: 17).

FIG. 40: Sense construct containing 127 bp of sense sequence from the 5'UTR of the mouse peripherin gene. (SEQ ID NO: 18).

EXAMPLE 1

Mouse Rhodopsin

Rib3 RNA targeting the mouse rhodopsin 5'non-coding sequence was cut with Xho I and expressed in vitro. The mouse rhodopsin cDNA and hybrid cDNA with altered 5'non-coding sequence (with the human peripherin 5'UTR sequence in place of the mouse rhodopsin 5'UTR sequence) were cut with Eco47111, expressed and both RNAs mixed separately and together with Rib3 RNA to test for cleavage. RNAs were mixed with varying concentrations of $MgCl_2$ and for varying amounts of time to optimize cleavage of RNA by Rib3 RNA (FIGS. 2–7). Likewise, a second hybrid with a small modification of the 5'UTR sequence was cut with Fspl, expressed and tested for cleavage with Rib3 RNA alone and together with the original unadapted mouse rhodopsin RNA. This alteration is a single base change at the ribozyme cleavage site involving a U→G, that is, altering the ribozyme cleavage site from GUC to GGC thereby removing the target site. In all cases the expressed RNA was the correct size. In all cases cleavage of the larger unadapted mouse rhodopsin RNA product was achieved. In some cases cleavage was complete and all cleavage products were of the predicted size. Notably hybrid mouse rhodopsin RNAs with altered 5'UTR sequences were not cleaved by Rib3 RNA either when mixed alone with Rib3 RNA or when combined with Rib3 RNA and the unadapted mouse rhodopsin RNA (FIGS. 2–7). This highlights the sequence specificity of the Rib3 RNA target in that small sequence alterations may be all that is required to prevent cleavage. Likewise small modifications in the targets for the antisense arms of ribozymes or more generally for any antisense may result in the inability of a suppression effector to attack the modified RNA. The first hybrid described above could be used to prevent ribozyme cleavage or antisense binding of many ribozymes or antisense suppression effectors and therefore would be particularly useful if more than one suppression effector was required to achieve suppression.

Example 2

Human Rhodopsin

The human rhodopsin cDNA clone (with a full length 5'UTR) and the human rhodopsin hybrid cDNA clone with altered 5'non-coding sequence (shorter 5'UTR) were cut with BstEII and expressed in vitro. The Rib15 clone was cut with Xbal and expressed in vitro. The resulting ribozyme and human rhodopsin RNAs were mixed with varying concentrations of $MgCl_2$ to optimize cleavage of the template RNA by Rib15 RNA. (FIGS. 8–12). The human rhodopsin cDNA and hybrid cDNA with altered 5'non-coding sequence were cut with Acyl, expressed and both RNAs mixed separately (due to their similar sizes) with Rib15 RNA to test for cleavage (FIGS. 8–12). The human rhodopsin cDNA was cut with BstEII and the hybrid cDNA with altered 5'non-coding sequence cut with Fspl, expressed and mixed separately and together with Rib15 RNA to test for cleavage (FIGS. 8–12). In all cases the expressed RNA was the correct size. Similarly in all cases the unadapted RNA template was cut into cleavage products of the predicted sizes. The cleavage of the unadapted RNA template was incomplete with some residual uncleaved RNA remaining. This may be due, for example, to the inability of the ribozyme to access RNA in some conformations. In all cases RNA expressed from the altered hybrid human rhodopsin cDNA with a shorter 5'UTR remained intact, that is, it was not cleaved by Rib15 RNA. It is worth noting that Acyl enzyme cuts after the stop codon of the coding region of the gene and therefore the resulting RNA includes all of the coding sequence that gives rise to the protein. The RNA from the original unadapted human rhodopsin cDNA clone cut with AcyI is cleaved by Rib15 RNA. In contrast, RNA from the hybrid clone with an altered 5'UTR sequence is not cleaved by Rib15 RNA. (FIGS. 8–12). The sequence of the ribozyme target site and of the antisense flanks are not present in the altered human rhodopsin RNA. Clearly, altering the sequence in non-coding regions masks the resulting altered gene from being suppressed by antisense or ribozymes targeting sites in non-coding regions.

Example 3

Mouse Peripherin

Rib17 targeting mouse peripherin 5'non-coding sequence was cut with XbaI and expressed in vitro. The mouse peripherin cDNA and mouse peripherin hybrid cDNA with an altered 5'non-coding sequence (in which the mouse peripherin 5'UTR sequence has been replaced by mouse rhodopsin 5'UTR sequence) were cut with BglII, expressed in vitro and both RNAs mixed separately and together with Rib17 RNA to test for cleavage. RNAs were mixed with varying concentrations of $MgCl_2$ and for varying times to optimize cleavage of RNAs by Rib17 RNA (FIGS. 13–16). Partial cleavage of the unadapted mouse peripherin RNA by Rib17 RNA was obtained—all RNAs expressed and all cleavage products were the predicted sizes. Partial cleavage may be due to the inaccessibility of some RNA conformations to antisense binding and/or ribozyme cleavage. In contrast the adapted hybrid mouse peripherin RNA containing mouse rhodopsin non-coding sequences remained intact (FIGS. 13–16). This again highlights that RNAs can be designed so that they code for a correct protein, in this case, mouse peripherin and such that they are masked from a suppression effector(s), in this case, a ribozyme with antisense flanks.

Example 4

Human Peripherin

Rib8 and Rib9 clones targeting human peripherin 5'non-coding sequence were cut with XbaI and expressed in vitro. The human peripherin cDNA and human peripherin hybrid cDNA with altered 5'non-coding sequence (with part of the human peripherin 5'UTR sequence replaced by mouse peripherin 5'UTR sequence) were cut with BglII and AvrII respectively, expressed in vitro and both RNAs mixed separately and together with Rib9 RNA to test for cleavage. RNAs were mixed with varying concentrations of $MgCl_2$ to optimize cleavage of RNAs by Rib9 RNA (FIGS. 17–20). Notably the majority of the larger unadapted RNA product was cleaved while the adapted RNA product with altered noncoding sequence remained intact (FIGS. 17–20). Similar results were obtained with Rib8 RNA which targets a different open loop than Rib9 RNA in the non-coding sequence of human peripherin. However, in the case of Rib8 RNA, the extent of the cleavage was significantly less than Rib9 RNA (FIGS. 17–20) suggesting the important role of RNA structure in antisense binding and RNA cleavage.

Example 5

Human COL1A2

Rib18 which has been cloned into pcDNA3 (SEQ ID NO:16) targets the 5'UTR sequence of the human type I collagen COL1A2 gene, multiple mutations in which can cause autosomal dominantly inherited osteogenesis imperfecta involving bone fragility, amongst other symptoms. A clone containing the 5'UTR sequence together with exon I of the human COL1A2 gene has also been generated (SEQ ID NO:15) to apply suppression and replacement strategies to this human gene.

Antisense constructs

A number of constructs have been generated in pcDNA3 and pZEOSV containing tracks of sense and antisense sequence from the non-coding regions of the mouse rhodopsin and peripherin genes. An example of these sequences is given in SEQ ID NOS:17 and 18. Antisense effects are under evaluation.

DISCUSSION

In the first four examples outlined above, RNA was expressed from cDNAs coding for four different proteins: mouse and human rhodopsin and mouse and human peripherin. All four RNAs have been significantly attacked in vitro using suppression effectors directed towards the non-coding regions of the RNA. In all four examples the ribozymes directed to 5'UTR sequences were successful in cleaving target RNAs in the predicted manner. Antisense targeting non-coding sequences was used successfully to elicit binding and cleavage of target RNAs in a sequence specific manner.

In some cases it is possible that cleavage of the RNA at the 5'UTR would not effect the functioning of the resulting RNA cleavage products in generating protein. Moreover although lowering RNA levels may often lead to a parallel lowering of protein levels this is not always the case. In some situations mechanisms may prevent a significant decrease in protein levels despite a substantial decrease in levels of RNA. However in many instances suppression at the RNA level has been shown to be effective. In some cases it is thought that ribozymes elicit suppression not only by cleavage of RNA but also by an antisense effect due to the antisense arms in the ribozyme. Notably we have demonstrated sequence specific attack of target RNAs in non-coding regions, which is an important stage in gene suppression.

In the four examples provided ribozymes were designed to target 5'UTR sequences, however, they could be readily designed to target any non-coding sequences. Suppression could be achieved using antisense or ribozymes targeting for example, the 3'UTR sequences or any combination of non-coding sequences.

Additionally, in all four examples, cDNAs with altered sequences in the non-coding regions targeted by ribozymes were generated. RNAs expressed from altered cDNAs were protected entirely from cleavage due the absence of the ribozyme target by each of the ribozymes tested. Alterations involved replacement of UTR sequence with UTR sequence from another gene expressed in the same tissue or UTR sequence from the same gene but from a different mammalian species (e.g., mouse peripherin, human peripherin, mouse rhodopsin). In one case the target site was deleted (human rhodopsin). Of particular interest is the second mouse rhodopsin hybrid cDNA for Rib3 which contains a single base change thereby preventing RNA cleavage. In some cases the non-coding sequences of a gene may be essential to the overall efficient expression and functioning of the gene. Therefore it may be useful to alter replacement genes in subtle ways to prevent ribozyme cleavage or nucleic acid binding. Changing a few nucleotides in many instances may be sufficient to prevent nucleolytic attack.

As highlighted before in this text using this invention the same method of suppression (targeting non-coding sequences) and gene replacement (using a gene with altered non-coding sequences) may be used as a therapeutic approach for any mutation within a given gene.

REFERENCES

Carter G and Lemoine N R. (1993) Cancer Res. 67: 869–876.

Cazenave et al. (1989) Nucl. Acid Res. 17: 42554273.

Dosaka-Akita H et al. (1995) Cancer Res. 55: 1559–1564.

Dryja T P et al. (1990) Nature 343: 364–366.

Duval-Valentin et al. (1992) Proc. Natl. Acad. Sci. USA 89: 504–508.

Ellis and Rodgers (1993) Nucl. Acid Res. 21: 5171–5178.

Farrar G J et al. (1991) Nature 354: 478–480.

Farrar G J et al. (1991) Genomics 14: 805–807.

Farrar G J et al. (1995) Invest. Ophthamol. Vis. Sci. (ARVO) 36: (4).

Feng M, Cabrera G, Deshane J, Scanlon K and Curiel D T. (1995) Cancer Res. 55: 2024–2028.

Gaughan D J, Steel D M, and Whitehead S A. (1995) FEBS Letters 374: 241–245.

Hanvey J C et al. (1992) Science 258:1481–1485.

Hardenbol P and Van Dyke M W. (1996) Proc. Natl. Acad. Sci. USA 93: 2811–2816.

Herschlag D, Khosla M, Tsuchihashi Z and Karpel R L. (1994) EMBO 13: (12) 29132924.

Herskowitz et al. (1987) Nature 329: 219–222.

Jankowsky E and Schwenzer B. (1996) Nucl. Acid Res. 24: (3) 423 429.

Jones J T, Lee S-W and Sullenger B A. (1996) Nature Medicine 2: 643–648.

Jordan S A et al. (1993) Nature Genetics 4: 54–58.

Quattrone A, Fibbi G, Anichini E, Pucci M et al. (1995) Cancer Res. 55: 90–95.

Kajiwara et al. (1991) Nature 354: 480–483.

Knudsen H and Nielsen P E. (1996) Nucl. Acid Res. 24: (3) 494–500.

Lange W et al. (1993) Leukemia 7: 1786–1794.

Mansergh F et al. (1995) J. Med. Genet. 32: 855–858.

Mashhour B et al. (1994) Gene Therapy 1:122–126.

McKay R A, Cummins L L, Graham M J, Lesnik E A et al. (1996) Nuc Acid Res 24: (3) 411–417.

McWilliam P et al. (1989) Genomics 5: 612–619.

Ohta Y, Kijima H, Ohkawa T, Kashani-Sabet M and Scanlon K J. (1996) Nucl. Acid. Res. 24: (5) 938–942.

Ott J et al. (1989) Proc. Natl. Acad. Sci. 87: 701–704.

Oyama T et al. (1995) Pathol. Int. 45: 45–50.

Postel et al. (1991) Proc. Natl. Acad. Sci. USA 88: 8227–8231.

Porumb H, Gousset, Letellier R, Salle V, et al. (1996) Cancer Res. 56: 515–522.

Rimsky et al. (1989) Nature 341: 453–456.

Sullenger B A and Cech T R. (1994) Nature 371: 619–622.

Sun J S et al. (1989) Proc. Natl. Acad. Sci. USA 86: 9198–9202.

Trauger J W, Baird E E and Dervan P B. (1996) Nature 382: 559–561.

Valera A et al. (1994) J. Biol. Chem. 269: 28543–28546.

Van Soest S et al. (1994) Genomics 22: 499–504.

Wei Z, Tung C-H, Zhu T, Dickerhof WA et al. (1996) Nucl. Acid Res. 24: (4) 655–661.

---

SEQUENCE LISTING

```
<160> NUMBER OF SEQ ID NOS: 26

<210> SEQ ID NO 1
<211> LENGTH: 624
<212> TYPE: DNA
<213> ORGANISM: Artificial Sequence
<220> FEATURE:
<223> OTHER INFORMATION: Mouse Rhodopsin cDNA sequences mouse rhodopsin
      5'UTR sequences/the ATG start site/mouse rhodopsin coding
      sequences are included.
<220> FEATURE:
<221> NAME/KEY: n
<222> LOCATION: (1)..(624)
<223> OTHER INFORMATION: any

<400> SEQUENCE: 1
nnnncttnct tanngcttgg taccganctc ggatccacta gtnaacggcc gccagtgtgc     60
tggaaattcc cagaggnact ctggggcaga caagatgaga caccctttcc tttctttacc    120
taagggcctc caccgatgt caccttggcc cctctgcaag ccaattaggc cccggtggca    180
```

```
gcagtgggat tagcgttagt atgatatctc gcggatgctg aatcagcctc tggcttaggg      240
agagaaggtc actttataag ggtctggggg gggtcagtgc ctggagttgc gctgtgggag      300
ccgtcagtgg ctgagctcgc caagcagcct tggtctctgt ctacgaaaan cccgtggggc      360
agcctcnana accgcagcca tgaacggcac agaaggcccc aatttttatg tgcccttctc      420
caacgtcaca ngcgtggtgc ggaacccctt cnancanccg cagtactacc tggcggaacc      480
atggcagttc tccatgctgg cancgtacat gtcctgctca tcgtgctggg nttcccatca      540
actcctcacg ctctagttca ccgtaaanna naaaaaactg cgcaacccct caactaaatc      600
ctgctcaatt gggcgtgggt gaac                                             624
```

<210> SEQ ID NO 2
<211> LENGTH: 624
<212> TYPE: DNA
<213> ORGANISM: Artificial Sequence
<220> FEATURE:
<223> OTHER INFORMATION: Forward mouse Rhodopsin cDNA with altered
      non-coding sequences mouse rhodopsin 5'UTR sequences with a 1 base
      change/the ATG start site/mouse rhodopsin coding sequences are
      included.
<220> FEATURE:
<221> NAME/KEY: n
<222> LOCATION: (1)..(624)
<223> OTHER INFORMATION: any

<400> SEQUENCE: 2

```
tnccttttt  tncaatttcc ttcnanaccc aggancacga tatcccctgc tcaagctgtg       60
attccgaaac ccctgccacc actactgcat tcacggggta tcccaggcta gtgggactcn     120
acatgggtag cccccagggc agctccctac agcttgggcc atctgcactt ttcccaaggc     180
cctaagtctc cgcctctggg ctcgttaagg tttggggtgg gagctgtgct gtgggaagca     240
acccggacta cacttggcaa gcatgaacgg cacagagggc cccaattttt atgtgccctt     300
ctccaacgtc acaggcgtgg tgcggaccc cttcgagcag ccgcagtact acctggcgga     360
accatggcag ttctccatgc tgggcancgt tacatgttcc tggcccatcg tgctgggctt     420
ccccatcaac ttcctcacgc tctacgtcan cgtacagcan aaaaanctgc gcacacccct     480
caactacatc ctgctcaact tgggcgtgg ctgaccccttc atggtctcgg aagatcacac     540
caccctctaa catcactcca tggctaattc ctctttnggg ccanaggcnt gtaatcncna     600
aggnttcttt gccancttgg aggt                                            624
```

<210> SEQ ID NO 3
<211> LENGTH: 620
<212> TYPE: DNA
<213> ORGANISM: Artificial Sequence
<220> FEATURE:
<223> OTHER INFORMATION: Forward Mouse Rhodopsin cDNA with altered
      non-coding sequences mouse rhodopsin 5'UTR sequences with a 1 base
      change/the ATG start site/mouse rhodopsin coding sequences are
      included.
<220> FEATURE:
<221> NAME/KEY: n
<222> LOCATION: (1)..(620)
<223> OTHER INFORMATION: any

<400> SEQUENCE: 3

```
tgnnttnctt aaangcttgg ttaccgagct cggatccact nagtaacggc cgccagtgtg       60
ctggaaattc ccagaggcac tctggggcag acaagatgag acacccttttc ctttctttac     120 ctaagggcct ccaccgatg tcaccttggc ccctctgcaa gccaattagg ccccggtggc      180
agcagtggga ttagcgttag tatgatatct cgcggatgct gaatcagcct ctggcttagg     240
```

```
gagagaangt cactttataa gggtctgggg ggggtcagtg cctggagttg cgctgtggga    300
gccgtcagtg gctgagctcg ccaagcagcc ttggtctctg gctacnaaaa ncccgtgggg    360
cancctcnaa anccgcancc atgaacggca cagaaggccc caatttttat gtttccctto    420 tccaacgtca cangcgtngt gcggaacctc ttcnaacaac cgcaatncta cctggcggaa    480
ccatggcagt tctccatgct ggcancgtaa tnttctgctc atcgtgctgg gttcccatca    540
anttcctcac ccctaatttc cgtnaanaaa aaaactgccc caccoccaaa taattctgnn    600 caanttggcg tggtnaccct                                                620
```

```
<210> SEQ ID NO 4
<211> LENGTH: 705
<212> TYPE: DNA
<213> ORGANISM: Artificial Sequence
<220> FEATURE:
<223> OTHER INFORMATION: Ribozyme 3 cloned in pcDNA3.
<220> FEATURE:
<221> NAME/KEY: n
<222> LOCATION: (1)..(705)
<223> OTHER INFORMATION: any

<400> SEQUENCE: 4
ngnttnnnnn nttacaganc nctcgctaan tagagaacca ctgcttactg gcttatcgaa    60
attaatacga ctcactatag ggagacccaa gcttcttcgt actgatgagt ccgtgaggac    120
gaaacagaga ctcgagcatg catctagagg gccctattct atagtgtcac ctaaatgcta    180
gagctcgctg atcagcctcg actgtgcctt ctagttgcca gccatctgtt gtttgcccct    240
cccccgtgcc ttccttgacc ctggaangtg ccactcccac tgtcctttcc taataaaatg    300
aggaaattgc atcgcattgt ctgagtangt gtcattctat tctgggggt ggggtggggc    360 anggacanca aggggaaga ttgggaaaaa caatancagg catgctgggg gatncngtgg    420
ggctctatgg cttctgangc ggaaagaaca actggggctc tangggtat ccccacncgc    480 cctgtaacgg cgcattaaac cccgcgggtg ttgtngttac cccacnttac cgctacactt    540
gccancgcct acgcccctcc tttcccttct cccttccttt ctcccacttc ccogcttccc    600 ctcaactcta atcggggccc cttaggttcc attaattctt acggncccca ccccaaaact    660
nataggtang gtcccttntt ggccncccct anaanggttt tccct                    705
```

```
<210> SEQ ID NO 5
<211> LENGTH: 617
<212> TYPE: DNA
<213> ORGANISM: Artificial Sequence
<220> FEATURE:
<223> OTHER INFORMATION: Human Rhodopsin cDNA sequence human rhodopsin
      5'UTR sequences/the ATG start site/human rhodopsin coding
      sequences are included.
<220> FEATURE:
<221> NAME/KEY: n
<222> LOCATION: (1)..(617)
<223> OTHER INFORMATION: any

<400> SEQUENCE: 5
tcccttntgn tagattgcan nncccaataa aanaaggncc cgcttaaagg cttatcgaaa    60
ttaatacgac tcactatang gagacccaag cttagagtca tccagctgga gccctgagtg    120
gctgagctca ggccttcgca gcattcttgg gtgggagcag ccacgggtca gccacaaggg    180
ccacagccat gaatggcaca gaaggcccta actctacgt gcccttctcc aatgcgacgg    240
gtgtggtacg cagccccttc gagtacccac agtactacct ggctgagcca nggcagntcr    300
```

| | |
|---|---|
| ccatgctggc cgcctacatg tttctgctga tcgtgctggg cttcccatc aacttcctca | 360 |
| cgctctacgt caccgtccag cacaagaagc tgcgcacgcc tctcaactac atcctggctc | 420 |
| aacctagccg tggctgaact cttcatggtc ctangtggct tcaccagcac ctctacanct | 480 |
| ctctgcatgg atactcgtct tcgggcccac aggatgcaat tgganggctc tttgcacctg | 540 |
| gngggaaatt gcctgtggtc ctngtggtcn ggncaccaac gtactggtng tgtntanccc | 600 |
| agaacaactc cgctccg | 617 |

<210> SEQ ID NO 6
<211> LENGTH: 574
<212> TYPE: DNA
<213> ORGANISM: Artificial Sequence
<220> FEATURE:
<223> OTHER INFORMATION: Human Rhodopsin cDNA with altered non-coding
      sequences human rhod opsin 5'UTR sequences (shorter UTR)/the AT
      G start site/human rhodopsin coding sequences are included.
<220> FEATURE:
<221> NAME/KEY: n
<222> LOCATION: (1)..(574)
<223> OTHER INFORMATION: any

<400> SEQUENCE: 6

| | |
|---|---|
| nnacttcttc nggaatacct gcgganaata nagaaccact gcttactggc ttatcgaaat | 60 |
| taatacgact cactataggg agacccaagc ttggtaccga gctcggatcc actagtaacg | 120 |
| gccgccagtg tgctggaatt ccggaaggcc tgagctcagc acaagggcc acagccatga | 180 |
| atggcacaga aggccctaac ttctacgtgc cttctccaa tgcgacgggt gtggtacgca | 240 |
| gcccttcga gtacccacag tactacctgg ctgagccatg gcagttctcc atgctggccg | 300 |
| cctacatgtt tctgctgatc gtgctgggct tccccatcaa cttcctcacg ctctacgtca | 360 |
| ccgtccagca caagaagctg cgcacgcctc tcaactacat cctggctcaa cctanccgtg | 420 |
| ggtgaactct tcatggtcct aggtgggttc accaacaccc tctaaaacct ctctgcatgg | 480 |
| atattcgtct tcgggccaca ggatgcaatt ggagggttct ttggcacctg ggngggaaat | 540 |
| gcctgtggtc ctgggngntc nggccaccaa cggt | 574 |

<210> SEQ ID NO 7
<211> LENGTH: 601
<212> TYPE: DNA
<213> ORGANISM: Artificial Sequence
<220> FEATURE:
<223> OTHER INFORMATION: Ribozyme 15 cloned in pcDNA3.
<220> FEATURE:
<221> NAME/KEY: n
<222> LOCATION: (1)..(601)
<223> OTHER INFORMATION: any

<400> SEQUENCE: 7

| | |
|---|---|
| cntncttttn anntttngnt cgcactctct ggctaactca gagaacccac tgcttactgg | 60 |
| cttatcgaaa ttaatacgac tcactatagg gagacccaag cttacccaag ctgatgagtc | 120 |
| cgtgaggacg aaatgctgct ctagagggcc ctattctata gtgtcaccta aatgctagag | 180 |
| ctcgctgatc agcctcgact gtgccttcta gttgccagcc atctgttgtt tgccctccc | 240 |
| ccgtgccttc cttgaccctg gaaggtgcca ctcccactgt cctttcctaa taaaatgagg | 300 |
| aaattgcatc gcattgtctg agtaagtgtc attctattct gggggtggg gtngggcang | 360 |
| acaacnaggg gaagattggg aananaataa caggcatgct ggggatgcng tgggctctat | 420 |
| ggcttcctga agcggaaaga aacactnggn tctagggggtn tcccccncc ctgtacnggc | 480 |
| attaacncgn ggtttgtngt tacccacnn ancctaattc agcctaccc ccttctcctc | 540 |

```
ctcttnccat tccggttccc taacntangg ggccttngtc caatatttn gcccccccca    600
a                                                                    601
```

<210> SEQ ID NO 8
<211> LENGTH: 626
<212> TYPE: DNA
<213> ORGANISM: Artificial Sequence
<220> FEATURE:
<223> OTHER INFORMATION: Mouse peripherin cDNA sequences mouse
      peripherin 5'UTR sequences/ the ATG start site/mouse peripherin
      coding sequences are included.
<220> FEATURE:
<221> NAME/KEY: n
<222> LOCATION: (1)..(626)
<223> OTHER INFORMATION: any

<400> SEQUENCE: 8

```
ttcnntgnaa attgcgccna aaananaagg gcngcttact ggcttatcna anttaatacg    60
actcactata gggagaccca agcttgcatg cctgcagggg gggggaagg actctgcaga   120
tacggcggcc taaattaact ccggctaccg ttactgantt aacggggatc ccaagctagg   180
gaggccccaa aatgggcaac tccctgcagc ttgggcccat ggtgctcttc cctanaccct   240
agcggtccag ccccgganct cactcggatt angagtggaa gctgaaccgt gggangctgc   300
tgaacgcact cngtaagcat ggcgctgctc aaagtcnagt ttgaccagaa gaaacnggtc   360
aagttggccc aagggctctg gctttatgaa ctggctgtcc gtgttnggcg gcatcgtccc   420
tcntcagctt ggggctgttc ttgaanattg aactttcccc aagaagaacc aaagtgatga   480
ataatttctg aaanccnctt ttgtncccaa ctccctgata ggggtgggg tcctgtccnt    540
nttcttnact ctctggctgg gaaaatttgc tnttnaancc ctggancccg ccaantncnc   600
cnnttggaaa ccctgctcga aaccct                                        626
```

<210> SEQ ID NO 9
<211> LENGTH: 617
<212> TYPE: DNA
<213> ORGANISM: Artificial Sequence
<220> FEATURE:
<223> OTHER INFORMATION: Mouse peripherin cDNA with altered non-coding
      sequences mouse rhodopsin 5'UTR sequences/the ATG start site/mouse
      peripherin coding sequences are included.
<220> FEATURE:
<221> NAME/KEY: n
<222> LOCATION: (1)..(617)
<223> OTHER INFORMATION: any

<400> SEQUENCE: 9

```
tnaccattcg nntaaanctn tcnnnccta ananaaccca ctggcttact ggcttatcga    60
aattaatacg actcactata gggagaccca agcttgagtt gcgctgtggg agccgtcagt   120
ggctgagctc gccaagcagc cttggtctct gtctacgaag agcccgtggg gcagcctcga   180
gagccgcagc catggcgctg ctcaaagtca gtttgacca gaagaagcgg gtcaagttgg   240
cccagggggct ctggcttatg aactggctgt ccgtgttggc cggcatcgtc ctcttcagct   300
tgggctgtt cttgaagatt gaacttcgca agaggagcga agtgatgaat aattctgaga   360
gccactttgt gcccaactcc ctgatangg tggggtcct gtcctgtgtc ttcaactctc    420
tggctgggaa gatctgctat gatgccctgg aaccggccaa gtacgccaag tggaanccct   480
ggctgaagcc gtacctggct gtctgcatct tcttaacgt catcctcttc cggtggntct   540
ctgctgcttc tgttgcnggg tccctggaaa acaccnggct tacggacnca aaatngggat   600
``` gaatttttt cnggata                                                617

<210> SEQ ID NO 10
<211> LENGTH: 610
<212> TYPE: DNA
<213> ORGANISM: Artificial Sequence
<220> FEATURE:
<223> OTHER INFORMATION: Ribozyme 17 sequence is included.
<220> FEATURE:
<221> NAME/KEY: n
<222> LOCATION: (1)..(610)
<223> OTHER INFORMATION: any

<400> SEQUENCE: 10

```
nnctnnntnt ttnatcgccc tctctggcta antcanagaa cccactgctt actggcttat      60
cgaaattaat acgactcact atagggtaga cccaagcttc actcctctga tgagtccgtg     120
aggacgaaat ccgagttcta gagggccta ttctatagtg tcacctaaat gctagagctc     180
gctgatcagc ctcgactgtg ccttctagtt gccagccatc tgttgtttgc cctcccccg     240
tgccttcctt gaccctggaa ggtgccactc ccactgtcct ttcctaataa aatgaggaaa    300
ttgcatcgca ttgtctgagt aagtgtcatt ctattctggg gggtggggtg gggcangaca    360
acaaggggga agattgggaa acaataaca ggcatgctgg ggatgcggtg ggctctatgg    420
ctcctgaagc gaaaaaacca ctggggctct aggggtttcc ccccccctg tacngccatt    480
aacncgnggt ntgtggtacc ccacnnacgt aattgcaccc tacccncttc ntctcctctt    540
ctccattcng gttcccccaa cnaaaggggc ccttggttca attttttnn gccccccna      600
nntnaagttc                                                            610
```

<210> SEQ ID NO 11
<211> LENGTH: 630
<212> TYPE: DNA
<213> ORGANISM: Artificial Sequence
<220> FEATURE:
<223> OTHER INFORMATION: Human peripherin cDNA sequences human
      peripherin 5'UTR sequences/ the ATG start site/human
      peripherin coding sequences are included.
<220> FEATURE:
<221> NAME/KEY: n
<222> LOCATION: (1)..(630)
<223> OTHER INFORMATION: any

<400> SEQUENCE: 11

```
nnncttntta ttcttcagcg tgccngacca ngantatccc ctgctcaagc tgtgattccg      60
agacccctgc caccactact gcattcacgg ggnatcccag gctagtggga ctcgacatgg    120
gtanccccca gggcagctcc ctacagcttg ggccatctgc acttttccca aggccctaag    180
tctccgcctc tgggctcgtt aaggtttggg gtgggagctg tgctgtggga agcaaccgg    240
actacacttg gcaagcatgg cgctactgaa agtcaagttt gaccaaaaaa agcgggtcaa    300
gttggcccaa gggctctggc tcatgaactg gttctccgtg ttggctggca tcatcatctt    360
cagcctagga ctgttcctga anattgaact ccgaaagaag ancgatgtga tgaataaatt    420
ctgaaancca ttttgtgccc aactcattga tanggatggg ggtgctatcc tgtgtcttca    480
actcnctggn tgggaanatc tgctacaacg ccctggaacc anccaatttg ccaaatggaa    540
ccctggctga aaccgtacct ggctatctgt nttcncctcc aaatcatccc cttccttgtg    600
ggtctctgct gctttccngc tccggggccc                                     630
```

<210> SEQ ID NO 12
<211> LENGTH: 612

```
<212> TYPE: DNA
<213> ORGANISM: Artificial Sequence
<220> FEATURE:
<223> OTHER INFORMATION: Human peripherin cDNA with altered non-coding
      sequences. Partial human and mouse peripherin 5'UTR sequences/the
      ATG start site/human peripherin coding sequences are included.
<220> FEATURE:
<221> NAME/KEY: n
<222> LOCATION: (1)..(612)
<223> OTHER INFORMATION: any

<400> SEQUENCE: 12
cnctattcaa acttgnccct gcaagtcgac nntanaggat cttcccagcc agcgagttga     60
agacacagga tagcaccccc atccctatca atgagttggg cacaaaatgg ctctcagaat    120
tattcatcac atcgctcctc tttcggagtt cgatcttcag gaacagtcct aggctgaaga   180
tgatgatgcc agccaacacg gagaaccant tcatgagcca gagcccttgg gccaacttga   240
cccgcttctt ctggtcaaac ttgactttca gtagcgccat gcttaccgag tgcgttcagc   300
agcctcccac ggttcagctt ccactcctaa tccgagtgag ctccggggct ggaccgctan   360
ggtctaagga anancaccat gggcccaagc tgcagggant tgcccatttt ggggcctgga   420
tccccgtgaa tgcantaatg gtggcagggg tctcggaatc acagcttgag cagggatagt   480
cctggtcctg ggcgctgaaa aaatcnccta tantgagtcg tatacaatca ctgggcgtcg   540
tttacaacgt ctgaatggga aaccctggnt tacccaactt aatcgcctgg aacacatccc   600
ctttcncanc tg                                                       612

<210> SEQ ID NO 13
<211> LENGTH: 619
<212> TYPE: DNA
<213> ORGANISM: Artificial Sequence
<220> FEATURE:
<223> OTHER INFORMATION: Ribozyme 8 sequence cloned in pcDNA3.
<220> FEATURE:
<221> NAME/KEY: n
<222> LOCATION: (1)..(619)
<223> OTHER INFORMATION: any

<400> SEQUENCE: 13
ctcnnntttn aacaganctg cngctaacta nagaaccact gcttactggc ttatcgaaat     60
taatacgact cactataggg agacccaagc ttccaagtgc tgatgagtcc gtgaggacga    120
aagtccggtc tagagggccc tattctatag tgtcacctaa atgctagagc tcgctgatca    180
gcctcgactg tgccttctag ttgccagcca tctgttgttt gcccctcccc cgtgccttcc    240
ttgaccctgg aangtgccac tcccactgtc ctttcctaat aaaatgagga aattgcatcg    300
cattgtctga gtaggtgtca ttctattctg gggggtgggg tggggcanga cancaagggg   360
gaagattggg aagacaatan cangcatgct ggggatgcgg tgggctctat ggcttctgaa   420
gcggaaagaa ccanctgggg ctctaagggg tatcccacg cnccctgtaa cggcgcatta   480
accccgcggt gttgttgtta cccccaacnt gaccgctaca cttgccaacc cctaaccccg   540
ctcctttcct ttcttccttc cttctcncac tttcccngct tcccntcaac tctaatcggg   600
gccccttagg ttcaattat                                                619

<210> SEQ ID NO 14
<211> LENGTH: 760
<212> TYPE: DNA
<213> ORGANISM: Artificial Sequence
<220> FEATURE:
<223> OTHER INFORMATION: Ribozyme 9 sequence cloned in pcDNA3.
<220> FEATURE:
```

```
<221> NAME/KEY: n
<222> LOCATION: (1)..(760)
<223> OTHER INFORMATION: any

<400> SEQUENCE: 14
nnnnnntttt naacaganct ccggctaact anagaaccac tgcttactgg cttatcgaaa      60
ttaatacgac tcactatagg gagacccaag cttcaaacct tctgatgagt ccgtgaggac     120
gaaacgagcc tctagagggc cctattctat agtgtcacct aaatgctaga gctcgctgat     180
cagcctcgac tgtgccttct agttgccagc catctgttgt ttgcccctcc ccgtgcctt     240
ccttgaccct ggaangtgcc actcccactg tcctttccta ataaaatgag gaaattgcat     300
cgcattgtct gagtangtgt cattctattc tggggggtgg ggtggggcaa ggacancaag     360
ggggaagatt gggaagacaa tancangcat gctggggatg cggtgggctc tatggcttct     420
gaagcggaaa gaaccanctg gggctctaag gggtatcccc acgcgccctg taaccgcgca     480
ttaaccccgc nggtntgttg gttaccccca cgtgaccgct acacttgcca acccctaacc     540
ccgctccttt ccctttcttc cttccttctc ccactttncc ggnttcccct caactctaat     600
cngggcncct taggttcaat tatcttacgn cncanccaaa atgataggta angtcntttt     660
ggccncccta aaaaggtttc ccttnattga tcccttctta natgancttt ccaatgaaaa     720
ccaccnncgt cttcttaata angattgcat cgccttgtaa                          760

<210> SEQ ID NO 15
<211> LENGTH: 620
<212> TYPE: DNA
<213> ORGANISM: Artificial Sequence
<220> FEATURE:
<223> OTHER INFORMATION: Human type I collagen (COL1A2) sequence - 5'UTR
      and exon 1 sequence are included.
<220> FEATURE:
<221> NAME/KEY: n
<222> LOCATION: (1)..(620)
<223> OTHER INFORMATION: any

<400> SEQUENCE: 15
cnnctnnntn ttttntngcn tctcnggcta acngacagaa cccactgctt actggcttat      60
cgaaattaat acgactcact atagggagac ccaagcttag caccacggca gcaggaggtt     120
tcggctaagt tggaggtact ggccacgact gcatgcccgc gcccgccatg tgatacctcc     180
gccggtgacc cagggctctg cgacacaagg agtcgcatgt ctaagtgcta gacatgctca     240
gctttgtgga tacgcggact ttgttgctgc ttgcagtaac ctcatgccta gcaacatgcc     300
aatctcgagc atgcatctan anggccctat tctatagtgt cncctanatg ctaganctcg     360
ctgatnagcc tcgactgtgc cttctaattg ccagccatct gtngtttggc cctccccgt     420
gccttccttg aacctggaag gtgccactcc cactgtcctt tcctaataaa atgaagaaat     480
tgcatcncat gtctgantag tgtcatctat ctgggggtgg gtngggcagg anaccaggga     540
gatggaaaaa atacagcttc tgggaacgtg gcctatgctc tnagngaaaa aactggggct     600
agggttcccc ccccntncgc                                                 620

<210> SEQ ID NO 16
<211> LENGTH: 621
<212> TYPE: DNA
<213> ORGANISM: Artificial Sequence
<220> FEATURE:
<223> OTHER INFORMATION: Ribozyme 18 sequence cloned in pcDNA3.
<220> FEATURE:
<221> NAME/KEY: n
<222> LOCATION: (1)..(621)
```

-continued

<223> OTHER INFORMATION: any

<400> SEQUENCE: 16

| | | | | | |
|---|---|---|---|---|---|
| agcagantct | ctggctaact | anagaaccca | ctgcttactg | gcttatcgaa | attaatacga | 60 |
| ctcactatag | ggagacccaa | gcttagacat | gcctgatgag | tccgtgagga | cgaaactcct | 120 |
| ttctagaggg | ccctattcta | tagtgtcacc | taaatgctag | agctcgctga | tcagcctcga | 180 |
| ctgtgccttc | tagttgccag | ccatctgttg | tttgcccctc | ccccgtgcct | tccttgaccc | 240 |
| tggaaggtgc | cactcccact | gtcctttcct | aataaaatga | ggaaattgca | tcgcattgtc | 300 |
| tgagtaggtg | tcattctatt | ctgggggtg | gggtgggca | ngacancaag | ggggangatt | 360 |
| gggaagacaa | tancangcat | gctggggatg | cggtgggctc | tatggcttct | gangcggaaa | 420 |
| gaaccanctg | gggctctagg | ggtatcccca | cnccoctgta | ccggccatta | agcccgcggt | 480 |
| gttgtngtta | ccccaantga | cgctacactg | ccacgcctac | gccctccttc | cttctccctc | 540 |
| cttctcccat | tccccggttc | ccctcancct | aatcggggcc | cttaggttcc | aatattctta | 600 |
| cgncnccacc | caaantaatn | g | | | | 621 |

<210> SEQ ID NO 17
<211> LENGTH: 644
<212> TYPE: DNA
<213> ORGANISM: Artificial Sequence
<220> FEATURE:
<223> OTHER INFORMATION: Antisense construct containing 127 bp of antisense sequence targeting the 5'UTR of the mouse peripherin gene.
<220> FEATURE:
<221> NAME/KEY: n
<222> LOCATION: (1)..(644)
<223> OTHER INFORMATION: any

<400> SEQUENCE: 17

| | | | | | |
|---|---|---|---|---|---|
| atggttatcg | aattaatacg | actcactata | nggagaccca | agcttccatg | cttaccgagt | 60 |
| gcgttcagca | gcctcccacg | gttcagcttc | cactcctaat | ccgagtgagc | tccggggctg | 120 |
| gaccgctagg | gtctanggaa | gagcaccatt | ctagagggcc | ctattctata | gtgtcaccta | 180 |
| aatgctagag | ctcgctgatc | agcctcgact | gtgccttcta | nttgccagcc | atctgttgtt | 240 |
| tgcccctccc | ccgtgccttc | cttgaccctg | gaangtgcca | ctcccactgt | nctttcctaa | 300 |
| aaaaatgagg | aaattgcatc | gcattgtctg | actaagtgtc | attctattct | gggggtggg | 360 |
| gtggggcacg | acaacaangg | ggaagattgg | gaanacaata | acacgcatgc | ngggatgcc | 420 |
| gtggggctct | atggcttctg | aagcggaaag | aacaactggg | gcnctagggg | tatcccacac | 480 |
| gccctgtacc | gggctttaac | gcggnggtgt | tgtggttacc | ccaacttgac | gctacacttt | 540 |
| ccaacgccta | ncgccgctct | ttcctttctt | ccctccattc | ccccaattcc | ccgntttccc | 600 |
| cccnnnnnnn | nnnnncncnc | nnnaantnng | ggggccctn | nggg | | 644 |

<210> SEQ ID NO 18
<211> LENGTH: 603
<212> TYPE: DNA
<213> ORGANISM: Artificial Sequence
<220> FEATURE:
<223> OTHER INFORMATION: Sense construct containing 127 bp of sense sequence from the 5'UTR of the mouse peripherin gene.
<220> FEATURE:
<221> NAME/KEY: n
<222> LOCATION: (1)..(603)
<223> OTHER INFORMATION: any

<400> SEQUENCE: 18

-continued

```
nngnnnnnnn ncntatggtt atcgaattaa tacgactcac tatagggaga cccaagctta      60
tggtgctctt ccctanaccc tancggtcca gccccggagc tcactcggat taggagtgga     120
agctgaaccg tgggaggctg ctgaacgcac tcggtaagca tggtctanag ggccctattc     180
tatagtgtca cctaaatgct agagctcgct gatcagcctc gactgtgcct tctagttgcc     240
agccatctgt tgtttgcccc tcccccgtgc cttccttgac cctggaaggt gccactccca     300
ctgtcctttc ctaataaaat gaggaaattg catcgcattg tctgagtaag tgtcattcta     360
ttctgggggg tggggtgggg cangacaaca aggggggaaga ttgggaanac aataacangc    420
atgctgggga tgccgtgggc tctatggctt ctgaagcgga aanaaccact ggggctctaa     480
ggggtatccc caccccctg taccggccat aacccgcgg tttgtggtta ccccactnac      540
gtaccttgca cgcctacccc cnccttcctc ttcctccttc cccnttccgg ttcccnnann    600 nnn                                                                  603
```

<210> SEQ ID NO 19
<211> LENGTH: 607
<212> TYPE: DNA
<213> ORGANISM: Artificial Sequence
<220> FEATURE:
<223> OTHER INFORMATION: Reverse Mouse Rhodopsin cDNA with altered non-coding sequences mouse rhodopsin 5'UTR sequences with a 1 base change/the ATG start site/mouse rhodopsin coding sequences are included.
<220> FEATURE:
<221> NAME/KEY: n
<222> LOCATION: (1)..(607)
<223> OTHER INFORMATION: any

<400> SEQUENCE: 19

```
nnccttctt anngtnngct gccagcatgg agaatgccat ggttccgcca ggtagtactg      60
cggctgctcg aagggctcc gcaccacgcc tgtgacgttg gagaagggca cataaaatt     120 tgggccctct gtgccgttca tgtttgccaa gtgtagtccg ggttgcttcc cacagcacag    180
ctcccacccc aaaccttaac gagcccagag gcggagactt agggccttgg gaaaagtgca    240
gatggcccaa gctgtangga gctgccctgg gggctaccca tgtcgagtcc cactagcctg    300
ggatccccgt gaatgcanta ntggtggcag gggtctcgga atcacagctt gagcagggga    360
tagtcctggt cctgggcgct gaancttggg tctccctata ntgagtcgta ttaatttcga    420
taagccanta agcantgggt tctctagtta gccagaaanc tctgcttata tagaactccc    480
accgtacacg cctaccgccc atttgcgtca tgggggagt gttacaaatt tggaaatccn    540
ttgaattngg ggccaaaaaa atcccatgan ttcatgggtg gaaattgaaa tccctgatt    600 caaccct                                                             607
```

<210> SEQ ID NO 20
<211> LENGTH: 615
<212> TYPE: DNA
<213> ORGANISM: Artificial Sequence
<220> FEATURE:
<223> OTHER INFORMATION: Reverse Mouse Rhodopsin cDNA with altered non-coding sequences mouse rhodopsin 5'UTR sequences with a 1 base change/the ATG start site/mouse rhodopsin coding sequences are included.
<220> FEATURE:
<221> NAME/KEY: n
<222> LOCATION: (1)..(615)
<223> OTHER INFORMATION: any

<400> SEQUENCE: 20

```
ttnnntntnn ttngactgtt gnccgccaan atggaganngt gccatggttc cgccaggtag    60
```

-continued

```
tactgcggct gctcgaagag gctccgcacc acgcctgtga cgttggagaa gggcacataa      120
aaattggggc cctctgtgcc gttcatggct gcggctctcg aggctgcccc acgggctctt      180
cgtagccaga gaccaaggct gcttggcgag ctcagccact gacggctccc acagcgcaac      240
tccaggcact gaccccccc agacccttat aaagtgacct tctctcccta agccagangc       300
tgattcagca tccgcgagat atcatactaa cgctaatccc actgctgcca ccggggccta     360
attggcttgc agangggcca aggtgacatc gggtggaagc ccttangtaa agaaaggaaa     420
nggtgtctca tcttgtctgc cccagantcc tctgggaatt ccagcacact ggcgggcgtt    480
actantggat ccganctcng taccaagctt gggtctccta taatgagtcc tattaatttc    540
gataaccata acagtgggtt ctctanttac cagaaactct gcttatataa actcccacgt    600
acacnctacg ccatt                                                     615
```

```
<210> SEQ ID NO 21
<211> LENGTH: 37
<212> TYPE: RNA
<213> ORGANISM: Artificial Sequence
<220> FEATURE:
<223> OTHER INFORMATION: Rib3

<400> SEQUENCE: 21
cuucguacug augaguccgu gaggacgaaa cagagac                              37

<210> SEQ ID NO 22
<211> LENGTH: 36
<212> TYPE: RNA
<213> ORGANISM: Artificial Sequence
<220> FEATURE:
<223> OTHER INFORMATION: Rib15

<400> SEQUENCE: 22
acccaagcug augaguccgu gaggacgaaa ugcugc                               36

<210> SEQ ID NO 23
<211> LENGTH: 37
<212> TYPE: RNA
<213> ORGANISM: Artificial Sequence
<220> FEATURE:
<223> OTHER INFORMATION: Rib17

<400> SEQUENCE: 23
cacuccucug augaguccgu gaggacgaaa uccgagu                              37

<210> SEQ ID NO 24
<211> LENGTH: 36
<212> TYPE: RNA
<213> ORGANISM: Artificial Sequence
<220> FEATURE:
<223> OTHER INFORMATION: Rib8

<400> SEQUENCE: 24
ccaagugcug augaguccgu gaggacgaaa guccgg                               36

<210> SEQ ID NO 25
<211> LENGTH: 37
<212> TYPE: RNA
<213> ORGANISM: Artificial Sequence
<220> FEATURE:
<223> OTHER INFORMATION: Rib9

<400> SEQUENCE: 25
```

```
caaaccuucu gaugaguccg ugaggacgaa acgagcc                    37
```

<210> SEQ ID NO 26
<211> LENGTH: 37
<212> TYPE: RNA
<213> ORGANISM: Artificial Sequence
<220> FEATURE:
<223> OTHER INFORMATION: Rib18

<400> SEQUENCE: 26

```
agacaugccu gaugaguccg ugaggacgaa acuccuu                    37
```

What is claimed is:

1. A therapeutic composition for treating a genetic disease, the composition comprising:
   a) a suppression effector that binds to an untranslated region of a mature RNA encoding a mutant allele, wherein said suppression effector inhibits the expression of the mutant allele; and
   b) a replacement nucleic acid that encodes a wild-type or non-disease causing allele and that is not inhibited by the suppression effector.

2. The composition of claim 1, wherein the suppression effector is a nucleic acid or peptide nucleic acid (PNA).

3. The composition of claim 1, wherein the suppression effector is a peptide.

4. The composition of claim 1, wherein the suppression effector is an antisense nucleic acid.

5. The composition of claim 1, wherein the suppression effector cleaves or degrades mRNA.

6. The composition of claim 1, wherein the suppression effector is a ribozyme.

7. The composition of claim 1, wherein the suppression effector is a nucleic acid that forms a triple helix with a portion of the untranslated region of the mutant allele.

8. The composition of claim 1, wherein the suppression effector is specific for mammalian rhodopsin RNA.

9. The composition of claim 1, wherein the suppression effector is specific for mammalian peripherin RNA.

10. The composition of claim 1, wherein the suppression effector is specific for mammalian collagen RNA.

11. The composition of claim 1, wherein the replacement nucleic acid does not hybridize with, or is only partially suppressed by, the suppression effector.

12. The composition of claim 1, wherein the replacement nucleic acid encodes a protein selected from the group consisting of mammalian rhodopsin, collagen 1A2 and peripherin.

13. The composition of claim 1, wherein the suppression effector comprises a nucleic acid sequence selected from the group consisting of SEQ ID NOS: 7, 13, 14 and 16.

14. The composition of claim 1, wherein suppression effector is operatively linked to an expression vector.

15. The composition of claim 1, wherein the replacement nucleic acid is operatively linked to an expression vector.

16. The composition of claim 1, wherein the suppression effector and the replacement nucleic acid are operatively linked to the same expression vector.

17. The composition of claim 1, wherein the untranslated region is essentially a 5' untranslated region.

18. The composition of claim 1, wherein the untranslated region is essentially a 3' untranslated region.

19. The composition of claim 17 or 18, wherein the suppression effector binds to said untranslated region and to a portion of the coding sequence.

20. The composition of claim 1, wherein the genetic disease is an autosomal dominant disease or a polygenic disease.

21. The composition of claim 1, wherein the genetic disease is osteogenesis imperfecta, retinitis pigmentosa, age-related macular degeneration, glaucoma, manic depression or cancer.

22. A therapeutic composition for suppressing the expression of a mutant allele of a protein, the composition comprising:
   a) a ribozyme that targets an untranslated region of a mature RNA encoding a mutant allele; and
   b) a replacement nucleic acid that encodes a wild-type or non-disease causing allele and that is not targeted by the ribozyme.

23. The composition of claim 22, wherein the ribozyme cleavage site is an NUX site.

24. The composition of claim 22, wherein the ribozyme is specific for mammalian rhodopsin RNA.

25. The composition of claim 22, wherein the ribozyme is specific for mammalian peripherin RNA.

26. The composition claim 22, wherein the ribozyme is specific for mammalian collagen RNA.

27. The composition of claim 22, wherein the replacement nucleic acid does not hybridize with, or is only partially suppressed by, the ribozyme.

28. The composition of claim 22, wherein the replacement nucleic acid encodes a protein selected from the group consisting of mammalian rhodopsin, collagen 1A2 and peripherin.

29. The composition of claim 22, wherein the suppression effector comprises a nucleic acid sequence selected from the group consisting of SEQ ID NOS: 7, 13, 14 and 16.

30. The composition of claim 22, wherein the ribozyme is operatively linked to an expression vector.

31. The composition of claim 22, wherein the replacement nucleic acid is operatively linked to an expression vector.

32. The composition of claim 22, wherein the ribozyme and the replacement nucleic acid are operatively linked to the same expression vector.

33. The composition of claim 22, wherein the untranslated region is essentially a 5' untranslated region.

34. The composition of claim 22, wherein the untranslated region is essentially a 3' untranslated region.

35. The composition of claim 33 or 34, wherein the ribozyme binds to said untranslated region and to a portion of the coding sequence.

36. The composition of claim 22, wherein the genetic disease is an autosomal dominant disease or a polygenic disease.

37. The composition of claim 22, wherein the genetic disease is osteogenesis imperfecta, retinitis pigmentosa, age-related macular degeneration, glaucoma, manic depression or cancer.

38. The composition of claim 1, wherein the suppression effector suppresses an endogenous gene.

39. The composition of claim 22, wherein the ribozyme suppresses an endogenous gene.

* * * * *